(12) United States Patent
Bughrara et al.

(10) Patent No.: US 7,317,098 B2
(45) Date of Patent: Jan. 8, 2008

(54) RYEGRASS CBF3 GENE: IDENTIFICATION AND ISOLATION

(75) Inventors: Suleiman Bughrara, East Lansing, MI (US); Zhoa Han, East Lansing, MI (US); Yuexia Wang, New York, NY (US)

(73) Assignee: The Board of Trustees of Michigan State University, Lansing, MI (US)

( * ) Notice: Subject to any disclaimer, the term of this patent is extended or adjusted under 35 U.S.C. 154(b) by 223 days.

(21) Appl. No.: 10/883,512

(22) Filed: Jul. 1, 2004

(65) Prior Publication Data

US 2006/0005265 A1    Jan. 5, 2006

(51) Int. Cl.
*C07H 21/02* (2006.01)
*C07H 21/04* (2006.01)
*C12N 15/63* (2006.01)

(52) U.S. Cl. .................. 536/23.1; 536/23.6; 435/320.1

(58) Field of Classification Search ............... None
See application file for complete search history.

(56) References Cited

OTHER PUBLICATIONS

Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*

* cited by examiner

*Primary Examiner*—David H. Kruse
*Assistant Examiner*—Vinod Kumar
(74) *Attorney, Agent, or Firm*—Medlen & Carroll, LLP

(57) ABSTRACT

The present invention relates to genes, proteins and methods comprising or utilizing C-repeat binding factors (CBF), specifically CBF3 in the ryegrass family. In a preferred embodiment, the present invention relates to using ryegrass CBF3 for altering cold tolerance and growth in plants, specifically in warm season grasses, turfgrasses, fodder plants and microorganisms.

13 Claims, 54 Drawing Sheets

Fig. 3a

Ryegrass cbf3 gene cloning and identification

The band of ryegrass is amplified by the primer of rice CBF gene (Tm=70°C)

Based on the rice sequence primers
O18065
(GGCCGGGGCGGGGAACCAAGTTCC),
O18066
(AGGCAGAGTCGGCGAAGTTGAGGC)
were synthesized and PCR for ryegrass genome The band of ryegrass is amplified by the CBF degenerated primer (Tm=50°C)

CBF Forward Primer
CC(AGCT)AA(AG)AA(AG)CC(AGCT)GC(ACGT)GG(ACGT)

CBF Reverse Primer
GG(AGCT)A(AG)(AGCT)A(AG)CAT(AGCT)CC(CT)TC(AGCT)GCC

>gi|22594968|gb|AF300970.1| Oryza sativa DRE-binding protein 1A mRNA, complete cds
Length = 895

Score = 198 bits (103), Expect = 2e-48
Identities = 168/198 (84%), Gaps = 1/198 (0%)
Strand = Plus / Plus

```
Query:    1  ggcggggcgaaccaagttccgggagacgcggcacccggtatcgcggtgtgcgtcgtag   60
             |||||||||||||||||| |||||||| |||||||||||| ||||||||| ||| |||
Sbjct:  177  ggcggggcgaccaagttcagggagacgaggacccggtgttccgcggcgtgcgggcgag  236

Query:   61  gggcaatgccggagggtgggtatgcgaggtgcgggtgcccaggagcgcgggagcaggct  120
             |||||||||||||||||||||| |||||||||||||||  |||||| ||| |||||||
Sbjct:  237  gggcaatgccggagggtgggtgtgcgaggtgcgggtgcccggtgcccgcgctgcaggct  296

Query:  121  gtgggtcggcaccttcgacactgccgagatcgccgcgcgagcacaagagggccgccatgc  180
             |||||||||||| ||||||||| |||||||| |||||||| ||||||| |||||||||
Sbjct:  297  ctggctcggcacgttcgacaccgccgagggcgcggcgcgcacga-cgccgccatgc    355

Query:  181  tcgccctcgccgcgggcg  198
             ||||| |||| ||||||
Sbjct:  356  tcgccatcaacgccggcg  373
```

Northern analysis

Cbf core sequence as probe

Cbf downstream gene(COR39 homologous gene) express analysis

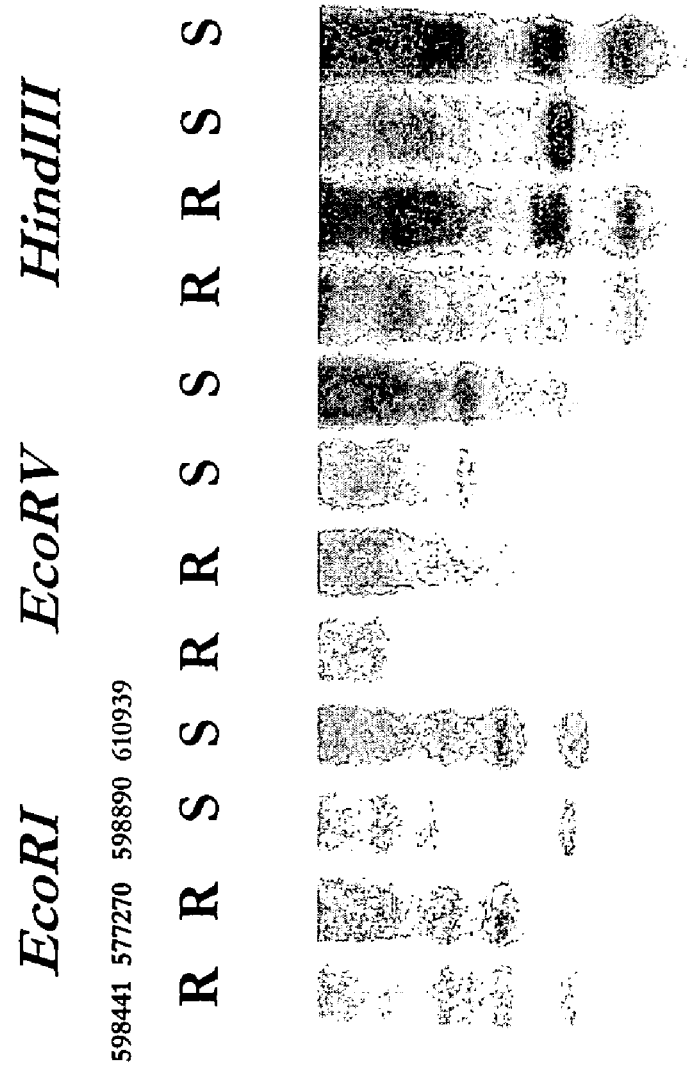
Fig. 5 Southern analysis

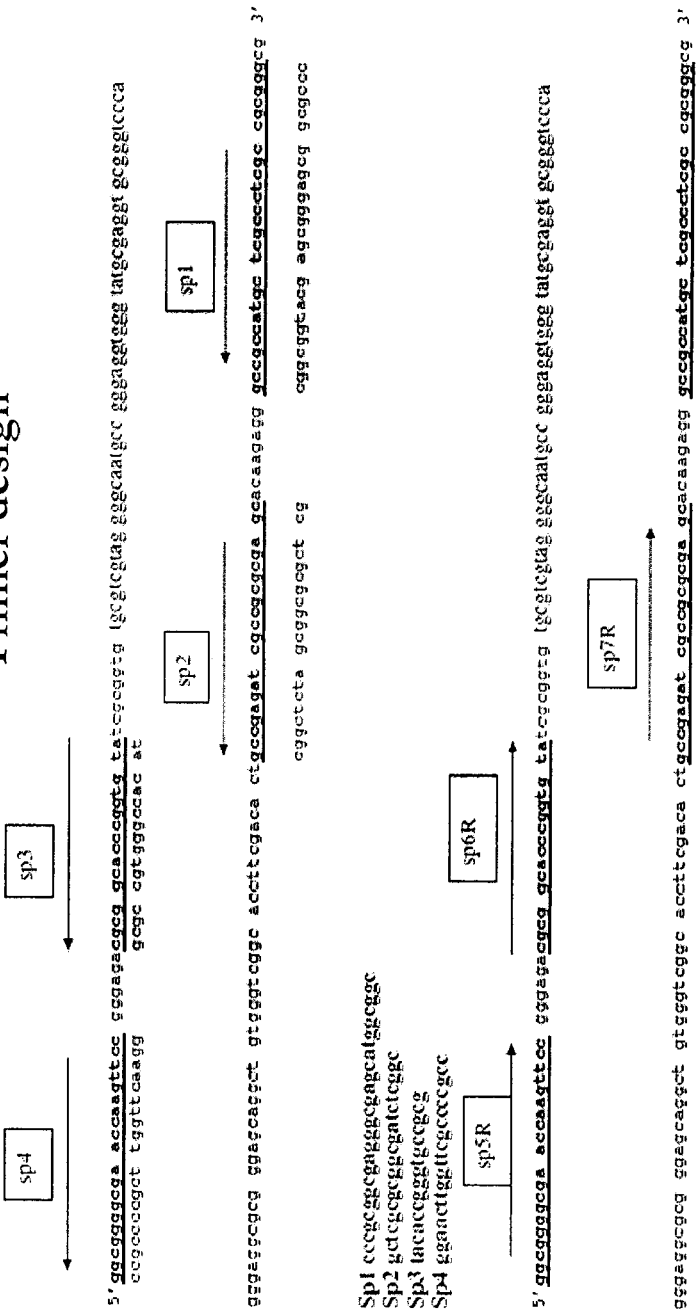

Lpcbf3 gene amplification

Primer design

The cbf gene in pGEM™ Vector amplified by T7 and sp6 primers

DNA sequence alignment

Fig. 8

SEQ ID NO:01:
Lolium perenne (perennial ryegrass) CBF3 full-length cDNA
nucleotide sequence:

```
attaaatttctcatcgcagagcaaaaccacttcacttcagcaaacaaaaagcatcaagagccctccaaggc
gaacagagacactgaggtagcgctagctcctattagattgtgattcggatcaacactcaattcgccatcag
aagatgtgtccgatcaaggaggagatgggcggggagtcaggctcgccgtgcagcggggactattactcgcc
ctcgacgtcgtcggagctgcagcaggtgcatagtcagaaccagacgccgtggacgaagcggccggcggggc
ggaccaagttcagggagacgcggcacccggtgtatcgcggtgtgcgtcgtaggggcaatgccgggaggtgg
gtatgcgaggtgcgcgtcccagggaggcgcgggagcaggctgtgggtcggccttcgacactgccgagat
cgccgcgcgagcacacgacgccgccatgctcgccctcgccgcgggcgattcctgcctcaacttcgctgact
ccgctgagctgctcgccgtgtcggcatcctcctaccgcagcctcgacgaggtgcgccacgctgtcaccgag
gccgtcgacgaattcgagcgacaccacgcgctgggcgaggaggacgccctgtccggcacgtcggcgtcgac
gccctcctcctcttcctccgtcaccgacgacgagacgtcgtcttcgtgggccgcggattcgcccttcgagc
tggaagtcatgggtgatatgggcagggatctgtactactcgagcttggcgcagggaatgctcatggcgccg
ccgaccgcagctgcagcgctcggtgattacggcgaggccaacctcgccgatgtggcactgtggagttacca
gagctagttttgttcgcgccacttcaaattttacctctctccttcggtgtcgtcttggacaaatttggtt
ctgtacggtcactgctagcagtttctggtaatgtgattgtgcaaattcagg
```

SEQ ID NO:02:
Lolium perenne (perennial ryegrass) CBF3 amino acid
sequence:

MCPIKEEMGGESGSPCSGDYYSPSTSSELQQVHSQNQTPWTKRPAGRTKFRETRHPVYR
GVRRRGNAGRWVCEVRVPGRRGSRLWVGTFDTAEIAARAHDAAMLALAAGDSCLNFADS
AELLAVSASSYRSLDEVRHAVTEAVDEFERHHALGEEDALSGTSASTPSSSSSVTDDET
SSSWAADSPFELEVMGDMGRDLYYSSLAQGMLMAPPTAAAALGDYGEANLADVALWSYQ
S

SEQ ID NO:03:
Lolium perenne (perennial ryegrass) CBF3 AP DNA-binding
domain amino acid sequence:

VYRGVRRRGNAGRWVCEVRVPGRRGSRLWVGTFDTAEIAARAHDAAMLALAAGDSCLNF
A

SEQ ID NO:04:
CBF motif bracket sequences for CBF3 AP DNA-binding domain
amino acid sequence:

PKK/RPAGRxKFxETRHP/AP DNA-binding domain/DSAWR

SEQ ID NO:5:
Lolium perenne (perennial ryegrass) bracket sequences for
CBF3 AP DNA-binding domain amino acid sequence:

WTK/RPAGRTKFRETRHP/AP DNA-binding domain/DSAEL
PWT/RPAGRTKFRETRHP/AP DNA-binding domain/DSAEL

Fig. 9

Fig. 10.
LpCBF3 AP Binding Domain Area Variants

| | |
|---|---|
| SEQ. ID. No.:06 | FRGVRRRGNAGRWVCEVRVPGRRGSRLWVGTFDTAEIAARAHDAAMLALAAGDSCLNFADSAEL |
| SEQ. ID. No.:07 | YRGVRQRGNAGRWVCEVRVPGRRGSRLWVGTFDTAEIAARAHDAAMLALAAGDSCLNFADSAEL |
| SEQ. ID. No.:08 | YRGVRRR-NSGKWVCEVRVPGRRGSRLWVGTFDTAEIAARAHDAAMLALAAGDSCLNFADSAEL |
| SEQ. ID. No.:09 | YRGVRRRGAAGRWVCEVRVPGRRGSRLWVGTFDTAEIAARAHDAAMLALAAGDSCLNFADSAEL |
| SEQ. ID. No.:10 | YRGVRRRGRVGQWVCEVRVPGRRGSRLWVGTFDTAEIAARAHDAAMLALAAGDSCLNFADSAEL |
| SEQ. ID. No.:11 | YRGVRRRGNTERWVCELREPGRRGSRLWVGTFDTAEIAARAHDAAMLALAAGDSCLNFADSAEL |
| SEQ. ID. No.:12 | YRGVRRRGNAGRWVCELREPGRRGSRLWVGTFDTAEIAARAHDAAMLALAAGDSCLNFADSAEL |
| SEQ. ID. No.:13 | YRGVRRRGNAGRWVCEVRVPNKK-TRLWVGTFDTAEIAARAHDAAMLALAAGDSCLNFADSAEL |
| SEQ. ID. No.:14 | YRGVRRRGNAGRWVCEVRVPGRRGSRIWVGTFDTAEIAARAHDAAMLALAAGDSCLNFADSAEL |
| SEQ. ID. No.:15 | YRGVRRRGNAGRWVCEVRVPGIKGSRLWVGTFDTAEIAARAHDAAMLALAAGDSCLNFADSAEL |
| SEQ. ID. No.:16 | YRGVRRRGNAGRWVCEVRVPGRRGCRLWVGTFDTAEIAARAHDAAMLALAAGDSCLNFADSAEL |
| SEQ. ID. No.:17 | YRGVRRRGNAGRWVCEVRVPGRRGARLWVGTFDTAEIAARAHDAAMLALAAGDSCLNFADSAEL |
| SEQ. ID. No.:18 | YRGVRRRGNAGRWVCEVRVPGRRGSRLWLGTFDTAEIAARAHDAAMLALAAGDSCLNFADSAEL |
| SEQ. ID. No.:19 | YRGVRRRGNAGRWVCEVRVPGRRGSRLWVGTYDTAEIAARAHDAAMLALAAGDSCLNFADSAEL |
| SEQ. ID. No.:20 | YRGVRRRGNAGRWVCEVRVPGRRGSRLWVGTFDTAEGAARAHDAAMLALAAGDSCLNFADSAEL |
| SEQ. ID. No.:21 | YRGVRRRGNAGRWVCEVRVPGRRGSRLWVGTFATAEVAARAHDAAMLALAAGDSCLNFADSAEL |
| SEQ. ID. No.:22 | YRGVRRRGNAGRWVCEVRVPGRRGSRLWVGTFLAAEAAARAHDAAMLALAAGDSCLNFADSAEL |
| SEQ. ID. No.:23 | YRGVRRRGNAGRWVCEVRVPGRRGSRLWVGTFDTAEMAARAHDAAMLALAAGDSCLNFADSAEL |
| SEQ. ID. No.:24 | YRGVRRRGNAGRWVCEVRVPGRRGSRLWVGTFNTAEIAARAHDAAMLALAAGDSCLNFADSAEL |
| SEQ. ID. No.:25 | YRGVRRRGNAGRWVCEVRVPGRRGSRLWVGTFQTAEIAARAHDAAMLALAAGDSCLNFADSAEL |
| SEQ. ID. No.:26 | YRGVRRRGNAGRWVCEVRVPGRRGSRLWVGTFNTAEMAARAHDAAMLALAAGDSCLNFADSAEL |
| SEQ. ID. No.:27 | YRGVRRRGNAGRWVCEVRVPGRRGSRLWVGTFQTAEMAARAHDAAMLALAAGDSCLNFADSAEL |
| SEQ. ID. No.:28 | YRGVRRRGNAGRWVCEVRVPGRRGSRLWVGTFDTAEIAARANDAAMLALAAGDSCLNFADSAEL |
| SEQ. ID. No.:29 | YRGVRRRGNAGRWVCEVRVPGRRGSRLWVGTFDTAEIAARAHDVAAIALAAGDSCLNFADSAEL |
| SEQ. ID. No.:30 | YRGVRRRGNAGRWVCEVRVPGRRGSRLWVGTFDTAEIAARAHDAAILALAAGDSCLNFADSAEL |
| SEQ. ID. No.:31 | YRGVRRRGNAGRWVCEVRVPGRRGSRLWVGTFDTAEIAARAHDAAVLALAAGDSCLNFADSAEL |

Fig. 10. (continued)

LpCBF3 AP Binding Domain Area Variants (continued)

| | |
|---|---|
| SEQ. ID. No.:32 | YRGVRRRGNAGRWVCEVRVPGRRGSRLWVGTFDTAEIAARAHDAAMLAINAGACCLNFADSAEL |
| SEQ. ID. No.:33 | YRGVRRRGNAGRWVCEVRVPGRRGSRLWVGTFDTAEIAARAHDAAMLALGGRSATCLNFADSDSAEL |
| SEQ. ID. No.:34 | YRGVRRRGNAGRWVCEVRVPGRRGSRLWVGTFDTAEIAARAHDAAMLALQGRGAGRLNFADSAEL |
| SEQ. ID. No.:35 | YRGVRRRGNAGRWVCEVRVPGRRGSRLWVGTFDTAEIAARAHDAAMLALSGRAACLNFADSAEL |
| SEQ. ID. No.:36 | YRGVRRRGNAGRWVCEVRVPGRRGSRLWVGTFDTAEIAARAHDAAMLALRGRSACLNFADSAEL |
| SEQ. ID. No.:37 | YRGVRRRGNAGRWVCEVRVPGRRGSRLWVGTFDTAEIAARAHDAAMLAGRDACLNFPDSAEL |
| SEQ. ID. No.:38 | YRGVRRRGNAGRWVCEVRVPGRRGSRLWVGTFDTAEIAARAHDAAMLALAGRGAGRLNFPDSAEL |
| SEQ. ID. No.:39 | YRGVRRRGNAGRWVCEVRVPGRRGSRLWVGTFDTAEIAARAHDAAMLALAAGDSRLNFPDSAEL |
| SEQ. ID. No.:40 | YRGVRRRGNAGRWVCEVRVPGRRGSRLWVGTFDTAEIAARAHDAAMLALAAGDSCLNFPDSAEL |
| SEQ. ID. No.:41 | YRGVRRRGNAGRWVCEVRVPGRRGSRLWVGTFDTAEIAARAHDAAMLALAAGDSCLNFADSAWL |
| SEQ. ID. No.:42 | YRGVRRRGNAGRWVCEVRVPGRRGSRLWVGTFDTAEIAARAHDAAMLALAAGDSCLNFADSARL |
| SEQ. ID. No.:43 | YRGVRRRGNAGRWVCEVRVPGRRGSRLWVGTFDTAEIAARAHDAAMLALAAGDSCLNFPDSARL |
| SEQ. ID. No.:44 | YRGVRRRGNAGRWVCEVRVPGRRGSRLWVGTFDTAEIAARAHDAAMLALAAGDSCLNFADSAWRL |
| SEQ. ID. No.:45 | YRGVRRRGNAGRWVCEVRVPGRRGSRLWVGTFDTAEIAARAHDAAMLALAAGDSCLNFADSAWRM |
| SEQ. ID. No.:46 | YRGVRRRGNAGRWVCEVRVPGRRGSRLWAGTFDTARIAARAHDAAMLALAAGDSCLNFADSAEL |
| SEQ. ID. No.:47 | YRGVRRRGNAGRWVCEVRVPGRRGSRLWVGTFDTARIAARAHDAAMLALAAGDSCLNFADSAEL |
| SEQ. ID. No.:48 | YRGVRRRGNAGRWVCEVRVPGRRGSRLWAGTFDTARIAARAHDAAMLALAAGDSCLNFADSAEL |

Fig. 11

SEQ ID NO:49:
PCR primer (Fig. 3a):
O18065: GGC CGG CGG GGC GAA CCA AGT TCC

SEQ ID NO:50:
PCR primer (Fig. 3a):
O18066: AGG CAG AGT CGG CGA AGT TGA GGC

SEQ ID NO:51:
CBF3 degenerate primers (Fig. 3a):
Forward:
5'-CC(AGCT)AA(AG)AA(AG)CC(AGCT)GC(ACGT)GG(ACGT)-3'

SEQ ID NO:52:
CBF3 degenerate primers (Fig. 3a):
Reverse:
5'-GG(AGCT)A(AG)(AGCT)A(AG)CAT(AGCT)CC(CT)TC(AGCT)GCC-3'

SEQ ID NO:53:
3'-5' RACE primers (Fig. 6a):
Sp1: CCC GCG GCG AGG GCG AGC ATG GCG GC SEQ ID NO:54:
3'-5' RACE primers (Fig. 6a):
Sp2: GCT CGC GCG GCG ATC TCG GC SEQ ID NO:55 (Fig. 6a):
3'-5' RACE primers:
Sp3: TAC ACC GGG TGC CGC G SEQ ID NO:56 (Fig. 6a):
3'-5' RACE primers:
Sp4: GGAACTTGGTTCGCCCCGCC SEQ ID NO:57 (Fig. 6a):
5'-3' RACE primers:
sp5R: GGC GGG GCG AAC CAA GTT CC SEQ ID NO:58 (Fig. 6a):
5'-3' RACE primers:
sp6R: CGC GGC ACC CGG TGT A

Fig. 11

SEQ ID NO:59 (Fig. 6a):
5'-3' RACE primers:
sp7R: GCC GAG ATC GCC GCG CGA GC

SEQ ID NO:60 (Fig. 7a):
5'-3' Lpcbf3 gene amplification primers:
CBF1: AAA TTT CTC ATC GCA GAG CAA AAC SEQ ID NO:61 (Fig. 7a):
5'-3' Lpcbf3 gene amplification primers:
CBF2: CAG CAA ACA AAA AGC ATC AAG AAC SEQ ID NO:62 (Fig. 7a):
5'-3' Lpcbf3 gene amplification primers:
CBF3: CAA GGC GAA CAG AGA CAC TG SEQ ID NO:63 (Fig. 7a):
5'-3' Lpcbf3 gene amplification primers:
CBF4: CGC CAT CAG AAG ATG TGT CCG SEQ ID NO:64:
Forward-Primer Cbf3-4F:   5'-ACTGAGGTAGCGCTAGCTCCTATT-3'

SEQ ID NO:170:
Reverse-Primer Cbf3-4R:   5'-CACAATCACATTACCAGAAACTGC-3'

SEQ ID NO:65:
C-repeat element:
5'-TGGCCGAC -3'

SEQ ID NO:66:
dehydration - responsive element:
5'-TACCGACAT-3'

SEQ ID NO:67:
C-repeat/dehydration-responsive element:
5'-CCGAC-3'

SEQ ID NO:68:
GCC box comprising:
5'-TAAGAGCCGCC-3'

SEQ ID NO:69:
AGC box:
5'-AGCCGCC-3

Fig. 12

| Plant Name | Ryegrass | Rice | Barley | Maize | Tomato | Arabidposis | Rye | Brassica napus |
|---|---|---|---|---|---|---|---|---|
| Identities | LpCBF | OsCBF | HvCBF | CBF | CBF | CBF | CBF | BNCBF |
|  |  | 50% | 38% | 38% | 23% | 23% | 26% | 23% |
|  | USA-MSU | Japan | USA CA | China | MSU | MSU | MSU | Canada |

Fig. 13A

SEQ ID NO:70:
Oryza sativa (rice) DRE-binding protein 1A (GenBank
AF300970) amino acid sequence:
MCGIKQEMSGESSGSPCSSASAERQHQTVWTAPPKRPAGRTKFRETRHPVFRGVRRRGN
AGRWVCEVRVPGRRGCRLWLGTFDTAEGAARAHDAAMLAINAGGGGGGACCLNFADSA
WLLAVPRSYRTLADVRHAVAEAVEDFFRRRLADDALSATSSSSTTPSTPRTDDDEESAA
TDGDESSSPASDLAFELDVLSDMGWDLYYASLAQGMLMEPPSAALGDDGDAILADVPLW
SY SEQ ID NO:71:
Oryza sativa (rice) transcription factor RCBF3 (EMBL
AY345233) amino acid sequence:
MCGIKQEMSGESSGSPCSSASAERQHQTVWTAPPKRPAGRTKFREFTTRHPVFRGVRRR
GNAGRWVCEVRVPGRRGCRLWLGTFDTAEGAARAHDAAMLAINAGGGFTGGGGACCLNF
ADSAWLLAVRRSYRTLADVRHAVAEAVEDFFRRRLADDALSATSSSSTTFTPSTPRTDD
DEESAATDGDESSSPASDLAFELDVLSDMGWDLYYASLAQGMLMEPPSAALFTGDDGDA
ILADVPLWSY SEQ ID NO:72:
Hordeum vulgare subsp. vulgare (two-rowed barley) CBF3-like
protein BCBF3 (BCBF3) (GenBank AF298231) amino acid
sequence:
MSPTLSLKLKKSSHTPQSSVSSSTMLRLFKKEAACQSPSTLPVAMDMGLEVSSSSPSSS
SVSSSPEHAARRASPAKRPAGRTKFRETRHPVYRGVRRRGNTERWVCEVRVPGKRGARL
WLGTYATAEVAARANDAAMLALGGRSATCLNFADSAWLLAVPSALSDLADVRRAAVEAV
ADFQRREAADGSLAIAVPKEASSGAPSLPSSGSDSAGSTGTSEPSANGVFEGPVVMDS
EMFRLDLFPEMDLGSYYMSLAEALLMDPPPTATIIHAYEDNGDGGADVRLWSYSVDM SEQ ID NO:73:
Hordeum vulgare subsp. vulgare CRT/DRE-binding factor (CBF)
mRNA (GenBank AF239616) amino acid sequence:
MDMGLEVSSSSPSSSSVSSSPEHAARRASPAKRPAGRTKFRETRHPVYRGVRRRGNTER
WVCEVRVPGKRGARLWLGTYATAEVAARANDAAMLALGGRSATCLNFADSAWLLAVPSA
LSDLADVRRAAVEAVADFQRREAADGSLAIAVPKEASSGAPSLPSSGSDSAGSTGTSE
PSANGVFEGPVVMDSEMFRLDLFPEMDLGSYYMSLAEALLMDPPPTATIIHAYEDNGDG
GADVRLWSYSVDM SEQ ID NO:74:
Oryza sativa (rice) apetala2 domain-containing CBF1-like
protein (EMBL AAQ06658) amino acid sequence:
MCGIKQEMSGESSGSPCSSASAERQHQTVWTAPPKRPAGRTKFRETRHPVFRGVRRRGN
AGRWVCEVRVPGRRGCRLWLGTFDTAEGAARAHDAAMLAINAGGGGGGACCLNFADSA
WLLAVPRSYRTLADVRHAVAEAVEDFFRRRLADDALSATSSSSTTPSTPRTDDEEESAA
TDGDESSSPASDLAFELDVLSDMGWDLYYASLAQGMLMEPPSAALGDDGDAILADVPLW
SY

Fig. 13B

SEQ ID NO:75:
Oryza sativa (rice) CRT/DRE binding factor (CBF) (GenBank
AF243384) amino acid sequence:
MEKNTAASGQLMTSSAEATPSSPKRPAGRTKFQETRHLVFRGVRWRGCAGRWVCKVRVPGSRGDR
FWIGTSDTAEETARTHDAAMLALCGASASLNFADSAWLLHVPRAPVVSGLRPPAARCATRCLQGH
RRVPAPGRGSTATATATSGDAASTAPPSAPVLSAKQCEFIFLSSLDCWMLMSKLISSSRAKGSLC
LRKNPISFCMVTNSYTALLLEYIILQMNSMIVLIHELSKYQVFLLLTMITHHLFQWRR SEQ ID NO:76:
Oryza sativa (rice) Similar to Arabidopsis thaliana mRNA
for DREB1B (GenBank AB023482) amino acid sequence:
MSGGAAATVAPGWRRELAGLLVPLVRSAMEARGCGHHHRDRLDASAIKSLPSVMTVRSCGQRGRQ
RRYARMPSPPSSPPPTLTNCLRRRTRHGEEHRRQRAIDDLLRGGDAVVAEAAGGANQVPGDEAPS
VPWGAMAWVRGAVGVQGTSDTAEETARTHDAAMLALCGASASLNFADSAWLLHVPRAPVVSGLRP
PAARCATRCLQGHRRVPAPGRGSTATATATSGDAASTAPPSAPVLSHASSSSMLATSVQQLNRLA
TSSHLSPPSHERTMRPSGAESLAPLLPIRSRARLLLSPPLRHRARPPTPPRPAAVLPFSHVSAAA
SLLPHRRQAVKPPCSHVAAAMQVETGEAPGHGGGAQRSPPIGWLSHSLLPAAAALLPRQPSVRHS
SPAGCAPREEKSERGKERRERGCWERGSADVAS SEQ ID NO:77:
Schedonorus arundinaceus (Festuca arundinacea) (tall
fescue) (GenBank AAQ98965) putative DRE-binding protein
DREB1 amino acid sequence:
MDAAVAASLSLQSGEQEYRTVWSEPPKPRSGRTKFQETRHPVYRGVRRRGRAGQWVCEMRVHGTK
GSRLWLGTFDTAEMAARAHDAAALALSGRDACLNFADSAWRMQPVLPAGAGSVCFGGAQEVKDAV
AAAVEAFQEEEHHVESTAETAKDEESALSMSSDLSEHDDERWIDGMDAGSYYASLAQGMLVEPPD
AGAWREDGEHGGVETSLWSYL SEQ ID NO:78:
Secale cereale (rye) clone 80 CBF-like protein (GenBank
AF370729) amino acid sequence:
MDVADIASRSGQQQQGHRTVSSEPPKRPAGRTKFHETRHPLYRGVRRRGRVGQWVCEVRVPGIKG
SRLWLGTFNTAEMAARAHDAAVLALSGRAACLNFADSAWRMLPVLAAGSFGFDSAREVKAAVAVA
VVAFQRKQIIPVAVAVVALQKQQVPVAVAVVALQQRQVPVTVAVVALQKLQVPVAVAVVALQKKQ
IILPAACLAPEFYMSSGDLLELDEEQWFGGMDAGSYYASLAQGMLVAPPDDRARPENGEQSGVQT
PLWSCLFD SEQ ID NO:79:
Triticum aestivum (bread wheat) AP2-containing protein
(Dreb1)(GenBank AF303376) amino acid sequence:
METGGSKREGDCPGQERKKKVRRRSTGPDSVAETIKKWKEENQKLQQENGSRKAPAKGSKKGCMA
GKGGPENSNCAYRGVRQRTWGKWVAEIREPNRGNRLWLGSFPTAVEAARAYDDAARAMYGAKARV
NFSEQSPDANSGCTLAPPLPMSNGATAASHPSDGKDESESPPSLISNAPTAALHRSDAKDESESA
GTVARKVKKEVSNDLRSTHEEHKTLEVSQPKGKALHKAANVSYDYFNVEEVLDMIIVELSADVKM
EAHEEYQDGDDGFSLFSY

Fig. 13C

SEQ ID NO:80:
Brassica napus (rape) (GenBank AF370733) clone 662 CBF-like
amino acid sequence:
MNSVSTFSELLGSENESPVGGDYCPMLAASCPKKPAGRKKFRETRHPIYRGVRLRKSGK
WVCEVREPNKKSRIWLGTFKTAEIAARAHDVAALALRGRGACLNFADSAWRLRIPETTC
AKDIQKAAAEAALAFEAEKSDTTTNDHGMNMASQAEVNDTTDHGLDMEETMVEAVFTEE
QRDGFYMAEETTVEGVVPEEQMSKGFYMDEEWMFGMPTLLADMAAGMLLPPPSVQWGHN
DDFEGDVDMNLWNY SEQ ID NO:81:
Brassica napus (rape) (GenBank AF370734) clone 662 CBF-like
amino acid sequence:
MNSVSTFSELLRSENESPVNTEGGDYILAASCPKKPAGRKKFQETRHPIYRGVRLRKSG
KWVCEVREPNKKSRIWLGTFKTAEIAARAHDVAALALRGRGACLNFADSAWRLRIPETT
CAKDIQKAAAEAALAFEAEKSDTTTNDHGMNMASQVEVNDTTDHDLDMEETIVEAVFRE
EQREGFYMAEETTVVGVVPEEQMSKGFYMDEEWMFGMPTLLADMAAGMLLPLPSVQWGH
NDDFEGDADMNLWNY SEQ ID NO:82:
Brassica napus (rape) (GenBank AF084185) dehydration
responsive element binding protein:
MTSFSTFSEMLGSEYESPVTLGGEYCPKLAASCPKKPAGRKKFRETRHPVYRGVRLRNS
GKWVCEVREPNKKSRIWLGTFLTAEIAARAHDVAAIALRGKSACLNFADSAWRLRIPET
TCPKEIQKAAAEAALAFQAEINNTTTDHGLDMEETIVEAIFTEENNDVFYMDEESMLEM
PALLASMAEGMLLPPPSVHFGHNYDFDGDADVSLWSY SEQ ID NO:83:
Glycine max (soybean) dehydration responsive element
binding protein (DREB1) (GenBank AF514908) amino acid
sequence:
MEDRDHCCSNNSTMITTTKKRTGRRSPTSDKLKNQHREKQSMKPYRGIRMRKWGKWVAE
IREPNKRSRIWLGSYTTPVAAARAYDTAVFYLRGPTARLNFPELLFQDDDQEGSDSVQH
GAAGNMSADSIRRKATQVGARVDALQTALHHHAPSTNSLNLKPDLNEFPKLEELQD SEQ ID NO:84:
Capsicum annuum (Bell pepper) dehydration responsive
element binding protein (DREB1) (EMBL; AY368483) amino acid
sequence:
MNIFRSYYSDPLTESSSSFSDSSIYSPNRAIFSDEEVILASNNPKKPAGRKKFRETRHP
VYRGVRKRNSGKWVCEVREPNKKSRIWLGTFPTAEMAARAHDVAAIALRGRSACLNFAD
SAWRLPVPASSDTKDIQKAAAEAAEAFRPLKLEGISKESSSSTPESMFFMDEEALFCMP
GLLTNMAEGLMLPPPQCAEIGDHVETADADTPLWSYSI

Fig. 13D

SEQ ID NO:85:
Capsicum annuum (Bell pepper) dehydration responsive
element binding protein (DREB1) (EMBL; AY496155) amino acid
sequence:
MNIFRSYYSDPLTESSSSFSDSSIYSPNRAIFSDEEVILASNNPKKPAGRKKFRETRHP
VYRGVRKRNSGKWVCEVREPNKKSRIWLGTFPTAEMAARAHDVAAIALRGRSACLNFAD
SAWRLPVPASSDTKDIQKAAAEAAEALRPLKLEGISKESSSSTPESMFFMDEEALFCMP
GLLTNMAEGLMLPPPQCAEIGDHVETADADTPLWSYSI SEQ ID NO:86:
Lycopersicon esculentum (Tomato) putative transcriptional
activator CBF1 (GenBank AY034473) amino acid sequence:
MNIFETYYSDSLILTESSSSSSSSSFSEEEVILASNNPKKPAGRKKFRETRHPIYRGIR
KRNSGKWVCEVREPNKKTRIWLGTFPTAEMAARAHDVAALALRGRSACLNFSDSAWRLP
IPASSNSKDIQKAAAQAVEIFRSEEVSGESPETSENVQESSDFVDEEAIFFMPGLLANM
AEGLMLPPPQCAEMGDHCVETDAYMITLWNYSI SEQ ID NO:87:
Lycopersicon esculentum (Tomato) dehydration responsive
element binding protein (DREB1) (GenBank AF370729) amino
acid sequence:
MAIMDEAANMVCVPLDYSRKRKSRSRRDRTKNVEETLAKWKEYNEKLDNEGKGKPVRKV
PAKGSKKGCMRGKGGPENWRCKYRGVRQRIWGKWVAEIREPKRGSRLWLGTFGTAIEAA
LAYDDAARAMYGPCARLNLPNYACDSVSWATTSASASASDCTVASGFGEVCPVDGALHE
ADTPLSSVKDEGTAMDIVEPTSIDEDTLKSGWDCLDKLNMDEMFDVDELLAMLDSTPVF
TKDYNSDGKHNNMVSDSQCQEPNAVVDPMTVDYGFDFLKPGRQEDLNFSSDDLAFIDLD
SELVV SEQ ID NO:88:
Cucumis melo (muskmelon) CMe-DREB1 mRNA for DREB-like
protein (GenBank AB125974) amino acid sequence:
MSSSKEQSPSPETESSSSSSSDSNKKPKRINSNSSSNSKHAVYRGVRMRNWGKWVSEIR
EPRKKSRIWLGTFPSPEMAARAHDVAALSIKGNSAILNFPDLVHLLPRPVSLAPRDVQA
AAAKAAHMHNLSSNANTNNHNTNSNSSSAFSDELSEIVELPALGTSYDGGVGVGGEFVF
VESELESAAWLYQPPWVQSLQEDYDDIDGDGDCGKLGMGFVSNGFKGFLFDY SEQ ID NO:89:
Zea mays (maize) DREB-like protein (DREB1A) (GenBank
AF450481) amino acid sequence:
MDTAGLVQHATSSSSTSTSASSSSSEQQSRKAAWPPSTASSPQQPPKKRPAGRTKFRET
RHPVFRGVRRRGAAGRWVCEVRVPGRRGARLWLGTYLAAEAAARAHDAAILALQGRGAG
RLNFPDSARLLAVPPPSALPGLDDARRAALEAVAEFQRRSGSGSGAADEATSGASPPSS
SPSLPDVSAAGSPAAALEHVPVKADEAVALDLDGDVFGPDWFGDMGLELDAYYASLAEG
LLVEPPPPPAAWDHGDCCDSGAADVALWSYY

Fig. 13E

SEQ ID NO:90:
Zea mays (maize) DREB-like protein (dreb1) (GenBank
AF448789) amino acid sequence:
MAQELHETSSCSATTTSSCTTSCCSSTVTDSSSSPPSPAAANAAPATRKRQALEAEAEA
EAGGEEEEEEEGCAGNKAAPAKKRPRGSEGKHPTFRGVRMRAWGKWVSEIREPRKKSR
IWLGTFPTAEMAARAHDVAALAIKGRAAHLNFPDLAGALPRAASAAPKDVQAAAALAAA
FTSPSSEPGAGAHEEPAAKDGAAPEEAAADAQAPVPVALPPPAASRPGTPSSGVEDERQ
LFDLPDLLLDIRDGFGRFPPMWAPLTDVEEVVNAELRLEEPLLWE SEQ ID NO:91:
Gossypium hirsutum (upland cotton) DREB-like protein
(DREB1A) mRNA (GenBank AY321150 (AAP83936)) amino acid
sequence:
MDFVVQDYDMVDSGSVSESGTDRPVNFSDEYVMLASSYPKRPAGRKKFRETRHPVYRGV
RRRNPGKWVSEVREPNKKSRIWLGTFPKADMAARAHDVAAIALRGKSACLNFADSAWKL
PVPASSDPKDIQKTVAEVAETFRTAEHSSGNSRNDAKRSENTEMEKGFYLDEEALFGTQ
RFWANMAAGMMMSPPRSGHDGGWEEHEVDDYVPLWSYSI SEQ ID NO:92:
Capsella bursa-pastoris (shepherd's purse) Cbcbf mRNA
(GenBank AY391121 (AAR26658)) amino acid sequence:
MNSSFSAFSEMFGSEYESPVSSGGGDYCPTLATSCPKKPAGRKKFRETRHPVYRGVRRR
NSGKWVCEVREPNKKSRIWLGTFPTADMAARAHDVAAIALRGRSACLNFADSAWRLRIP
ESTGAKEIQKAAAEAALAFQDEMMMSDTTTTDHGFDMEETFVEAIVTAEQSASLYIDEE
DMFGMPSLMASMAEGMLLPLPSVQWNHNYDIDGDDDVSLWSY SEQ ID NO:93:
Prunus avium (sweet cherry) (GenBank AB080966) amino acid
sequence:
MDMFFSQLSDSVDQPQSSLLSDASVTTRGASCSGDVILASSRPKKRAGRRVFKETRHP
VYRGVRRRNNDKWVCEMREPNKKKSRIWLGTYPTAEMAARAHDVAALAFRGKLACINFA
DSAWRLPVPASMDTMDIRRAAAEAAEGFRPVEFGGVCSGSSDEKERMVVQVEEKNKKGS
VNLERSRSLSLSYWDEEEVFHMPRLLHDMAEGLLLSPSQCLGGYMNLDDMGTDADVKLW
SFSI SEQ ID NO:94:
Prunus avium (sweet cherry) (GenBank AB080965) amino acid
sequence:
MDMIYSQLSDLASMENPDTSSFSDASVTARRASLSDEEVILASSCPKRRAGRRVFKETR
HPVYRGVRRRNNNKWVCELRAPNKKKARIWLGTYPTAEMAARAHDVAVLAFRGKLACLN
FADSAWRLPVPASTDAAEIRRAATEAAEAFRQAEDGGVDEKESKAVVSEEKGCVGMEGS
SNLFYLDEDEIFEMPRLLDDMADGIMLCPPQCLDGYMDWNDVETVDDLKLWSFSI

Fig. 13F

SEQ ID NO:95:
Arabidopsis thaliana (thale cress) DREB1A (GenBank
AB013815(BAA33434)) amino acid sequence:
MNSFSAFSEMFGSDYESSVSSGGDYIPTLASSCPKKPAGRKKFRETRHPIYRGVRRRNS
GKWVCEVREPNKKTRIWLGTFQTAEMAARAHDVAALALRGRSACLNFADSAWRLRIPES
TCAKDIQKAAAEAALAFQDEMCDATTDYGFDMEETLVEAIYTAEQSENAFYMHDEAMFE
MPSLLANMAEGMLLPLPSVQWNHNHEVDGDDDDVSLWSY SEQ ID NO:96:
Arabidopsis thaliana (thale cress) DREB1A; DRE-binding
factor 3 (CBF3) (GenBank AB007787 (BAA33791); NM_118680
(NP_567720); AF074602; AF076155; T51830; JE0297) amino acid
sequence:
MNSFSAFSEMFGSDYESSVSSGGDYIPTLASSCPKKPAGRKKFRETRHPIYRGVRRRNS
GKWVCEVREPNKKTRIWLGTFQTAEMAARAHDVAALALRGRSACLNFADSAWRLRIPES
TCAKDIQKAAAEAALAFQDEMCDATTDHGFDMEETLVEAIYTAEQSENAFYMHDEAMFE
MPSLLANMAEGMLLPLPSVQWNHNHEVDGDDDDVSLWSY SEQ ID NO:97:
Arabidopsis thaliana (thale cress) DREB1B; DRE-binding
factor 1 (CBF1) (GenBank AAC99369) amino acid sequence:
MNSFSAFSEMFGSDYEPQGGDYCPTLATSCPKKPAGRKKFRETRHPIYRGVRQRNSGKW
VSEVREPNKKTRIWLGTFQTAEMAARAHDVAALALRGRSACLNFADSAWRLRIPESTCA
KDIQKAAAEAALAFQDETCDTTTTDHGLDMEETMVEAIYTPEQSEGAFYMDEETMFGMP
TLLDNMAEGMLLPPPSVQWNHNYDGEGDGDVSLWSY SEQ ID NO:98:
Arabidopsis thaliana (thale cress) DREB1C; DRE-binding
factor 2 (CBF2) (GenBank AAC99371) amino acid sequence:

MNSCSAFSEMFGSDYESPVSSGGDYSPKLATSCPKKPAGRKKFRETRHPIYRGVRQRNS
GKWVCELREPNKKTRIWLGTFQTAEMAARAHDVAAIALRGRSACLNFADSAWRLRIPES
TCAKEIQKAAAEAALNFQDEMCHMTTDAHGLDMEETLVEAIYTPEQSQDAFYMDEEAML
GMSSLLDNMAEGMLLPSPSVQWNYNFDVEGDDDVSLWSY

SEQ ID NO:99:
Arabidopsis thaliana (thale cress) CBF4 amino acid
sequence:
MNPFYSTFPDSFLSISDHRSPVSDSSECSPKLASSCPKKRAGRKKFRETRHPIYRGVRQ
RNSGKWVCEVREPNKKSRIWLGTFPTVEMAARAHDVAALALRGRSACLNFADSAWRLRI
PETTCPKEIQKAASEAAMAFQNETTTEGSKTAAEAEEAAGEGVREGERRAEEQNGGVFY
MDDEALLGMPNFFENMAEGMLLPPPEVGWNHNDFDGVGDVSLWSFDE

Fig. 13G

SEQ ID NO:100:
Thellungiella salsuginea (close relative of Arabidopsis
thaliana)(GenBank AAC99371):
MNSFSAFAEMFGSEYESPVTVGGDYCPTLATSCPKKPAGRKKFRETRHPIYRGVRRRNS
GKWVCEVREPNKKSRIWLGTFPTAEMAARAHDVAAIALRGRSACLNFADSAWRLRIPES
TCAKDIQKAAAEAAVAFQAEMSDTMTSDHGLDMEETTVEVIVTEEEQSEGFYMDEEAMF
GMPRLLANMAEGMLLPPPSVQWGHNYDCDGDADVSLWSY SEQ ID NO:101:
Oryza sativa (indica cultivar-group) CRT/DRE binding
protein gene, (GenBank AY502052):
MEKNTAASGQLMTSSAEATPSSPKRPAGRTKFQETRHLVFRGVRWRGCAGRWVCKVRVP
GSRGDRFWIGTSDTAEETARTHDAAMLALCGASASLNFADSAWLLHVPRAPVVSGLRPP
AARCATRCLQGHRRVPAPGRGSTATATATSGDAASTAPPSAPVLSAKQCEFIFLSSLDC
WMLMSKLISSSRAKGSLCLRKNPISFCMVTNSYTALLLEYIILQMNSMIVLIHELSKYQ
VFLLLTMITHHLFQWRR SEQ ID NO:102:
Oryza sativa Dre-binding protein gene (GenBank AY319971)
amino acid sequence:
MEVEEAAYRTVWSEPPKRPAGRTKFRETRHPVYRGVRRRGGRPGAAGRWVCEVRVPGAR
GSRLWLGTFATAEAAARGHDAAALALRGRAACLNFADFAWRMPPVPASAALAGARGVRD
PVAVAVEAFQRQSAAPSSPAETFANDGDEEEANKEVLPVAAAEVFDAGAFELDDGFRFG
GMDAGSYYASLAQGLLVEPPAAGAWWEDGELADSDMPLWSY SEQ ID NO:103:
Oryza sativa (japonica cultivar-group) DRE binding factor 2
(DBF2) (GenBank AY305028) amino acid sequence:
MAAAIDLSGEELMRALEPFIRDASGSPPVCSQFSPTSPFSFPHALAYGGGLAQQPELSP
AQMHYIQARLHLQRQAAQAGPLGPRAQPMKASSSSASAAGAAATPPRPQKLYRGVRQRH
WGKWVAEIRLPRNRTRLWLGTFDTAEEAALAYDQAAYRLRGDAARLNFPDNAASRGPLH
ASVDAKLQTLCQNIAAAKNAKKSSVSASAAATSSAPTSNCSSPSSDDASSCLESADSSP
SLSPSSAATTAETPATVPEMQQLDFSEAPWDEAAAFALTKYPSYEIDWDSLLAAN SEQ ID NO:104:
Oryza sativa DRE-binding protein 1A mRNA (GenBank AF300970)
amino acid sequence:
MCGIKQEMSGESSGSPCSSASAERQHQTVWTAPPKRPAGRTKFRETRHPVFRGVRRRGN
AGRWVCEVRVPGRRGCRLWLGTFDTAEGAARAHDAAMLAINAGGGGGGACCLNFADSA
WLLAVPRSYRTLADVRHAVAEAVEDFFRRRLADDALSATSSSSTTPSTPRTDDDEESAA
TDGDESSSPASDLAFELDVLSDMGWDLYYASLAQGMLMEPPSAALGDDGDAILADVPLW
SY

Fig. 13H

SEQ ID NO:105:
Oryza sativa (japonica cultivar-group) AP2-domain DRE
binding factor DBF1 (GenBank AY297448) amino acid sequence:
AAAIEGNLMRALGEAPSPQMQKIAPPPFHPGLPPAPANFSSAGVHGFHYMGPAQLSPAQ
IQRVQAQLHMQRQAQSGLGPRAQPMKPASAAAPAAAAARAQKLYRGVRQRHWGKWVAEI
RLPRNHPRLWLGTFDTAEEAALTYGQAAYRLRGDAARLNFPDNAASRGPLDAAVDAKLQ
AICDTIAASKNASSRSRGGAGRAMPINAPLVAAASSSSGSDHSGGGDDGGSETSSSSAA
ASPLAEMEQLDFSEVPWDEAEGFALTKYPSYEIDWDSLLNNNN SEQ ID NO:106:
Oryza sativa putative DRE-binding protein 1B mRNA (GenBank
AF300972) amino acid sequence:
MEVEEAAYRTVWSEPPKRPAGRTKFRETRHPVYRGVRRRGGRPGAAGRWVCEVRVPGAR
GSRLWLGTFATAEAAARAHDAAALALRGRAACLNFADFAWRMPPVPASAALAGARGVRD
PVAVAVEAFQRQSAAPSSPAETFANDGDEEEANKDVLPVAAAEVFDAGAFELDDGFRFG
GMDAGSYYASLAQGLLVEPPAAGAWWEDGELAGSDMPLWSY SEQ ID NO:107:
Oryza sativa (indica cultivar-group) putative DRE-binding
protein1B (GenBank AY166833) amino acid sequence:
MEVEEAAYRTVWSEPPKRPAGRTKFRETRHPVYRGVRRRGGRPGAAGRWVCEVRVPGAR
GSRLWLGTFATAEAAARAHDAAALALRGRAACLNFADSAWRMPPVPASAALAGARGVRD
AVAVAVEAFQRQSAAPSSPAETFADDGDEEEDNKDVLPVAAAEVFDAGAFELDDGFRFG
GMDAGSYYASLAQGLLVEPPAAGAWWEDGELAGSDMPLWSY SEQ ID NO:108:
Oryza sativa DRE binding protein 2 (GenBank AF300971) amino
acid sequence:
MERGEGRRGDCSVQVRKKRTRRKSDGPDSIAETIKWWKEQNQKLQEENSSRKAPAKGSK
KGCMAGKGGPENSNCAYRGVRQRTWGKWVAEIREPNRGRRLWLGSFPTALEAAHAYDEA
ARAMYGPTARVNFADNSTDANSGCTSAPSLMMSNGPATIPSDEKDELESPPFIVANGPA
VLYQPDKKDVLERVVPEVQDVKTEGSNGLKRVCQERKNMEVCESEGIVLHKEVNISYDY
FNVHEIVEMIIVELSADQKTEVHEEYQEGDDGFSLFSY

Fig. 14A

SEQ ID NO:109:
Oryza sativa DRE-binding protein 1A mRNA (GenBank
AF300970.1) nucleic acid sequence:
cactcgagcagagcaaatacagttcaggaatcaggagcaagcagaaacacacacacaaatccgaagatgtg
cgggatcaagcaggagatgagcggcgagtcgtcggggtcgccgtgcagctcggcgtcggcggagcggcagc
accagacggtgtggacggcgccgccgaagaggccggcggggcggaccaagttcagggagacgaggcacccg
gtgttccgcggcgtgcggcggaggggcaatgccgggaggtgggtgtgcgaggtgcgggtgcccgggcggcg
cggctgcaggctctggctcggcacgttcgacaccgccgagggcgcggcgcgcgcacgacgccgccatgc
tcgccatcaacgccggcggcggcggcggcggggagcatgctgcctcaacttcgccgactccgcgtggctc
ctcgccgtgccgcgctcctaccgcaccctcgccgacgtccgccacgccgtcgccgaggccgtcgaggactt
cttccggcgccgcctcgccgacgacgcgctgtccgccacgtcgtcgtcctcgacgacgccgtccaccccac
gcaccgacgacgacgaggagtccgccgccaccgacggcgacgagtcctcctccccggccagcgacctggcg
ttcgaactggacgtcctgagtgacatgggctgggacctgtactacgcgagcttggcgcaggggatgctcat
ggagccaccatcggcggcgctcggcgacgacggtgacgccatcctcgccgacgtcccactctggagctact
agagctcaatcaactgtacaattttgcctctttttctctcttttctggcttccgatgccaaaattttggt
actgtacggacactactttcggtaatgtgatggaacaagttgc SEQ ID NO:110:
Oryza sativa (japonica cultivar-group) cDNA clone (GenBank
AK105599.1) nucleic acid sequence:
aaaaaaaaaaaaaaaaaaaaaaaaaaaaaaaaaaaatcgccattaccacactcgagcagagcaaatacagt
tcaggaatcaggagcaagcagaaacacacacacaaatccgaagatgtgcgggatcaagcaggagatgagcg
gcgagtcgtcggggtcgccgtgcagctcggcgtcggcggagcggcagcaccagacggtgtggacggcgccg
ccgaagaggccggcggggcggaccaagttcagggagacgaggcacccggtgttccgcggcgtgcggcggag
gggcaatgccgggaggtgggtgtgcgaggtgcgggtgcccgggcggcgcggctgcaggctctggctcggca
cgttcgacaccgccgagggcgcggcgcgcgcacgacgccgccatgctcgccatcaacgccggcggcggc
ggcggcggggagcatgctgcctcaacttcgccgactccgcgtggctcctcgccgtgccgcgctcctaccg
caccctcgccgacgtccgccacgccgtcgccgaggccgtcgaggacttcttccggcgccgcctcgccgacg
acgcgctgtccgccacgtcgtcgtcctcgacgacgccgtccaccccacgcaccgacgacgacgaggagtcc
gccgccaccgacggcgacgagccctcctccccggccagcgacctggcgttcgaactggacgtcctgagtga
catgggctgggacctgtactacgcgagcttggcgcaggggatgctcatggagccaccatcggcggcgctcg
gcgacgacggtgacgccatcctcgccgacgtcccactctggagctactagagctcaatcaactgtacaatt
ttgcctctttttctctcttttctggcttccgatgccaaaattttggtactgtacggacactactttcggt
aatgtgatggaacaagttgcaaaacacagagc SEQ ID NO:111:
Schedonorus arundinaceus (Festuca arundinacea) (tall
fescue) putative DRE-binding protein DREB1 (GenBank
AY423713) nucleic acid sequence:
aatccaaaataacctccaccctccagctaagaacatactagtaccttcgcctcaccagagcaacccacaa
gcaagcatctccactatatcgacgctgcgagtgatggacgctgccgttgccgcctcgctgtcgctgcag
tcgggggagcaagagtacaggacggtatggtcggagccgccgaagccacgatcggggcgcaccaagttcca
ggagacgcggcacccggtgtaccgcggcgttcggcgccggggcgtgccgggcagtgggtgtgcgagatgc
gcgtccacgggacgaaggggtccaggctctggctcggcaccttcgacaccgctgagatggctgcacgcgcg
cacgacgccgccgcgctcgcgctctccggccgcgacgcatgcctcaacttcgctgactccgcctggcggat
gcagcccgtcctccctgccggtgccgggtcggtctgcttcggcggagcgcaggaggtcaaggacgccgtcg
ccgccgccgtcgaggcgttccaggaggaggagcaccacgttgagtccacggcggagacggccaaggacgag
gagagcgcgctgtccatgtccagcgacttgtcggagcacgacgacgagcgctggattgacggcatggacgc
cgggtcgtactacgcgagcttggcgcagggcatgctcgtggagccaccggacgccggagcgtggcgggagg
acggcgaacacggcggtgtcgagacgtcgctatggagctacttgtagtgtacgtggagttttaccaggaac
tactactagaactagttctgttctcgcttccaaatatgggaagacgcagagtaatcatcgagggcaattt
tacccccatatgtgaaaggaaaacgctctctttcctccggacgatacgacgcgatgcgtcctccgccttgcg
cacgcaacacgtgtctggggcccacctccaccgcttcaaaaaaaaaaaaaaaaaaaaaaaaaaaa

Fig. 14B

SEQ ID NO:112:
Oryza sativa DRE-binding protein 1A (GenBank AF243384)
nucleic acid sequence:

cactcgagcagagcaaatacagttcaggaatcaggagcaagcagaaacacacacacaaatccgaagatgtg
cgggatcaagcaggagatgagcggcgagtcgtcggggtcgccgtgcagctcggcgtcggcggagcggcagc
accagacggtgtggacggcgccgccgaagaggccggcggggcggaccaagttcagggagacgaggcacccg
gtgttccgcggcgtgcggcggaggggcaatgccgggaggtgggtgtgcgaggtgcgggtgcccgggcggcg
cggctgcaggctctggctcggcacgttcgacaccgcgagggcgcggcgcgcgcacgacgccgccatgc
tcgccatcaacgccggcggcggcggcggcggggagcatgctgcctcaacttcgccgactccgcgtggctc
ctcgccgtgccgcgctcctaccgcaccctcgccgacgtccgccacgccgtcgccgaggccgtcgaggactt
cttccggcgccgcctcgccgacgacgcgctgtccgccacgtcgtcgtcctcgacgacgccgtccacccac
gcaccgacgacgacgaggagtccgccgccaccgacggcgacgagtcctcctccccggccagcgacctggcg
ttcgaactggacgtcctgagtgacatgggctgggacctgtactacgcgagcttggcgcaggggatgctcat
ggagccaccatcggcggcgctcggcgacgacggtgacgccatcctcgccgacgtcccactctggagctact
agagctcaatcaactgtacaattttgcctcttttttctctcttttctggcttccgatgccaaaatttttggt
actgtacggacactactttcggtaatgtgatggaacaagttgc SEQ ID NO:113:
Oryza sativa apetala2 domain-containing CBF1-like protein
(EMBL AAQ06658) nucleic acid sequence:

atgtgcgggatcaagcaggagatgagcggcgagtcgtcggggtcgccgtgcagctcggcgtcggcggagcg
gcagcaccagacggtgtggacggcgccgccgaagaggccggcggggcggaccaagttcagggagacgaggc
acccggtgttccgcggcgtgcggcggaggggcaatgccgggaggtgggtgtgcgaggtacgggtgcccggg
cggcgcggctgcaggctctggctcggcacgttcgacaccgcgagggcgcggcgcgcgcgcacgacgccgc
catgctcgccatcaacgccggcggcggcggcggcggggagcatgctgcctcaacttcgccgactccgcgt
ggctcctcgccgtgccgcgctcctaccgcaccctcgccgacgtccgccacgccgtcgccgaggccgtcgag
gacttcttccggcgccgcctcgccgacgacgcgctgtccgccacgtcgtcgtcctcgacgacgccgtccac
cccacgcaccgacgacgaggaggagtccgccgccaccgacggcgacgagtcctcctccccggccagcgacc
tggcgttcgaactggacgtcctgagtgacatgggctgggacctgtactacgcgagcttggcgcaggggatg
ctcatggagccaccatcggcggcgctcggcgacgacggtgacgccatcctcgccgacgtcccactctggag
ctactag SEQ ID NO:114:
Oryza sativa transcription factor RCBF3 (EMBL AY345233)
nucleic acid sequence:

cgagcagaggaaatacagtttaggaatccggagcaagcagaaacacacacacaaatccgaagatgtgcggg
atcaagcaggagatgagcggcgagtcgtcggggtcgccgtgcagctcggcgtcggcggagcggcagcacca
gacggtgtggacggcgccgccgaagaggccggcggggcggaccaagttcagggagacgaggcacccggtgt
tccgcggcgtgcggcggaggggcaatgccgggaggtgggtgtgcgaggtgcgggtgcccgggcggcgcggc
tgcaggctctggctcggcacgttcgacaccgcgagggcgcggcgcgcgcacgacgccgccatgctcgc
catcaacgccggcggcggcggcggcggggagcatgctgcctcaacttcgccgactccgcgtggctcctcg
ccgtgcggcgctcctaccgcaccctcgccgacgtccgccacgccgtcgccgaggccgtcgaggacttcttc
cggcgccgcctcgccgacgacgcgctgtccgccacgtcgtcgtcctcgacgacgccgtccacccacgcac
cgacgacgacgaggagtccgccgccaccgacggcgacgagtcctcctccccggccagcgacctggcgttcg
aactggacgtcctgagtgacatgggctgggacctgtactacgcgagcttggcgcaggggatgctcatggag
ccaccatcggcggcgctcggcgacgacggtgacgccatcctcgccgacgtcccactctggagctactagag
ctcaatcaactgtacaattttgcctcttttttctctcttttctgccttccgatgccaaaatttttttaa

Fig. 14C

SEQ ID NO:115:
Oryza sativa CRT/DRE binding factor (CBF) mRNA (GenBank
AF243384) nucleic acid sequence:

actgcttgagacgtcgcacacgtcatggagaagaacaccgccgccagcgggcaattgatgacctcctccgc
ggaggcgacgccgtcgtcgccgaagcggccggcggggcgaaccaagttccaggagacgaggcacctagtgt
tccgtggggtgcgatggcgtgggtgcgcggggcggtgggtgtgcaaggtgcgtgtcccgggcagccgcggt
gaccgtttctggataggcacgtctgacaccgccgaggagaccgcgcgcacgcacgacgccgccatgctcgc
cttgtgcggggcctccgccagcctcaacttcgccgactctgcctggctgctccacgtcccgcgcgcccccg
tcgtctccggactccggccaccagctgcccgatgtgcaacgcgctgcctgcaaggccatcgccgagttcca
gcgccgggccggggagcaccgccactgccactgccacctccggcgatgctgcatcgaccgctcctccgtc
ggcacccgttctgtcagccaaacaatgcgaattcatctttctttcttcactagattgttggatgttaatgt
caaagcttatcagcagtagcagagcaaaaggatcgttgtgcctgcgaaaaaatcccatttcattttgcatg
gttacaaattcttacactgctcttttgctcgaatacattatattgcagatgaattcaatgatcgttttaat
ccacgaattatcaaaatatcaagtctttctgctactaaccatgataacacaccaccttttcaatggagga
ggtaggcgcggacgccctcgccatcatcgtcgatgtcgccactgatgacgaggtccgcgccgctcaccagc
tcgcacgcctcgtcgtcgtccatgctcgccacctcggtccagcagctgaacc SEQ ID NO:116:
Oryza sativa Similar to Arabidopsis thaliana mRNA for
DREB1B (GenBank AB023482) nucleic acid sequence:

atgtcaggtggtgcggccgcgacggtggctcccgggtggcggcgcgagctcgccggcctcctcgt
ccccctcgtgcggtcggcgatggaggcgcgcggctgcggccatcatcaccgagatcgactcgacg
cctctgccatcaagtcgctgccgtcggtgatgacggtgcgcagctgtggccaacggggaggcag
aggaggtacgcacggatgccctcgccccgtcgtcgccgccgccaacactaaccaactgcttgag
acgtcgcacacgtcatggagaagaacaccgccgccagcgggcaattgatgacctcctccgcggag
gcgacgccgtcgtcgccgaagcggccggcggggcgaaccaagttccaggagacgaggcacctagt
gttccgtggggtgcgatggcgtgggtgcgcggggcggtgggtgtgcaaggtgcgtgtcccgggca
gccgcggtgaccgtttctggataggcacgtctgacaccgccgaggagaccgcgcgcacgcacgac
gccgccatgctcgccttgtgcggggcctccgccagcctcaacttcgccgactctgcctggctgct
ccacgtcccgcgcgccccgtcgtctccggactccggccaccagctgcccgatgtgcaacgcgct
gcctgcaaggccatcgccgagttccagcgccgggccggggagcaccgccactgccactgccacc
tccggcgatgctgcatcgaccgctcctccgtcggcacccgttctgtcagccaaacaatgcgaatt
catctttctttcttcactagattgttggatgttaatgtcaaagcttatcagcagtagcagagcaa
aaggatcgttgtgcctgcgaaaaaatcccatttcattttgcatggttacaaattcttacactgct
cttttgctcgaatacattatattgcagatgaattcaatgatcgttttaatccacgaattatcaaa
atatcaagtctttctgctactaaccatgataacacaccaccttttcaatggaggaggtaggcgc
ggacgccctcgccatcatcgtcgatgtcgccactgatgacgaggtccgcgccgctcaccagctcg
cacgcctcgtcgtcgtccatgctcgccacctcggtccagcagctgaaccgcctggcgacgtcctc
tcacctcagtcctccctcccagtgagcgaacaatgaggccgagcggcgcagagtcgttggcgccg
ctgctccccatccgcagccgcgctcgcctgctgctgtcgccgcctctccgccaccgcgctcgccc
gccgacgccgcctcgccccgccgccgtcctcccttctcccatgtctccgccgccgtcgctgc
tgccacatcgccggcaggctgtcaaacctccctgctcccacgtcgccgctgcgatgcaagtggag
actggagaggccccggggcatggtggaggggcacagcgttctccccctatcggctggctgtcgca
ctccctcctgccggccgcggcggccctcctaccccggcagccgtcggtgcggcactcctcccctg
ccggttgtgctcctcgagaggagaaaagtgagagaggaaaggaaaggagggagaggggctgctgg
gagagagggagtgctgatgtggcatcctga

Fig. 14D

SEQ ID NO:117:
Hordeum vulgare subsp. vulgare (two-rowed barley) CBF3-like protein BCBF3 (BCBF3) (GenBank AF298231.1) nucleic acid sequence:

acaattcacatctaaatttgtcttttcttgttttcaatgtgtatttagaatttgcatgtgaaatttttgg
gggatgtgcattcatgcgatgtggacatccgcaattattttcagaacttttttgagatgtttaaaattaata
tttttgaatgatatcatggaagcatttggaagatggtatcaccggatactctccctctcggggaacaagac
gacctcattcagcagtgaccgctgtcttctctttctggccgatcagccggcggaccaatcaggcaaggcaa
tcaccgctgcattaacactgttaagccagaagaaagttcgctttttttcttttgagaggagcaggaagtt
gcctttttgcttaacactgcaatgccaaaagcccccacacgcccagcaggagaaaagtctcatgaacacc
acttgatttcatccattgtcaccagctgtccggacaccgcatccctaccgccgtcccaagcgcgttcata
cacttcaacctccagcaccacgcatacctataaatatgtctcccacactctcgctcaagctcaagaaatca
tctcacactcctcagtcctcagtaagctcaagcaccatgctcagactgttcaagaaggaagccgcctgcca
atcacccagcactctgccggtagccatggacatgggccttgaggtctcgagctcctcccctcctcctcgt
cggtgtcgtcctcgcccgagcacgcggcgaggcgggcgtcgccggcgaagcgccccgctgggcgcaccaag
ttccgggagacgcggcacccggtgtaccgcggcgtgcggcgccggggcaacaccgaacggtgggtctgcga
ggtgcgcgtccccggcaagcgcggtgctcggctctggctcgggacgtacgccacggctgaggtcgccgcgc
gcgcgaacgacgctgccatgctcgccctgggcggccgctccgccacgtgcctcaacttcgccgattccgcg
tggctgctcgccgtgccgtccgccctgtccgatctcgcagacgtccggcgcgcggctgtcgaggccgtcgc
ggatttccagcgacgggaggctgccgatggctccctcgccatcgctgtccctaaggaggcctcctctggcg
ctccttcactatctccgtcgtctgggtccgacagtgccggttcgacggggacgtcggaaccttccgccaat
ggagtgttcgaggggccgttgtaatggacagtgaaatgttcaggcttgacttgttcccggaaatggacct
gggctcgtactacatgagcctcgcggaggcgctgctcatggacccgccgcctacagcgaccatcatccacg
cgtacgaagacaacggcgacgggggagctgatgtccggctctggagctatagtgtcgatatgtgatttccc
agatgattctgctctgttttgactgtgtactgactgctgagtagtttttttgtttccttaggaaagttttc
ctcttttagagtgaagatgttgtagctaataaactgaagctgcttccaatccagcactgaatgaaacagtt
ttagtcgctgcaattcttatgccacctttatgactccggctcttttattcctgaaacatttcgtgcaattt
caaactataaaaaggaaaacaagaacgacagatcaaagcagatactttgttggttgagatttgagacgggt
tgcaaaggattccagaaacagaaagtgttccttcatgcgccatgaccttagaacatctacaatcagaccct
tcatactgatttaaaagctcgtgcaagtcgtccggtcactaaccggtcatagaattttgacccagctagac
cttcgaaatgggctcaaacttccgggttgacatatacccttacatccagcccaaatataaggaggatatg
gaagc SEQ ID NO:118:
Hordeum vulgare subsp. vulgare (barley) CRT/DRE-binding factor (CBF) mRNA (GenBank AF298616.1) nucleic acid sequence:

gcacactcctcagtcctcagtaagctcaagcaccatgctcagactgttcaagaaggaagccgcctgccaat
cacccagcactctgccggtagccatggacatgggccttgaggtctcgagctcctcccctcctcctcgtcg
gtgtcgtcctcgcccgagcacgcggcgaggcgggcgtcgccggcgaagcgccccgctgggcgcaccaagtt
ccgggagacgcggcacccggtgtaccgcggcgtgcggcgccggggcaacaccgaacggtgggtctgcgagg
tgcgcgtccccggcaagcgcggtgctcggctctggctcgggacgtacgccacggctgaggtcgccgcgcgc
gcgaacgacgctgccatgctcgccctgggcggccgctccgccacgtgcctcaacttcgccgattccgcgtg
gctgctcgccgtgccgtccgccctgtccgatctcgcagacgtccggcgcgcggctgtcgaggccgtcgcgg
atttccagcgacgggaggctgccgatggctccctcgccatcgctgtccctaaggaggcctcctctggcgct
ccttcactatctccgtcgtctgggtccgacagtgccggttcgacggggacgtcggaaccttccgccaatgg
agtgttcgaggggccgttgtaatggacagtgaaatgttcaggcttgacttgttcccggaaatggacctgg
gctcgtactacatgagcctcgcggaggcgctgctcatggacccgccgcctacagcgaccatcatccacgcg
tacgaagacaacggcgacgggggagctgatgtccggctctggagctatagtgtcgatatgtgatttcccag
atgattctgctctgttttgactgtgtactgactgctgagtagtttttttgtttccttaggaaagttttcct
cttttagagtgaagatgttgtagctaataaactgaagctgcttccaatccagcactgaatgaaacagtttt
agtcgctgcaattcttatgcc

Fig. 14E

SEQ ID NO:119:
Secale cereale (rye) clone 80 CBF-like protein mRNA
(GenBank AF370729) nucleic acid sequence:

```
accgatcgatcaaaacctcccaacacagctgctgattccagtactagtactactccacacctctcacgagc
atcatctccgccagctctcgactcggatggacgtcgccgacatcgcctcccggtctggccagcagcagcag
gggcaccggaccgtgtcgtcggagccgccgaagcgccccgcggggaggaccaagttccacgagacgcgcca
cccgctgtaccgcggcgtgcggcgccgtggccgcgtcgggcagtgggtgtgcgaggtgcgcgtgcccggga
tcaagggctccaggctctggctcggccacttcaacacggccgagatggcggcgcgcgcacgacgctgcc
gtgctcgcgctctccggccgcgccgcctgcctcaacttcgccgactccgcctggcggatgctgcccgtgct
cgcggccggctccttcggctttgatagcgcgcgggaggtcaaggccgccgtcgccgtcgccgtcgtcgcgt
tccagcggaaacagattattccagtcgccgtcgctgtcgttgctctccagaagcagcaggttccggtcgcc
gtggccgtcgtggcgctccagcagaggcaggttccggtcaccgtcgccgtcgtggcgctccagaagctgca
ggttccggtcgccgtcgccgtcgtggcgctccagaagaagcagattattcttccagccgcgtgtctggcgc
cggagttttacatgtcttccggcgacctgttggagctcgacgaggagcagtggtttggcggcatggacgcc
gggtcgtactacgccagcttggcgcaggggatgctcgtggcgccgccggacgacagagcgaggccggagaa
cggcgagcagagcggcgtccagactccgctatggagctgcttgttcgactaatttagcaccacaactgtca
agttgtagatagtcgtgttcttcccgatttggaagaagcagagtagagttcccgatttctactttggggga
aaagggctatattgcttactcgagtaatacattttcttttgatttt
```

SEQ ID NO:120:
Triticum aestivum (bread wheat) AP2-containing protein
(Dreb1)(GenBank AF303376) nucleic acid sequence:

```
caaaaccaaggcggcggcagcggggcgggagagcggggagcaccgaccgacaccggccgacaggg
tgggctgcatgcggagctgaggcgaggcgaggcgaggcggggagagatccggcgcgggtgccacc
gccggccggccgcgggagatctggttggtggcgccgcccggataagggagaggcggcgaggggag
agcagccggggagaccgaggcgagaggagatctctctcgtccctcttctcgctccatggagacc
ggggggtagcaagcgggaaggagactgccccgggcaggaaaggaagaagaaagtgcgcaggagaag
cactggtcctgattcggttgctgaaaccatcaagaagtggaaggaggaaaaccagaagctccagc
aagagaatggatcccggaaagcaccggccaagggttccaagaaagggtgcatggcagggaaagga
ggtccagagaattcaaactgcgcttaccgcggtgtgaggcagaggacgtggggaaatgggttgc
tgagatccgtgagcccaaccgtggcaatcggctgtggcttggttcattccctaccgcagtcgaag
ctgcacgtgcatatgatgatgcggcaagggcaatgtatggcgccaaagcacgtgtcaacttctca
gagcagtccccggatgccaactctggttgcacgctggcacctccattgccgatgtctaatggggc
aaccgctgcgtcacatccttctgatgggaaggatgaatcggagtctcctccttctcttatctcaa
atgcgccgacagctgcgctgcatcggtctgatgctaaggatgagtctgagtctgcagggaccgtg
gcacgtaaggtgaaaaaagaagtgagcaatgatttgaagtacccatgaggagcacaagaccct
ggaagtatcccaaccaaagggaaggctttacataaagcagcgaacgtaagttatgattacttca
acgtcgaggaagttcttgacatgataattgtggaattgagtgctgatgtaaaaatggaagcacat
gaagagtaccaagatggtgatgatgggtttagtctttctcatattagggttttagctatgaggg
ttgcagtcatgcggagcaatagggataactttcattctagctgctaggaaatacttcaaatctgc
aacccgaagctttgtagtcacttatggttttcatcttactggagagaatagctttataccataag
tcaacgggtacaagaagttgtcctgtgcgttgagttcatgtactatggtaaaagttg
```

Fig. 14F

SEQ ID NO:121:
Brassica napus (rape) (GenBank AF370733) clone 662 CBF-like nucleic acid sequence:

gtaattcgattaccgctcgagtacttactatactacactcagccttatccagtttttca
aaagaagttttcaactatgaactcagtctctactttttctgaacttcttggctctgaga
acgagtctccggtaggtggtgattactgtcccatgttggcggcgagctgtccgaagaag
ccggcgggtaggaagaagtttcgggagacacgtcacccatttaccgaggagttcgcct
tagaaaatcaggtaagtgggtgtgtgaagtgagggaaccaaacaaaaaatctaggattt
ggctcggaactttcaaaacagctgagatcgcagctcgtgctcacgacgtcgccgcctta
gctctccgtggaagaggcgcctgcctcaacttcgccgactcggcttggcggctccgtat
cccggagacaacctgcgccaaggatatccagaaggctgctgctgaagccgcattggctt
ttgaggccgagaagagtgataccacgacgaatgatcatggcatgaacatggcttctcag
gccgaggttaatgacacaacggatcatggcctggacatggaggagacgatggtggaggc
tgttttactgaggagcagagagacgggttttacatggcggaggagacgacggtggagg
gtgttgttccggaggaacagatgagcaagggttttacatggacgaggagtggatgttc
gggatgccgaccttgttggctgatatggcggcagggatgctcttaccgccgccgtccgt
acaatggggacataatgatgacttcgaaggagatgttgacatgaacctctggaattatt
agtactcatatttttttaaattatttttgaacgaataatattttatt SEQ ID NO:122:
Brassica napus (rape) (GenBank AF370734) clone 662 CBF-like nucleic acid sequence:

aataaatatcttatcaaaccagtcagaacagagatcttgttacttactatactacactc
agccttatccagttttcaaaaaaagtattcaacgatgaactcagtctctactttttctg
aactgctccgctccgagaacgagtctccggttaatacggaaggtggtgattacattttg
gcggcgagctgtcccaagaaacctgctggtaggaagaagtttcaggagacacgccaccc
catttacagaggagttcgtctgaggaagtcaggtaagtgggtgtgtgaagtgagggaac
caaacaagaaatctagaatttggctcggaactttcaaaacagctgagatcgcagctcgt
gctcacgacgttgccgccttagctctccgtggaagaggcgcctgcctcaacttcgccga
ctcggcttggcggctccgtatcccggagacgacctgcgccaaggatatccagaaggctg
ctgctgaagccgcattggcttttgaggccgagaagagtgataccacgacgaatgatcat
ggcatgaacatggcttctcaggttgaggttaatgacacgacggatcatgacctggacat
ggaggagacgatagtggaggctgttttagggaggaacagagagaagggttttacatgg
cggaggagacgacggttgtgggtgttgttccggaggaacagatgagcaagggttttac
atggacgaggagtggatgttcgggatgccgaccttgttggctgatatggcggcagggat
gctcttaccgctgccgtccgtacaatggggacataatgatgacttcgaaggagatgctg
acatgaacctctggaattattagtactcatatttttttaaattatttttgaacgaata
atattttattgaa

Fig. 14G

SEQ ID NO:123:
Brassica napus (rape) (GenBank AF084185) dehydration
responsive element binding protein nucleic acid sequence:

ggcacgaggataaattaaacatttatcaaaccaacgaaacatagatctttgtagttact
tatccagtttatttttaaaaaattataaagagatttcaacaatgacctcattttctac
cttttctgaaatgttgggctccgagtatgagtctccggttacgttaggcggagagtatt
gtccgaagctggccgcgagctgtccgaagaaaccagccggtcgtaagaagtttcgggag
acgcgtcacccagtttatagaggagttcgtctgagaaactcaggtaaatgggtgtgtga
agtgagggagccaaacaagaaatccaggatttggctcggtacttcttaaccgccgaga
tcgcagctcgtgctcacgacgtcgccgccatagccctccgcggcaaatcagcttgtctc
aatttgctgactcggcttggcggctccgtatcccggagacaacatgccccaaggagat
tcagaaggcggctgctgaagccgccttggcttttcaggctgagataaataatacgacga
cggatcatggcctggacatggaggagacgatcgtggaggctatttcacggaggaaaac
aacgatgtgtttatatggacgaggagtccatgttagagatgccggccttgttggctag
tatggcggaaggaatgcttttgccgccgccgtccgtacatttcggacataactatgact
ttgacggagatgctgacgtgtccctttggagttattagtgcaaaggttttttttcaatt
ttttcgtataatacttcttttggattttcggattctgccttttatgggaatctttttt
ttttggtaatgtggaagctgagtgtgaatgtttaaacaattgtgttatcaaatgctag
tattttttgtgcagcataatcatcttattggctctccaaaaaaaaaaaaaaaaaaaaa
aaaaaaaaaaaaaaaaaaaaa SEQ ID NO:124:
Glycine max (soybean) dehydration responsive element
binding protein (DREB1) (GenBank AF514908) nucleic acid
sequence:

gcacctctatatatacatagacacatgtaaatggttgcaaagaaagataagataggtac
cagctttcacatagtttatttaatccgttatatgccacctgatatataggcatattagc
tagttaggtaggtatagtagttaagttaattcaaccatggaagacagggatcactgttg
ttccaacaattcaacgatgatcacaacaacaaagaaaagaacgggtagaagaagtccaa
catcggataagctcaagaatcaacaccgcgagaagcagtcgatgaaaccttaccgtgga
ataaggatgcggaagtgggggaagtgggtggcggagatcagagaacccaacaaaaggtc
gaggatatggttgggttcttacacgacacccgtggccgccgcacgtgcctacgacaccg
ctgtcttttacctccggggtcccaccgcgcgccttaacttccccgaactcttgttccag
gacgacgaccaggagggcagtgattcggtgcagcacggcgcagcagggaacatgtccgc
tgattccattcgccgaaaagccacgcaagtcggcgccagagtcgacgctctccaaaccg
cgcttcaccaccacgcgccaagtaccaactctctcaatctcaagcccgacttgaacgag
tttccaaaactcgaagagcttcaagattgatataaatcaaatatcaatatcaatcaata
tatttaatttcctaagttctttattaatatatagttttatgtgtgtatatatagatgat
gatgcctcggagttggggcttgaaactaattaaccccttcccttccccttaatttagat
atatcccttttcttgtttttccgtatcttcaatcataatatcaaatcaaagaagtatta
ttattttctaaaaaaaaaaaaaaaa

Fig. 14H

SEQ ID NO:125:
Cucumis melo (muskmelon) CMe-DREB1 mRNA for DREB-like
protein (GenBank AB125974) nucleic acid sequence:

aaaaaccccaaaatccaaaatccctgttttctctcctctaaaatcaccaataatgagtagtagt
aagaacagagcccttctccggaaacagagtcctcttcttcatcttcttccgattcaaacaaaaa
acccaaaagaattaattccaattccagttccaattcaaaacacgcagtttacagaggagttcgaa
tgagaaattgggggaaatgggtatcagaaattcgagaaccaagaaagaaatcccgcatttggtta
gggactttccccagccctgaaatggctgctcgagctcatgatgttgctgccctaagcatcaaagg
aaattccgccattcttaatttccctgatcttgttcatcttcttcctcgtcctgtttctcttgctc
ctcgtgatgttcaagctgctgctgctaaagctgctcatatgcataatctttcatctaatgctaat
actaacaaccataatactaattctaattcctcctctgccttttccgatgaacttagtgagattgt
tgagttgccggctctgggaacgagttacgacggcggagttggtgttggtggggagtttgtgtttg
ttgagtcggaattggaatcagcggcttggctttaccagccaccgtgggtgcagagcttgcaggag
gattatgatgatatagatggagatggagattgtggtaagttgggaatgggatttgtttccaatgg
atttaaagggtttctgtttgattattgaaaaaaaatatttgtatttaaaaaaaaaaaaaaaa
aaaaaaaaaaaaaaaaaaaaaaaaaa SEQ ID NO:126:
Capsicum annuum (Bell pepper) CaCBF1B (CBF1B) (EMBL;
AY368483) nucleic acid sequence:

ggcacgagccaacataccataaaataataatgaacatctttagaagctattattcggacccactt
actgaatcttcatcatcttttttctgatagtagcatttactcccctaatagagctattttttctga
tgaggaagttatattagcatcaaataacccgaaaaagccagctgggaggaagaagtttcgagaaa
ctcgacatccagtatacaggggagttaggaagaggaattcaggcaaatgggtttgtgaagtcaga
gaacccaataagaaatcaagaatttggcttggtacttttcctacagctgaaatggctgctagagc
tcatgacgtggcggctatagcattaagaggtcgttctgcttgtttgaactttgctgattctgctt
ggaggttgcctgttccggcttcctctgacactaaagatattcaaaaggcggccgctgaggccgcg
gaagccttccgaccattgaagttggaaggaatttcaaaagaatcatctagcagtactccagagag
tatgttctttatggatgaggaagcgctcttctgcatgccgggattacttacgaatatggctgaag
ggctaatgttaccaccacctcaatgtgcagaaattggagatcatgtggaaactgctgatgcggat
acccctttatggagctattccatttaagtaattatgttactacttattttggatgcagtactctt
ctagctatgatcttccctataagtataatcagattaatgctgaaagaagttccttaaattaggat
atacttcgtgctcaatatttgggtatggtgcgaattattgtaaaggtattgtaatatgtggatat
tataagtatgtatttctatctattatatacgtgtagcagcataagtaagtggttggggctaaatg
aaaatcattggcctagagcgtgcggataagactatgatatttatgacggtggtctaaagttttt
tctagtttaggcaagtgaaaagtagatttgtggagtctattttcaagttggtagttgtatttga
atgaaataaatgggcaagttttgaaacctattttcttctgtttttgaattctcaatatcttttg
ggcaagttacctatttcaactgccaatgtacggcagtatataggagcatttagaagaagaccaag
ctttgttttggtcaaagattttgtaagtatttttgaaaaaattcagcattaactttaaatttgg
gaattggtgcaacgtttgatagagttttaaaaaaaaaaaaaaaaaa

Fig. 14I

SEQ ID NO:127:
Capsicum annuum (Bell pepper) DREB-like protein 1 (EMBL; AY496155) nucleic acid sequence:

ggcacgaggataccataaaataataatgaacatctttagaagctattattcggacccacttactgaatctt
catcatctttttctgatagtagcatttactcccctaatagagctattttttctgatgaggaagttatatta
gcatcaaataacccgaaaaagccagctggggaggaagaagtttcgagaaactcgacatccagtatacagggg
agttaggaagaggaattcaggcaaatgggtttgtgaagtcagagaacccaataagaaatcaagaatttggc
ttggtacttttcctacagctgaaatggctgctagagctcatgacgtggcggctatagcattaagaggtcgt
tctgcttgtttgaactttgctgattctgcttggaggttgcctgttccggcttcctctgacactaaagatat
tcaaaaggcggccgctgaggccgcggaagccctccgaccattgaagttggaaggaatttcaaaagaatcat
ctagcagtactccagagagtatgttctttatggatgaggaagcgctcttctgcatgccgggattacttacg
aatatggctgaagggctaatgttaccaccacctcaatgtgcagaaattggagatcatgtggaaactgctga
tgcggatacccctttatggagctattccatttaagtaattatgttactacttattttggatgcagtactct
tctagctatgatcttccctataagtataatcagattaatgctgaaagaagttccttaaattaggatatact
tcgtgctcaatatttgggtatggtgcgaattattgtaaaggtattgtaatatgtggatattataagtatgt
atttctatctattatatacgtgtagcagcataagtaagtggttgggggctaaatgaaaatcattggcctaga
gcgtgcggataagactatgatatttatgacggtggtctaaagtttttttctagtttaggcaagtgaaaagt
agatttgtggagtctattttttcaagttggtagttgtatttgtaatgaaataaatgggcaagtttttgaaac
ctaaaaaaaaaaaaaaaaa SEQ ID NO:128:
Lycopersicon esculentum (Tomato) putative transcriptional activator CBF1 (GenBank AY034473) nucleic acid sequence:

ggcaccagctttctattttttagctctcaacaacaatgaatatctttgaaacctattattcagactcgttaa
ttttaaccgaatcatcttcttcttcatcgtcatcgtcgttttctgaagaggaagttatttttagcttcgaat
aacccgaaaaagccagctggcaggaagaagtttcgagaaacacggcatccgatatacaggggaatcaggaa
gaggaattcaggaaaatgggtttgtgaagtcagagaacccaataagaagacaaggatttggcttggtactt
ttcctacggctgaaatggcggctagagctcatgacgtggcggctttagcattaagaggccgttctgcttgt
ttgaatttctctgattctgcttggaggctgcctatccctgcttcctccaactctaaagatattcaaaaggc
ggccgctcaggccgtcgaaatcttccgatcggaagaagtttcaggagaatctcctgaaacgtcagaaaatg
tgcaagagagtagtgacttcgtggatgaggaggcgatctttttcatgccaggattacttgcaaatatggca
gaaggacttatgctacctccacctcaatgtgcagaaatgggagatcattgtgtggaaactgatgcctacat
gataactttatggaattattctatctaaaatagtagtacaatttatcaaattactaggatttagaagattt
tggtagttttggtattcagtatttagatactaagaatgtatattattagtatttttatttttggcc

Fig. 14J

SEQ ID NO:129:
Lycopersicon esculentum (Tomato) dehydration responsive
element binding protein (DREB1) (GenBank AF370729) nucleic
acid sequence:
ctctacaagcttttgttaagagactaaaaaaaacaaaaaaaccttgaagaactcaccaatttgatcaatt
catttattaaaaaaaaaaacagagaagaaaagagaaatggctattatggatgaagctgctaatatggtttg
tgtgccgttggattatagtagaaagaggaaatcaaggagtagaagggacagaacaaaaaatgtggaagaga
cactagctaaatggaaggagtataatgagaaactagacaatgaagggaagggaagccagtgcgtaaagtt
cctgctaaaggttcaaagaaggggtgtatgagaggtaaaggggggaccagaaaattggcggtgtaaatacag
aggtgttagacagaggatatggggtaaatggggttgctgagattagggaacctaaaagaggtagtaggttat
ggttgggtacatttggtacagcaattgaagctgctttagcatatgatgatgctgcaagagctatgtatggt
ccttgtgcaaggcttaatttgccaaattacgcgtgtgattctgtttcctgggcaactacatctgcatctgc
atctgcatctgattgcaccgttgcttctggtttcggcgaggtatgtccggttgatggtgctcttcatgaag
ctgacacaccattgagctcagtgaaagacgaagggaccgcgatggatattgttgaacctacgagtattgat
gaagatacgcttaagtctggatgggattgtctagataaattaaatatggatgagatgtttgatgtagatga
gctattggctatgttagattctactccagttttcaccaaggactacaattcagatggaaagcacaacaata
tggtatcagattcgcaatgtcaggagccgaatgcagtggtagatcctatgactgttgactatggctttgat
tttctgaaaccaggcaggcaagaagatcttaatttcagttcggatgaccttgcattcatagacttggattc
tgaacttgtcgtttgatagttttcgcagttgaaagatgcaatgcaagataacatgtatcgtcattgattga
gatataggacgcgaggaagagaaaactcgagatgttgagtttggacaatgttttcgtatcgttcaattttt
ttttatttcatgttgggcagcattggttgccttttcccaggccagctgattctcgataagtttttgcatc
gaagattatgcatttggtgttctggaggactaatcttgtacagatctaaccggcctagtgagtcaataatt
gttcgttttggtgtgttgatatgacgaataaagatgtttctgggattcatagtttgttgtaaagtttgctt
gacaattagaggtactgattttgtgctttcattggaacaatgtagaatgcattgacggcatttacagttc
attcataacttgaacaataagtttggcagtgtgtatttgtgttactttgtgaagtattcccaggggattcg
ccaacgaatgctgtgttgtgtgttcaagtgtttcgagtagatcagagaagtactggaagcagtggtgctat
agtgttttatgttagccctcatcgtggtttggtagatttgtgtagttctgttttgcacttaggcttttta
tctctatcagaagttgtactcaggatgtaatagtagacgttttgagacgtttcaaaatgttccagttcatg
ttctttaccacattgtaattcaataaattctgcggtaatcttaagatgtggaaaaaaaaaaaaaaaaaaa
aaaaaaa SEQ ID NO:130:
Zea mays (maize) DREB-like protein (DREB1A) mRNA (GenBank
AF448789) nucleic acid sequence:
ccagagtaccagacaccactgcgcatcagtgcaaagaggtagctaccctatctgccatggctcaagagctc
cacgaaacgtcctcttgctctgccaccaccacctcgtcgtgcaccacatcctgctgctcgtccactgtcac
agactcgtcctcttcgcccccgtcaccggcggcggccaatgccgcgcccgcgacacggaagcggcaggcgt
tggaggccgaggccgaggccgaggcgggcggtgaggaggaggaggaggaggaggaaggctgtgctggtaat
aaggcggcgccggccaagaagcgaccgcggggcagcgaggggaagcacccgacgttccgcggcgtgcggat
gcgggcgtggggcaagtgggtgtcggagatccgcgagccgcgcaagaagtcgcgcatatggctcggcacgt
tccccaccgccgagatggccgcgcgcgcccacgacgtcgcggcgctcgccatcaagggccgcgccgcgcac
ctcaacttcccggacctcgccggcgcgctcccgcgcgccgcgtccgcggcgcccaaggacgtccaggcagc
cgccgcattggccgctgcgttcacgtcgccgtcatcggagcccggcgccggcgcgcacgaggagcccgctg
ccaaggacggcgccgcgcccgaggaggcagccgccgacgcacaggcaccagtaccagtagcactaccaccg
ccggcggcctctcggccagggacgccgtcgagcggcgtggaggacgagcggcagctgttcgacctgccgga
cctgctcctcgacatccgggacgggttcgggcgcttcccgccgatgtgggccccgctcactgacgtggagg
aggtggtcaatgcggagctgcgcctcgaggagccgctgctttgggagtagcggtcagagatgctcgttgcc
tgcattgcaaacgaggtctaaacaatagtagcagtggtatcccatttcttctcgtttttgcttctcgccctc
tcctttttttctctcttcttgcttactttgggggaaaacagctagttctttttttcttcttcttcttct
tcttttattaaattgagttttaataagtataaacatatataaacgagagagagagatataagctgtgtactta
aaagtgtaagacgagtacctatcagttcattattacgtatctactagtggtaccagtagtgatcatgttgt
cccggccgtgtgtgaattccagcggtagttgttgaccttgctagattttatagttgcttgtgttgtgtgc
tgtaccaaaattccccagggaaaagggcaggaagcaaacgaatgtaacgggaacacaagcagcatctaat
ctctattactgctgacaacgaaaaaaaaaaaaaaaaaaa

Fig. 14K

SEQ ID NO:131:
Zea mays (maize) DREB-like protein (DREB1A) mRNA (GenBank
AF450481) nucleic acid sequence:
gctcaagctcgagacaagaaaccagaaccagctcactcctcactccacttccactccca
acagcaagctcaagcagtcagtcaccggcaggggtcagggtcacagtcacagcagcagc
catggacacggccggcctcgtccagcacgcgacctcctcgtcttccacctccacctcgg
cgtcgtcgtcctcgtccgagcagcagagccgcaaggcggcgtggccgccgtcgaccgct
tcctcaccacagcagccgcccaagaagcgccccgcggggcgcacaaagttccgggagac
gcggcaccggtgttccgcggcgtgcggcggcggggcgccgcgggccggtgggtgtgcg
aggtgcgcgtcccggggaggcgcggcgcgcggctgtggctcggcacctacctcgccgcc
gaggcggcggcgcgcgcgcacgacgccgcgatactcgccctgcagggccgcggcgcggg
gcgcctcaacttcccggactccgcgcggctgctcgccgtgccgccccgtccgcgctcc
cgggcctggacgacgcccgccgcgcggcgctcgaggccgtcgcggagttccagcgccgc
tctgggtccgggtccggggccgccgacgaagcgacctcgggcgcgtctcctccctcctc
gtcgccgtcgctgccggacgtttctgcggctggctcgccggcggcggcgcttgagcacg
tgcctgtgaaggccgacgaagcagtggcgttggacttggacggcgacgtgttcgggccc
gactggttcggggacatggcctggagttggatgcgtactacgccagcctcgcggaagg
gttgctcgtggagccgccgccgccgccggcggcctgggatcatggagactgctgtgact
ccggagctgcggacgtcgcgctctggagctactactagcaaagttaacaataataagct
tgacagccaaccccaaaagccccccaactgattgtattcacctctgtaacaaaattcaa
attgatttcccagcaaatgaacttcaaaagaagtctttggttccgatttaaaaaaaaaa
aaaaaaaaaaaaaaaaaaaaaa SEQ ID NO:132:
Gossypium hirsutum (upland cotton) DREB-like protein
(DREB1A) mRNA (GenBank AY321150) nucleic acid sequence:
ggccattacggccggggagaaaagaaagctcatttagttaatattttcccttgcattt
ccaaattcggaagttcatacagcaagtgatttcctaaaatacttggatcctaagtacga
atatccttttcttgaaatatactcttttaagtcaaaagctttgtttaactgaaactta
aactgattactgtttgggtttttttttaaatggattttgtagttcaagattatgatat
ggttgattctgggtcggtttctgaaagtggaactgatcgtccggtgaattttccgatg
aatatgtgatgttagcttcgagttatccaaagaggcccgcgggaaggaagaagttccgg
gagactcgacacccggtgtaccgtggagttcgccggaggaatcccgggaagtgggtttc
tgaagtgagggagcctaataagaagtcgaggatttggcttggaactttcccgaaggcgg
atatggcggcgcgtgctcacgacgtggcagctatagcactgagagggaagtcagcttgt
ttgaacttcgctgactcagcttggaagcttccggtccggcttcttccgacccaaagga
tatccaaaagacggtggcggaggtggcggagactttcagaacggctgagcattcgagcg
ggaattctagaaacgatgcaaagagaagtgaaaacacggagatggagaaagggttttac
ttggacgaagaagcgttgtttgggacacaaagatttgggcaaatatggctgccggtat
gatgatgtcacctcctcgttccggtcatgacggaggatgggaggaacatgaagtcgatg
attatgtacctttatggagttattctatttaaaagtaaaattttcagacatttcaag
cattcattggaattttagttcacagaaatcgccaccggcaattgcctttatgttttg
tacgtacaacgattttttggattgtacgggtagtgctgtaagtaaaagattaatgtg
tatatatacgatgtatatatacttcatagcttctccaaacaataaatttatagcttcat
atctattttaccatcaaaaaaaaaaaaaaaaaaaaaaaaaa

Fig. 14L

SEQ ID NO:133:
Capsella bursa-pastoris (shepherd's purse) CBF mRNA
(GenBank AY391121) nucleic acid sequence:

acgcgggttcttctaactacaaacttaaacaagaatccacctgaaaagaaaatagggagagagaaatatat
atatatatatattaacaactaaagagatttcttcttttagttactctctactttttatccagttttttttct
tctttatctcgaacagagtattctcaaacaatgaactcatctttctctgctttctctgaaatgtttggttc
cgagtacgagtctccggtttcttcaggcggcggagattactgtccgacgctggccacgagctgtcccaaaa
aaccagcgggtaggaagaagtttcgtgagacccgtcacccagtttacagaggagttcgtcggagaaactcc
ggcaagtgggtttgtgaggttagagagccaaacaagaaatctaggatttggctcggaactttccctacggc
cgatatggctgctcgtgctcacgacgtcgccgctatagccctccgtggcaggtcagcctgtctcaatttcg
ctgactctgcttggcggctacggatccccgagtcaacaggcgccaaggaaatccagaaggcggcggctgaa
gctgcgctggcttttcaggatgagatgatgatgagcgataccacgacgacggatcatggctttgacatgga
ggaaacgtttgtggaagcaattgtgacggcggaacagagcgcttcgttatatatagacgaagaggacatgt
tcggtatgccgagtttgatggctagtatggccgaaggtatgcttttgcctctgccgtccgtacaatggaac
cataactatgacatcgacggcgatgatgacgtctcgctatggagttattaaacttttctgattttctcat
ctccattaatattttggtactactgtgtgatatttattttgtttggatccttttttagaacggatcctt
catttgttgttgtttgggtagttgtgagaagtgaatgtaaatgattcagtatggctggattttacttaaat
gcaaagagtgcagaaaaagttcatgatcaaaaaaaaaaaa SEQ ID NO:134:
Prunus avium (sweet cherry) (GenBank AB080966) nucleic acid
sequence:

tacttacttttgctgtgactaccactctctctcacctccttctctctagaccaccaacttttcgactttta
ctctctctctctctctctctctctgctttgttgataagatttgagttatgagtaagcactgtgg
gacctcagctgagcttgggagtgggagccagttacagtaataaaatatcacatttcagaagcacttaaatg
caggggcaaaatagtattttttatattatttttaattttatcatcagaatatttctttcattaaaaaaat
aaaaataaaaactgaaaaaccttcttcgtatcctcgccatcactggatggtgggtatgatttgagcggggg
tatggttgtgagagcaccatcagttgttgcgggggtggtgggttatttggctcggtgtcgggtagagatt
gaccatgactttgttgaaatagtcagattgtgaaaattaaaattaatacaaaaaataaaaaaccattttgt
acctgtatttaatataaaaaattaacaaaactgacaacatgaccatttctcctaataaaactaaaattgaa
aatcatggaaacaattttaaaaattaaggaatcaaaatacaaatagggtcaaaattatggtgatattgaac
ctaaaaaccccacttgcccccccactatactttttaaacttgcgccccaatttacttagactagttagttca
gtgtgtgtttccgccacgtggcggagccaagtctaatctatttcttttcctccatctctcctccaatcc
ccttttgtctgttttgtgagggaacttgctgagccacattccgacctggccccaccggcctcctcacact
ccgtgttatcgtgtccacacctgggcccacctgccacgcaatccctaatctataaaagccattctccctca
cttccaatttcagctcaaggaaactcaaacaagctaaaacaccaaaccattcatacataaagcttagtcta
atggacatgttcttctctcaactttcagactcggtcgaccagccccagtcgagtttgttgtccgacgccag
cgtcaccactcgaggggcttcttgttccgacggggacgtcatattggcgtcgagccggccgaagaagcgag
cggggaggagggttttcaaggagacgaggcaccggtttataggggtgtgaggaggaggaacaatgacaag
tgggtgtgtgaaatgagagagcccaacaagaagaagtccaggatatggctcgggacttatccgacggcgga
gatggctgctcgtgcccatgacgtggccgcattggcgtttagagggaagcttgcatgcatcaactttgctg
actcagcgtggaggctgcccgtgccggcttccatggataccatggatattcggagggcggccgcagaggca
gctgaggggtttaggccggtggagtttggtggagtgtgcagcggcagcagtgatgagaaggagagaatggt
ggtgcaggtggaagagaagaacaagaagggtagtgtgaacttggaaagaagcagaagcttgagcttgtcct
attgggatgaggaggaagtgtttcacatgccaggttgcttcatgacatggctgaagggcttcttctttct
ccatcgcaatgcttaggtggctacatgaatttggatgacatgggcaccgatgctgatgtcaaattgtggag
tttctccatttaataatcgacgtttattttagtcgattactagaatttatttattgtttgattcttatgca
tttatttacttgtaacaaaaaagattaaccttggttgttcgctgtaagtggacagattggaaatatattt
tggatatttgtggtcgagatagatattttgggttatatactgcacaaaagtttcctaaatttagaattatt

Fig. 14M

SEQ ID NO:135:
Prunus avium (sweet cherry) (GenBank AB080965) nucleic acid sequence:

```
atgatattgtattaagtaaggtcttgcagttcaagtagttaagactattttattcattc
atatgagattttaagttcgactcttctctccctgactatcgtttatatctaaaaaataa
ttattgtaatcgaaattatatttacaaattttgacctagcctccttacgatacataaac
taacccccaaaaagagtttccttgccatttctattttgaagtatatgattttacatata
ccgccgtcctttccacagaacaaaaagaggagaatgcattcgattcgaagatatacaaa
tacttgtgatttcctctaagtgagacaacaaaagcgaagaagacgatgaaaaatttatt
gcaggatttgagttgggcaccacctcacacacattgcacacgttgcattaaaaaacgtg
acaaattttgtaaccaaaaaatcacacgtgctaaatacccactttacttagcttagtaa
gtcaagccaaagccaaagtcaaattaatctatttctctacaatcctctttgctttcca
gtgtgaacacgcccacattaggccgctgatttccatgtggcgtctcgccaaatcatcac
gctccgtgttcgcgcgtccacttcgcataaacatggcccaacccaaaatctataaaaaa
gccaccaccacactcgaactctctccattttcagcccagaaaaaacccaaccctactaa
aacacaaagtcggaaagctttacactaagggcttgcaaaaatggacatgatctacagcc
agctctctgatttagcttctatggaaaacccggatacgtcttcgttttcggacgccagc
gttacggcccggcgagcttctctttcagatgaggaggtcatactggcgtccagctgccc
gaaaaggcgggcggggaggagggttttcaaggagaccaggcacccggtttataggggtg
tgaggaggaggaacaacaacaagtgggtgtgtgagctgagagcccccaacaacaagaag
gccaggatatggctcgggacttatccgacggctgagatggcggctcgtgcccatgatgt
cgctgtattggcgtttaggggggaagcttgcctgcctcaactttgctgactcggcttggc
ggctgcctgtgcctgcctccaccgatgccgcggagattaggagggcggccaccgaggcc
gctgaagcgtttaggcaggcggaggatggtggtgttgatgagaaggagagtaaggcagt
ggtgagtgaggagaagggttgtgtaggaatggagggaagcagcaacttgttttatttgg
acgaggacgaaatatttgagatgccaaggttgcttgatgacatggctgatgggattatg
ctttgtccacctcaatgcttagatggctacatggattggaatgacgtggaaactgttga
cgatttgaaactgtggagttttctatttgatcgacctctatagaaatcccacattcta
tagtaaatcagaatgattgtaatttgtaggccctacttactttatttttaaatggaaa
catatttatgttttagaccctacttactttgctgtgactaccactctctctcacctcc
ttctctctagaccaccaactttttcgacttttactctctctctctctctctctctctc
```

Fig. 14N

SEQ ID NO:136:

Arabidopsis thaliana DREB1A (GenBank AB013815) nucleic acid sequence:

```
atttttgagtgagaggagtgcgctggctggagagaaagagaggaaaggagtttcgaagtgagagagagggc
gttgagattgtggatcaacttaatgtaatatgttcttttattaacatttttcttttgtcatataactcaaa
ccttttactattttgtttcataaatctaacacaccccaccatttgttaatgcatgatggtagaaaatatta
aatataattaactactttatgtgatcaaaattaggtttcagactcgtttcgcgatccgatctacaattac
aactgcatgcttctaattgatctaaattctaattttttatacatattaaaaaaacaactttttgttaaat
tctcaatcatcatttttgtgattaacaattttttataactctaaaccaataatatttgattatttatttta
tatgtataatgatgattgagaatttttaattagcagtctatttagggttttcctaaagttacaatatgttgt
tacccttctagttaaattttccaaaataccatatttcataacttttcaaactgtttattaattcaaccgta
aaaagcactaaaatgttacatttgatcattcacccaaattaaattcaaaagttttttccgccaaaactactt
ggtgacttacgtgcttatatacggacgactattattatgttctatacttttttatactttgttgcacaaat
atctactctcccaattcatattctagaaggatgtgctataagaatgggagaaattacacaagaagagcatc
tttaaatatcctctcacaatctttatgtctaatacacgggtgaacaattaacgacaatttctttattcagg
aatataataatgaataacggttaccctacacctagtacactaaatccttaacagccacacattcatacgca
aagagtttataaaactcataaaggtataataataacgagtgaataagtcaaaaaaagtcttctctggacac
atggcagatcttaatgagtgaatccttaaactactcattttacaattgcttcgctgtgtatagtttacgtg
gcattaccagagacacaaactccgtcttcgccttttcttttgcctctaaaatatcttccgccattataaaa
cagcatgctctcactccaacttttatttatctacaaacattaaatccacctgaactagaacagaaagagag
agaaactattatttcagcaaaccataccaacaaaaagacagagatcttttagttaccttatccagtttct
tgaaacagagtactcttctgatcaatgaactcatttctgcttttctgaaatgtttggctccgattacga
gtcttcggttcctcaggcggtgattatattccgacgcttgcgagcagctgcccaagaaaccggcgggtc
gtaagaagtttcgtgagactcgtcacccaatatacagaggagttcgtcggagaaactccggtaagtgggtt
tgtgaggttagagaaccaaacaagaaaacaaggatttggctcggaacatttcaaaccgctgagatggcagc
tcgagctcacgacgttgccgctttagcccttcgtggccgatcagcctgtctcaatttcgctgactcggctt
ggagactccgaatcccggaatcaacttgcgctaaggacatccaaaaggcggcggctgaagctgcgttggcg
tttcaggatgagatgtgtgatgcgacgacggattatggcttcgacatggaggagacgttggtggaggctat
ttacacggcggaacagagcgaaaatgcgtttatatgcacgatgaggcgatgtttgagatgccgagtttgt
tggctaatatggcagaagggatgcttttgccgcttccgtccgtacagtggaatcataatcatgaagtcgac
ggcgatgatgacgacgtatcgttatggagttattaaaactcagattattatttccattttagtacgatac
ttttattttattattatttttagatcctttttagaatggaatcttcattatgtttgtaaaactgagaaa
cgagtgtaaattaaattgattcagtttcagtataagtgtgggctattcttaaatgcaagtattttagagc
agtaacaaaaaaatgttgtttaaattagagtataaaaccgaaacaaccgattcagcaaaacctccaataat
agaccgtacaccataaacagaaatatgggtcccacaagagagcactgtccgtagcttcccttcattggcc
ctctacgtggctcctcttgtaaccaatgtcatgtcatttcaagttttactttctttttttatactaatat
cttgttgtcgttttctgtaccttaaggtcctaaaccactttctttcgcgcaccattccttgtcgtattat
ttctccgaatatgtcaataccgtgagacgacaattgatagcgagaggtagcgagagagagaaacgttcgtt
gtgaagatatttttattgctgttgttgagattgagatattttatagctattattggaatttgaaagtgatgt
ataacttgctactatatcggctaaatccttgggcttaaaccagttttatttagtaaattttatgctcctg
tattattatctggaagtatttttctccgaaatatatgagtcgagtttaaggaatatataagcgaaaaaccn
caaattatatatataagcggggttaatagatcaccacaatcaatttaatttggactttagaattaataaaa
ttgtttcttcgtaattattattattttgttgttctggcaaatctgataatccagattattattagacaag
tagcgaagggacggtgaacatttatgatttttaatttgtatgttgtaaggaaaacaaaacaaataagttctg
taaaaaggtttaccttctactttgccggaaaactcaactcacggtggcgtccggcgagttttcagacca
aaaagaaggttggaagaaatgaagatgaagaggagaggacaaaagatagagatggtggttgaacaaaagaa
gagtaaagaggacgaagacgctctaagtctaagccaaggggggagaagaagagaagaggtatgaggaggaac
catactttgttagagagatgctggaaattgtgatcaactacatgcaaaatgtcttttcgcctaaccactt
accatatttgatattttccttttgccaaattacacaaaccctatcttgtctctcacatatatatccaatta
atacaccctgccacttgttaattctcgaccatgtatgtatacttatgtaaagaatatccaaaagctt
```

Fig. 140

SEQ ID NO:137:
Arabidopsis thaliana DREB1A (GenBank AB007787 (BAA33791))
nucleic acid sequence:

cctgaactagaacagaaagagagagaaactattatttcagcaaaccataccaacaaaaa
agacagagatcttttagttaccttatccagtttcttgaaacagagtactcttctgatca
atgaactcatttctgcttttctgaaatgtttggctccgattacgagtcttcggtttc
ctcaggcggtgattatattccgacgcttgcgagcagctgcccaagaaaccggcgggtc
gtaagaagtttcgtgagactcgtcacccaatatacagaggagttcgtcggagaaactcc
ggtaagtgggtttgtgaggttagagaaccaaacaagaaaacaaggatttggctcggaac
atttcaaaccgctgagatggcagctcgagctcacgacgttgccgctttagcccttcgtg
gccgatcagcctgtctcaatttcgctgactcggcttggagactccgaatcccggaatca
acttgcgctaaggacatccaaaaggcggcggctgaagctgcgttggcgtttcaggatga
gatgtgtgatgcgacgacggatcatggcttcgacatggaggagacgttggtggaggcta
tttacacggcggaacagagcgaaaatgcgttttatatgcacgatgaggcgatgtttgag
atgccgagtttgttggctaatatggcagaagggatgcttttgccgcttccgtccgtaca
gtggaatcataatcatgaagtcgacggcgatgatgacgacgtatcgttatggagttatt
aaaactcagattattatttccattttagtacgatacttttatttattattattttt
agatccttttagaatggaatctncattatgtttgtaaaactgagaaacgagtgtaaa
ttaaattgattcagtttcagtat SEQ ID NO:138:
Arabidopsis thaliana DRE-binding protein (DREB1A) /
CRT/DRE-binding factor 3 (CBF3) (At4g25480) mRNA (GenBank
NM_118680) nucleic acid sequence:

cctgaactagaacagaaagagagagaaactattatttcagcaaaccataccaacaaaaa
agacagagatcttttagttaccttatccagtttcttgaaacagagtactcttctgatca
atgaactcatttctgcttttctgaaatgtttggctccgattacgagtcttcggtttc
ctcaggcggtgattatattccgacgcttgcgagcagctgcccaagaaaccggcgggtc
gtaagaagtttcgtgagactcgtcacccaatatacagaggagttcgtcggagaaactcc
ggtaagtgggtttgtgaggttagagaaccaaacaagaaaacaaggatttggctcggaac
atttcaaaccgctgagatggcagctcgagctcacgacgttgccgctttagcccttcgtg
gccgatcagcctgtctcaatttcgctgactcggcttggagactccgaatcccggaatca
acttgcgctaaggacatccaaaaggcggcggctgaagctgcgttggcgtttcaggatga
gatgtgtgatgcgacgacggatcatggcttcgacatggaggagacgttggtggaggcta
tttacacggcggaacagagcgaaaatgcgttttatatgcacgatgaggcgatgtttgag
atgccgagtttgttggctaatatggcagaagggatgcttttgccgcttccgtccgtaca
gtggaatcataatcatgaagtcgacggcgatgatgacgacgtatcgttatggagttatt
aaaactcagattattatttccattttagtacgatacttttatttattattattttt
agatccttttagaatggaatcttcattatgtttgtaaaactgagaaacgagtgtaaa
ttaaattgattcagtttcagtat

Fig. 14P

SEQ ID NO:139:
Arabidopsis thaliana CRT/DRE binding factor 3 (CBF3) mRNA
(GenBank AF074602) nucleic acid sequence:

ctagaacagaaagagagagaaactattatttcagcaaaccataccaacaaaaaagacag
agatcttttagttaccttatccagtttcttgaaacagagtactcttctgatcaatgaac
tcatttctgcttttctgaaatgtttggctccgattacgagtcttcggtttcctcagg
cggtgattatattccgacgcttgcgagcagctgccccaagaaaccggcgggtcgtaaga
agtttcgtgagactcgtcacccaatatacagaggagttcgtcggagaaactccggtaag
tgggtttgtgaggttagagaaccaaacaagaaacaaggatttggctcggaacatttca
aaccgctgagatggcagctcgagctcacgacgttgccgctttagcccttcgtggccgat
cagcctgtctcaatttcgctgactcggcttggagactccgaatcccggaatcaacttgc
gctaaggacatccaaaaggcggcggctgaagctgcgttggcgtttcaggatgagatgtg
tgatgcgacgacggatcatggcttcgacatggaggagacgttggtggaggctatttaca
cggcggaacagagcgaaaatgcgttttatatgcacgatgaggcgatgtttgagatgccg
agttgttggctaatatggcagaagggatgcttttgccgcttccgtccgtacagtggaa
tcataatcatgaagtcgacggcgatgatgacgacgtatcgttatggagttattaaaact
cagattattatttccattttagtacgatactttttatttattattattttagatcc
ttttttagaatggaatcttcattatgtttgtaaaactgagaaacgagtgtaaattaaat
tgattcagtttcagtat SEQ ID NO:140:
Arabidopsis thaliana DREB1A (GenBank AF076155 combined
CBF1, CBF2 and CBF3) nucleic acid sequence:

aacatatcatcacacgtggaatgagaacgagtttcgacttttcaaatatgccataaagcctcaattatctt
cttatctagcttgaatatgcaacaaaaagctattaagatattcataaaatagaggcgtctcaaatctacca
acaaaaagctacaaaagatccagtccaatccactgaagaatcccaaaacagagtagaaacccaaacaaccc
gattcagcaaataattcaaaaacgaacgtccgtacgattttccaaaaacagaaagatgggttccacaagat
aatgcgtggggacgtcaaaatcctctaaaccgtggttcggccgcggaaacactgtccctaccttccccac
cagccttcactggccccatacgtcactctcaagctttacttctctattttccactaaagccaattttgttgt
tttcttcaccttaccactctttttttccctctttgttgtgtcttcttttctcctaaatgtcaataacgtga
gagcgagaggtaacgagagagatattttgtcagcgaatatatttcatgcatatcttattgtgaagattttt
ttataccttttttttgtcaatacaatatagctattattgagattgagatatttgtggaattattgggatt
caagataacttgctatttgtattggtcttatccttcgcttagtcctgtcctggtccatttacatgttttt
ggttatagtttgtttaaactgaataattttgttcatcatatgcattaatgactcattttaaccgtccatc
gaaattgataattatccattaccaaatctgattaatttttttaaaaatcaagcttttctatattgtagta
ttattttggttaaatattaggacatctacttccaatacaaatactacatgagtatttaaaatatcatttc
acagagatatttatgtctattatgttatagacgggtgacaattaatgacaatttgtttattcataggaatt
taaaaacgattgtaacaacagcagccagccaaccacacaggcacacactcgatagaatttaaagaactcat
aaaggttaacgagtgaagagtcaaaagtctctttacaagggtcaaaggacacacgtcagacagcgagtgga
acatcgtgggattgcttcgctatgtactatacacgtgtcattcacagagacaaaaactccgtgtgcacccc
acatatccgttatctctcctccggccaatataaacaccaattctcactctcactttttatactaactacac
acttgaaaagaatctacctgaaaagaaaaaaaagagagagagatataaatagctttaccaagacagatat
actatcttttattaatccaaaaagactgagaactctagtaactacgtactacttaaaccttatccagtttc
ttgaaacagagtactctgatcaatgaactcattttcagctttttctgaaatgtttggctccgattacgagc
ctcaaggcggagattattgtccgacgttggccacgagttgtccgaagaaaccggcgggccgtaagaagttt
cgtgagactcgtcacccaatttacagaggagttcgtcaaagaaactccggtaagtgggtttctgaagtgag

Fig. 14P

SEQ ID NO:140 (continued):
Arabidopsis thaliana DREB1A (GenBank AF076155 combined
CBF1, CBF2 and CBF3) nucleic acid sequence:

```
agagccaaacaagaaaaccaggatttggctcgggactttccaaaccgctgagatggcagctcgtgctcacg
acgtcgctgcattagccctccgtggccgatcagcatgtctcaacttcgctgactcggcttggcggctacga
atcccggagtcaacatgcgccaaggatatccaaaaagcggctgctgaagcggcgttggcttttcaagatga
gacgtgtgatacgacgaccacggatcatggcctggacatggaggagacgatggtggaagctatttataca
cggaacagagcgaaggtgcgttttatatggatgaggagacaatgtttgggatgccgactttgttggataat
atggctgaaggcatgcttttaccgccgccgtctgttcaatggaatcataattatgacggcgaaggagatgg
tgacgtgtcgctttggagttactaatattcgatagtcgtttccattttgtactatagtttgaaaatattc
tagttccttttttagaatggttccttcatttattttatttattgttgtagaaacgagtggaaaataatt
caatacaaaacaaatcgttttctacttctttgcttcacataagttaaaagtcaaatatttaacaaaaaaga
tattaaaagtcatattgtagttgctttcaaggcaaaatatgtggacagaatcattacacgtggatgatgtt
tgtaaatatgccacaaaacctgcattacattatttttattctatctcatgtaagttacagatcttacaattt
tagcaacagaaagccacaaaatattacataaattggctcgtctcgaatctagcaaccaaaaaattcagtc
cagttcactataaagaataaaaaaaaagtttcctaaaatagtgtataaaaccgaaacaaactaattcaac
aaacccgaaataaacaaatccgtacgacaaccaaaaatatctttcagatgggttccacaagataacccagt
gccaatcagaattctgaaagcgtggctcgaccgcggaaaccattgtccataccttctctcttctttgtccccc
cttacgtggctcgctgtggagtctcgtaccacgtgtcgcgtcacttcactctttactttctatttccact
aaaatcataatttgtcttttttcttgaccatacccactcttttttcttctcgttgtcgtcttgcttctccta
aatatctcaaataacgtgagagacttgagtgtgagaggtaggtaacgaggcagacttttttggaagcgaa
tataacttatgctgatattttatttagctttctgattggagttgagatattataggtattattgagata
ttatatacgtattattgagatttgagatatttgtagattttatagttctatcggactaattcttggctta
atccactaacatgttttgtttagttaattaaactgattatttctgcgctatagttttgttaaacacctt
ttagacgtaacaaagcaattacgcttgatcattcatcgtagactcttttctttttttacatctcatgaa
gttttgtttaaacacagcaggaagtaaattatttcttattacgtacgtatgattgttttagactatttt
agtactttgagaagtaaaattggggatacgagataaaagacaattgattaacatgcttttatttgactt
ccgaaactaatcatggttgtctatgtttataaattgtgttattttgttgaaaaacttagataattattaa
atcagtagcgaatggatggagaacacatgattttagattgcataccgtaaaacaaaaaaaaatcatgatgg
atgtagaacattcaaatggatcaaataaataagtatgtgatcaaaagaaagtatgtaatcaaaagggttag
cacgagtaccttgggaggaaattcttctaattatgaattatgcaagaattttcgtcaagggaaggtgggga
agaggtagctaaattaaagaatagagaatcatatgactaaggacgtggtggttgaaggaaatgagagaata
catgaagaagagaaacttctttgagtgagaaggaagtgcgctggctgaaggcaatagagagaaaagagttt
cgagtgagagagagggcgttgagattgtgatcaacttaatgtaatatgttcttttattacatttttctttt
gtcatatactcaaaccttttactattttgtctcataaatctaacacaccccaccatttgttaatgcatgat
ggtagaaaatattaaatataattaactactttatgtgatcaaaattaggtttcagactcgtttcgcgatc
cgatttacaattacaactgcatgcttctaattgatctaaattctaagttttttatacatattaaaaaata
acttttttgttaaattctcaatcatcattttgtgattaacaattttttataactctaaaccaataatattt
gattatttattttatatgtataatgatgattgagaattttaattagcagtctatttagggttttcctaaag
ttacaatatgttgttacccttctagttaaatttccaaaataccatatttcataacttttcaaactgttta
ttaattcaaccgtaaaaagcactaaaatgttacatttgatcattcacccaaattaaattcaaaagttttc
cgccaaaactacttggtgacttacgtgcttatatacggacgactattattatgttctatacttttttatac
tttgttgcacaaatatctactctcccaattcatattctagaaggatgtgctataagaatgggagaaattac
acaagaagagcatctttaaatatcctctcacaatctttatgtctaatacacgggtgaacaattaacgacaa
tttctttattcaggaatataataatgaataacggttaccctacacctagtacactaaatccttaacagcca
cacattcatacgcaaagagtttataaaactcataaaggtataataataacgagtgaataagtcaaaaaaag
tcttctctggacacatggcagatcttaatgagtgaatccttaaactactcattttacaattgcttcgctgt
gtatagtttacgtggcattaccagagacacaaactccgtcttcgccttttcttttgcctctaaaatatctt
ccgccattataaaacagcatgctctcactccaacttttatttatctacaaacattaaatccacctgaacta
gaacagaaagagagagaaactattatttcagcaaaccataccaacaaaaaagacagagatcttttagttac
cttatccagtttcttgaaacagagtactcttctgatcaatgaactcatttttctgctttttctgaaatgttt
ggctccgattacgagtcttcggtttcctcaggcggtgattatattccgacgcttgcgagcagctgcccaa
```

Fig. 14P

SEQ ID NO:140 (continued):
Arabidopsis thaliana DREB1A (GenBank AF076155 combined
CBF1, CBF2 and CBF3) nucleic acid sequence:

```
gaaaccggcgggtcgtaagaagtttcgtgagactcgtcacccaatatacagaggagttcgtcggagaaact
ccggtaagtgggtttgtgaggttagagaaccaaacaagaaaacaaggatttggctcggaacatttcaaacc
gctgagatggcagctcgagctcacgacgttgccgctttagcccttcgtggccgatcagcctgtctcaattt
cgctgactcggcttggagactccgaatcccggaatcaacttgcgctaaggacatccaaaaggcggcggctg
aagctgcgttggcgtttcaggatgagatgtgtgatgcgacgacggatcatggcttcgacatggaggagacg
ttggtggaggctatttacacggcggaacagagcgaaaatgcgttttatatgcacgatgaggcgatgtttga
gatgccgagtttgttggctaatatggcagaagggatgcttttgccgcttccgtccgtacagtggaatcata
atcatgaagtcgacggcgatgatgacgacgtatcgttatggagttattaaaactcagattattatttccat
ttttagtacgatacttttatttttattattattattttagatcctttttttagaatggaatcttcattatgttt
gtaaaactgagaaacgagtgtaaattaaattgattcagtttcagtataagtgtgggctattcttaaatgca
agtattttagagcagtaacaaaaaaatgttgtttaaattagagtataaaaccgaaacaaccgattcagca
aaacctccaataatagaccgtacaccataaacagaaatatgggtcccacaagagagcactgtccgtagctt
cccccttcattggccctctacgttgctcctctgtaaccaatgtcatgtcatttcaagttttactttctttt
tttatactaatatcttgtttgtcgttttctgtaccttaaggtcctaaaccactttctttcgcgcaccattc
cttgtcgtattatttctccgaatatgtcaataccgtgagacgacaattgatagcgagaggtagcgagagag
agaaacgttcgttgtgaagatattttattgctgttgttgagatttgagatattttatagctattattggaa
tttgaaagtgatgtataacttgctactatatcggtctaatccttggcttaaaccagttttatttagtaat
ttaaactcaatgtccttatgctcctgtattattattcggtggaagtatttttttctcaaaaaatatatgag
tcgagtttaagaaatatataagcgaaaaaacaaaaaaatatatataagcgggggttaatagatcaaccacaa
tcaatttaatttggactttagaattaataaaattgtttacttcgtaattattattattttttgttgttctgg
caaatctgataatccagattattattagacaagtagcaaagggacggtgaacatttatgattttaatttgt
atgttgtgaggaaaacaaaacaaataagttctgtaaaaaaggtttaccttctactttgccggaaaactca
actcacggtggcgtccggcgagttttcagaccaaaagaaggttggaagaaatgaagatgaagaggagagg
acaaaagatagagatggtggttgaacaaaagaagagtaaagaggacgaagacgctctaagtctaagccaag
ggggagaagaagagaagaggtatgaggaggaaccatactttgttagagagatgctggaaattgtgatcaa
ctacatgcaaaatgtcttttcgcctaaccacttaccatatttgatattttccttttgccaaattacacaaa
ccctatcttgtctctcacatatatatccaattaatacacccctgccacttgttaattctcgaccatgtatg
tatacttatgtaaagaatatccaaaagctttcttttttgttccttcgatttttaagcaacttgtgttctcatt
tctcaatatattaaagaaatcctgagtaaaagttatagcctccgtgaatcttaggaaattactctagcata
ttcaaattttttgagacaatatataaatttttctgaataattaaatttacatatctatgctacgaaacttg
attaattaaattaaatatatatatataataataataataataatataacatttttttttaggacacaaa
tatctaatctcactatactctagaagtatttgcaatgcacgatatgtgaatggagaaaagacagaaagagc
atttgaaaatatctcgtttcacggatcattatgtctaattattttaccatagaaaagcgacaattataaac
aatttgttattcgtggaaaaataatatttaataatggttgtcgtacctataactacagccacacattca
tacaataagaagttaaaaaaattcatccctaaaggcatcaaccagtgaagggtcagaaacttcccaagat
gggtcaaaggacacatgtcagattctcagtgattgacagccttgataattacaaaaccgtgggatcgctta
gctgtttcttatccacgtggcattcacagagacagaaactccgcgttcgaccccacaaatatccaaatatc
ttccggccaatataaacagcaagctctcactccaacatttctataacttcaaacacttacctgaattagaa
aagaaagatagagagagaaataaatatttttatcataccatacaaaaaaagacagagatctttctacttact
ctactctcataaaccttatccagtttcttgaaacagagtactcttctgatcaatgaactcatgttctgctt
tttctgaaatgtttggctccgattacgagtctccggtttcctcaggcggtgattacagtccgaagcttgcc
acgagctgccccaagaaaccagcgggaaggaagaagtttcgtgagactcgtcacccaatttacagaggagt
tcgtcaaagaaactccggtaagtgggtgtgtgagttgagagagccaaacaagaaaacgaggatttggctcg
ggactttccaaaccgctgagatggcagctcgtgctcacgacgtcgccgccatagctctccgtggcagatct
gcctgtctcaatttcgctgactcggcttggcggctacgaatcccggaatcaacctgtgccaaggaaatcca
aaaggcggcggctgaagccgcgttgaattttcaagatgagatgtgtcatatgacgacggatgctcatggtc
ttgacatggaggagaccttggtggaggctatttatacgccggaacagagccaagatgcgttttatatggat
gaagaggcgatgttggggatgtctagtttgttggataacatggccgaagggatgcttttaccgtcgccgtc
ggttcaatggaactataattttgatgtcgagggagatgatgacgtgtccttatggagctattaaaattcga
ttttatttccattttggtattatagcttttatacatttgatccttttttagaatggatcttcttctttt
ttttggttgtgagaaacgaatgtaaatggtaaaagttgttgtcaaatgcaaatgttttgagtgcag
```

Fig. 14Q

SEQ ID NO:141:
Thellungiella salsuginea (close relative of Arabidopsis thaliana) nucleic acid sequence:

caggccaatataaacaccaaccctcactcccacttttcttcaaactacaaactttaaaa
tccaacctgaaaaaaaagagagagataaaaataaaatatttctatcaaaaaccatcag
gacggaagatcttttaacctactacttaaaccttatccagttttctcaaaaaagagtt
ttcttttttcttaaagatcaaaaatgaactcattttctgcgttcgctgaaatgtttgg
ctccgagtacgagtctccggtcaccgtaggcggcgattactgtccgacgctagcgacta
gctgtccgaagaaaccagccggtcggaagaagtttcgggagacacgtcacccaatctac
agaggagttcgtcggagaaactccggtaagtgggtgtgtgaggttagagagccaacaa
gaaatctaggatttggctcggaacttttccaacagccgagatggcagctcgtgctcatg
acgtcgccgccatagctctacgtggcagatccgcctgtctaaatttcgcagactcggct
tggcggcttagaatcccggagtcaacttgcgctaaagatatacagaaagcggctgctga
agcggcggttgcttttcaggctgagatgagtgatacgatgacatcggatcatggccttg
acatggaggagacgacggtggaggttattgtaacggaggaggaacaaagcgaagggttt
tatatggacgaggaagccatgtttggcatgccgaggttgctggctaatatggcggaagg
tatgcttttgcctcctcgtccgtacaatggggacataattatgactgcgacggagatg
ctgacgtgtccctttggagttattaaaaaaatttggtactataatttttttttttttt
tctgagattttaggattccacaatttttttataggatgaatccctcttttttttttttt
tggtggtcactgagagacgatgtaaatctttcaaaaacaatattttcaatgcgagtatt
ttttgtgcaaaaaaaaaaaaaaaaaaaaaaaaaaa

Fig. 15

SEQ ID NO:142:
Triticum aestivum (bread wheat) COR39 (GenBank ACCESSION
AF058794):

MENQAHIAGEKKGIMEKIKEKLPGGHGDHKETAGTHGHAATATHGAPATGGAYGQQGHA
GTTGTGLHGAHAGEKKGVMENIKDKLPGGHEDHQQTGGHYGQQGHAGTATHGTPATAGT
YGQQGHTGTATHGTPATGGTYGEQGHTGVTGTGTHGTGEKKGLMENIKEKLPGGHGDHQ
QTAGTYGQQGHVGTGTHGAPATGGAYGQHEHAGVAGAGTYGTGEKKGVMENIKDKLPGG
HGDHQQTGGTYGQQGHTGTATHGTPAGGGTYEQHGHTGMTGTGTHGTGEKKGVMENIKE
KLPGGHGDHQQTGGAYGQQGHTGTATHGTPAGGGTYGQHAHTGMTGTETHGTTATGGTH
GQHGHAGTTGTGTHGTDGVGEKKSLMDKIKDKLPGQH

SEQ ID NO:143:
Capsella bursa-pastoris (shepherd's purse) dehydrin COR29
(new COR47) (GenBank ACCESSION AY513787):

MAEENKNNVPEHETPKVATTEEPSTTTTTPEVTDRGMFDFLSKKKEEVKPQETTTLESE
FDHKAQISEPALAAEHEEVKENKITLLEELQEKTEEDEENKPSVIEKLHRSNSSSSSSS
DEEGEEKKKKKTVEGEEEKKGAMDKIKEKLPGHHDKETEDHDVPVVSTIQVPVSESVVE
HHETEGEEKKGVMDKIKEKLPGRNDKETEDSPVPTSTPLVVTEHPVGHSTEQPAEKKGI
IEKIKEKLPGYHAKTEEEKKEKESA

SEQ ID NO:144:
Arabidopsis thaliana (thale cress) dehydrin COR47 (GenBank
ACCESSION NM_101894):

MAEEYKNNVPEHETPTVATEESPATTTEVTDRGLFDFLGKKEEEVKPQETTTLESEFDH
KAQISEPELAAEHEEVKENKITLLEELQEKTEEDEENKPSVIEKLHRSNSSSSSSSDEE
GEEKKEKKKKIVEGEEDKKGLVEKIKEKLPGHHDKTAEDDVPVSTTIPVPVSESVVEHD
HPEEEKKGLVEKIKEKLPGHHDEKAEDSPAVTSTPLVVTEHPVEPTTELPVEHPEEKKG
ILEKIKEKLPGYHAKTTEEEVKKEKESDD

SEQ ID NO:145:
Arabidopsis thaliana (thale cress) COR47 (GenBank ACCESSION
X59814):

NHLKATTQVLKFSHIFYLLYKLLIKSRLTMAEEYKNNVPEHETPTVATEESPATTTEVT
DRGLFDFLGKKEEEVKPQETTTLESEFDHKAQISEPELAAEHEEVKENKITLLEELQEK
TEEDEENKPSVIEKLHRSNSSSSSSSDEEGEEKKEKKKKIVEGEEDKKGLVEKIKEKLP
GHHDKTAEDDVPVSTTIPVPVSESVVEHDHPEEEKKGLVEKIKEKLPGHHDEKAEDSPA
VTSTPLVVTEHPVEPTTELPVEHPEEKKGILEKIKEKLPGYHAKTTEEEVKKEKESDD

Fig. 15

SEQ ID NO:146:
Triticum aestivum (bread wheat) COR39 (GenBank ACCESSION AF058794):

gtaaacacatcagcactagtagatttcacgagtcagaagctcagcgcaagatggagaaccaggca
cacatcgccggcgagaagaagggcatcatggagaagatcaaggagaagctccccggcggccacgg
cgaccacaaggagaccgctggtacccacgggcacgccgccacggcgacgcatggtgccccggcca
ccggtggtgcctacgggcagcagggtcacgctggaaccaccggcacggggttgcatggcgcccac
gccggcgagaagaagggcgtgatggagaacatcaaggacaagctccctggtggccacgaggacca
ccagcagaccggtggccactacgggcagcagggacacgccggcacggcgacgcatggcaccccgg
ctaccgctggcacctatgggcaacaggggcataccggcacggcgacgcatggcaccccagcgacc
ggtggcacctatggggagcagggacacaccggagtgaccggcacggggacgcacggcaccggcga
gaagaagggcctcatggagaacatcaaggagaagctccctggtggccatggtgaccaccagcaga
ccgctggcacctacgggcagcagggacacgtcggcacggggacacatggcgccccggctaccggc
ggggcctacgggcagcatgaacacgccggagtggccggcgcgggaacatacggcaccggcgagaa
gaagggcgtcatggagaacatcaaggacaagctccctggcggccacggcgaccaccagcagaccg
gtggcacctacgggcagcagggacacaccggcacggcgacgcatggcaccccggccggcggcggc
acctatgagcagcacggacacaccgggatgaccggcacggggacacacggcaccggcgagaagaa
gggcgtcatggagaacatcaaggagaagctccccggtggccacggcgaccaccagcagaccggtg
gagcctacgggcagcagggacacaccggcacggcgacgcatggcactccggctggcggcggcacc
tacgggcagcatgcacacactggaatgaccggcacggagacgcacggcaccacggccaccggcgg
cacccatgggcagcacggacacgccggaacgactggcactgggacacacggcaccgacggggtgg
gcgagaagaagagcctcatggacaagatcaaggacaagctgcctggacagcactgagcccggtgt
gccgacgg SEQ ID NO:147:
Capsella bursa-pastoris (shepherd's purse) COR47 (GenBank ACCESSION AY513787):

ggcgccatacgcgggggtctcaaacatcgatactcatcatctcacacacacctcttcaaaaccaa
tctttttagcaacttcaaagttctttaaactttctgtttatcaaaccgtttcagtccattcaga
ttataactatggcggaagagaacaagaacaacgttcccgagcacgagacccccaaggttgcaaca
acagaagagccatcaaccactactactacaccagaggttacggatcgtgggatgttcgatttctt
gagcaagaagaaagaggaagtgaaacctcaagagactacgacgctcgagtctgagttcgaccata
aggctcagatctcagaaccggcgttagctgcggagcacgaggaagtgaaggagaacaagattact
ctcctcgaggagcttcaggagaagaccgaggaagatgaggagaacaagcctagtgtcatcgaaaa
gcttcaccgatccaacagctcttcttcctcttcaagcgatgaagaaggtgaggaaaagaaaaaga
agaagaccgttaaggagaagaagagaagaaaggggcaatggataagatcaaagagaagcttcca
ggccaccacgacaaggaaacagaggatcatgacgtaccagtggtcagcaccatccaggtaccagt
atcggagagtgtggtggagcatcacgaaaccgagggcgaagaaagaaaggagtaatggataaga
tcaaggagaagcttccaggccgcaacgacaaggagacagaggattcacctgtcccaaccagcacg
ccactggttgtaactgagcacccggtgggacactcgacggagcaaccggcggagaagaagggaat
catcgaaaagattaaagagaagcttccaggttatcacgccaagacagaggaagagaagaaagaaa
aagagtctgcttaagcaaaatgatgaaacgatgaaataatgatattgggagtgggacatttgttg
tgtttttgtgatcattatctttctctttttcttttaagttgttcttgtggctttcatttgatc
ctgtggtttgtattttcattttatctttttatatatataaatggtttgcataaaaaaaaaaaa
aaaa

Fig. 15

SEQ ID NO:148:
Arabidopsis thaliana (thale cress) dehydrin COR47 (GenBank ACCESSION NM_101894):

ggcgccatacgcgggggtctcaaacatcgatactcatcatctcacacacacctcttcaaaaccaa
tcttttttagcaacttcaaagttctttaaactttctgtttatcaaaccgtttcagtccattcaga
ttataactatggcggaagagaacaagaacaacgttcccgagcacgagacccccaaggttgcaaca
acagaagagccatcaaccactactactacaccagaggttacggatcgtgggatgttcgatttctt
gagcaagaagaaagaggaagtgaaacctcaagagactacgacgctcgagtctgagttcgaccata
aggctcagatctcagaaccggcgttagctgcggagcacgaggaagtgaaggagaacaagattact
ctcctcgaggagcttcaggagaagaccgaggaagatgaggagaacaagcctagtgtcatcgaaaa
gcttcaccgatccaacagctcttcttcctcttcaagcgatgaagaaggtgaggaaaagaaaaaga
agaagaccgttgaaggagaagaagagaagaaaggggcaatggataagatcaaagagaagcttcca
ggccaccacgacaaggaaacagaggatcatgacgtaccagtggtcagcaccatccaggtaccagt
atcggagagtgtggtggagcatcacgaaccgagggcgaagaaagaaaggagtaatggataaga
tcaaggagaagcttccaggccgcaacgacaaggagacagaggattcacctgtcccaaccagcacg
ccactggttgtaactgagcacccggtgggacactcgacggagcaaccggcggagaagaagggaat
catcgaaaagattaaagagaagcttccaggttatcacgccaagacagaggaagagaagaaagaaa
aagagtctgcttaagcaaaatgatgaaacgatgaaataatgatattgggagtgggacatttgttg
tgttttgtgatcattatctttctcttttttcttttaagttgttcttgtggctttcatttgatc
ctgtggtttgtattttcattttatctttttatatatataaatggtttgcataaaaaaaaaaa
aaaa SEQ ID NO:149:
Arabidopsis thaliana (thale cress) COR47 (GenBank ACCESSION X59814):

aaaaccatcttaaagcaactacacaagtcttgaaattttctcatattttctatttactatataaa
cttttaatcaaatcaagattaactatggctgaggagtacaagaacaacgttcccgagcacgagac
accaacggtcgcaacagaggaatcaccagcgacgacaacagaggttacggatcgtggattgtttg
atttcttggggaagaaggaagaggaagtgaaacctcaagagacaacgacgctcgagtctgagttc
gatcataaggctcagatctctgaaccggagttagctgcggagcacgaggaagtgaaggagaacaa
gattactctgctagaggagcttcaagaaagaccgaggaagatgaggagaacaagcctagtgtca
tcgaaaagcttcaccgatccaacagctcttcttcctcttcgagcgatgaagaaggtgaggaaaag
aaggagaagaagaagaagatcgttgaaggagaggaagataagaaaggactagtggagaagatcaa
ggagaagctcccaggacaccacgacaagacagcagaggatgatgtaccagtttccactaccatcc
cggtaccagtgtcggagagtgtggtggagcatgaccatcccgaggaagagaagaaaggattagtt
gagaagatcaaggagaagcttcctggtcaccacgacgagaaagcagaggattcaccagctgtcac
gtccacgccgttggttgtaacggagcatccggtggagcctacgacggagcttccagtggaacatc
cggaggagaagaaggggattttggaaaagatcaaagagaagcttccaggttatcatgccaagacc
actgaagaggaagtgaagaaagaaaaagagtctgatgattaagcaaaatggttaaagaatgaata
atgatgtgggagtgggacattcgctgtgttttgtgatcattatctttctcttttaagttgttatt
gtggctttcgttgattgcatttgatccctttattttgtaatttcattctatcttttatataaagtt
tgcatatggtttatacttaaaaaaaaaaaaaaa

Fig.16

SEQ ID NO:150:
CBF probe (D1):
ttaggcagagtcggcgaagtcccttcaagaatcgcccgcggcgagggcgagcatggcgg
ccctcttgtgctcgcgcggcgatctcggcagtgtcgaaggtgccgacccacagcctgct
cccgcgcctccctgggacgcgcgcctcgcatacccacctcccggcattgcccctacgac
gcacaccgcgatacaccgggtgccgcgtctcccggaacttggttcgccccgcc

US 7,317,098 B2

RYEGRASS CBF3 GENE: IDENTIFICATION AND ISOLATION

FIELD OF THE INVENTION

The present invention relates to genes, proteins and methods comprising or utilizing C-repeat binding factors (CBF), specifically CBF3 in the ryegrass family. In a preferred embodiment, the present invention relates to using ryegrass CBF3 for altering cold tolerance and growth in plants, specifically in warm season grasses, turfgrasses, fodder plants and microorganisms.

BACKGROUND

Warm season grasses provide lush green carpets and ornamental borders for a wide range of commercial purposes such as lawns, parks, golf courses, ground covers, and sports fields. These grasses thrive well in warm weather climates and during the warm season of cold weather climes. However, during periods of cold, even of short duration, grasses such as bahiagrass, Bermudagrass, centipedegrass, St. Augustine grass, and zoysiagrass turn brown and often die. Further, under dry winter conditions, these grasses not only turn brownish, their growth is stunted and they tend to go to seed thus destroying their green carpet or ornamental effect. Natural grasses that remain green during cold weather for the most part do not provide the richness and visual beauty of warm season grasses.

Where warm season grasses are planted for warm weather use, attempts are made to hide the withering and browning effects of cold weather. These include overseeding warm grasses with cold season and transitional grasses such as Kentucky bluegrass, tall fescue, and perennial ryegrass to provide a green cover during the cold season. However, if the temperature goes too low, the desired warm season grass requires replanting in the spring. In some cases a green appearance is maintained during the cold season by using green paint to color brown grass or by spreading green pellets to maintain a green color on the ground. In addition to being high maintenance and costly, these solutions do not provide a suitable alternative for the lushness of a warm season grass turf.

Other solutions are to search for natural mutations of the desired grass known as "sports" or to conduct crossbreeding programs and screen for the desired traits including enhanced cold tolerance. However, few varieties of warm season grass produce low temperature tolerant sports, nor is crossbreeding very successful based upon the few commercially available crossbred grasses. The few known crossbreeds that tolerate cold are limited in variety; difficult to propagate over large areas, variable in temperature tolerance and typically must be sown from sod plugs, as other forms of propagation are not commercially available. Further, these grasses have variable abilities to withstand cold weather and are only available in a few out of thousands of varieties of natural grasses.

Therefore, it would be of considerable advantage to engineer warm season turfgrass and ornamental grasses for enhancement of cold tolerance. Further, it would be of considerable advantage to transform turfgrass, fodder plants (or non-plant) species to withstand colder temperatures in their native and adopted climates especially with abrupt changes in local climates.

SUMMARY OF THE INVENTION

The present invention relates to genes, proteins and methods comprising C-repeat binding factors (CBF), specifically CBF3 in the ryegrass family. In a preferred embodiment, the present invention relates to using ryegrass CBF3 for altering cold tolerance and growth in plants, specifically in warm season grasses, turfgrasses, fodder plants and microorganisms.

The present invention is not limited to any particular plant gene sequence encoding a protein comprising a C-repeat binding factor (CBF) having effects on environmental tolerance. In some embodiments, the invention provides a nucleic acid comprising a sequence selected from the group consisting of SEQ ID NO:01 and sequences at least 89% identical to SEQ ID NO:01, wherein said sequence encodes a protein that binds to a C-repeat/dehydration-responsive element. In other embodiments, the present invention provides nucleotide sequences at least 89%, 90%, 95%, 98%, 99% (or more) identical to any of SEQ ID NO:01.

In some embodiments, the invention provides an isolated nucleic acid molecule comprising a polynucleotide encoding a polypeptide at least 63% identical to SEQ ID NO:02, wherein the polypeptide binds to a C-repeat/dehydration-responsive element. In other embodiments, the present invention provides an isolated nucleic acid molecule comprising a polynucleotide encoding a polypeptide at least 63%, 65%, 70%, 75%, 80%, 85%, 90%, 95%, 98%, 99% (or more) identical to any of SEQ ID NO:02, wherein the polypeptide binds to a C-repeat/dehydration-responsive element. In other embodiments, said isolated nucleic acid molecule comprising a polynucleotide encoding a polypeptide further comprises an AP2 binding domain having at least 80% sequence identity to SEQ ID NO: 03. In other embodiments, said nucleic acid molecule comprising a polynucleotide encoding a polypeptide further comprises an AP2 binding domain having at least 80%, 85%, 90%, 95%, 98%, 99% (or more) identical to any of SEQ ID NO:03. Accordingly in other embodiments, said nucleic acid molecule comprising a polynucleotide encoding a polypeptide further comprises an AP2 binding domain having at least 80%, 85%, 90%, 95%, 98%, 99% (or more) identical to any of comparison windows of SEQ ID NOS: 03, and 06-48.

In some embodiments, the invention provides an isolated polypeptide having SEQ ID NO:02 and variants that are at least 63% identical thereto and encode a polypeptide that binds to a C-repeat/dehydration-responsive element. In other embodiments, the present invention provides an isolated polypeptide at least 63%, 65%, 70%, 75%, 80%, 85%, 90%, 95%, 98%, 99% (or more) identical to any of SEQ ID NO:02, wherein the polypeptide binds to a C-repeat/dehydration-responsive element. In other embodiments, said isolated polypeptide further comprises an AP2 binding domain having at least an 80% sequence identity to SEQ ID NO:03. In other embodiments, said isolated polypeptide further comprises an AP2 binding domain having at least 80%, 85%, 90%, 95%, 98%, 99% (or more) identical to any of SEQ ID NO:03.

In some embodiments, the invention provides a vector construct comprising a nucleic acid at least 89% identical to SEQ ID NO:01, wherein said sequence encodes a protein that binds to a C-repeat/dehydration-responsive element. In other embodiments, the present invention provides a vector construct comprising a nucleic acid at least 89%, 90%, 95%, 98%, 99% (or more) identical to any of SEQ ID NO:01, wherein said nucleic acid encodes a protein that binds to a C-repeat/dehydration-responsive element. In other embodiments said vector construct comprising a nucleic acid at least 89% identical to SEQ ID NO:01, wherein said sequence encodes a protein that binds to a C-repeat/dehydration-responsive element, is operably linked to an exogenous promoter. The present invention is not limited to any particular type of promoter. Indeed, the use of a variety of promoters is contemplated. In some embodiments, the promoter is a eukaryotic promoter. In further embodiments, the eukaryotic promoter is active in a plant. The present invention is not limited to any particular type of vector construct. Indeed, the use of a variety of vector constructs is contemplated. In some embodiments, the vector is a eukaryotic vector. In other embodiments, said eukaryotic vector is a plant vector. In other embodiments, said vector plant vector comprises a T-DNA vector. In other embodiments, said vector is a prokaryotic vector.

In some embodiments, the invention provides an expression vector comprising a nucleic acid molecule comprising a polynucleotide encoding a polypeptide at least 63% identical to SEQ ID NO:02, wherein the polypeptide binds to a C-repeat/dehydration-responsive element. In other embodiments, the present invention provides an expression vector comprising a nucleic acid molecule encoding a polypeptide at least 63%, 65%, 70%, 75%, 80%, 85%, 90%, 95%, 98%, 99% (or more) identical to any of SEQ ID NO:02. In other embodiments, the polypeptide further comprises an AP2 binding domain having at least an 80% sequence identity to SEQ ID NO:03, operably linked to an exogenous promoter. In other embodiments, the polypeptide further comprises an AP2 binding domain having at least 80%, 85%, 90%, 95%, 98%, 99% (or more) identical to any of SEQ ID NO:03. The present invention is not limited to any particular type of promoter. Indeed, the use of a variety of promoters is contemplated. In other embodiments, the nucleic acid molecule is operably linked to an exogenous promoter. In some embodiments, the promoter is a eukaryotic promoter. In further embodiments, the eukaryotic promoter is active in a plant. The present invention is not limited to any particular type of expression vector. In other embodiments, said vector is a eukaryotic vector. In further embodiments, said eukaryotic vector is a plant vector. In yet further embodiments the plant vector comprises a T-DNA vector. In some embodiments, the expression vector is a prokaryotic vector.

In some embodiments, the invention provides a transgenic plant comprising an exogenous nucleic acid molecule encoding a polypeptide at least 63% identical to SEQ ID NO:02, wherein the polypeptide binds to a C-repeat/dehydration-responsive element. In other embodiments, the transgenic plant comprises an exogenous nucleic acid molecule encoding a polypeptide at least 63%, 65%, 70%, 75%, 80%, 85%, 90%, 95%, 98%, 99% (or more) identical to any of SEQ ID NO:02, wherein the polypeptide binds to a C-repeat/dehydration-responsive element. In other embodiments, the polypeptide further comprises an AP2 binding domain having at least an 80% sequence identity to SEQ ID NO:03, operably linked to a heterologous promoter. In other embodiments, the polypeptide further comprises an AP2 binding domain having at least 80%, 85%, 90%, 95%, 98%, 99% (or more) identical to any of SEQ ID NO:03. The present invention is not limited to any particular type of heterologous promoter. Indeed a variety of heterologous promote are contemplated. In some embodiments, said exogenous nucleic acid molecule is operably linked to a eukaryotic promoter. In other embodiments, said eukaryotic promoter is active in a plant. The present invention is not limited to any particular type of plant. Indeed a variety of plants are contemplated. In some embodiments, said plant is chosen from one or more members of a grass family, a sedge family and a rush family. In some embodiments, said plant comprises one or more of annual and perennial plants. In some embodiments, the plant is a warm season plant. In one embodiment, said warm season plant is a turfgrass. In other embodiments, said turfgrass is one or more of bahiagrass, Bermudagrass, centipedegrass, St. Augustine grass, zoysiagrass, carpetgrass, centipedegrass, buffalograss, hurricanegrass, seashore paspalum and the like. The turfgrass of the present invention is not limited to wild-type turfgrass. Indeed a variety of turfgrasses are contemplated. In some embodiments, said turfgrass is one or more of a wild-type turfgrass. In some embodiments, said turfgrass is one or more of a sport, selectively bred, and cultivator. In some embodiments, said turfgrass is one or more of a cloned plant, transgenic plant, and the like. The present invention is not limited to any particular type of ornamental grass and ornamental sedge. Indeed a variety of ornamental grasses and ornamental sedges are contemplated. In one embodiment, said ornamental grass is an Indian grass. In one embodiment, said ornamental sedge is one or more of Cyperaceae; for example *Carex* spp., *Scirpus* spp., *Cyperus* spp., and the like. The present invention is not limited to any particular type of rush. In one embodiment, said rush is one or more of Juncaceae; for example *Juncus* spp., *Luzula* spp., *Eleocharis* spp., *Equisetum* spp., *Hierochloe* spp., *Hystrix* spp., and the like. In some embodiments, the plant is a cold season plant. The present invention is not limited to any particular cold season plant. In one embodiment, said cold season plant is a turfgrass. In some embodiments, said turfgrass is one or more of bluegrass (e.g. Kentucky bluegrass), tall fescue, Italian ryegrass and perennial ryegrass and the like. In other embodiments, said transgenic plant is a fodder plant. In some embodiments, said fodder plant is one or more of fescues, Sudan grass, clover, alfalfa, legumes, forage grasses, bentgrass, redtop, fiorin grass (e.g. *Agrostis* spp.); bluegrass (e.g. *Poa* spp.); Columbus grass (*Sorghum almum*); fescue (e.g. *Festuca* spp.); Napier, elephant grass (*Pennisetum purpureum*); orchard grass (*Dactylis glomerata*); Rhodes grass (*Chloris gayana*); Sudan grass (*Sorghum vulgare* var. *sudanense*); Timothy grass (*Phleum pratense*), and the like. In some embodiment a legume is one or more of birdsfoot trefoil (*Lotus corniculatus*); lespedeza (*Lespedeza* spp.); kudzu (*Pueraria lobata*); sesbania (*Sesbania* spp.); sainfoin, esparcette (*Onobrychis sativa*); sulla (*Hedysarum coronarium*), and the like.

In some embodiments, the invention provides a transgenic plant comprising an exogenous nucleic acid encoding a polypeptide at least 35% identical to SEQ ID NO:02, wherein the polypeptide binds to a C-repeat/dehydration-responsive element and wherein said plant is chosen from one or more members of a grass family, a sedge family and a rush family. In other embodiments, the transgenic plant comprises an exogenous nucleic acid molecule encoding a polypeptide at least 35%, 40%, 45%, 50%, 55%, 60%, 65%, 70%, 75%, 80%, 85%, 90%, 95%, 98%, 99% (or more) identical to any of SEQ ID NO:02, wherein the polypeptide binds to a C-repeat/dehydration-responsive element. The present invention is not limited to any particular type of plant. Indeed a variety of plants are contemplated. In some embodiments, said plant is chosen from one or more members of a grass family, a sedge family and a rush family. In some embodiments, said plant comprises one or more of annual and perennial plants. In some embodiments, the plant is a warm season plant. In one embodiment, said warm season plant is a turfgrass plant. The present invention is not limited to any particular type of turfgrass. Indeed, a variety of turfgrass are contemplated. In other embodiments, said turfgrass is one or more of bahiagrass, Bermudagrass, centipedegrass, St. Augustine grass, Zoysiagrass, carpetgrass, centipedegrass, buffalograss, hurricanegrass, seashore paspalum and the like.

In some embodiments, said turfgrass is one or more of a wild-type turfgrass. In some embodiments, said turfgrass is one or more of a sport, selectively bred, and cultivator turfgrass. In some embodiments, said turfgrass is one or more of a cloned plant, transgenic plant, and the like. The present invention is not limited to any particular type of grass, sedge and rush. Indeed a variety of ornamental grass, ornamental sedge and ornamental rush are contemplated. In one embodiment, said ornamental grass is an Indian grass. In one embodiment, said ornamental sedge is one or more of Cyperaceae; for example *Carex* spp., *Scirpus* spp., *Cyperus* spp., and the like. The present invention is not limited to any particular type of rush. In one embodiment, said rush is one or more of Juncaceae; for example *Juncuss* spp., *Luzula* spp., *Eleocharis* spp., *Equisetum* spp., *Hierochloe* spp., *Hystrix* spp., and the like. The present invention is not limited to any particular type vegetative propagation. Indeed a variety of ways to provide vegetative propagation are contemplated. In other embodiments, said plant comprises one or more parts for vegetative propagation. In other embodiments, said parts for vegetative propagation comprises one or more sprigs, plugs, stolons, rhizomes, callus, meristem and sod. In other embodiments, said transgenic plant is a seed. In other embodiments, said transgenic plant is a tiller. In other embodiments said transgenic plant comprises a cold season plant. The present invention is not limited to any particular cold season plant. In one embodiment, said cold season plant is a turfgrass. In some embodiments, said turfgrass is one or more of bluegrass (e.g. Kentucky bluegrass), tall fescue, Italian ryegrass and perennial ryegrass and the like. In other embodiments, said transgenic plant is a fodder plant. In some embodiments, said fodder plant is one or more of fescues, Sudan grass, clover, alfalfa, legumes, forage grasses, bentgrass, redtop, fiorin grass (e.g. *Agrostis* spp.); bluegrass (e.g *Poa* spp.); Columbus grass (*Sorghum almum*); fescue (e.g. *Festuca* spp.); Napier, elephant grass (*Pennisetum purpureum*); orchard grass (*Dactylis glomerata*); Rhodes grass (*Chloris gayana*); Sudan grass (*Sorghum vulgare* var. *sudanense*); Timothy grass (e.g. *Phleum pratense*), and the like. In some embodiment a legume is one or more of birdsfoot trefoil (e.g. *Lotus corniculatus*); lespedeza (e.g. *Lespedeza* spp.); kudzu (e.g. *Pueraria lobata*); sesbania (e.g. *Sesbania* spp.); sainfoin, esparcette (e.g. *Onobrychis sativa*); sulla (e.g. *Hedysarum coronarium*), and the like.

In some embodiments, the invention provides an expression vector, comprising a first nucleic acid sequence encoding a nucleic acid product that interferes with the expression of a second nucleic acid sequence encoding a polypeptide at least 63% identical to SEQ ID NO:02. In other embodiments, the second nucleic acid sequence encoding a polypeptide at least 63%, 65%, 70%, 75%, 80%, 85%, 90%, 95%, 98%, 99% (or more) identical to any of SEQ ID NO:02, wherein the polypeptide binds to a C-repeat/dehydration-responsive element. The present invention is not limited to any particular nucleic acid product that interferes with the expression of a second nucleic acid sequence. Indeed a variety of types of nucleic acids are contemplated. In other embodiments, said nucleic acid product that interferes is an antisense sequence. In other embodiments, said nucleic acid product that interferes is a dsRNA that mediates RNA interference. In other embodiments, said nucleic acid product that interferes is a siRNA sequence. In other embodiments, said nucleic acid product that interferes is hpRNA sequence. The present invention is not limited to any particular cold season plant. In one embodiment, said cold season plant is a turfgrass. In some embodiments, said turfgrass is one or more of bluegrass (e.g. Kentucky bluegrass), tall fescue, Italian ryegrass and perennial ryegrass and the like. In other embodiments, said transgenic plant is a fodder plant. In some embodiments, said fodder plant is one or more of fescues, Sudan grass, clover, alfalfa, legumes, forage grasses, bentgrass, redtop, fiorin grass (e.g. *Agrostis* spp.); bluegrass (*Poa* spp.); Columbus grass (*Sorghum almum*); fescue (e.g. *Festuca* spp.); Napier, elephant grass (*Pennisetum purpureum*); orchard grass (*Dactylis glomerata*); Rhodes grass (*Chloris gayana*); Sudan grass (*Sorghum vulgare* var. *sudanense*); Timothy grass (*Phleum pratense*), and the like. In some embodiment a legume is one or more of birdsfoot trefoil (*Lotus corniculatus*); lespedeza (e.g. *Lespedeza* spp.); kudzu (*Pueraria lobata*); sesbania (e.g. *Sesbania* spp.); sainfoin, esparcette (*Onobrychis sativa*); sulla (*Hedysarum coronarium*), and the like.

In some embodiments, the invention provides a method for altering the phenotype of a plant, comprising: providing; i) an expression vector comprising a nucleic acid sequence encoding a polypeptide at least 63% identical to SEQ ID NO: 02, wherein the polypeptide binds to a C-repeat/dehydration-responsive element and plant tissue; and ii) plant tissue, and; transfecting the plant tissue with the vector under conditions that alter the phenotype of a plant. In other embodiments, said plant tissue comprises one or more of calli and primordial meristem. In other embodiments, the nucleic acid encoding a polypeptide at least 63%, 65%, 70%, 75%, 80%, 85%, 90%, 95%, 98%, 99% (or more) identical to any of SEQ ID NO:02, wherein the polypeptide binds to a C-repeat/dehydration-responsive element.

In some embodiments, the invention provides a method for altering environmental tolerance, comprising: a) providing a vector construct comprising a nucleic acid encoding a polypeptide at least 63% identical to SEQ ID NO: 02, wherein the polypeptide binds to a C-repeat/dehydration-responsive element; and b) producing a plant comprising the vector, wherein the plant exhibits altered environmental tolerance. In other embodiments, the nucleic acid encoding a polypeptide at least 63%, 65%, 70%, 75%, 80%, 85%, 90%, 95%, 98%, 99% (or more) identical to any of SEQ ID NO:02, wherein the polypeptide binds to a C-repeat/dehydration-responsive element. In other embodiments, the nucleic acid encoding a polypeptide further comprises a polypeptide at least 80%, 85%, 90%, 95%, 98% (or more) identical to any of SEQ ID NO:03. It is not meant to limit the type of environmental tolerance. Indeed a variety of types of environmental tolerances are contemplated. In other embodiments, said environmental tolerance is low temperature tolerance. In other embodiments, said environmental tolerance is drought.

In some embodiments, the invention provides a method for altering plant growth, comprising: a) providing; i) an expression vector comprising a nucleic acid encoding a polypeptide at least 63% identical to SEQ ID NO:02, wherein the polypeptide binds to a C-repeat/dehydration-responsive element; and ii) plant tissue; and iii) introducing the vector into the plant tissue under conditions such that the polypeptide encoded by the nucleic acid sequence is expressed so that the plant tissue exhibits altered plant growth. In other embodiments, the nucleic acid encoding a polypeptide at least 63%, 65%, 70%, 75%, 80%, 85%, 90%, 95%, 98%, 99% (or more) identical to any of SEQ ID NO:02, wherein the polypeptide binds to a C-repeat/dehydration-responsive element. It is not meant to limit the type of altered plant growth. Indeed a variety of altered growth is contemplated. In some embodiments, altered plant growth is plant height. In some embodiments, altered plant growth is a delay in flowering. In some embodiments, plant growth is altered seed production.

In some embodiments, the invention provides a method for altering phenotype, comprising: providing a transgenic host cell comprising a heterologous nucleic acid sequence, wherein the heterologous nucleic acid sequence encodes a polypeptide at least 63% identical to SEQ ID NO: 02, wherein the polypeptide binds to a C-repeat/dehydration-responsive element under conditions sufficient for expression of the encoded protein; and b) culturing the transgenic host cell under conditions such that an altered phenotype is produced. In other embodiments, the nucleic acid encoding a polypeptide at least 63%, 65%, 70%, 75%, 80%, 85%, 90%, 95%, 98%, 99% (or more) identical to any of SEQ ID NO:02, wherein the polypeptide binds to a C-repeat/dehydration-responsive element. In other embodiments, the present invention provides a nucleic acid sequence encoding a polypeptide comprising a conserved AP binding domain at least 80%, 85%, 90%, 95%, 98% (or more) identical to any of SEQ ID NO:03.

In one embodiment, the present invention provides a transgenic plant comprising a nucleic acid sequence encoding a polypeptide at least 35% identical to SEQ ID NO:02, wherein the nucleic acid sequence is heterologous to the plant. Accordingly in other embodiments, the polypeptide is at least 35%, 40%, 60%, 70%, 80%, 90%, 95% (or more) identical to any of SEQ ID NOS: 02, 70-108.

The present invention is not limited to any particular transgenic plant. In some embodiments, transgenic plants are turfgrass plants. Indeed, a variety of transgenic plants are contemplated, including, but not limited to one or more of the following: Bermudagrass, buffalograss, centipedegrass, St. Augustine grass, zoysiagrass, bahiagrass, carpetgrass, Zoysiagrass spp., manilagrass, Japanese lawngrass, Mascarene grass, Indiangrass, big and little blue stemgrass, eastern gamagrass, switchgrass and the like.

In some embodiments, the present invention provides methods for altering the phenotype of a plant, comprising: a) providing; i) an expression vector as described in detail above, and ii) plant tissue; and b) transfecting the plant tissue with the vector under conditions that alter the phenotype of a plant. It is not meant to limit the type of phenotype. Indeed a variety of phenotypes are contemplated. In some embodiments, the plant phenotype is height. In some embodiments, the plant phenotype is width. In some embodiments, the plant phenotype is flowering. In some embodiments, the plant phenotype is seeding. In some embodiments, the plant phenotype is cold tolerance. In some embodiments, the plant phenotype is cold tolerance.

In one embodiment, the invention provides a method for altering environmental tolerance in a plant, comprising: a) providing a vector construct comprising a nucleic acid encoding a polypeptide at least 95% identical to SEQ ID NO: 02, 70-108, wherein the polypeptide binds to a C-repeat/dehydration-responsive element; and b) producing a plant, wherein said plant is a turfgrass plant, comprising the vector, wherein the plant exhibits altered environmental tolerance. Accordingly in other embodiments, the polypeptide is at least 95%, 96%, 97%, 98%, 99%, (or more) identical to any of 02, 70-108, wherein the polypeptide binds to a C-repeat/dehydration-responsive element.

DESCRIPTION OF THE FIGURES

FIG. 5. shows exemplary embodiments in which a Southern analysis reveals polymorphism in a ryegrass cbƒ3 gene between cold tolerant and non-tolerant plant materials.

FIG. 8. SEQ ID NO: 01: shows a full-length cDNA nucleotide sequence for cbƒ3. SEQ ID NO:02: shows an amino acid sequence for CBF3. SEQ ID NO:03: shows an amino acid sequence for an AP binding region of CBF3. SEQ ID NO:04: shows CBF motif bracket sequences for a putative AP DNA-binding domain comprising bracket sequences PKK or PPK or PAK or PK with RPAGRXK-FXETRHP (SEQ ID NO:151) or (SEQ ID NO:199), and DSAWR (SEQ ID NO:152) SEQ ID NO:05: shows *Lolium perenne* (perennial ryegrass) bracket sequences for CBF3 AP DNA-binding domain, comprising bracket amino acids PWXKRPAGRTKFRHP (SEQ ID NO:153) and DSAEL (SEQ ID NO:154), and putative AP DNA-binding domain. WTKRPAGRTKFRETRHPVYRGVRRRG-NAGRWVCEVRVPGRRGSRLWVGTFDTAEIAA RAH-DAAMLALAAGDSCLNFADSAEL (SEQ ID NO:155) and PWTKRPAGRTKFRETRHPVYRGVRRRG-NAGRWVCEVRVPGRRGSRLWVGTFDTAEIA ARAH-DAAMLALAAGDSCLNFADSAEL (SEQ ID NO:156) show *Lolium perenne* (perennial ryegrass) bracket sequences for CBF3 AP DNA-binding domain, comprising bracket amino acids WTK and/or PWXK (SEQ ID NOS: 157), and DSAEL (SEQ ID NO:154), and putative AP DNA-binding domain PAGRTKFRETRHPVYRGVRRRG-NAGRWVCEVRVPGRRGSRLWVGTFDTAEIAARAHD AAMLALAAGDSCLNFA (SEQ ID NO:158), respectively. SEQ ID NOS:159-162 show related CSF motif bracket sequences comprising WTKRPAGRTKFRETRHP (SEQ ID NO:163) and/or WTKXXXXXTXXR (SEQ ID NO:164) and/or PWTXRPAGRTKFRETRHP (SEQ ID NO:165) and/or PWTXXXXXXTXXR (SEQ ID NO:166), DSAEL (SEQ ID NO:154) and/or AP DNA-binding donmain.

FIG. 9. (SEQ ID NOS:2, 196, 197, 89, 78, and 198) shows an exemplary embodiment that demonstrates sequence alignments comparing ryegrass cbƒ3 with cbƒ genes from other plants.

FIG. 10. SEQ ID NOS:06-48 shows embodiments that demonstrate variant sequences of ryegrass cbf3 comprising AP2 binding domain variants.

FIG. 11. SEQ ID NOS:49-63 shows exemplary embodiments that demonstrate PCR primers for obtaining ryegrass cbf segments, RACE, and amplification of cbf gene. SEQ ID NOS:64 and 170 show PCR primer sequences used for obtaining a full-length sequence of ryegrass cbf3. SEQ ID NOS:65-69 shows embodiments that demonstrate DNA binding element motifs.

FIG. 12. shows percent identities of ryegrass CBF3 (LpCBF3) compared to other plant CBF proteins.

FIG. 13. shows amino acid sequences for plant CBF related genes SEQ ID NOS: 70-108.

FIG. 14. shows nucleic acid sequences for plant cbf related genes SEQ ID NO:109-141.

FIG. 15. SEQ ID NO:142 shows an amino acid sequence for *Triticum aestivum* (bread wheat) COR39 (homologous to *Arabidopsis thaliana* COR47). SEQ ID NO:143 shows an amino acid sequence for *Capsella bursa-pastoris* (shepherd's purse) dehydrin cor29 (new COR47). SEQ ID NO:144 and 145 shows amino acid sequences for *Arabidopsis thaliana* (thale cress) COR47. SEQ ID NO:146 shows a nucleic acid sequence for *Triticum aestivum* (bread wheat) COR39, a CBF downstream gene (FIG. 4*b*) (homologous to *Arabidopsis thaliana* COR47). SEQ ID NO:147 shows a nucleic acid sequence for *Capsella bursa-pastoris* (shepherd's purse) dehydrin cor29 (new COR47). SEQ ID NO:148 and 149 shows nucleic acid sequences for *Arabidopsis thaliana* (thale cress) COR47 (COR39 homologous gene).

FIG. 16. SEQ ID NO:150 shows a nucleic acid sequence for a ryegrass cbf Northern probe (D1 fragment).

DEFINITIONS

Figure 1:
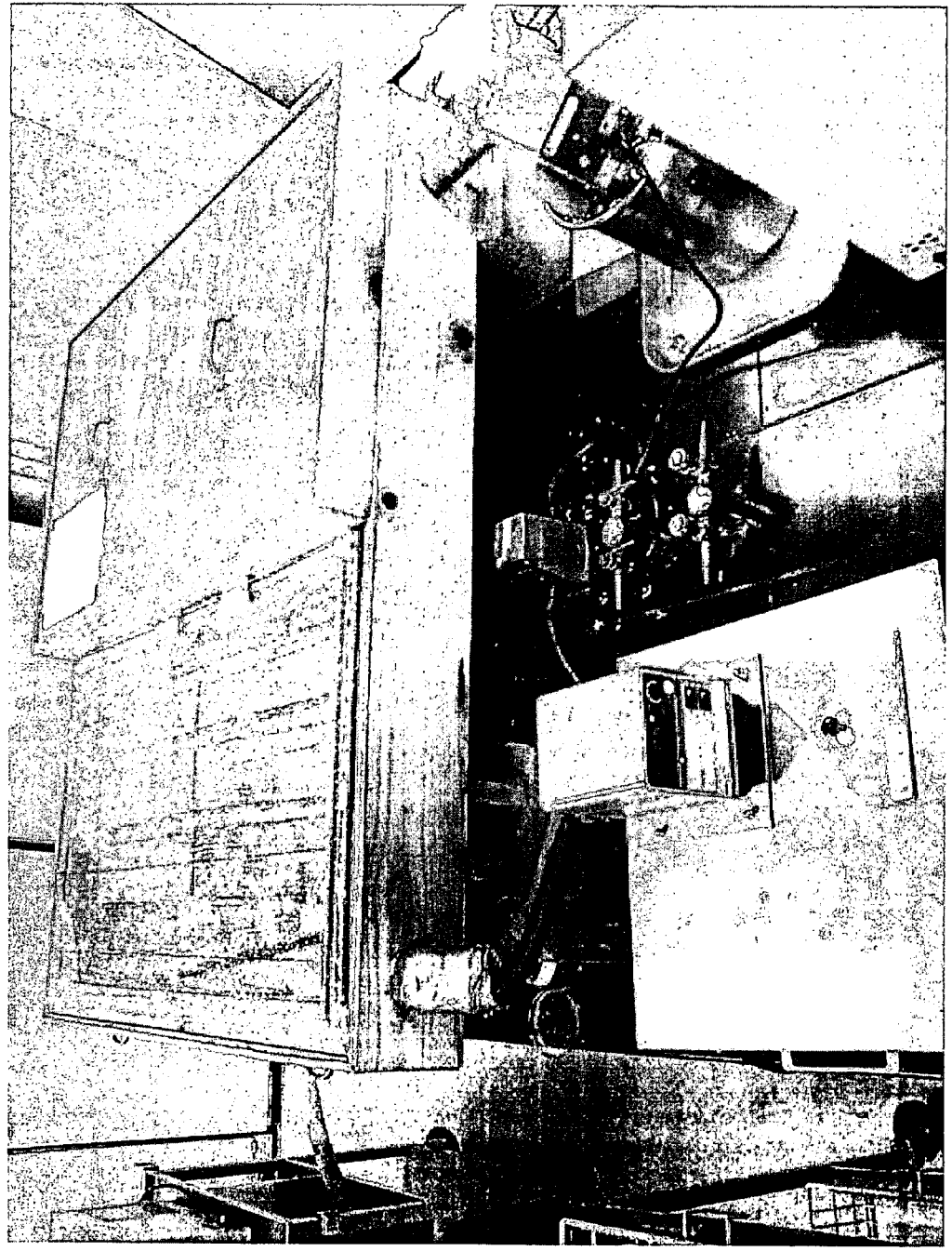
FIG. 1. shows embodiments for a screen of over 300 PI accessions of perennial ryegrass (*Lolium perenne*) for seed germination in a cold environment using thermogradient plate.

To facilitate an understanding of the present invention, a number of terms and phrases as used herein are defined below:

The use of the article "a" or "an" is intended to include one or more.

As used herein, when one molecule has two or more names they will be named with a forward slash between the names (e.g. CBF/DREB).

As used herein, terms defined in the singular are intended to include those terms defined in the plural and vice versa.

For the purposes of the present invention, family assignment is based upon a combination of sequence identity, phylogeny and gene organization (as described herein).

The term "CBF" refers to a member of the "Core Binding Factor β family."

The terms "cis-acting cold-regulatory C-repeat binding factors," "C-repeat binding factor," "CBF," "CBF transcription factor," refer to proteins that can function as transcription factors (Stockinger et al. Proc. Natl. Acad. Sci. 94:1035-1040 (1997)) comprising an AP2/EREBP domain motif and further comprising a C-repeat binding element.

The terms "cis-acting cold-regulatory C-repeat binding factors," "C-repeat binding factor," "CBF," "CBF transcription factor," are used interchangeably with the terms "dehydration-responsive element binding protein," "DREB," "dehydration-responsive element binding proteins," and further are interchangeable with terms "cis-acting cold-regulatory C-repeat binding factor/dehydration-responsive element binding protein," "CRT/DRE binding protein," and "CRT/DREB protein."

The term "C-repeat binding element" refers to an area of a CBF protein that binds to a "C-repeat" and "CRT" DNA motif found in the promoter region of genes comprising 5'-TGGCCGAC -3' (SEQ ID NO:65) (e.g. cold-inducible cor15a (Baker et al., Plant Mol Biol March;24(5):701-13 (1994)).

The terms "dehydration-responsive element" and "DRE" refer to a 9-bp conserved sequence comprising 5'-TACCGA-CAT-3' (SEQ ID NO:66) for the regulation of dehydration responsive gene expression (e.g. also functions as a cis-acting element involved in the induction of genes such as rd29A expression by low-temperature stress).

The term "DRE-related motifs" refers to sequences similar to 5'-TACCGACAT-3' (SEQ ID NO:66) found in the promoter regions of cold- and drought-inducible genes such as kin1, cor6.6, and rd17 (Wang et al., Eur J Pharmacol October 6;293(3):191-205 (1995); Iwasaki et al., Plant Physiol. 115:1287-1289 (1997)) (e.g. C repeat comprising 5'-TGGCCGAC-3' (SEQ ID NO:65)).

The terms "C-repeat/dehydration-responsive element," "CRT/DRE," refer to a DNA regulatory element in the promoter region of stress-inducible genes comprising a core motif "5'-CCGAC-3'" (SEQ ID NO:67) whose binding state controls the expression of stress-inducible proteins in plants (e.g. *Arabidopsis thaliana*, etc.), microorganisms (e.g. yeasts, etc.).

The terms, "CBF genes," "DREB genes," "CBF/DREB genes," refer to genes that code for proteins that bind to a CRT/DRE DNA regulatory element.

The terms, "CBF," "CBF polypeptide," "CBF-related polypeptide," refer to a protein transcription factor that binds to a promoter comprising a "CRT/DRE element."

As used herein, the terms "CBF," "CBF polypeptide," "CBF-like polypeptide," "CBF-related polypeptide," "DREB," "DREB polypeptide," "DRE-binding polypeptide," "DRE binding polypeptide," "DREB-like polypeptide," are interchangeable.

As used herein, "low-temperature-responsive elements," "LTREs," "RD elements," "responsive-to-desiccation elements" refer to DNA elements in promoter regions of genes that in some cases are interchangeable with CRT DNA elements.

As used herein, "DRE/CRT/LTRE" refers to a 9-bp DNA element, 5'-TACCGACAT-3' (SEQ ID NO:66), in the promoter region of that recognize a "low temperature induced/cold regulated" and "LTI/COR" genes that respond to low temperature, drought and high salinity (e.g. CBF1, CBF2 and CBF3 and CRT binding factor and DREB1B, DREB1C and DREB1A and DRE-binding protein).

The terms "CBF3 gene" or "CBF3" or "cold tolerance gene" refer to a plant gene that can alter environmental tolerance, and alters cold tolerance, allowing adaptation to colder temperatures (e.g., ryegrass SEQ ID NO:01). Alleles are referred to by a number, for example, CBF3, CBF1, CBF2, CBF4, CBF16 and CBF17. The present invention identifies a ryegrass CBF3 polypeptide encoded by a CBF3 gene e.g., ryegrass SEQ ID NO:02.

The terms "inducers of CBF" and ICE" refer to proteins and their genes that function as upstream transcription factor that regulates the transcription of CBF genes in the cold (Zarka et al., Plant Physiol. October;133(2):910-8 (2003) Epub 2003 Sep. 18 and Chinnusamy et al., Genes Dev. 2003 Apr. 15;17(8):1043-54 (2003) Epub 2003 Apr. 02); Gong, et al., Proc Natl Acad Sci USA, 99(17):11507 (2002).

The terms "ICE1" and "inducer of CBF expression 1" refer to proteins and genes constitutively expressed comprising a MYC-like bHLH transcriptional activator that binds specifically to the MYC recognition sequences in the CBF3 promoter. The term "ice1 mutant" is a mutant *Arabidopsis thaliana* ice1 gene whose mutation significantly reduces plant chilling and freezing tolerance and also blocks the expression of CBF3 and decreases the expression of many genes downstream of CBFs. Thus ICE1 is an upstream activator of CBF3. ICE 1 is expressed constitutively and its overexpression in wild-type plants enhances the expression of CBF regulon genes, through CBF expression, in the cold and improves freezing tolerance of the transgenic plants (Chinnusamy et al., Genes Dev. April 15;17(8):1043-1054 (2003) Epub 2003 Apr. 02 and Zarka et al., Plant Physiol. October;133(2):910-918 (2003) Epub 2003 Sep. 18).

The terms "ICEr1" and "ICEr2" refer to regions of an *Arabidopsis* CBF2 promoter referred to as "induction of CBF expression region 1" and "induction of CBF expression region 2, " respectively (Zarka et al., Plant Physiol. October; 133(2):910-918 (2003) Epub 2003 Sep. 18).

The terms "AP2" and "APETALA2" refer to a homeotic gene originally discovered in *Arabidopsis* thaliana, wherein the gene encodes a protein comprising at least two AP2 binding domain motifs and further comprises a putative nuclear localization signal that functions in gene regulation including genes expressed during flower, seed, and ovule development (Okamuro et al., Proc Natl Acad Sci USA June 24;94(13):7076-81 (1977)).

The terms "AP2," "AP2 protein," and "AP2 polypeptide" refer to a specific polypeptide product of the AP2 gene that contains an "AP2 domain binding domain motif" and generally to a protein comprising at least one domain similar to an "AP2 protein DNA binding domain."

The terms "AP2 binding domain," "AP2 binding motif," "AP2 DNA-binding motif," and "APETALA2 binding domain," refer to a region comprising about a 60-70 amino acid motif found within a polypeptide further comprising about an 18-amino acid core region that is predicted to form an amphipathic alpha-helix and bind to an "AP2 protein DNA binding domain."

The terms "AP2 protein DNA binding domain," "AP2 domain," "AP2 like domain," and "APETALA2 domain," refer to a region of DNA that binds to an AP2 binding domain.

The term "AP2 family" refers to a plant-specific family of "transcriptional regulators" and/or "transcription factors" comprising at least two DNA binding domains comprising an "AP2 binding motif."

The term "AP2 gene family" refers to two groups designated as EREBP-like and AP2-like on the basis of whether they possess one or two of the AP2 repeats, respectively (Okamuro et al., Proc Natl Acad Sci USA June 24;94(13): 7076-81 (1997)).

The term "AP2/EREBP family of plant transcription factors" refers to transcription factors found in a range of higher plants comprising a conserved, approximately 60- to 70-amino acid region required for DNA binding, a part of which has been predicted to form an amphipathic alpha-helix (Okamuro et al., Proc Natl Acad Sci USA June 24;94(13):7076-81 (1997)). The AP2/EREBP domain is found in a large number of plant proteins including more than 140 proteins in *Arabidopsis* (Riechmann et al., Plant Physiol October;130(2):639-48 (2000)).

The term "AP2 domain class of transcription factors in *Arabidopsis*" refers to at least 110 members. For example, the ABI4 subgroup contains at least 30 members, of which several members have been shown to be involved in environmental and stress responses (e.g. ABI4, TINY, CBF3/DREB1A, CBF1/DREB1B, CBF2/DREB1C, DREB2A, DREB2B, and the like).

As used herein, "AP2/EREBP family" refers to a group of DNA-binding proteins (Riechmann and Meyerowitz, Biol. Chem. 379:633-646 (1998)), comprising at least one "AP2 DNA-binding motif" herein used interchangeably with an "ethylene response element binding domain motif" and AP2/EREBP domain (Riechmann and Meyerowitz, Biol. Chem. 379:633-646 (1998)).

The terms "ethylene response element binding domain," "EREB domain," "EREBP DNA binding domain," "ethylene response element binding domain motif" refer to a DNA binding domain in proteins originally discovered in tobacco plants that comprise at least one "ethylene response element binding domain" that is similar to an "AP2 protein DNA binding domain" and "AP2 binding motif."

The terms "EREBP/AP2 DNA binding domain" and AP2/EREBP DNA binding domain" refer to DNA binding domains that include at least one of AP2 DNA binding domains and EREBP DNA binding domains.

The terms "ERF," "ethylene response factor," "EREBP," "ethylene response element binding protein," "AP2/EREBP," and "EREBP/AP2" refer to transcription factors that comprise at least one of AP2 DNA binding domains and EREBP DNA binding domains and as used herein are used interchangeably to include AP2 proteins and EREBPs (Weigel, The Plant Cell, April;7(4):388-389 (1995)).

As used herein, "EREBP family" and "ethylene response element binding protein family," refers to a group of DNA-binding proteins (Riechmann and Meyerowitz, Biol. Chem. 379:633-646 (1998)), comprising at least one "AP2 binding domain" herein used interchangeably with an "ethylene response element-binding domain."

The terms, "ethylene responsive element binding proteins," "EREBPs," and "ERE binding proteins" refer to a group of transcription factors comprising proteins that bind to a secondary ethylene response element in the 5' upstream region of ethylene-inducible genes in some plants (e.g. EREBP-1, EREBP-2, EREBP-3 and EREBP-4) and further comprise an "AP2 binding domain motif." The term "secondary ethylene response element" refers to a conserved DNA sequence comprising a GCC box (SEQ ID NO:68).

The terms "GCC box" and "GCC element" refer to an "ethylene-responsive element" and "ERE" comprising an 11-bp sequence 5'-TAAGAGCCGCC-3' (SEQ ID NO:68) found in the promoters of a large number of ethylene responsive genes (Ohme-Takagi and Shinshi, The Plant Cell, Vol. 7, 173-182 (February 1995)).

The terms "AGC box" and "AGCCGCC sequence" refer to a portion of the GCC box comprising 5'-AGCCGCC-3' (SEQ ID NO:69).

The term "RAP" refers to proteins and their "rap" genes that are "related to AP2 proteins" (e.g RAP 2.1, RAP 2.6, etc.).

The terms, "basic leucine zipper" and "bZIP" refer to a group of DNA binding proteins such as soybean SGBF1, and the like.

The terms, "ABA," and "abscisic acid" refer to molecules that induce "ABA-responsive proteins" comprising "abscisic acid responsive elements" and "ABA responsive elements" that refer to DNA regions of in the promoter region that bind to ABA of genes that respond to ABA mediated environmental stress. The ABA-mediated signal pathway leading to expression of low temperature induced genes appears to encompass similar second messengers and signal components as the ABA independent activated these genes such as CBF genes and lead to an increased freezing tolerance.

The term "cold acclimation" refers to an increase in freezing tolerance in response to exposure to low nonfreezing temperatures. The terms "cold tolerance," "freezing tolerance," "cold hardiness," and "response to cold" refer to the ability of a plane to live at or following exposure to a low temperature. The freezing tolerance of a plant can be measured quantitatively as the lethal temperature at which freezing injury occurs (e.g. quantitatively as a LT50, lethal temperature at which all plants die, etc.). As used herein, freezing tolerance of plants is not constitutive but is induced in response to low temperatures (below approximately 10° C.), a phenomenon known as "cold acclimation" (Thomashow, Annu Rev Plant Physiol Plant Mol Biol 50:571-599 (1999)). For example, nonacclimated wheat (*Triticum aestivum* L. cv Norstar) plants are killed at freezing temperatures of about −5° C., but after cold acclimation, can survive temperatures down to about −20° Celsius.

The terms "altered cold tolerance" and "altering cold tolerance" refer to any changes in cold tolerance.

The terms, "DRE," "dehydration responsive element," "CRT," "C-repeat," "CRT/DRE," "C-repeat/dehydration responsive element" and refer to a cis-acting DNA regulatory element that has about a core sequence of "CCGAC" or "G/ACCGAC" herein designated a "C-repeat" and "C-repeat element." A C-repeat element is present in one to multiple copies in the promoters of many cold-regulated plant genes, including the *Arabidopsis* genes COR15a and COR78/RD29A (COR78 and RD29A are alternative designations for the same gene) and the *Brassica napus* (canola) gene BN115.

The terms "cold-regulated" and "COR" refer to genes involved in cold acclimation and cold tolerance (e.g. COR15a, COR6.6, COR78, etc).

The terms "late embryogenesis abundant," "LEA" and "LEA-related" refer to genes related to environmental tolerance expressed during embrogenesis (e.g. COR15a, HVA-1, etc.).

The terms "leaf" and "leaves" refer to a usually flat, green structure of a plant where photosynthesis and transpiration take place and attached to a stem or branch.

The terms "calli" and "callus" refer to a tough, often hairy, swelling at the base or insertion of the lemma.

The term "lemma" refers to the lower of the two bracts enclosing the flower in the spikelet of grasses.

The term "bract" refers to a leaf from the axil of which a flower arises.

The term "axil" refers to the angle between a branch or leaf and the stem from which it grows.

The term "spikelet" refers to one of the small few-flowered bracted spikes that make up the compound inflorescence of grasses further comprising two glumes and one or more florets.

The term "inflorescence" refers to a flowering part of a plant.

The term "glume" refers to the chaffy bract, one of two bracts of the base of the spikelet in grasses.

The term "floret" refers to a small flower comprising one of a cluster of small flowers that form the head of a plant such as clover.

The term "meristem" refers to undifferentiated tissue from which new cells are formed, e.g., the tips of roots or stems; the growing tip.

The term "meristem cloning" refers to artificial propagation of a plant using cells taken from the meristem of a parent plant and yielding genetically identical offspring.

The term "stem" refers to a main ascending axis of a plant.

The terms "stolen" and "runner" refer to an elongated horizontal stem (or shoot) that grows above the soil or just under the soil surface that roots at nodes and can form new plants. The term "stoloniferous" refers to spreading by means of stolons.

The term "rhizome" refers to a specialized slender or swollen stem with branching close to the soil surface that can produce a root, a stem, a leaf and a flower, along its length and at its apex.

The term "sprig" refers to a small part of a plant comprising a short piece of the stolon or rhizome, roots and leaves, but not soil, (e.g. stolon, used for propagations).

The term "tiller" refers to a portion of a plant where a lateral stem (or shoot), usually erect, develops from the central crown, often used for propagation of grass plants. Also refers to the branch or shoot that originates at a basal node.

The term "node" refers to the joint of a stem and the region of attachment of leaves on a stem.

The term "rhizome" refers to an underground stem capable of sending out roots and leafy shoots.

The term "crown" refers to a portion of a plant at the base of the stem where roots arise and the point where stem and root join in a seed plant.

The term "plug" refers to a small piece of sod usually two or more inches wide comprising 2 to 3 inches of soil and grass roots.

The term "sod" refers to a plugs, squares of turfgrass and strips of turfgrass, with adhering soil that are used in vegetative planting for example top few centimeters of soil permeated by and held together with grass roots or grass-legume roots.

The term "sodformer" refers to grass that propagates by seed and vegetatively by rhizomes and/or stolons to form a sod.

The term "variety" refers to a biological classification for an intraspecific group or population, that can be distinguished from the rest of the species by any characteristic (for example morphological, physiological, cytological, etc.). A variety may originate in the wild but can also be produced through selected breeding (for example, see, cultivar).

The terms "cultivar," "cultivated variety," and "cv" refer to a group of cultivated plants distinguished by any characteristic (for example morphological, physiological, cytological, etc.) that when reproduced sexually or asexually, retain their distinguishing features to produce a cultivated variety. An example of a turfgrass cultivar is shown in U.S. Pat. No. 5,977,450; herein incorporated by reference.

The term "seed" refers to a ripened ovule, consisting of the embryo and a casing.

The term "propagation" refers to the process of producing new plants, either by vegetative means involving the rooting or grafting of pieces of a plant, or by sowing seeds. The terms "vegetative propagation" and "asexual reproduction" refer to the ability of plants to reproduce without sexual reproduction, by producing new plants from existing vegetative structures that are clones, i.e., plants that are identical in all attributes to the mother plant and to one another. For example, the division of a clump, rooting of proliferations, or cutting of mature crowns can produce a new plant.

The terms "tissue culture" and "micropropagation" refer to a form of asexual propagation undertaken in specialized laboratories, in which clones of plants are produced from small cell clusters from very small plant parts (e.g. buds, nodes, leaf segments, root segments, etc.), grown aseptically (free from any microorganism) in a container where the environment and nutrition can be controlled.

The term plant cell "compartments or organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, thylakoid membranes and nuclear membranes, and the like.

The term "tetraploid plant" refers to a plant that has 4 sets of chromosomes per cell. As used herein, the term "tetraploid grasses" refers to grasses that have 4 sets of chromosomes per cell (e.g. tetraploid varieties of grasses such as ryegrass, red clover, lotus, etc.).

The term "diploid plant" refers to a plant with 2 sets of chromosomes (e.g. the majority of wild-type grass plants).

The term "triploid plant" refers to a plant with 3 sets of chromosomes. As used herein, the term "triploid grasses" refers to grasses that have 3 sets of chromosomes per cell (e.g. Bermudagrass varieties such as Midfield, Midlawn, Midway, Tifgreen, Santa Anna, etc.). The term "portion" when used in reference to a protein (as in "a portion of a given protein") refers to fragments of that protein. The fragments may range in size from four amino acid residues to the entire amino sequence minus one amino acid.

The term "gene" encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region termed "exon" or "expressed regions" or "expressed sequences" interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation.

The terms "allele" and "alleles" refer to each version of a gene for a same locus that has more than one sequence. For example, there are multiple alleles for eye color at the same locus.

The terms "recessive," "recessive gene," and "recessive phenotype" refer to an allele that has a phenotype when two alleles for a certain locus are the same as in "homozygous" or as in "homozygote" and then partially or fully loses that phenotype when paired with a more dominant allele as when two alleles for a certain locus are different as in "heterozygous" or in "heterozygote." The terms "dominant," "dominant allele," and "dominant phenotype" refer to an allele that has an effect to suppress the expression of the other allele in a heterozygous (having one dominant allele and one recessive allele) condition.

The term "heterologous" when used in reference to a gene or nucleic acid refers to a gene that has been manipulated in some way. For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The terms "nucleic acid sequence," "nucleotide sequence of interest" or "nucleic acid sequence of interest" refer to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, and the like.

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "polynucleotide" refers to refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

The term "an oligonucleotide (or polypeptide) having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region of the gene if needed to permit proper initiation of transcription and/or correct processing of the primary RNA transcript. Alternatively, the coding region utilized in the expression vectors of the present invention may contain endogenous enhancers, exogenous promoters, splice junctions, intervening sequences, polyadenylation signals, etc., or a combination of both endogenous and exogenous control elements.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "SNP" and "Single Nucleotide Polymorphism" refer to a single base difference found when comparing the same DNA sequence from two different individuals.

The terms "EST" and "expressed sequence tag" refer to a unique stretch of DNA within a coding region of a gene; approximately 200 to 600 base pairs in length.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The terms "protein," "polypeptide," "peptide," "encoded product," "amino acid sequence," are used interchangeably to refer to compounds comprising amino acids joined via peptide bonds and a "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence. The term "X" may represent any amino acid.

The terms "homolog," "homologue," "homologous," and "homology" when used in reference to amino acid sequence or nucleic acid sequence or a protein or a polypeptide refers to a degree of sequence identity to a given sequence, or to a degree of similarity between conserved regions, or to a degree of similarity between three-dimensional structures or to a degree of similarity between the active site, or to a degree of similarity between the mechanism of action, or to a degree of similarity between functions. In some embodiments, a homolog has a greater than 20% sequence identity to a given sequence. In some embodiments, a homolog has a greater than 40% sequence identity to a given sequence. In some embodiments, a homolog has a greater than 60% sequence identity to a given sequence. In some embodiments, a homolog has a greater than 70% sequence identity to a given sequence. In some embodiments, a homolog has a greater than 90% sequence identity to a given sequence. In some embodiments, a homolog has a greater than 95% sequence identity to a given sequence. In some embodiments, homology is determined by comparing internal conserved sequences to a given sequence. In some embodiments, homology is determined by comparing designated conserved functional regions. In some embodiments, homology is determined by comparing designated conserved "motif" regions. In some embodiments, means of determining homology are described in the Experimental section (Examples 4 and 8).

The term "homology" when used in relation to nucleic acids or proteins refers to a degree of identity. There may be partial homology or complete homology. The following terms are used to describe the sequence relationships between two or more polynucleotides and between two or more polypeptides: "identity," "percentage identity," "identical," "reference sequence," "sequence identity," "percentage of sequence identity," and "substantial identity." "Sequence identity" refers to a measure of relatedness between two or more nucleic acids or proteins, and is described as a given as a percentage "of homology" with reference to the total comparison length. A "reference sequence" is a defined sequence used as a basis for a sequence comparison; a reference sequence may be a subset of a larger sequence, for example, the sequence that forms an active site of a protein or a segment of a full-length cDNA sequence or may comprise a complete gene sequence. Since two polynucleotides or polypeptides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of in internal region of a polypeptide. In one embodiment, a comparison window is at least 77 amino acids long. In another embodiment, a comparison window is at least 84 amino acids long. In another embodiment, conserved regions of proteins are comparison windows. In a further embodiment, an amino acid sequence for a conserved transmembrane domain is 24 amino acids. Calculations of identity may be performed by algorithms contained within computer programs such as the ClustalX algorithm (Thompson, et al. Nucleic Acids Res. 24, 4876-4882 (1997)), herein incorporated by reference); MEGA2 (version 2.1) (Kumar, et al. Bioinformatics 17, 1244-1245 (2001)); "GAP" (Genetics Computer Group, Madison, Wisconsin), "ALIGN" (DNAStar, Madison, Wisconsin), BLAST (National Center for Biotechnology Information; NCBI as described at http://,followed by,www., followed by,ncbi.nlm.nih.gov/BLAST/blast_help.,followed by,shtml) and MultAlin (Multiple sequence alignment) program (Corpet, Nucl. Acids Res., 16 (22), 10881-10890 (1988) at http:, followed by,//prodes.,followed by,toulouse.inra.fr/multalin/multalin.,followed by,html), all of which are herein incorporated by reference).

For comparisons of nucleic acids, 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2:482 (1981)) by the homology alignment algorithm of Needleman and Wunsch (Needleman and Wunsch, J. Mol. Biol. 48:443 (1970), herein incorporated by reference), by the search for similarity method of Pearson and Lipman (Pearson and Lipman, Proc. Natl. Acad. Sci. (U.S.A.) 85:2444 (1988), herein incorporated by reference), by computerized implementations of these algorithms (GAP, BEST-FIT, FASTA, and TFASTA in the Wisconsin Genetics Software Package Release 7.0, Genetics Computer Group, 575 Science Dr., Madison, Wis., herein incorporated by reference), or by inspection, and the best alignment (i.e., resulting in the highest percentage of homology over the comparison window) generated by the various methods is selected. The term "sequence identity" means that two polynucleotide or two polypeptide sequences are identical (i.e., on a nucleotide-by-nucleotide basis or amino acid basis) over the window of comparison. The term "percentage of sequence identity" is calculated by comparing two optimally aligned sequences over the window of comparison, determining the number of positions at which the identical nucleic acid base (e.g., A, T, C, G, U, or I) or amino acid, in which often conserved amino acids are taken into account, occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (for e.g. in FIG. 10).

The term "ortholog" refers to a gene in different species that evolved from a common ancestral gene by speciation. In some embodiments, orthologs retain the same function. The term "paralog" refers to genes related by duplication within a genome. In some embodiments, paralogs evolve new functions. In further embodiments, a new function of a paralog is related to the original function.

The term "partially homologous nucleic acid sequence" refers to a sequence that at least partially inhibits (or competes with) a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence that is completely complementary to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial-degree of identity (e.g., less than about 30% identity); in the absence of non-specific binding the probe will not hybridize to the second non-identical target.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. Melting temperature $T_m$ is the midpoint of the temperature range over which nucleic acids are denatured (e.g. DNA:DNA, DNA:RNA and RNA:RNA, etc.). Methods for calculating the $T_m$ of nucleic acids are well known in the art (Sambrook, et al., *Molecular Cloning: A Laboratory Manual*, $2^{nd}$ ed., Cold Spring Harbor Laboratory Press, New York (1989) pp. 9.50-51, 11.48-49 and 11.2-11.3, herein incorporated by reference).

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent (50× Denhardt's contains per 500 ml:05 g Ficoll (Type 400, Pharmacia):05 g BSA (Fraction V; Sigma)) and 100 µg/ml denatured salmon sperm DNA followed by washing in a solution comprising 5× SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q replicase, MDV-1 RNA is the specific template for the replicase (Kacian et al., Proc. Natl. Acad. Sci. USA, 69:3038-3042 (1972), herein incorporated by reference). Other nucleic acids will not be replicated by this amplification enzyme. Similarly, in the case of T7 RNA polymerase, this amplification enzyme has a stringent specificity for its own promoters (Chamberlin et al., Nature, 228:227 (1970), herein incorporated by reference). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 (1989), herein incorporated by reference). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989), herein incorporated by reference).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used-in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew has reported (Curr. Opin. Cell Biol. 13(2):244-248 (2001)) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, and the like.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237 (1987), herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al., supra (1987), herein incorporated by reference).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length. Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy.

Promoters may be "constitutive" or "inducible." The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098, herein incorporated by reference), and ubi3 promoters (see e.g., Garbarino and Belknap, Plant Mol. Biol. 24:119-127 (1994), herein incorporated by reference). Such promoters have been used successfully to direct the expression of heterologous nucleic acid sequences in transformed plant tissue.

In contrast, an "inducible" promoter is one that is capable of directing a level of transcription of an operably linked nucleic acid sequence in the presence of a stimulus (e.g., heat shock, chemicals, light, etc.) that is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, and the like.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2$^{nd}$ ed., Cold Spring Harbor Laboratory Press, New York (1989) pp. 16.7-16.8, herein incorporated by reference). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6-16.7).

The term "vector" refers to nucleic acid molecules that transfer DNA segment(s). Transfer can be into a cell, cell to cell, etc. The term "vehicle" is sometimes used interchangeably with "vector."

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The terms "stable transfection" and "stably transfected" refer to the introduction and integration of foreign DNA into the genome of the transfected cell. The term "stable transfectant" refers to a cell that has stably integrated foreign DNA into the genomic DNA.

The terms "transient transfection" and "transiently transfected" refer to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb in Virol., 52:456 (1973), herein incorporated by reference, has been modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, herein incorporated by reference), and are commercially available (e.g. the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgene" refers to a foreign gene that is placed into an organism by the process of transfection. The term "foreign gene" refers to any nucleic acid (e.g., gene sequence) that is introduced into the genome of an organism by experimental manipulations and may include gene sequences found in that organism so long as the introduced gene does not reside in the same location, as does the naturally occurring gene.

The terms "transformants" and "transformed cells" include the primary transformed cell and cultures derived from that cell without regard to the number of transfers. Resulting progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 (1987) and U.S. Pat Nos. 6,074,859; 5,976,796; 5,674,713; and 5,618,682; all of which are herein incorporated by reference), green fluorescent protein (e.g., GenBank Accession Number U43284; GFP variants commercially available from CLONTECH Laboratories, Palo Alto, Calif., herein incorporated by reference), chloramphenicol acetyltransferase, β-galactosidase (lacZ gene), alkaline phosphatase, and horse radish peroxidase. An example of using lacZ as a reporter gene for *Arabidopsis* DREB1A is provided in U.S. Pat. No. 6,495,742, herein incorporated by reference. Methods for using luciferase as a reporter gene for *Arabidopsis* DREB1A are disclosed in U.S. Pat. Nos. 6,495,742; 6,670,528; all of which are herein incorporated by reference.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The terms "hpRNA" and "hairpin RNA" refer to self-complementary RNA that forms hairpin loops and functions to silence genes (e.g. Wesley et al., The Plant Journal 27(6):581-590 (2001), herein incorporated by reference). The term "ihpRNA" refers to intron-spliced hpRNA that functions to silence genes.

The term "target RNA molecule" refers to an RNA molecule to which at least one strand of the short double-stranded region of a siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The terms "posttranscriptional gene silencing" and "PTGS" refers to silencing of gene expression in plants after transcription, and appears to involve the specific degradation of mRNAs synthesized from gene repeats.

The term "cosuppression" refers to silencing of endogenous genes by heterologous genes that share sequence identity with endogenous genes. The term "overexpression" generally refers to the production of a gene product in transgenic organisms that exceeds levels of production in normal or non-transformed organisms. The term "cosuppression" refers to the expression of a foreign gene that has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "overexpression" and "overexpressing" and grammatical equivalents, are specifically used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots).

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook, et al., *Molecular Cloning: A Laboratory Manual*, $2^{nd}$ ed., Cold Spring Harbor Laboratory Press, New York (1989) pp. 9.31-9.58, herein incorporated by reference).

The term "Northern blot analysis," "Northern blot," and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al. supra, pp 7.39-7.52, (1989), herein incorporated by reference).

The terms "RACE" and "Rapid Amplification of cDNA Ends" refer to a PCR technique used to obtain the 3' end of a cDNA as in 3' RACE and to obtain the 5' end of a cDNA as in 5' RACE.

The terms "blot analysis," "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "isolated" when used in relation to a nucleic acid or polypeptide, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences that are removed from their natural environment isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the terms "purified" and "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "host cell" refers to any cell capable of replicating and/or transcribing and/or translating a heterologous gene. Thus, a "host cell" refers to any eukaryotic or prokaryotic cell (e.g., plant cells, algal cells such as *C. reinhardtii*, bacterial cells such as *E. coli*, yeast cells, insect cells, etc.), whether located in vitro or in vivo. For example, host cells may be located in a transgenic plant. The terms "eukaryotic" and "eukaryote" are used in it broadest sense. It includes, but is not limited to, any organisms containing membrane bound nuclei and membrane bound organelles. Examples of eukaryotes include but are not limited to animals, plants, alga, diatoms, and fungi.

The terms "prokaryote" and "prokaryotic" are used in it broadest sense. It includes, but is not limited to, any organisms without a distinct nucleus. Examples of prokaryotes include but are not limited to bacteria, blue-green algae, archaebacteria, actinomycetes and mycoplasma. In some embodiments, a host cell is any microorganism. As used herein the term "microorganism" refers to microscopic organisms and taxonomically related macroscopic organisms within the categories of algae, bacteria, fungi (including lichens), protozoa, viruses, and subviral agents.

The terms "expression vector" and "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

The term "*Agrobacterium*" refers to a soil-borne, Gram-negative, rod-shaped phytopathogenic bacterium that causes crown gall. *Agrobacterium* is a representative genus of a soil-borne, Gram-negative, rod-shaped phytopathogenic bacterium family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. *Agrobacterium tumefaciens* causes crown gall disease by transferring some of its DNA to the plant host. The transferred DNA (T-DNA) is stably integrated into the plant genome, where its expression leads to the synthesis of plant hormones and thus to the tumorous growth of the cells. A putative macromolecular complex forms in the process of T-DNA transfer out of the bacterial cell into the plant cell. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain GV3101, LBA4301, C58, A208, etc.) are referred to as "nopaline-type" *Agrobacteria*; *Agrobacterium* strains which cause production of octopine (e.g., strain LBA4404, Ach5, B6, etc.) are referred to as "octopine-type" *Agrobacteria*; and *Agrobacterium* strains which cause production of agropine (e.g., strain EHA105, EHA101, A281, etc.) are referred to as "agropine-type" *Agrobacteria*.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

The term "plant" is used in it broadest sense. It includes, but is not limited to, any species of grass (e.g. turfgrass), sedge, rush, ornamental or decorative, crop or cereal, fodder or forage, fruit or vegetable, fruit plant or vegetable plant, woody, flower or tree. It is not meant to limit a plant to any particular structure. Such structures include, but are not limited to, a seed, a tiller, a sprig, a stolen, a plug, a rhizome, a shoot, a stem, a leaf, a flower petal, a fruit, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). In one embodiment, transgenic seeds of the present invention may contain at least 2x as much CBF3 over wild-type seeds. Plant tissue may be in planta, in organ culture, tissue culture, or cell culture. The term "plant part" as used herein refers to a plant structure or a plant tissue. Plant parts may comprise one or more of a tiller, plug, rhizome, sprig, stolen, meristem, crown, and the like. In some embodiments of the present invention transgenic plants are fodder plants. The term "fodder plant" and "forage plant" is used in its broadest sense and used interchangeably herein. The term includes, but is not limited to any species of plant used as a feed for animals or birds, or fish, or reptiles, or marine animals. Examples of transgenic forage plants are described in U.S. patent application Pub. No. 20020019997A1 and 20020023279A1; and U.S. Pat. No. 5,985,666; all of which are herein incorporated by reference.

The terms "crop" and "crop plant" is used herein its broadest sense. The term includes, but is not limited to, any species of plant or alga edible by humans or used as a feed for animals or fish or marine animals, or consumed by humans, or used by humans, or viewed by humans (flowers) or any plant or alga used in industry or commerce or education.

The term "ground cover" refers to a use of a plant to fill in areas of land (e.g. sunny area, shaded area, and the like.

The terms "transgenic" when used in reference to a plant or leaf or fruit or seed or plant part for example a "transgenic plant," "transgenic leaf," "transgenic fruit," "transgenic seed," and a "transgenic host cell" refer to a plant or leaf or fruit or seed or part or cell that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitution refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on). Thus, nucleotide sequences of the present invention can be engineered in order to introduce or alter a CBF3 coding sequence for a variety of reasons, including but not limited to initiating the production of environmental stress tolerance; alterations that modify the cloning, processing and/or expression of the gene product (such alterations include inserting new restriction sites and changing codon preference), as well as varying the protein function activity (such changes include but are not limited to differing binding kinetics to nucleic acid and/or protein or protein complexes or nucleic acid/protein complexes, differing binding inhibitor affinities or effectiveness, differing reaction kinetics, varying subcellular localization, and varying protein processing and/or stability) (e.g. FIG. 10).

The term "fusion" when used in reference to a polypeptide refers to a chimeric protein containing a protein of interest joined to an exogenous protein fragment (the fusion partner). The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms. The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The "basic region-helixloop-helix-leucine zipper" and "b-HLH-Zip" domains consist of an α-helix and a three-stranded antiparallel β-sheet that interacts with base pairs within the DNA major groove (Allen et al., EMBO J September 15;17(18):5484-96 (1998)).

The term "signature sequences" refers to amino acid sequences that are present in CBF-like proteins from numerous plants including *Arabidopsis, B. napus*, wheat, rye, tomato and the like. Conservation of these sequences across evolutionarily diverse plant species suggests that they have an important functional role. The resemblance of the RPAGRxKFxETRHP (SEQ ID NO:151) motif sequence cnmprising SEQ ID NO:04 to nuclear transport signals (Smith and Raikhel, Plant Physiol. Apr;119(4):1157-64) (1999)) indicates that it might be involved in protein trafficking as previously suggested (Stockinger et al., EMBO J August 15;21(16):4259-67 (1997)). The signature sequences would not appear to be involved in recognition of the CRT/DRE regulatory element because they (or closely related sequences) are not present in the *Arabidopsis* AP2/EREBP protein DREB2a (Liu et al., Plant Cell, 10(8):1391-1406 (1998)). DREB2a binds to a CRT/DRE element and activates gene expression in *Arabidopsis* in a transient assay (though not in stable *Arabidopsis* transformants; Liu et al., Plant Cell, 10(8): 1391-1406 (1998)). The DREB2a gene is not induced by low temperature, but instead is induced in response to dehydration stress (Liu et al., Plant Cell, 10(8): 1391-1406 (1998)). Expression of the DREB2a protein in drought-stressed plants is proposed to account, at least in part, for the dehydration responsiveness of the CRT/DRE element (Liu et al., Plant Cell, 10(8):1391-1406 (1998)).

The term "accession" when used herein associated with sources of plants refers to a plant or group of similar plants or group of seeds from these plants received from a single source at a single time. The term "accession number" when used herein associated with sources of plants refers to a unique identifier for each accession and is assigned when an accession is entered into a plant collection. As used herein "PI" used before an accession number indicates the identity of the genebank or national system that in this case refers to an accession cataloged within the USA system where the term "PI" refers to "plant introductions."

The term "accession" when used herein associated with sequences of genes and proteins refers to a gene or group of similar genes or proteins from these genes or proteins received from a single source at a single time. The term "accession number" when used herein refers to a unique identifier for protein and gene sequences and is assigned when an accession is entered into a database (for example GenBank at NCBI, European Molecular Biology Laboratory (EMBL), SWISS-PROT, and the like.

The term "R" in reference to a plant refers to cold tolerant plants.

The term "S" in reference to a plant refers to non-cold tolerant plants.

The term "mowing frequency" refers to the number of times a turf-grass area is mowed per week, month, or growing season. The term "mowing interval" refers to the number of days, weeks, etc., between successive mowing.

The term "fiber content" refers to the indigestible or slowly digesting components of forage that occupy space in the gastrointestinal tract of animals (for example, the lower the percent ADF, the more forage an animal can digest). The terms "acid detergent fiber" and "ADF" refers to the percentage of highly indigestible plant material (lignified cellulose) in a feed or forage. The lower the percent ADF, the more forage an animal can digest.

The term "digestibility" refers to a measure of the amount of forage that is ingested and retained in the body versus that amount passed as fecal material.

DESCRIPTION OF THE INVENTION

The present invention relates to genes, proteins and methods comprising or utilizing C-repeat binding factors (CBF), specifically CBF3 in the ryegrass family. In a preferred embodiment, the present invention relates to using ryegrass CBF3 for altering cold tolerance and growth in plants, specifically in warm season grasses, turfgrasses, fodder plants and microorganisms.

Environmental Stress Response in Plants.

Environmental stress such as low temperature, high temperature, high salt and drought threaten the survival of plants, especially those unable to withstand these types of extreme conditions. Under environmental stress many plants respond by increasing expression of relevant stress response genes that allow them to adapt in order to live and even thrive under otherwise harsh environmental conditions. However, other plants do not have an innate ability to adapt to certain alien or extreme environments. For example, warm season grasses (e.g. Bermudagrass, St. Augustine grass, etc.) will grow as rich green carpets in colder northern regions of the U.S. during the warm summer months but then during the fall and winter they wither, turn brown and become dormant and frequently die from cold temperatures, thus requiring seasonal reseeding or resodding, and the like in the spring. At the same time, cold season grasses (e.g. Kentucky bluegrass, perennial ryegrass, etc.) will live and sometimes thrive under these colder conditions but often with reduced growth and/or a substantial loss of green color. Further, even cold season grasses show a range of tolerance for low temperature conditions, a tolerance that can be enhanced with cold adaptation prior to exposure to low temperatures and with genetic manipulation (Jaglo-Ottosen et al., Science 280:104-106 (1998); Liu et al., Plant Cell, 10(8):1391-1406 (1998); Kasuga et al., Nature Biotechnol. March;17(3):287-91(1999); and Gilmour et al., Plant Physiol. December; 124(4):1854-1865 (2000).

Conversely, cold season grasses often do not grow well in warm climates, especially in the hot sun. In addition, grasses that grow well in transition zones, zones between warm and cold climates (e.g. many types of fescue spp., etc.), tend not to grow well in either extreme of hot or cold.

Environmental response genes for cold responses, drought responses and salt responses can be regulated through environmental stress response transcription factors. For example, a cold (low temperature) response in plants (e.g. in *Arabidopsis*) can be mediated by one or more of cis-acting CBFs, bZIPs, and ABA responsive proteins.

The CBF multigene family consisting of six paralogs that include three intensively studied genes (CBF1/DREB1B, CBF2/DREB1C, and CBF3/DREB1A) in an 8.7-kb region on chromosome 4 (Gilmour et al., Plant J. November;16(4): 433-42 (1998); Liu et al., Plant Cell, 10(8):1391-1406 (1998)), and lesser studied genes on chromosome 5 (CBF4/DREBID; (Haake et al., Plant Physiol October;130(2):639-48 (2001)) and chromosome 1 (DREB1E and DREB1F; Sakuma et al., Biochem Biophys Res Commun January 25;290(3):998-1009 (2002)).

The association of CBF transcription factor expression with cold tolerance is demonstrated in *Arabidopsis* using transgenic plants overexpressing one of each gene (e.g. CBF3, CBF1, and CBF2) and generating microarray DNA expression information (Fowler and Thomashow, Plant Cell August;14(8):1675-90 (2002); Seki et al., Plant Cell, 13(1): 61-72 (2001); Seki et al., Plant J, 31(3):279-292 (2002), herein incorporated by reference. These studies further suggest that CBF genes have both separate and overlapping functions during low temperature environmental tolerance.

Recently, studies monitoring expression profiles of rice genes under cold, drought, and high-salinity stresses using cDNA microarray and RNA gel-blot analyses revealed 73 genes as stress inducible with 36 of these induced by cold and 15 induced by any one of cold, drought, ABA, and high-salinity stresses (Rabbani et al., Plant Physiol. December;133(4):1755-1767 (2003) Epub 2003 Nov. 26 (2003). Twenty-two of these were novel stress-inducible genes since orthologs not found in *Arabidopsis*. Thus although rice responds to cold tolerance in a similar manner, there are also differences in gene activation during cold responses between *Arabidopsis* and rice (Rabbani et al., Plant Physiol. December;133(4):1755-1767 (2003) Epub 2003 Nov. 26 (2003).

CBF and CBF-like proteins and genes comprising conserved AP binding domains are found in a variety of plants, even those not cold tolerant such as wheat, barley and rye, in addition to *Arabidopsis* and rice (e.g. Medina, et al., Plant Physiol, 119(2):463-470 (1999); Choi, et al., Plant Physiol, 129(4):1781-7178 (2002); and Dubouzet et al., Plant J, 33(4):751-763 (2003)). In *Arabadopsis thaliana*, there are at least 4 CBF genes that contain AP2 binding domains. Of these, CBF1-3 are about 86% identical overall to each other whereas CBF4 is about 63% identical to CBF1-3.

These environmental response transcription factors in turn regulate additional environmental response genes, either laterally or downstream by binding to promoter regions that contain CRT/DRE and/or ABA-responsive elements. In other words, C-repeat/dehydration-responsive transacting factors activate genes by binding to promoter regions of other stress response genes that contain CRT/DR response elements (e.g. CBF binds to the promoter region of target genes that express stress response proteins such as COR6.6, COR15, COR6.6, COR47, COR78, ERD10, P5CSb, and the like) in addition to activating genes that do not contain the core CCGAC sequence (SEQ ID NO:67) of the CRT/DRE element within 1 kb of the start of transcription for increasing production of stress response proteins (e.g. RAP2.1, RAP2.6, and the like). The CBF genes are induced within 15 min of plants exposed to low, nonfreezing temperatures followed at about 2 h by induction of COR genes that contain the CRT/DRE-regulatory element (CBF regulon). Over the next few days, expression of genes containing the CBF regulon leads to an increase in plant freezing tolerance. Further, expression of genes containing the CBF regulon often increases tolerance to both drought and high salinity stress (See, Fowler and Thomashow, Plant Cell August;14(8):1675-90 (2002)).

Effects of CBF3 Overexpression on Vegetative Growth, Time to Flowering, and Freezing Tolerance.

Overexpression of CBF3 (DREB1a) increases the freezing tolerance of nonacclimated plants. Where nonacclimated control plants were killed by freezing at −6° C. for 24 h whereas nonacclimated CBF3-overexpressing plants were not; results for *Arabidopsis* (L.). The freezing tolerance of cold-acclimated CBF3-overexpressing plants was significantly greater than that of both nonacclimated CBF3-overexpressing plants and cold-acclimated control plants (Gilmour et al., Plant Physiol. December;124(4):1854-65 (2000)).

Overexpression of CBF3 in *Arabidopsis* induces numerous target genes associated with cold tolerance (e.g. rd29A, cor78, kin1, kin2, cor15a, rd17 and erd10) and similar studies in rice overexpressing CBF3 showed that more than 36 environmental stress tolerance genes related to cold tolerance were affected. Therefore the ryegrass CBF3 of the present invention should regulate numerous cold tolerance genes.

Liu et al., (Plant Cell August;10(8):1391-406 (1998)), reported that transgenic *Arabidopsis* plants overexpressing *Arabidopsis* CBF3 (DREB1a) have a "dwarf" phenotype. CBF3-overexpressing plants had a pronounced prostrate growth habit; whereas the leaves of the control plants generally had an upright stature, those of the transgenic plants laid flat to the soil. The CBF3-overexpressing plants also had much shorter petioles when compared with those of the control plants. Also, there was a substantial difference in time to flowering between the control and CBF3-overexpressing plants; i.e. control plants bolted and formed flowers well before the CBF3-overexpressing plants did. The CBF3-overexpressing plants went on to form flowers and set seed, although as noted by Liu et al., (Plant Cell August;10(8): 1391-406 (1998)), the final plant mass and seed yield were considerably less than that obtained with control plants. The lower yield of seed was due at least in part to the CBF3-overexpressing plants producing fewer axillary shoots. The delay in flowering observed in the CBF3-overexpressing plants, significantly, did not "simply" involve a slower overall growth rate, but appeared to involve a developmental delay in flowering. In one experiment, for instance, the control plants produced an average of 4.5 and 4.6 leaves per rosette, whereas the transgenic plants produced 6.0, 9.7, and 12.5 leaves per rosette, respectively Liu et al., (Plant Cell August; 10(8):1391-406 (1998).

Further, overexpression studies of *Arabidopsis* CBF3, with the use of a strong constitutive 35S cauliflower mosaic virus (CaMV) promoter, was associated with stunted growth and a delay in flowering (Yamaguchi-Shinozaki and Shinozaki, Novartis Found Symp. 236:176-86 (2001); Liu et al., Plant Cell. August;10(8):1391-406 (1998); Gilmour et al., Plant Physiol. December;124(4):1854-65 (2000). This phenotype was altered when compared to overexpression of *Arabidopsis* CBF3 with a stress-inducible rd29A promoter which gave rise to minimal effects on plant growth while providing an even greater tolerance to stress conditions (Yamaguchi-Shinozaki and Shinozaki, Novartis Found Symp. 236:176-86 (2001)).

Overexpression of CBF3 also leads to elevated levels of proline and sugars that are normally associated with cold acclimation (Gilmour et al., Plant Physiol. December; 124 (4):1854-1865 (2000)). Genes associated with elevated sugar levels include genes that code for proteins with galactinol synthase activity. Of three *Arabidopsis* genes encoding proteins with galactinol synthase activity, one of these, AtGolS3 (which corresponds to probe set 18596_at), was induced in response to low temperature (Taji et al., Plant J. February 2002;29(4):417-26 (2002)) and overexpression of CBF3/DREB1.

Overexpression of DREB1A (CBF3) not only increases freezing tolerance, but also salt loading and drought tolerance in transgenic *Arabidopsis* (Kasuga et al., Nat Biotechnol. March;17(3):287-91 (1999)). Transgenic plants overexpressing DREB1A/CBF3 have severely compromised growth and development even under the benign growth conditions of controlled environments (U.S. patent application Pub. No. 20040019927A1; herein incorporated by reference).

Overexpression of *Arabidopsis* CBF1 in tomato plants (Hsieh et al., American Society of Plant Physiologists Plant Physiol. 130(2):618-626 (2002), canola oilseed rape (*Brassica napus*) (Jaglo-Ottosen et al., Science 280:104-106 (1998)) increases water deficit resistance and stunts growth including a decrease in fruit, seed number, and fresh weight in addition to enhancing chilling tolerance as compared with wild-type plants (Hsieh et al., American Society of Plant Physiologists Plant Physiol. 130(2):618-626 (2002)).

Overexpression of CBF1/DREB1B or CBF3/DREB1A leads to the constitutive expression of genes with promoters containing the DRE/CRT/LTRE element and to improved freezing, drought and salt tolerance of non-acclimated plants (Jaglo-Ottosen et al., Science 280:104-106 (1998); Kasuga et al., Nat Biotechnol. March 17(3):287-91 (1999)).

Other trans-acting factors, DREB2A and DREB2B, have been isolated which also bind the DRE/CRT element (Jaglo-Ottosen et al., Science 280:104-106 (1998); Kasuga et al., Nat Biotechnol. March 17(3):287-91 (1999); Liu et al., Plant Cell, 10(8):1391-1406 (1998)). The DREB2 proteins contain a Ser-/Thr-rich domain, and have no significant sequence similarity to CBF/DREB 1 proteins, except for the presence of NLS and AP2 domains. The DREB2 genes are induced by dehydration and salt stress, but not cold stress (Liu et al., Plant Cell, 10(8):1391-1406 (1998); Nakashima et al., Plant Mol Biol March;42(4):657-65 (2000)). In summary, there are two different types of DRE/CRT-binding factors, CBF/DREB1 and DREB2, keyed by at least somewhat separate signal transduction pathways.

Ryegrass CBF3 and Induction of Cold Tolerance.

The present invention provides methods for using ryegrass cbf3 genes and ryegrass CBF3 polypeptides. Such methods include, but are not limited to, use of these genes to produce transgenic plants, to produce cold tolerance, to increase cold tolerance, to decrease cold tolerance, to alter environmental tolerance, to alter phenotypes, and for controlled environmental tolerance. It is not meant to limit the present invention to alterations in cold tolerance. In some embodiments, cbf3 alters production of one or more of height, growth rate, shade tolerance, and drought resistance. In some embodiments, CBF3 polypeptides are overexpressed in transgenic plants, transgenic tissue, transgenic leaves, transgenic calli, transgenic meristem, transgenic stem, transgenic stolen, transgenic sprig, transgenic cultivar, transgenic tiller, transgenic seed, transgenic host cell. Examples of alteration of environmental tolerance in transgenic plants are provided in U.S. Pat. Nos. 6,025,542; 6,677,504; 6,025,542; 5,891,859; 6,417,428; 5,929,305; 5,296,462; 5,356,816; 5,892,009; 5,965,705; and U.S. patent application Pub. Nos. 20020160378A1; 20040009476A9; 20040019925A1; 20030226173A1; 20030217383A1; 20040019927A1; 20020157136A1; 20030140379A1; and PCT Patent WO 99/38977A2; all of which are herein incorporated by reference.

In some embodiments, ryegrass cbf3 alters production of one or more of the following cold response genes as shown in *Arabidopsis*, for example cor15a, cor15b, cor 6.6, rap 2.1, rap 2.6, Atgols3 (galactinol synthase), Δ1-pyrroline-5-carboxylate synthase (P5CS) and genes whose promoters contain the CRT/DRE regulatory element (Gilmour et al., Plant J. November;16(4):433-42 (1998); Liu et al., Plant Cell, 10(8):1391-1406 (1998); Shinwari et al., Biochem Biophys Res Commun. September 8;250(1):161-70 (1998)). An example of such alteration in cold response in a transgenic plant where expression of a cold response gene is altered is disclosed in U.S. Pat. Nos. 5,296,462 and 5,356,816, herein incorporated by reference.

In some embodiments, ryegrass CBF-like proteins alter production of one or more of the following cold response genes as shown in Brassica oilseed rape (canola) Bn115 (Weretilnyk et al., Plant Physiol January;101(1):171-177 (1993)), where *Arabidopsis* CBF genes inserted into *B. napus* resulted in an increase in freezing tolerance.

Other genes activate cbf genes, and upstream regulators such as ICE proteins in particular activate cbf3. In some embodiments, modulators of ryegrass cbf3 expression in transgenic plants produces alterations in environmental tolerance (e.g. increasing and decreasing ICE1 as demonstrated in U.S. patent application Pub. No. 20030233681A1 and PCT Patent WO 03/093411; all of which are herein incorporated by reference). Accordingly, in some embodiments, host plants may express ICE1 for increasing cbf expression.

Increased Cold Tolerance in Tetraploid Grasses.

Some embodiments of the present invention provide a transgenic tetraploid plant with enhanced cold tolerance. It is not meant to limit the tetraploid plant to any one species or variety of plant. In some embodiments, a tetraploid plant is a tetraploid grass. A tetraploid grass may be naturally or artificially derived. In some embodiments, the tetraploid grass is a grass artificially created by plant breeders. Examples of such tetraploid plants are ryegrass (e.g. varieties such as Tonga, Baristra, Barlatra, Citadel, Condesa, Fantoom, Barvestra, Bonita, etc.), bahiagrass (e.g. broad leafed cultivars of varieties such as Argentine, Paraguay-22, Wilmington, etc.), a Bermudagrass (e.g. cultivar of varieties NuMex Sahara, etc.). In some embodiments, a tetraploid plant is transgenically engineered (e.g. U.S. patent application Pub. No. 20040023395A1, herein incorporated by reference).

The present invention also provides methods for inhibiting cbf3 genes, and CBF3 polypeptides. Such methods include, but are not limited to, use of these genes in antisense constructs to produce transgenic plants, to suppress cold tolerance, to decrease cold tolerance, to increase heat tolerance of cold season plants, to alter phenotypes associated with cold tolerance, to decrease accumulation of sugars, to decrease accumulation of Proline, to alter phenotypes, to alter growth, to induce a tall phenotype, to decrease time until flowering, and to alter phenotypes for enhancing nutritional value. In some embodiments, cbf3 genes and CBF3 polypeptides are inhibited in transgenic plants, transgenic tissue, transgenic leaves, transgenic seeds, and transgenic host cells. Introduction of the nucleic acid sequence of interest into the plant cell genome may be achieved by, for example, heterologous recombination using *Agrobacterium*-derived sequences. Examples of antisense inhibition in ryegrasses and other plants are provided in Bhalla et al., Proc Natl Acad Sci USA, 96(20):11676-11680 (1999); U.S. patent application Pub. No. 20020062499A1; PCT Patent WO03/076612; Wesley et al., Plant J. 27(6):581-590(2001);

Fujisawa et al., Proc Natl Acad Sci USA, 96(13):7575-7580 (1999); Yamamuro et al., Plant Cell 12(9):1591-606 (2000); all of which are herein incorporated by reference).

The present invention is not limited to any particular mechanism of action. Indeed, an understanding of the mechanism of action is not needed to practice the present invention. The following description describes pathways involved in regulating environmental stress tolerance, with an emphasis on controlling cold tolerance or controlling drought tolerance or controlling growth or controlling nutrient content. Also described are methods for identifying genes involved in environmental stress tolerance or controlling cold tolerance, and of the ryegrass CBF3/CBF-like gene discovered through use of these methods. This CBF3 and CBF-like related gene has been identified, cloned, and characterized including determination of its relationship to other plant cbƒ and cbƒ-like genes. Further, using the sequence of the present invention, an additional AP2 binding domain identified and characterized for another AP2 binding domain consensus sequence for the constructs and methods of the present invention. This description also provides methods of identifying, isolated, characterizing and using this gene and its encoded protein. In addition, the description provides specific, but not limiting, illustrative examples of embodiments of the present invention.

The present invention also provides methods for using a combination of ryegrass cbƒ3 with other cbƒ genes (e.g. other ryegrass cbƒ and cbƒ-like genes, cbƒ and cbƒ-like genes from plants such as rice, fescue, barley, *Arabidopsis*, and the like), as contemplated by using one or more of SEQ ID NO:01, 109-141, and 150 for adding cold response genes (e.g. lateral and downstream genes such as cor39, cor47, and the like for example SEQ ID NO:146-149) and genes that would augment environmental tolerance and growth (e.g. fructan genes and the like). Such methods include, but are not limited to, use of these genes to produce transgenic plants, to produce cold tolerance, increasing cold tolerance of cold-acclimated plants, increasing cold tolerance of non-cold-acclimated plants, to alter cold tolerance, to alter phenotypes associated with cold tolerance, increasing accumulation of sugars, increasing accumulation of Proline, to alter phenotypes, to alter growth, inducing a dwarf phenotype, increasing time until flowering, and altering phenotypes for enhancing nutritional value.

I. CBF/DREB Genes, Coding Sequences and Polypeptides

The present invention is not limited to the use of any particular homolog or variant or mutant of a CBF3 protein or a cbƒ3 gene. Indeed, in some embodiments a variety of CBF3 proteins or cbƒ3 genes, variants and mutants may be used so long as they retain at least some of the activity of the corresponding wild-type protein. In some embodiments, proteins encoded by the nucleic acids of SEQ ID NOS:01, 109-141 and 150, find use in the present invention. In other embodiments, nucleic acids encoding proteins that comprise polypeptides at least 63%, 89%, 90%, 95%, 98%, 99% (or more) identical to SEQ ID NO:01 and the corresponding encoded proteins find use in the present invention. In still other embodiments, the nucleic acid sequence further comprises a sequence encoding an AP2 binding domain amino acid motif corresponding to SEQ ID NO:03. In other embodiments, the nucleic acid sequence further comprises sequences encoding conserved amino acid sequences, RPAGRxKFxETRHP (SEQ ID NO:151) and DSAWR (SEQ ID NO:152) within SEQ ID NO:04, that bracket the AP2/ERE DNA binding domains of CBF proteins (SEQ ID NO:151). In other embodiments, the nucleic acid sequence further comprises a sequence encoding ryegrass AP2 domain bracketing amino acid sequences, WTKRPAGRTK-FRETRHPVYRGVRRRGNAGR-WVCEVRVPGRRGTSRLWVGTFDTAEIAA RAH-DAAMLALAAGDSCLNFADSAEL (SEQ ID NO:155) and/or PWTKRPAGRTKFRETRHPVYRGVRRRG-NAGRWVCEVRVPGRRGSRLWVGTFDTAEIA ARAH-DAAMLALAAGDCLNFADSAEL (SEQ ID NO:156) further comprising RPAGRTKFRETRHP (SEQ ID NO:168) and DSAEL (SEQ ID NO:154) that bracket and further comprise the AP2/EREBP DNA binding domain VYRGVR-RRGNAGRWVCEVRVPGRRGSRLWVGTFD-TAEIAARAHDAAMLALAAGDSC LNFA (SEQ ID NO:169). Functional variants can be screened for by expressing the variant in an appropriate vector (described in more detail below) in a plant cell and analyzing the plant's response to environmental stress (e.g. tolerance to cold prior to death, $LT_{50}$, height, time to flowering, etc.).

A. Nucleic Acid Sequences

1. Ryegrass and Plant cbƒ3 Genes

The present invention provides plant cbƒ3 genes and proteins, including their homologs, orthologs, paralogs, variants and mutants. In some embodiments of the present invention, isolated nucleic acid sequences comprising cbƒ3 genes are provided. Mutations in these genes, which disrupt expression of the genes, result in altered environmental tolerance and growth phenotype. In some embodiments, isolated nucleic acid sequences comprising cbƒ3, or cbƒ or cbƒ-like are provided. These sequences include sequences comprising cbƒ3 and cbƒ and cbƒ-like cDNA/genomic sequences (for example, as shown in FIG. 7; SEQ ID NOS: 02, and 70-108, FIG. 9; SEQ ID NOS: 01, 109-141 and 150).

2. Additional Plant cbƒ and cbƒ-like Genes

The present invention provides nucleic acid sequences comprising additional cbƒ and cbƒ-like genes. For example, some embodiments of the present invention provide nucleic acid sequences that encode polypeptides that are homologous to at least one of SEQ ID NOS: 02, and 70-108. In some embodiments, the polypeptides are at least 89%, 90%, 95%, 98%, 99% (or more) identical to SEQ ID NO:02. In other embodiments, the present invention provides nucleic acid sequences that hybridize under conditions ranging from low to high stringency to at least one of SEQ ID NOS: 01, 109-141 and 150, as long as the polynucleotide sequence capable of hybridizing to at least one of SEQ ID NOS: 01, 109-141 and 150 encodes a protein that retains a desired biological activity of an environmental stress response protein. In some preferred embodiments, the hybridization conditions are high stringency. In preferred embodiments, hybridization conditions are based on the melting temperature ($T_m$) of the nucleic acid binding complex and confer a defined "stringency" as explained above (See e.g., Wahl et al., Meth. Enzymol., 152:399-407 (1987), incorporated herein by reference).

In other embodiments of the present invention, alleles of environmental stress response genes, and in particular of cbƒ and cbflike genes, are provided. In preferred embodiments, alleles result from a mutation, (i.e., a change in the nucleic acid sequence) and generally produce altered mRNAs or polypeptides whose structure or function may or may not be altered.

Any given gene may have none, one or many allelic forms. Common mutational changes that give rise to alleles are generally ascribed to deletions, additions, or insertions, or substitutions of nucleic acids. Each of these types of changes may occur alone, or in combination with the others, and at the rate of one or more times in a given sequence.

Mutational changes in alleles also include rearrangements, insertions, deletions, additions, or substitutions in upstream regulatory regions.

In other embodiments of the present invention, the polynucleotide sequence encoding a cbƒ gene is extended utilizing the nucleotide sequences (e.g., SEQ ID NOS:01, 109-141 and 150) in various methods known in the art to detect upstream sequences such as promoters and regulatory elements. For example, it is contemplated that for cbƒ3, cbƒ1, cbƒ2, cbƒ or related cbƒ-like genes, the sequences upstream of the start site or downstream from the poly A tail can be identified using information in databases containing plant genomic information such as TIGR Plant Gene Indices for rice, wheat, barley, rye, maize, sorghum, soybean, potato, cotton, rice etc. a CBF3 and/or a CBF, and/or a CBF-like protein (http:,followed by,//www,followed by,.tigr.org/tdb/tgi/plant.,followed by,shtml), GrainGenes for wheat, barley, rye, triticale, and oats (http:,followed by,// wheat.pw.usda.gov/QueryDB,followed by,.shtml), Gramene: A Comparative Mapping Resource for Grains (http://www.gramene.org), rice (http:,followed by,//rgp.dna.affrc.,followed by,go.jp/), maize (MaizeGDB http:,followed by,//www.maizegdb., followed by,org/), barley (http:, followed by,//hordeum.oscs.montana.,followed by,edu/), soybean (http://,followed by,stadler.agron.iastate.edublast/ blast.,followed by,html), and *Arabidopsis* (http,followed by,://www.arabidopsis.,followed by,org/) databases. An example of such a method for extending coding region information using a RACE PCR method is described herein for the identification of cbf3 segments upstream and downstream of the originally cloned segment, FIG. 3a. For ryegrass cbf3 specific information and for other ryegrass cbƒ and ryegrass cbƒ-like genes for which public genomic or expressed information is not available, or not complete, it is contemplated that polymerase chain reaction (PCR) methods in addition to RACE finds use in the present invention.

In another embodiment, inverse PCR is used to amplify or extend sequences using divergent primers based on a known region (Triglia et al., Nucleic Acids Res., 16:8186 (1988), herein incorporated by reference). In yet another embodiment of the present invention, capture PCR (Lagerstrom et al., PCR Methods Applic., 1:111-19 (1991), herein incorporated by reference) is used. In still other embodiments, walking PCR is utilized. Walking PCR is a method for targeted gene walking that permits retrieval of unknown sequence (Parker et al., Nucleic Acids Res., 19:3055-60 (1991), herein incorporated by reference). The PROMOTERFINDER kit (Clontech) uses PCR, nested primers and special libraries to "walk in" genomic DNA. This process avoids the need to screen libraries and is useful in finding intron/exon junctions. In yet other embodiments of the present invention, add TAIL PCR is used as a preferred method for obtaining flanking genomic regions, including regulatory regions (Liu and Whittier, Genomics, February 10;25(3):674-81 (1995); Liu et al., Plant J., September;8(3): 457-63 (1995), herein incorporated by reference). Preferred libraries for screening for full-length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic Libraries are useful for obtaining introns and extending 5' sequence.

3. Variant cbƒ3 Genes.

In some embodiments, the present invention provides isolated variants of the disclosed nucleic acid sequences encoding cbƒ3, or cbƒ or cbƒ-like genes, and in particular of cbƒ3, cbƒ1, cbƒ2, cbƒ, or related cold induced genes, and the polypeptides encoded thereby; these variants include mutants, fragments, fusion proteins or functional equivalents of genes and gene protein products.

a. Mutants.

Some embodiments of the present invention contemplate nucleic acid sequences encoding mutant forms of CBF proteins, and in particular of CBF3 proteins, (i.e., mutants), and the polypeptides encoded thereby. In preferred embodiments, mutants result from mutation of the coding sequence, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

Mutants of cbƒ3 genes can be generated by any suitable method well known in the art, including but not limited to EMS induced mutagenesis, site-directed mutagenesis, randomized "point" mutagenesis, and domain-swap mutagenesis in which portions of the cbƒ3 cDNA are "swapped" with the analogous portion of other cbƒ3-encoding cDNAs such as used for identifying functional regions of terpene cyclases (Back and Chappell, PNAS 93:6841-6845 (1996), herein incorporated by reference).

It is contemplated that is possible to modify the structure of a peptide having an activity (e.g., such as a CRT/DRE binding activity), for such purposes as increasing synthetic activity or altering the affinity of the CBF3 protein for a binding partner or a kinetic activity. Such modified peptides are considered functional equivalents of peptides having an activity of a CBF3 activity as defined herein. A modified peptide can be produced in which the nucleotide sequence encoding the polypeptide has been altered, such as by substitution, deletion, or addition. In some preferred embodiments of the present invention, the alteration increases or decreases the effectiveness of the cbƒ3 gene product to exhibit a phenotype caused by altered responses of environmental stress response genes. In other words, construct "X" can be evaluated in order to determine whether it is a member of the genus of modified or variant cbƒ3 gene of the present invention as defined functionally, rather than structurally. Accordingly, in some embodiments the present invention provides nucleic acids comprising cbƒ3 or cbƒ3 AP binding domain sequence or CRT/DRE that can complement the coding regions of any of SEQ ID NOS:01, and 109-141 and 150, as well as the polypeptides encoded by such nucleic acids.

Moreover, as described above, mutant forms of CBF3 proteins are also contemplated as being equivalent to those peptides that are modified as set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule.

Accordingly, some embodiments of the present invention provide nucleic acids comprising sequences encoding variants of cbƒ3 gene products containing conservative replacements, as well as the proteins encoded by such nucleic acids. Conservative replacements are those that take place within a family of amino acids that are related in their side chains.

Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, $2^{nd}$ ed, W H Freeman and Co., 1981, herein incorporated by reference).

Whether a change in the amino acid sequence of a peptide results in a functional homolog can be readily determined by assessing the ability of the variant peptide to function in a fashion similar to the wild-type protein. Peptides having more than one replacement can readily be tested in the same manner. Examples of such likely conservative mutations in the AP2 DNA-binding domain of ryegrass CBF3 are shown in SEQ ID NOS:06, 17, 21 and the like. A further example of a conservative mutation in the AP2 DNA-binding domain of ryegrass CBF3 based upon a functionally silent mutation of glutamic acid to aspartic acid in an equivalent location of *Arabidopsis* CBF3/DREB1A AP binding domain is shown in SEQ ID NO:47 (Cao et al., Biochemistry (Mosc). June; 66(6):623-627 (2001)).

More rarely, a mutant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.). Accordingly, other embodiments of the present invention provide nucleic acids comprising sequences encoding variants of cbf3 gene products containing non-conservative replacements where the biological activity of the encoded protein is retained, as well as the proteins encoded by such nucleic acids.

Accordingly, other embodiments of the present invention provide nucleic acids comprising sequences encoding variants of cbf3 gene products containing non-conservative replacements where the biological activity of the encoded protein is unchanged, increased or decreased, slightly or significantly (e.g. for decreasing biological activity as in Cao et al., Biochemistry (Mosc). June;66(6):623-627 (2001) and Sakuma et al., Biochem. and Biophys. Research Commun., 290(3):998-1009 (25 Jan. 2002); all of which are herein incorporated by reference). An example of such nonconservative mutations within the AP2 DNA-binding domain of ryegrass CBF3 that decrease function is shown in SEQ ID NOS:46 (alanine is substituted for valine) (Cao et al., Biochemistry (Mosc). June;66(6):623-627 (2001). Accordingly, other embodiments of the present invention provide nucleic acids comprising sequences encoding variants of cbf3 gene products containing a combination of conservative and non-conservative replacements where the biological activity of the encoded protein is unchanged, increased or decreased, slightly or significantly, as well as the proteins encoded by such nucleic acids. An example of such a combination of conservative and non-conservative replacements where the biological activity of the encoded protein is significantly decreased is shown in SEQ ID NO:48 (Cao et al., Biochemistry (Mosc), June;66(6):623-627 (2001).

b. Directed Evolution.

Variants of cbf3 genes or coding sequences may be produced by methods such as directed evolution or other techniques for producing combinatorial libraries of variants. Thus, the present invention further contemplates a method of generating sets of nucleic acids that encode combinatorial mutants of the CBF3 proteins, as well as truncation mutants, and is especially useful for identifying potential variant sequences (i.e., homologs) that possess the biological activity of the encoded CBF3 proteins. In addition, screening such combinatorial libraries is used to generate, for example, novel encoded cbf3 gene product homologs that possess novel binding or other kinetic specificities or other biological activities. The invention further provides sets of nucleic acids generated as described above, where a set of nucleic acids encodes combinatorial mutants of the CBF3 proteins, or truncation mutants, as well as sets of the encoded proteins. The invention further provides any subset of such nucleic acids or proteins, where the subsets comprise at least two nucleic acids or at least two proteins.

It is contemplated that cbf, and in particular cbf3, cbf1, cbf2, cbf-like, or related cold activated genes; genes and coding sequences (e.g., any one or more of SEQ ID NOS:01, 109-141, and 146-150 and fragments and variants thereof for example SEQ ID Nos:06-48) can be utilized as starting nucleic acids for directed evolution. These techniques can be utilized to develop encoded CBF3 product variants having desirable properties such as increased kinetic activity or altered binding affinity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458-67 (1996); Leung et al., Technique, 1:11-15 (1989); Eckert and Kunkel, PCR Methods Appln., 1:17-24 (1991); Caldwell and Joyce, PCR Methods Appln., 2:28-33 (1992); and Zhao and Arnold, Nuc. Acids. Res., 25:1307-08 (1997), all of which are herein incorporated by reference).

After mutagenesis, the resulting clones are selected for desirable activity (e.g., screened for abolishing or restoring hydroxylase activity in a constitutive mutant, in a wild type background where hydroxylase activity is required, as described above and below). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or special PCR procedures (e.g., Smith, Nature, 370: 324-25 (1994); U.S. Pat. Nos. 5,837,458; 5,830,721; 5,811, 238; 5,733,731; all of which are herein incorporated by reference). Gene shuffling involves random fragmentation of several mutant DNAs followed by their reassembly by PCR into full-length molecules. Examples of various gene shuffling procedures include, but are not limited to, assembly following DNase treatment, the staggered extension process (STEP), and random priming in vitro recombination.

c. Homologs.

In some embodiments, the present invention provides isolated variants of the disclosed nucleic acid sequence encoding a cbf gene, and in particular of cbf3, cbf1, cbf2, cbf-like, or related cold response genes, and the polypeptides encoded thereby; these variants include mutants, fragments, fusion proteins or functional equivalents genes and protein products.

Some homologs of encoded cbf products have intracellular half-lives dramatically different than the corresponding wild-type protein. For example, the altered protein is rendered either more stable or less stable to proteolytic degradation or other cellular process that result in destruction of, or otherwise inactivate the encoded cbf product. Such homologs, and the genes that encode them, can be utilized to alter the activity of the encoded cbf products by modulating the half-life of the protein. For instance, a short half-life can give rise to more transient cbf3 biological effects. Other homologs have characteristics which are either similar to wild-type cbf3, or which differ in one or more respects from wild-type cbf3.

In some embodiments the combinatorial mutagenesis approach are contemplated for the present invention, the amino acid sequences for a population of cbf3 gene product homologs are aligned, preferably to promote the highest homology possible. Such a population of variants can include, for example, cbf3 gene homologs from one or more species (e.g. FIG. 9), or cbf3 gene homologs from the same species but which differ due to mutation (e.g. FIG. 10). Amino acids that appear at each position of the aligned sequences are selected to create a degenerate set of combinatorial sequences.

In a preferred embodiment of the present invention, the combinatorial cbf3 gene library is produced by way of a degenerate library of genes encoding a library of polypeptides that each include at least a portion of candidate encoded CBF3-protein sequence. For example, a mixture of synthetic oligonucleotides is enzymatically ligated into gene sequences such that the degenerate set of candidate cbf3 sequences are expressible as individual polypeptides, or alternatively, as a set of larger fusion proteins (e.g., for phage display) containing the set of cbf3 sequences therein.

There are many ways by which the library of potential cbf3 homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential cbf3 sequences or any combination of cbf3 sequences and cbf3 sequences. The synthesis of degenerate oligonucleotides is well known in the art (see e.g., Narang, Tetrahedron Lett., 39:3 9 (1983); Itakura et al., Recombinant DNA, in Walton (ed.), Proceedings of the 3$^{rd}$ Cleveland Symposium on Macromolecules, Elsevier, Amsterdam, pp 273-289 (1981); Itakura et al., Annu. Rev. Biochem., 53:323(1984); Itakura et al., Science 198:1056 (1984); Ike et al., Nucl. Acid Res., 11:477 (1983); all of which are herein incorporated by reference). Such techniques have been employed in the directed evolution of other proteins (see e.g., Scott et al., Science, 249:386-390 (1980); Roberts et al., Proc. Natl. Acad. Sci. USA, 89:2429-2433 (1992); Devlin et al., Science, 249:404-406 (1990); Cwirla et al., Proc. Natl. Acad. Sci. USA, 87:6378-6382 (1990); as well as U.S. Pat. Nos. 5,223,409; 5,198,346; and 5,096,815; all of which are herein incorporated by reference).

d. Screening Gene Products.

A wide range of techniques are known in the art for screening gene products of combinatorial libraries made by point mutations, and for screening cDNA libraries for gene products having a certain property. Such techniques are generally adaptable for rapid screening of the gene libraries generated by the combinatorial mutagenesis of cbf3 and/or cbf3 homologs, paralogs, and orthologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Each of the illustrative assays described below are amenable to high throughput analysis as necessary to screen large numbers of degenerate sequences created by combinatorial mutagenesis techniques.

Accordingly, in some embodiments of the present invention, the gene library is cloned into the gene for a surface membrane protein of a bacterial cell, and the resulting fusion protein detected by panning (WO 88/06630; Fuchs et al., BioTechnol., 9:1370-1371 (1991); and Goward et al., TIBS 18:136-140 (1992); all of which are herein incorporated by reference. In other embodiments of the present invention, fluorescently labeled molecules that bind encoded CBF3 products can be used to score for potentially functional CBF3 and/or CBF3 homologs, paralogs, and orthologs. Cells are visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences are expressed on the surface of infectious phage in the filamentous phage system, thereby conferring two significant benefits. First, since these phages can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical $E.\ coli$ filamentous phages M13, fd, and f1 are most often used in phage display libraries, as either of the phage gIII or gVIII coat proteins can be used to generate fusion proteins without disrupting the ultimate packaging of the viral particle (See e.g., WO 90/02909; WO 92/09690; Marks et al., J. Biol. Chem., 267:16007-16010 (1992); Griffths et al., EMBO J., 12:725-734 (1993); Clackson et al., Nature 352:624-628 (1991); and Barbas et al., Proc. Natl. Acad. Sci., 89:4457-4461 (1992); all of which are herein incorporated by reference).

In another embodiment of the present invention, the recombinant phage antibody system (e.g., RPAS, Pharmacia Catalog number 27-9400-01) is modified for use in expressing and screening of encoded CBF3 and/or CBF homolog, paralog, and ortholog product combinatorial libraries. The pCANTAB 5 phagemid of the RPAS kit contains the gene that encodes the phage gIII coat protein. In some embodiments of the present invention, the cbf3 and/or cbf combinatorial gene library is cloned into the phagemid adjacent to the gIII signal sequence such that it is expressed as a gIII fusion protein. In other embodiments of the present invention, the phagemid is used to transform competent $E.\ coli$ TG1 cells after ligation. In still other embodiments of the present invention, transformed cells are subsequently infected with M13KO7 helper phage to rescue the phagemid and its candidate cbf3 gene insert. The resulting recombinant phage containing phagemid DNA encoding a specific candidate CBF3 protein and display one or more copies of the corresponding fusion coat protein. In some embodiments of the present invention, the phage-displayed candidate proteins that display any property characteristic of a CBF3 protein are selected or enriched by panning. The bound phage is then isolated, and if the recombinant phages express at least one copy of the wild type gIII coat protein, they will retain their ability to infect *E. coli*. Thus, successive rounds of reinfection of *E. coli* and panning will greatly enrich for CBF3 and/or CBF3 homologs, paralogs, and orthologs.

In light of the present disclosure, other forms of mutagenesis generally applicable will be apparent to those skilled in the art in addition to the aforementioned rational mutagenesis based on conserved versus non-conserved residues. For example, CBF3 homologs can be generated and screened using, for example, alanine scanning mutagenesis and the like (Ruf et al., Biochem, 33:1565-1572 (1994); Wang et al., J. Biol Chem, 269:3095-3099 (1994); Balint Gene 137:109-118 (1993); Grodberg et al., Eur. J. Biochem., 218:597-601 (1993); Nagashima et al., J. Biol. Chem., 268:2888-2892 (1993); Lowman et al., Biochem, 30:10832-10838 (1991); and Cunningham et al., Science, 244:1081-1085 (1989); all of which are herein incorporated by reference), by linker scanning mutagenesis (Gustin et al., Virol., 193:653-660 (1993); Brown et al., Mol. Cell. Biol., 12:2644-2652 (1992); McKnight and Kingsbury Science, July 23;217(4557):316-24 (1982), or by saturation mutagenesis (Myers et al., Science, 2;232(4750):613-618 (1986); all of which are herein incorporated by reference).

In some preferred embodiments, the ability of the CBF3 sequence to bind to its response element is tested in vitro (e.g. DREB1a/CFB3 binding to an intact DRE of a rd29 promoter in Liu et al., The Plant Cell 10:1391-1406 (1998)).

In some preferred embodiments, the ability of the CBF3 sequence to bind to its response element is tested in vivo. Examples of such in vivo tests include prokaryotic expression and detection systems (e.g. yeast transactivation systems that detect DRE binding in Liu et al., The Plant Cell 10:1391-1406 (1998); U.S. Pat. No. 6,670,528; all of which are herein incorporated by reference.

e. Truncation Mutants of CBF3.

In addition, the present invention provides isolated nucleic acid sequences encoding fragments of encoded CBF3 products like genes (i.e., truncation mutants), and the polypeptides encoded by such nucleic acid sequences. In preferred embodiments, the CBF3 fragment is biologically active. In some embodiments of the present invention, when expression of a portion of a CBF3 and/or CBF3-like protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751-757 (1987), herein incorporated by reference) and *Salmonella typhimurium* and its in vitro activity has been demonstrated on recombinant proteins (Miller et al., Proc. Natl. Acad. Sci. USA, 84:2718-1722 (1990), herein incorporated by reference). Therefore, removal of an N-terminal methionine, if desired, can be achieved either in vivo by expressing such recombinant polypeptides in a host that produces MAP (e.g., *E. coli* or CM89 or *S. cerevisiae*), or in vitro by use of purified MAP.

f. Fusion Proteins Containing CBF3 and/or CBF3-like Proteins.

The present invention also provides nucleic acid sequences encoding fusion proteins incorporating all or part of CBF3 and/or CBF3-like proteins, and the polypeptides encoded by such nucleic acid sequences. In some embodiments of the present invention, chimeric constructs code for fusion proteins containing a portion of a CBF3 and/or CBF3-like protein and a portion of another gene. In some embodiments, the fusion proteins have biological activity similar to the wild type CBF3 (e.g., have at least one desired biological activity of a CBF3 protein). In other embodiments, the fusion protein has altered biological activity. In addition to utilizing fusion proteins to alter biological activity, it is widely appreciated that fusion proteins can also facilitate the expression and/or purification of proteins, such as the CBF3 and/or CBF3-like protein of the present invention. Accordingly, in some embodiments of the present invention, a CBF3 protein is generated as a glutathione-S-transferase (i.e., GST fusion protein). It is contemplated that such GST fusion proteins enables easy purification of the CBF3 and/or CBF3-like protein, such as by the use of glutathione-derivatized matrices (See e.g., Ausabel et al. (eds.), Current Protocols in Molecular Biology, John Wiley & Sons, NY (1991), herein incorporated by reference).

In some embodiments, the fusion proteins have a CBF3 and/or a CBF3-like functional domain with a fusion partner. Accordingly, in some embodiments of the present invention, the coding sequences for the polypeptide (e.g., a CBF3 functional domain) are incorporated as a part of a fusion gene including a nucleotide sequence encoding a different polypeptide. It is contemplated that such a single fusion product polypeptide is able to provide a transgenic plant that produces one or more environmental tolerance, low temperature tolerance, increasing low temperature tolerance, decreasing height, altering growth rates and delaying flowering times.

In another embodiment of the present invention, a fusion gene coding for a purification leader sequence, such as a poly-(His)/enterokinase cleavage site sequence at the N-terminus of the desired portion of a CBF3 and/or CBF3-like protein allows purification of the expressed CBF3 and/or CBF3-like fusion protein by affinity chromatography using a $Ni^{2+}$ metal resin. In still another embodiment of the present invention, the purification leader sequence is then subsequently removed by treatment with enterokinase (See e.g., Hochuli et al., J. Chromatogr., 411:177 (1987); and Janknecht et al., Proc. Natl. Acad. Sci. USA, 88:8972, all of which are herein incorporated by reference). In yet other embodiments of the present invention, a fusion gene coding for a purification sequence appended to either the N or the C terminus allows for affinity purification; one example is addition of a hexahistidine tag to the carboxy terminus of a CBF3 and/or CBF3-like protein that is optimal for affinity purification.

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See e.g., Current Protocols in Molecular Biology, supra, herein incorporated by reference).

B. Encoded cbf3 Gene Polypeptides.

The present invention provides isolated CBF3 and/or CBF3-like polypeptides, as well as variants, homologs, mutants or fusion proteins thereof, as described above. In some embodiments of the present invention, the polypeptide is a naturally purified product, while in other embodiments it is a product of chemical synthetic procedures, and in still other embodiments it is produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention is glycosylated or non-glycosylated. In other embodiments, the polypeptides of the invention also include an initial methionine amino acid residue.

1. Purification of CBF3 Polypeptides.

The present invention provides or contemplates purified CBF3 and/or CBF3-like polypeptides as well as variants, homologs, mutants or fusion proteins thereof, as described above. In some embodiments of the present invention, CBF3 and/or CBF3-like polypeptides purified from recombinant organisms as described below are provided. In other embodiments, CBF3 and/or CBF3-like polypeptides purified from recombinant bacterial extracts transformed with ryegrass cbf3 and/or cbf3-like cDNA, and in particular any one or more of cbf3, and/or cbf3-like and or related transcription factor cDNA, are provided (SEQ ID NOS: 02-108).

The present invention also provides methods for recovering and purifying CBF3 and/or CBF3-like from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

The present invention further provides nucleic acid sequences having the coding sequence (or a portion of the coding sequence) for a CBF3 protein (or a portion of a CBF3 protein) (e.g., SEQ ID NOS:01, 109-141 and 150) and/or CBF3-like protein fused in frame to a marker sequence that allows for expression alone or for both expression and purification of the polypeptide of the present invention. A non-limiting example of a marker sequence is a hexahistidine tag that is supplied by a vector, for example, a pQE-30 vector which adds a hexahistidine tag to the N terminal of a cbf3 gene and/or cbf3-like gene and which results in expression of the polypeptide in a bacterial host, or, for example, the marker sequence is a hemagglutinin (HA) tag when a mammalian host is used. The HA tag corresponds to an epitope derived from the influenza hemagglutinin protein (Wilson et al., Cell, 37:767 (1984), herein incorporated by reference).

2. Chemical Synthesis of CBF3 and/or CBF3-like Polypeptides.

In an alternate embodiment of the invention, the coding sequence of cbf3 genes and/or cbf3-like genes, and in particular of any one or more of cbf3, and/or cbf3-like, or related transcription factor genes, is synthesized in whole or in part, using chemical methods well known in the art (See e.g., Caruthers et al., Nucleic Acids Symp Ser., 7:215-223 (1980); Crea and Horn, Nucl. Acids Res., May 24;8(10): 2331-2348 (1980); Matteucci and Caruthers, Tetrahedron Lett., 21:719 (1980); and Chow et al., Nucl. Acids Res., November 11;10(21):6695-714 (1981), all of which are herein incorporated by reference). In other embodiments of the present invention, the protein itself is produced using chemical methods to synthesize an entire CBF3 and/or CBF3-like amino acid sequence (for example, SEQ ID NOS:01, and 109-141 and 150) or a portion thereof. For example, peptides are synthesized by solid phase techniques, cleaved from the resin, and purified by preparative high performance liquid chromatography (See e.g., Creighton, Proteins Structures And Molecular Principles, W.H. Freeman and Co, New York N.Y. (1983), herein incorporated by reference). In other embodiments of the present invention, the composition of the synthetic peptides is confirmed by amino acid analysis or sequencing (See e.g., Creighton, supra, herein incorporated by reference).

Direct peptide synthesis can be performed using various solid-phase techniques (Roberge et al., Science, 269:202-204 (1995), herein incorporated by reference) and automated synthesis may be achieved, for example, using ABI 431A Peptide Synthesizer (Perkin Elmer) in accordance with the instructions provided by the manufacturer. Additionally, the amino acid sequence of CBF3 and/or CBF3-like, or any part thereof, may be altered during direct synthesis and/or combined using chemical methods with other sequences to produce a variant polypeptide.

3. Generation of CDF3 Antibodies.

In some embodiments of the present invention, antibodies are generated to allow for the detection and characterization of a CBF3 protein and/or CBF3-like proteins. The antibodies may be prepared using various immunogens. In one embodiment, the immunogen is an *Arabidopsis* CBF3 peptide (e.g., an amino acid sequence as depicted in SEQ ID NOS:01, 109-141 and 150), or CBF3-like, or a fragment thereof, to generate antibodies that recognize a plant CBF3 and/or CBF3-like protein. Such antibodies include, but are not limited to polyclonal, monoclonal, chimeric, single chain, Fab fragments, and Fab expression libraries.

Various procedures known in the art may be used for the production of polyclonal antibodies directed against a CBF3 protein. For the production of antibody, various host animals can be immunized by injection with the peptide corresponding to the CBF3 protein and/or CBF3-like protein epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface-active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward a CBF3 protein and/or CBF3-like protein, it is contemplated that any technique that provides for the production of antibody molecules by continuous cell lines in culture finds use with the present invention (See e.g., Harlow and Lane, Antibodies: A Laboratory Manual, Cold Spring Harbor Laboratory Press, Cold Spring Harbor, N.Y., herein incorporated by reference). These include but are not limited to the hybridoma technique originally developed by Köhler and Milstein (Köhler and Milstein, Nature, 256:495-497 (1975), herein incorporated by reference), as well as the trioma technique, the human B-cell hybridoma technique (See e.g., Kozbor et al., Immunol Today, 4:72 (1983), herein incorporated by reference), and the EBV-hybridoma technique to produce human monoclonal antibodies (Cole et al., in Monoclonal Antibodies and Cancer Therapy, Alan R. Liss, Inc., pp. 77-96 (1985), herein incorporated by reference).

In an additional embodiment of the invention, monoclonal antibodies are produced in germ-free animals utilizing technology such as that described in PCT/US90/02545). Furthermore, it is contemplated that plant tissue antibodies may be generated (e.g. Canas and Malmberg, Plant Sci 83:195-203 (1992), herein incorporated by reference) or by producing plant protein specific monoclonal antibodies by using mouse hybridomas (Lund et al., Plant Physiol 116:1097-1110 (1998), herein incorporated by reference).

In addition, it is contemplated that techniques described for the production of single chain antibodies (U.S. Pat. No. 4,946,778, herein incorporated by reference) find use in producing a CBF3 and/or CBF3-like protein-specific single chain antibodies. An additional embodiment of the invention utilizes the techniques described for the construction of Fab expression libraries (Huse et al., Science, 246:1275-1281 (1989), herein incorporated by reference) to allow rapid and easy identification of monoclonal Fab fragments with the desired specificity for a CBF3 and/or CBF3-like protein.

It is contemplated that any technique suitable for producing antibody fragments finds use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody is accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay. In some embodiments of the present invention, the foregoing antibodies are used in methods known in the art relating to the expression of a CBF3 protein (e.g., for Western blotting), measuring levels thereof in appropriate biological samples, etc. The antibodies can be used to detect a CBF3 and/or CBF3-like protein in a biological sample from a plant. The biological sample can be an extract of a tissue, or a sample fixed for microscopic examination.

The biological samples are then be tested directly for the presence of a CBF3 and/or CBF3-like protein using an appropriate strategy (e.g., ELISA or radioimmunoassay) and format (e.g., microwells, dipstick (e.g., as described in WO 93/03367 herein incorporated by reference), etc. Alternatively, proteins in the sample can be size separated (e.g., by polyacrylamide gel electrophoresis (PAGE), in the presence or not of sodium dodecyl sulfate (SDS), and the presence of a CBF3 and/or CBF3-like protein detected by immunoblotting (Western blotting). Immunoblotting techniques are generally more effective with antibodies generated against a peptide corresponding to an epitope of a protein, and hence, are particularly suited to the present invention.

C. Expression of Cloned cbf3.

In some embodiments, genes described above may be used to generate recombinant DNA molecules that direct the expression of the encoded protein product in appropriate host cells. As will be understood by those of skill in the art, it may be advantageous to produce cbf3-encoding nucleotide sequences possessing non-naturally occurring codons. Therefore, in some preferred embodiments, codons preferred by a particular prokaryotic or eukaryotic host (Murray et al., Nucl. Acids Res., 17(2):477-498 (1989), herein incorporated by reference) can be selected, for example, to increase the rate of cbf3 expression or to produce recombinant RNA transcripts having desirable properties, such as a longer half-life, than transcripts produced from naturally occurring sequence.

1. Vectors for Production of CBF3 and/or CBF3-like.

The nucleic acid sequences of the present invention may be employed for producing polypeptides by recombinant techniques. Thus, for example, the nucleic acid sequence may be included in any one of a variety of expression vectors for expressing a polypeptide.

In some embodiments of the present invention, vectors include, but are not limited to, chromosomal, nonchromosomal and synthetic DNA sequences (e.g., derivatives of plant tumor sequences, T-DNA sequences, derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic sequences as broadly described above (e.g., SEQ ID NOS:01, 109-141 and 150). In some embodiments of the present invention, the constructs comprise a vector, such as a plasmid or eukaryotic vector, or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors for incorporation into host cells include, but are not limited to, the following vectors and their derivatives: 1) Prokaryotic and other host cells—pBI221, pBI121 (Clonetech), pYeDP60, pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); pBI2113Not, pBI2113, pBI101, pBI121, pGA482, pGAH, PBIG, and 2) Eukaryotic and other host cells—pHISi-1, pMLBART, *Agrobacterium tumefaciens* strain GV3101, pSV2CAT, pOG44, PXT1, pSG (Stratagene); pSVK3, pBPV, pMSG, and pSVL (Pharmacia); pLGV23Neo, pNCAT, and pMON200. Any other plasmid or vector may be used as long as they are replicable and viable in the host.

In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences for expression in plants. In other embodiments, DNA sequences derived from the SV40 splice, and polyadenylation sites may be used to provide the required nontranscribed genetic elements.

In certain embodiments of the present invention, the nucleic acid sequence in the expression vector is operatively linked to an appropriate expression control sequence(s) (promoter) to direct mRNA synthesis. Promoters useful in the present invention include, but are not limited to, the LTR of SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, DNA encoding the polypeptides of the present invention is expressed with plant promoters. Plant promoters can by constitutive, leaky and transient. In some embodiments, a promoter is a transient promoter (e.g. transient rd29A promoter as in U.S. Pat. No. 6,495,742B1; U.S. Pat. No. 6,670,528; herein incorporated by reference). Examples of constitutive promoters contemplated for the present invention include a "cauliflower mosaic virus 35S promoter" and "CaMV35S promoter" as used for expression of *Arabidopsis thaliana* DREB1a and DREB2 (e.g. U.S. Pat. No. 6,495,742B1; U.S. Pat. No. 6,670,528; herein incorporated by reference). In some embodiments, promoters of the present invention are stress response promoters and comprise one or more of a rd29A gene promoter (Yamaguchi-Shinozaki, et al., The Plant Cell 6:251-264 (1994)); rd29B gene promoter (Yamaguchi-Shinozaki, et al., The Plant Cell 6:251-264 (1994)); rd17 gene promoter (Iwasaki, et al., Plant Physiol., 115:1287 (1997)); rd22 gene promoter (Iwasaki, et al., Mol. Gen. Genet., 247:391-398 (1995)); DREB1A gene promoter (Shinwari, et al., Biochem. Biophys. Res. Com. 250:161-170 (1988)); cor6.6 gene promoter (Wang, et al., Plant Mol. Biol. 28:619-634 (1995)); cor15a gene promoter (Baker, et al., Plant Mol. Biol. 24:701-713 (1994)); erd1 gene promoter (Nakashima et al., Plant J. 12:851-861 (1997)); kin1 gene promoter (Wang, et al., Plant Mol. Biol. 28:605-617 (1995)); all of which are herein incorporated by reference.

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of CBF3.

In a further embodiment, the present invention provides host cells containing the above-described constructs. In some embodiments of the present invention, the host cell is a higher eukaryotic cell (e.g., a plant cell). An example of a transgenic plant cell and methods thereof are provided in U.S. patent application Pub. No. 20030144192A1, herein incorporated by reference. In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175(1981), herein incorporated by reference), 293T, C127, 3T3, HeLa and BHK cell lines, NT-1 (tobacco cell culture line), root cell and cultured roots in rhizosecretion (Gleba et al., Proc Natl Acad Sci USA 96: 5973-5977 (1999), herein incorporated by reference).

The constructs in host cells can be used in a conventional manner to produce the gene product encoded by the recombinant sequence. In some embodiments, introduction of the construct into the host cell can be accomplished by calcium phosphate transfection; DEAE-Dextran mediated transfection, or electroporation (See e.g., Davis et al., Basic Methods in Molecular Biology, (1986), herein incorporated by reference). Alternatively, in some embodiments of the present invention, the polypeptides of the invention can be synthetically produced by conventional peptide synthesizers.

Proteins can be expressed in eukaryotic cells, yeast, bacteria, or other cells under the control of appropriate promoters. An example of eukaryotic production of *Arabidopsis* DREB1a/CBF3 is shown in Liu et al., The Plant Cell 10:1391-1406 (1998); U.S. patent application No. 20030207947A1; all of which are herein incorporated by reference. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual*, $2^{nd}$ ed., Cold Spring Harbor Laboratory Press, New York (1989), herein incorporated by reference.

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonification, mechanical disruption, or use of cell lysing agents.

II. Methods of Modifying Environmental Tolerance Phenotype by Manipulating cbf3 Gene Expression.

The present invention also provides methods of using cbf3 and/or cbf and/or cbf-like ortholog genes. In some embodiments, the sequences are used for research purposes. For example, nucleic acid sequences comprising coding sequences of a cbf3 and/or cbf and/or cbf-like orthologs, for example any one or more of CBF3and/or CBF and/or CBF-like or related AP2 binding domain containing polypeptide are used to discover other genes that affect environmental stress tolerance. In other embodiments, endogenous plant cbf3 genes, such as any one or more of cbf3 and/or cbf and/or cbf-like or related AP2 binding domain containing genes, are silenced, for example with antisense RNA, RNAi, siRNA, hpRNA, or by cosuppression, and the effects on environmental tolerance is observed. Examples of such antisense mediation in ryegrass include Bhalla et al., Proc Natl Acad Sci USA, 96(20):11676-11680 (1999). Examples of ihpRNA gene silencing in rice are provided by Wesley et al., The Plant Journal 27(6):581-590 (2001), herein incorporated by reference.

In other embodiments, heterologous plant cbf3 genes, such as any one or more of cbf3 and/or cbf and/or cbf-like or related AP2 DNA-binding domain containing genes, are silenced, for example with antisense RNA, RNAi or by cosuppression, in order to produce a plant with increased heat tolerance. Examples of such antisense mediation include U.S. patent application Pub. No. 20020062499A1; herein incorporated by reference.

In other embodiments, modifications to nucleic acid sequences encoding cbf3 genes, such as any one or more of cbf3 and/or cbf and/or cbf-like genes, are made, and the effects observed in vivo. For example, modified nucleic acid sequences encoding at least one cbf3 gene are utilized to transform plants in which endogenous cbf3 genes are silenced by antisense RNA technology, cosuppression or RNAi, and the effects observed. In other embodiments, cbf3 genes, either unmodified or modified, are expressed in vitro translation and/or transcription systems, and the interaction of the transcribed and/or translation product with other system components (such as nucleic acids, proteins, lipids, carbohydrates, or any combination of any of these molecules) observed.

In other embodiments, cbf3 gene sequences are utilized to alter environmental stress tolerance and/or to control the growth rate in a host. In some embodiments, cbf3 sequences alter the low temperature stress. In yet other embodiments, cbf3 gene sequences are utilized to confer a low temperature phenotype, and/or to decrease a low temperature phenotype or to increase a low temperature phenotype, or to promote the production of novel growth characteristics (e.g. delay in flowering, dwarfism, etc.). Thus, it is contemplated that nucleic acids encoding a CBF3 polypeptide of the present invention may be utilized to either increase or decrease the level of cbf3 mRNA and/or protein in transfected cells as compared to the levels in wild-type cells. An example of altered *Arabidopsis thalania* cbf3 expression in transgenic canola (*B. napus* cv. *Westar*) plants is provided in U.S. patent application No. 20030233680, herein incorporated by reference.

In some embodiments, the present invention provides methods to over-ride an environmental tolerance stress phenotype, and/or to promote overproduction of CBF, in plants that require CBF3, by disrupting the function of at least one cbf3 gene in the plant. In these embodiments, the function of at least one cbf3 gene is disrupted by any effective technique, including but not limited to antisense, co-suppression, and RNA interference, as is described above and below.

In yet other embodiments, the present invention provides methods to alter environmental stress tolerance or growth phenotype in plants in which CBF3 or CBF or CBF-like is not usually found and/or add a novel or environmental stress tolerance or growth phenotype in plants in which cold tolerance or dwarf phenotype or delay in flowering is not otherwise found, by expression of at least one heterologous cbf3 gene. Thus, in some embodiments, nucleic acids comprising coding sequences of at least one cbf3 gene, for example any one or more of cbf3, are used to transform plants without a pathway for producing a particular environmental stress tolerance or growth phenotype such cold tolerance or dwarf phenotype or delay in flowering. It is contemplated that some particular plant species or cultivars do not express any cbf3 genes. For these plants, it is necessary to transform a plant with the necessary cbf3 genes required to confer the preferred environmental stress tolerance or growth phenotype. It is contemplated that other particular plant species or cultivars may possess at least one cbf3 gene; thus, for these plants, it is necessary to transform a plant with those cbf3 genes that can interact with endogenous cbf3 genes in order to confer a preferred environmental stress phenotype.

The presence of cbf3 genes in a species or cultivar can be tested by a number of ways, including but not limited to using probes from genomic and cDNA from CBF and downstream CBF activated genes, or by using PCR analysis or by using Northern blotting (examples in FIGS. 3a-d), or antibodies specific to CBF3 polypeptides. The additional cbf3 or cbf or cor gene(s) needed to confer the desired phenotype can then be transformed into a plant to confer the phenotype. In these embodiments, plants are transformed with cbf3 or cbf or cor gene(s) genes as described above and below.

As described above, in some embodiments, it is contemplated that the nucleic acids encoding a CBF3 polypeptide of the present invention may be utilized to decrease the level of cbf3 mRNA and/or protein in transfected cells as compared to the levels in wild-type cells. In some of these embodiments, the nucleic acid sequence encoding a CBF3 protein of the present invention is used to design a nucleic acid sequence encoding a nucleic acid product that interferes with the expression of the nucleic acid encoding a CBF3 polypeptide, where the interference is based upon a coding sequence of the encoded CBF3 polypeptide.

One method of reducing cbf3 expression utilizes expression of antisense transcripts. Antisense RNA has been used to inhibit plant target genes in a tissue-specific manner (e.g., van der Krol et al. Biotechniques 6:958-976 (1988), herein incorporated by reference). Antisense inhibition has been shown using the entire cDNA sequence as well as a partial cDNA sequence (e.g., Sheehy et al. Proc. Natl. Acad. Sci. USA 85:8805-8809 (1988); Cannon et al. Plant Mol. Biol. 15:39-47 (1990), herein incorporated by reference). There is also evidence that 3' non-coding sequence fragment and 5' coding sequence fragments, containing as few as 41 basepairs of a 1.87 kb cDNA, can play important roles in antisense inhibition (Ch'ng et al. Proc. Natl. Acad. Sci. USA 86:10006-10010 (1989), herein incorporated by reference).

Accordingly, in some embodiments, a cbf3 encoding-nucleic acid of the present invention are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full-length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch-viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff, et al. Nature 334:585-591 (1988). Ribozymes targeted to the mRNA of a lipid biosynthetic gene, resulting in a heritable increase of the target enzyme substrate, have also been described (Merlo A O et al., Plant Cell 10:1603-1621 (1998), herein incorporated by reference).

Another method of reducing cbf3 expression utilizes the phenomenon of cosuppression or gene silencing (See e.g., U.S. Pat. No. 6,063,947, herein incorporated by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (e.g., Napoli et al. Plant Cell 2:279-289 (1990); van der Krol et al. Plant Cell 2:291-299 (1990); Smith et al. Mol. Gen. Genetics 224:477-481 (1990), herein incorporated by reference). Accordingly, in some embodiments the nucleic acid sequences encoding a cbf3 of the present invention are expressed in another species of plant to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants that are over-expressers. A higher identity in a shorter than full-length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Another method to decrease expression of a gene (either endogenous or exogenous) is via siRNAs. siRNAs can be applied to a plant and taken up by plant cells; alternatively, siRNAs can be expressed in vivo from an expression cassette. RNAi refers to the introduction of homologous double stranded RNA (dsRNA) to target a specific gene product, resulting in post-transcriptional silencing of that gene. This phenomenon was first reported in *Caenorhabditis elegans* by Guo and Kemphues Cell, 81(4):611-620 (1995) and subsequently Fire et al. Nature 391:806-811) (1998) discovered that it is the presence of dsRNA, formed from the annealing of sense and antisense strands present in the in vitro RNA preps, that is responsible for producing the interfering activity. The present invention contemplates the use of RNA interference (RNAi) to downregulate the expression of cbf3 genes. In preferred embodiments, the dsRNA used to initiate RNAi, may be isolated from native source or produced by known means, e.g., transcribed from DNA. The promoters and vectors described in more detail below are suitable for producing dsRNA. RNA is synthesized either in vivo or in vitro. In some embodiments, endogenous RNA polymerase of the cell may mediate transcription in vivo, or cloned RNA polymerase can be used for transcription in vivo or in vitro. In other embodiments, the RNA is provided transcription from a transgene in vivo or an expression construct. In some embodiments, the RNA strands are polyadenylated; in other embodiments, the RNA strands are capable of being translated into a polypeptide by a cell's translational apparatus. In still other embodiments, the RNA is chemically or enzymatically synthesized by manual or automated reactions. In further embodiments, the RNA is synthesized by a cellular RNA polymerase or a bacteriophage RNA polymerase (e.g., T3, T7, SP6). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. In some embodiments, the RNA is dried for storage or dissolved in an aqueous solution. In other embodiments, the solution contains buffers or salts to promote annealing, and/or stabilization of the duplex strands.

In some embodiments, the dsRNA is transcribed from the vectors as two separate stands. In other embodiments, the two strands of DNA used to form the dsRNA may belong to the same or two different duplexes in which they each form with a DNA strand of at least partially complementary sequence. When the dsRNA is thus produced, the DNA sequence to be transcribed is flanked by two promoters, one controlling the transcription of one of the strands, and the other that of the complementary strand. These two promoters may be identical or different. In some embodiments, a DNA duplex provided at each end with a promoter sequence can directly generate RNAs of defined length, and which can join in pairs to form a dsRNA. See, e.g., U.S. Pat. No. 5,795,715; incorporated herein by reference. RNA duplex formation may be initiated either inside or outside the cell.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases.

There is no upper limit on the length of the dsRNA that can be used. For example, the dsRNA can range from about 21 base pairs (bp) of the gene to the full length of the gene or more. In one embodiment, the dsRNA used in the methods of the present invention is about 1000 bp in length. In another embodiment, the dsRNA is about 500 bp in length. In yet another embodiment, the dsRNA is about 22 bp in length. In some preferred embodiments, the sequences that mediate RNAi are from about 21 to about 23 nucleotides. That is, the isolated RNAs of the present invention mediate degradation of the target RNA (e.g., major sperm protein, chitin synthase, or RNA polymerase II). In preferred embodiments, dsRNAs corresponding to all or a portion of nucleic acids encoding a polypeptide comprising SEQ ID NOS:02, 03, and 70-108, or nucleic acids corresponding to SEQ ID NOS:01, 109-141 and 150 are utilized.

The double stranded RNA of the present invention need only be sufficiently similar to natural RNA that it has the ability to mediate RNAi for the target RNA. In one embodiment, the present invention relates to RNA molecules of varying lengths that direct cleavage of specific mRNA to which their sequence corresponds. It is not necessary that there be perfect correspondence of the sequences, but the correspondence must be sufficient to enable the RNA to direct RNAi cleavage of the target mRNA. In a particular embodiment, the RNA molecules of the present invention comprise a 3' hydroxyl group. In some embodiments, the amount of target RNA (e.g., CBF3mRNA) is reduced in the cells of the plant exposed to target specific double stranded RNA as compared to cells of the plant or a control plant that have not been exposed to target specific double stranded RNA.

In still further embodiments, knockouts may be generated by homologous recombination. In some embodiments, knockouts may be generated by heterologous recombination. In some embodiments knockouts may be generated by *Agrobacterium* transfer-DNA. Generally, plant cells are incubated with a strain of *Agrobacterium* that contains a targeting vector in which sequences that are homologous to a DNA sequence inside the target locus are flanked by *Agrobacterium* transfer-DNA (T-DNA) sequences, as previously described.

Homologous recombination may be achieved using targeting vectors that contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

A. Transgenic Plants, Seeds, and Plant Parts.

The present invention also provides a transgenic plant, a transgenic plant part, a transgenic plant cell, or a transgenic plant seed, comprising any of the nucleic acid sequences of the present invention described above, wherein the nucleic acid sequence is heterologous to the transgenic plant, a transgenic plant part, a transgenic plant cell, or a transgenic plant seed. In some embodiments, the nucleic acid sequence is operably linked to any of the promoters described above. In other embodiments, the nucleic acid is present in any of the vectors described above.

The present invention also provides a method for producing CBF3 and/or CBF, and/or CBF-like polypeptide, comprising culturing a transgenic host cell comprising a heterologous nucleic acid sequence, wherein the heterologous nucleic acid sequence is any of the nucleic acid sequences of the present invention described above which encode a CBF3 and/or a CBF, and/or a CBF-like polypeptide or variant thereof, under conditions sufficient for expression of an encoded CBF3 and/or CBF, and/or CBF-like polypeptide, and producing CBF3 and/or CBF, and/or CBF-like polypeptide in the transgenic host cell.

The present invention also provides a method for altering the phenotype of a plant, comprising providing an expression vector comprising any of the nucleic acid sequences of the present invention described above, and plant tissue, and transfecting plant tissue with the vector under conditions such that a plant is obtained from the transfected tissue and the nucleic acid sequence is expressed in the plant and the phenotype of the plant is altered. In some embodiments, the nucleic acid sequence encodes CBF3 and/or CBF, and/or CBF-like polypeptide or variant thereof. In other embodiments, the nucleic sequence encodes a nucleic acid product that interferes with the expression of a nucleic acid sequence CBF3 and/or CBF, and/or CBF-like polypeptide or variant thereof, wherein the interference is based upon the coding sequence of CBF3 and/or CBF, and/or CBF-like protein or variant thereof.

The present invention also provides a method for altering the phenotype of a plant, comprising growing a transgenic plant comprising an expression vector comprising any of the nucleic acid sequences of the present invention described above under conditions such that the nucleic acid sequence is expressed and the phenotype of the plant is altered. In some embodiments, the nucleic acid sequence is CBF3 and/or CBF, and/or CBF-like polypeptide or variant thereof. In other embodiments, the nucleic sequence encodes a nucleic acid product which interferes with the expression of a nucleic acid sequence encoding CBF3 and/or CBF, and/or CBF-like polypeptide or variant thereof, wherein the interference is based upon the coding sequence of CBF3 and/or CBF, and/or CBF-like polypeptide or variant thereof.

Accordingly, in some embodiments, the present invention provides plants transformed with at least one heterologous gene encoding a cbf3 or cbf or cbf-like gene, or encoding a sequence designed to increase cbf3 or cbf or cbf-like gene expression. It is contemplated that these heterologous genes are utilized to increase the level of the polypeptide encoded by heterologous genes, or to decrease the level of the protein encoded by endogenous genes.

1. Plants and Seeds.

The present invention is not limited to any particular plant comprising a heterologous nucleic acid (e.g., plants comprising a heterologous nucleic acid encoding a polypeptide comprising SEQ ID NOS:02-05, 155 and 156, or nucleic acids corresponding to SEQ ID NOS:01 and 150). Indeed, a variety of plants are contemplated, including but not limited to turfgrasses, sedges and rushes. The present invention is not meant to limit the varieties of plants and include natural, cultivated, selectively bred, engineered (transgenic), natural mutants, cultivated mutants, engineered mutants and the like.

Some embodiments contemplate altering one or more of an environmental stress tolerance phenotype, enhancing cold tolerance, increasing time to flowering, and decreasing height in turfgrasses such as bahiagrass (e.g. Tifton 9 Bahiagrass), Bermudagrass (e.g. Ranchero Frio), centipedegrass, St. Augustine grass (e.g. cultivated varieties in U.S. Pat. Nos. PP6,922; PP6,921; PP6,372; PP4,097; all of which are herein incorporated by reference), zoysiagrass, carpetgrass, buffalograss (e.g. *Buchloe* spp.), hurricanegrass and seashore paspalum; switch grass (*Panicum* spp.), big and little bluestems (e.g. *Calamagrostis* spp., *Schizachyrium* spp., *Andropogon* spp., and the like), Grama grasses (e.g. *Bouteloua* spp.), Indian grass (*Sorghastrum* spp.), love grasses, panic grasses, fountain grass (*Pennisetum* spp.), Johnson grass, limpo grass, digit grass, woodoats (e.g. *Chasmanthium* spp.), tall moor grass (e.g. *Sesleria* spp. and *Molinia* spp.), ravenna grass (*Saccharum* spp.), greybeard grass (*Spodiopogon* spp.), praire dropseed grasses (e.g. *Sporobolus* spp.), Korean Feather Grass (*Stipa* spp.), fountain grass (*Pennisetum* spp.), Blue Lymegrass (*Elymus* spp.), reed grass (e.g. *Calamagrostis* spp.), pampas grass/Plume Grass (*Erianthus* spp.), Ribbon Grass (*Phalaris* spp.), Annual Quaking Grass (*Briza* spp.), Rabbit's Tail Grass (*Lagurus* spp.); and the like.

Some embodiments contemplate altering one or more of an environmental stress tolerance phenotype, enhancing cold tolerance, increasing time to flowering, and decreasing height in transgenic turfgrasses engineered for specific purposes such as alterations in color (e.g. U.S. patent application No. 20020188964A1; herein incorporated by reference), using color changes as indicators of stress conditions (e.g. U.S. patent application No. 20020188964A1; herein incorporated by reference); enhancement of salt tolerance in plants (e.g. PCT Patent WO 00/11138); herein incorporated by reference); enhancement of herbicide resistance in plants (e.g., U.S. Pat. No. 6,066,786); herein incorporated by reference), enhancement of insect resistance in plants (e.g. U.S. Pat. No. 5,593,881; and U.S. patent application Nos. 20030144192A1 and 20020128192A1; and Geiser et al. Gene 48:109-118 (1986); all of which are herein incorporated by reference), and the like.

The present invention is not limited to any particular use of the transgenic plant. Indeed, a variety of purposes are contemplated. In some embodiments, the transgenic grass is for a sports field. For example warm season grasses, (such as Bermudagrass (e.g. Princess 77), Bahiagrass, etc.) and cool season grasses (such as creeping bentgrasses, Kentucky bluegrass, Perennial Ryegrass, and tall fescue, etc.). In some embodiments the transgenic grass is used as a lawn either individually or in blends (examples of lawn Bermudagrasses and blends include Sahara, Yuma, Mohawk, Yukon, Rivera, EnviroBermuda, La Prima, Mohawk, Panama, Royal Blend, Savannah, Sultan, Sydney, etc.). In further embodiments, the transgenic grass is utilized as forage.

In some embodiments, the transgenic grass is used as part of a Golf course. For example, bentgrass spp. is used for tee areas (e.g. Penncross), bluegrass spp., and combinations of grasses for roughs, fairways and hazards (e.g. bentgrass spp., bluegrass spp. and other grasses).

In some embodiments, the transgenic grass of the present invention is a dwarf transgenic grass. Such a dwarf grass would require less maintenance, for example a turfgrass with a lower mowing frequency. It is not meant to limit the use of such a dwarf grass. In some embodiments, the dwarf grass is used as part of a lawn, golf course, sports field and the like. In some embodiments, a dwarf grass would also produce an enhanced tolerance to low temperatures. It is not meant to separate the grasses from the sedges as grasses and sedges are often interchangeably categorized; however in general sedges have edges and grasses are flat.

Some embodiments contemplate altering one or more of an environmental stress tolerance phenotype, enhancing cold tolerance, increasing time to flowering, and decreasing height in ornamental grasses and sedges including members of Cyperaceae for example *Carex phyllocephala* 'Sparkler', *Festuca glauca* 'Elijah Blue', *Calamagrostis acutiflora* 'Karl Foerster', *Calamagrostis acutiflora* 'Overdam', *Calamagrostis arundinacea* v. "Brachytricha", *Miscanthus oligostachyus* 'Purpurascens', *Miscanthus sinensis* 'Adagio'x, *Leymus arenarius* (also named *Elymus arenarius*), *Cymbopogon citratus*, *Chasmanthium latifolium*, *Miscanthus sinensis* 'Autumn Light', *Miscanthus sinensis* 'Bluetenwunder', *Miscanthus sinensis* 'Gracillimus', *Miscanthus sinensis* 'Gracillimus', *Miscanthus sinensis* 'Graziella', *Miscanthus sinensis* 'Malepartus', *Miscanthus sinensis* 'Sarabande', *Miscanthus sinensis* 'Silberfeder', *Miscanthus sinensis* 'Strictus', *Miscanthus sinensis* 'Variegatus', *Miscanthus sinensis* 'Zebrinus', *Miscanthus sinensis* var. *condensatus* 'Cabaret', *Miscanthus sinensis* var. *condensatus* 'Central Park', *Miscanthus sinensis* var. *condensatus* 'Cosmopolitan', *Panicum virgatum*, *Panicum virgatum* 'Cloud Nine', *Cortaderia selloana*, *Cortaderia selloana* 'Rosea', *Erianthus ravennae*, (also named *Saccharum ravennae*) and the like.

Some embodiments contemplate altering one or more of an environmental stress tolerance phenotype, enhancing cold tolerance, increasing time to flowering, and decreasing height in rushes (e.g. *Juncus* spp., *Luzula* spp., *Eleocharis* spp., *Equisetum* spp., *Hierochloe* spp., *Hystrix* spp., and the like).

In some embodiments plants include warm season grasses, cool season grasses, and transitional grasses. Some embodiments contemplate altering one or more of an environmental stress tolerance phenotype, enhancing cold tolerance, increasing time to flowering, and decreasing height in warm season grasses such as Bermuda Grass (*Cynodon dactylon*), Big Bluestem (*Andropogon geradii*), Sand Bluestem (*Andropogon hallii*), Sideoats Grama (*Boteloua curtipendula*), Little Bluestem (*Schizachyrium scoparium*), Blue Grama (*Boeteloua gracillis*), Buffalograss (*Buchloe dactyloides*), Prairie Sandreed (*Calamovifa longifolia*), Inland Saltgrass (*Distichlis stricta*), Switchgrass (*Panicum virgatum*), Indian Grass (*Sorghastrum nutans*), Alkali Sacaton (*Sporobolus airoides*), Sand Dropseed (*Sporobolus crypatandrus*), Yellow Sweet clover (*Melilotus officinalis*), and the like.

Some embodiments contemplate altering one or more of an environmental stress tolerance phenotype, enhancing cold tolerance, increasing time to flowering, and decreasing height in cool season grasses such as Siberian Wheat Grass (*Agropyron sibericum*), Crested Wheat Grass (*Agropyron cristatum*), Thickspike Wheatgrass (*Agropyron dasystachyum*), Standard Crested Wheatgrass (*Agropyron desertorum*), Tall Wheatgrass (*Agropyron elongatum*), Western Wheatgrass (*Agropyron smithii*), Steambank Wheatgrass (*Agropyron riparium*), Crested Wheatgrass (hybrid) (*Agropyron cristatum ×desertorum*), Beardless Bluebunch Wheatgrass (*Agropyron inerme*), Intermediate Wheatgrass (*Agropyron intermedium*), Bluebunch Wheatgrass (*Agropyron spicatum*), Newhy Wheatgrass (*Agropyron spicafum ×repens*), Slender Wheatgrass (*Agropyron trachycaulum*), Pubescent Wheatgrass (*Agropyron trichophorum*), Pubescent Wheatgrass (*Agropyron trichophorum*), Redtop (*Agrostis alba*), Creeping Bentgrass (*Agrostis palustris*), Creeping Foxtail (*Alopecurus arundinaceus*), Meadow Foxtail (*Alopecurus pratensis*), Polargrass (*Arcatagrostis latifolia*), American Slough Grass (*Beckmannia syzigachne*), Meadow Brome (*Bromus biebersteinii*), California Brome (*Bromus carinatus*), Rescuegrass (*Bromus catharticus*), Smooth Brome (*Bromus inermis*), Mountain Brome (*Bromus marginatus*), Soft Chess or Blando Brome (*Bromus mollis*), Orchardgrass (*Dactylis gomerata*), Tufted Hairgrass (*Deschampsia caespitosa*), Bering Hairgrass (*Deschampsia caespitosa* (L) Beauv. ssp. *Beringensis*), Altai Wildrye (*Elymus angustus*), Canada Wildrye (*Elymus canadensis*), Great Basin Wildrye (*Elymus cinereus*), Dahurian Wildrye (*Elymus dahuricus*), Blue Wildrye (*Elymus glaucus*), Russian Wildrye (*Elymusjunceus*), Beardless Wildrye (*Elymus triticoides*), Arizona Fescue (*Festuca arizonica*), Tall Fescue (*Festuca arundinacea*), Hard Fescue (*Festuca duriuscula*), Meadow Fescue (*Festuca eliator*), Turf Type Tall Fescue (*Festuca eliator arundinacea*), Hard Fescue (turf type) (*Festuca longifolia*), Foxtail Fescue (*Festuca megalura*), Sheep Fescue (*Festuca ovina*), Creeping Red Fescue (*Festuca rubra*), Chewings Fescue (*Festuca rubra* var. *commutata*), Native Red Fescue (*Festuca rubra* var. *rubra*), Meadow Barley (*Hordeum brachyantherum*), Prairie Junegrass (*Koeleria cristata*), Annual Ryegrass (*Lolium multiflorum*), Perennial Ryegrass (*Lolium perenne*), Indian Ricegrass (*Oryzopsis hymenoides*), Reed Canarygrass (*Phalaris arundinacea*), Alpine Timothy (*Phleum alpinum*), Common Reed (*Phragmites australis*), Alpine Bluegrass (*Poa alpina*), Big Bluegrass (*Poa ampla*), Bulbous Bluegrass (*Poa bulbosa*), Canby Bluegrass (*Poa canbyi*), Canada Bluegrass (*Poa compressa*), Upland Bluegrass (*Poa glauca*), Fowl Bluegrass (*Poa palustris*), Kentucky Bluegrass (*Poa prantensis*), Sandburg Bluegrass (*Poa sandbergii*), Rough Bluegrass (*Poa trivialis*), Alkaligrass (*Puccinellia distans*), Cereal Rye (*Secale cereale*), Bottlebrush Squirltail (*Sitanion hystrix*), Needle and Thread (*Stipa cornata*), Green Needlegrass (*Stipa viridula*), Wheat (*Triticum aestivum*, spp.), Meadow Barley (*Hordeum brachyantherum*) and the like. Some embodiments contemplate altering one or more of an environmental stress tolerance phenotype, enhancing cold tolerance, increasing time to flowering, and decreasing height in transitional grasses such as *Festuca* spp. (e.g. Blue Fescue, etc.) and the like. It is not meant to separate the transitional grasses from the warm season or the cool season grasses because transitional grass varieties are often classified as one or the other.

In some embodiments plants include ornamental plants, forage plants, and crop plants.

Some embodiments contemplate altering one or more of an environmental stress tolerance phenotype, enhancing cold tolerance, increasing time to flowering, and decreasing height in warm season ornamental grasses such as Pampas grass (*Cortaderia selloana*), Lemon grass (*Cymbopogon citratus*), Amur silver grass (*Miscanthus floridulus*), Switchgrass (*Panicum virgatum*), Fountain grass (*Pennisetum setaceum* 'Cupreum'), miscanthus spp (e.g. silver grass, giant silver grass, Japanese silver grass, Porcupine Grass, Maiden Grass, Purple Flame Grass, zebra grass, variegated eulalia, and the like.

Some embodiments contemplate altering one or more of an environmental stress tolerance phenotype, enhancing cold tolerance, increasing time to flowering, and decreasing height in warm season ornamental sedges such as *Scirpus* spp., (also known as Bulrush and Club Grass) a group of decorative hardy and frost-tender sedges and the like.

Some embodiments contemplate altering one or more of an environmental stress tolerance phenotype, enhancing cold tolerance, increasing time to flowering, and decreasing height in warm season ornamental rushes such as *Juncus* spp. (e.g. *Juncus effusus spiralis*, Corkscrew Rush) and the like.

Some embodiments contemplate altering one or more of an environmental stress tolerance phenotype, enhancing cold tolerance, increasing time to flowering, and decreasing height in ornamental cool season grasses such as Feather reed grass (*Calamagrostis acutiflora*), Sedge (*Carex* spp.), Tufted hair grass (*Deschampsia caespitosa*), Blue oat grass (*Helictotrichon sempervirens*), Squirreltail grass (*Hordeum jubatum*), and the like.

Some embodiments contemplate altering one or more of an environmental stress tolerance phenotype, enhancing cold tolerance, increasing time to flowering, and decreasing height in forage plants including one or more of fescue spp., (e.g. *Festuca* spp.); Sudan grass (*Sorghum vulgare* var. *sudanense*); *Brassica* spp., clover, alfalfa, legumes, forage grasses, and the like. Some embodiments contemplate altering one or more of a growth phenotype in forage plants that would lead to a decrease in fiber content and increase digestibility in animals (e.g. decreasing lignin, altering one or more of acid detergent fiber (ADF), neutral detergent fiber (NDF), and the like). In some embodiments forage grasses are one or more of bentgrass, redtop, fiorin grass (e.g. *Agrostis* spp.); bluegrass (e.g. *Poa* spp.); Columbus grass (*Sorghum almum*); Napier grass, elephant grass (*Pennisetum purpureum*); orchard grass (*Dactylis glomerata*); Rhodes grass (*Chloris gayana*); Timothy grass (*Phleum pratense*), and the like. In some embodiment a legume is one or more of birdsfoot trefoil (*Lotus corniculatus*); lespedeza (*Lespedeza* spp.); kudzu (*Pueraria lobata*); sesbania (*Sesbania* spp.); sainfoin, esparcette (*Onobrychis sativa*); sulla (*Hedys-

*arum coronarium*), annual ryegrass, perennial ryegrass, smooth brome grass, orchard grass, wheatgrasses, oatgrass, Kentucky bluegrass (e.g. U.S. Pat. Nos. PP4,223; PP6,279; U.S. Patent No., PP4,336; PP8,490; PP6,585; PP9,036; PP6,537; PP6,538; PP7,831; PP6,280; all of which-are herein incorporated by reference), Canada bluegrass, annual bluegrass, redtop reed canary grass, timothy, wheats, ryes, clovers, millets, sorghums, wheat, rye, indigo, clover, millet, sorghum, redtop, fiorin grass (*Agrostis* spp.); bluegrass (*Poa* spp.); columbus grass (e.g. *Sorghum almum*); fescue (e.g. *Festuca* spp.); napier, elephant grass (e.g. *Pennisetum purpureum*); cocksfoot/orchard grass (e.g. *Dactylis glomerata*); rhodes grass (e.g. *Chloris gayana*); sudan grass (e.g. *Sorghum vulgare* var. *sudanense*); timothy grass (e.g. *Phleum pratense*); (e.g. *Dactylis glomerata*), switchgrass, gamagrass and caucasian bluestem and the like. Examples of transgenic forage plants contemplated in the present invention are provided in U.S. Pat. No. 5,985,666; U.S. patent application Nos. 20030237108A1; 20030180751A1; 20030180751A1; 20020019997A1; 20020023279A1; all of which are herein incorporated by reference).

Some embodiments contemplate altering one or more of an environmental stress tolerance phenotype, enhancing cold tolerance, increasing time to flowering, and decreasing height in crop plants such as vegetable and vegetable-like plants, rice, corn, barley, wheat, *Brassica* spp., *Arabidopsis*, tomato, musk melon, soybean and the like. In some embodiments of the present invention transgenic plants are any type of crop plants. Examples of transgenic crop plants are described in U.S. Pat. No. 6,486,384; U.S. patent application Pub. No. 2003/0217386A1; all of which are herein incorporated by reference.

2. Vectors.

The methods of the present invention contemplate the use of at least one heterologous gene encoding CBF3 or CBF or CBF-like gene, or encoding a sequence designed to decrease or increase, CBF3 or CBF or CBF-like gene expression, as described previously (e.g., vectors encoding a nucleic acid encoding a polypeptide comprising SEQ ID NOS:02, 03-48, 70-108, 142-145 or nucleic acids corresponding to SEQ ID NOS: 01, 109-141 and 146-150). Heterologous genes include but are not limited to naturally occurring coding sequences, as well variants encoding mutants, variants, truncated proteins, and fusion proteins, as described above.

Heterologous genes intended for expression in plants are first assembled in expression cassettes comprising a promoter. Methods, which are well known to or developed by those skilled in the art, may be used to construct expression vectors containing a heterologous gene and appropriate transcriptional and translational control elements. These methods include in vitro recombinant DNA techniques, synthetic techniques, and in vivo genetic recombination. Exemplary techniques are widely described in the art (see e.g., Sambrook, et al., *Molecular Cloning: A Laboratory Manual*, 2$^{nd}$ ed., Cold Spring Harbor Laboratory Press, New York (1989) and Ausubel, F. M. et al. (1989) Current Protocols in Molecular Biology, John Wiley & Sons, New York, N.Y., herein incorporated by reference).

In general, these vectors comprise a nucleic acid sequence encoding a CBF3 or a CBF or a CBF-like gene, or encoding a sequence designed to decrease CBF3 or CBF or CBF-like gene expression, (as described above) operably linked to a promoter and other regulatory sequences (e.g., enhancers, polyadenylation signals, etc.) required for expression in a plant.

Promoters include but are not limited to constitutive promoters, tissue-, organ-, and developmental-specific promoters, and inducible promoters. Examples of promoters include but are not limited to: constitutive promoter 35S of cauliflower mosaic virus; a wound-inducible promoter from tomato, leucine amino peptidase ("LAP," Chao et al., Plant Physiol 120:979-992 (1999), herein incorporated by reference); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (e.g. U.S. Pat. No. 5,187,267, herein incorporated by reference); a tetracycline-inducible promoter (e.g. U.S. Pat. No. 5,057,422, herein incorporated by reference); and seed-specific promoters, such as those for seed storage proteins (e.g., phaseolin, napin, oleosin, and a promoter for soybean beta conglycin (Beachy et al., EMBO J. 4:3047-3053 (1985), herein incorporated by reference).

The expression cassettes may further comprise any sequences required for expression of mRNA. Such sequences include, but are nt limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (see e.g., Odell et al., Nature 313:810 (1985); Rosenberg et al., Gene 56:125 (1987); Guerineau et al., Mol. Gen. Genet. 262:141 (1991); Proudfoot, Cell 64:671 (1991); Sanfacon et al., Genes Dev. 5:141; Mogen et al., Plant Cell 2:1261 (1990); Munroe et al., Gene, 91:151 (1990); Ballas et al., Nucleic Acids Res. 17:7891 (1989); Joshi et al., Nucleic Acid Res., 15:9627 (1987); all of which are incorporated herein by reference).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Callis et al., Genes Develop. 1:1183 (1987), herein incorporated by reference). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Kalderon et al., Cell 39:499 (1984); Lassner et al., Plant Molecular Biology 17:229 (1991)), a plant translational consensus sequence (Joshi, Nucleic Acids Research 15:6643 (1987)), an intron (Luehrsen and Walbot, MolGen Genet. 225:81 (1991)), and the like, operably linked to the nucleic acid sequence encoding a CBF3 gene.

In preparing the construct comprising the nucleic acid sequence encoding a cbf3 gene, or encoding a sequence designed to decrease cbf3 gene expression, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, Gene 19:259 (1982); Bevan et al., Nature 304:184 (1983), all of which are incorporated herein by reference), the bar gene which confers resistance to the herbicide phosphinothricin (White et al., Nucl Acids Res. 18:1062 (1990); Spencer et al., Theor. Appl. Genet. 79:625 (1990), all of which are incorporated herein by reference), the hph gene which confers resistance to the antibiotic hygromycin (Blochlinger and Diggelmann, Mol. Cell. Biol. 4:2929 (1984), incorporated herein by reference)), and the dhfr gene, which confers resistance to methotrexate (Bourouis et al., EMBO J., 2:1099 (1983), herein incorporated by reference).

In some preferred embodiments, the (Ti (T-DNA) plasmid) vector is adapted for use in an *Agrobacterium* mediated transfection process (see e.g., U.S. Pat. Nos. 5,981,839; 6,051,757; 5,981,840; 5,824,877; and 4,940,838; all of which are herein incorporated by reference). In some embodiments, strains of *Agrobacterium tumefaciens* are C58, LBA4404, EHA101, C58C1Rif.sup.R, EHA105, and the like. Examples of *Agrobacterium* mediated transfection in turfgrasses are provided in PCT Patents WO00/04133; WO00/11138; and U.S. patent application Pub. Nos. 20030106108A1; 20040010816A1; and U.S. Pat. No. 6,646,185; all of which are herein incorporated by reference.

Construction of recombinant Ti and Ri plasmids in general follows methods typically used with the more common vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The use of T-DNA as a flanking region in a construct for integration into a Ti- or Ri-plasmid has been described in EPO No. 116,718 and PCT Appln. Nos. WO 84/02913, 02919 and 02920 all of which are herein incorporated by reference). See also Herrera-Estrella, Nature 303:209-213 (1983); Fraley et al., Proc. Natl. Acad. Sci, USA 80:4803-4807 (1983); Horsch et al., Science 223:496-498 (1984); and DeBlock et al., EMBO J. 3:1681-1689 (1984), all of which are herein incorporated by reference).

The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available. In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (e.g U.S. Patent No., 5,501,967, herein incorporated by reference). Homologous recombination may be achieved using targeting vectors that contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention are utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted $cbf3$ polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785; all of which are incorporated herein by reference.

In some embodiments of the present invention the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (e.g. WO 93/07278; herein incorporated by reference).

3. Transformation Techniques.

Once a nucleic acid sequence encoding a $cbf3$ gene is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See e.g., U.S. Pat. Nos. 5,451,513; 5,545,817; 5,545,818; and PCT Patent WO 95/16783; all of which are incorporated herein by reference). The basic technique for chloroplast transformation involves introducing regions of cloned plastid DNA flanking a selectable marker together with the nucleic acid encoding the RNA sequences of interest into a suitable target tissue (e.g., using biolistic or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., PNAS, 87:8526-8530 (1990); Staub and Maliga, Plant Cell, 4:39-45 (1992), all of which are incorporated herein by reference). The presence of cloning sites between these markers allowed creation of a plastid targeting vector introduction of foreign DNA molecules (Staub and Maliga, EMBO J., 12:601 (1993)). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, PNAS, 90:913-917 (1993)). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (e.g. Crossway, Mol. Gen. Genet, 202:179 (1985)). In still other embodiments, the vector is transferred into the plant cell by using polyethylene glycol ((e.g. Krens et al., Nature, 296:72 (1982); Crossway et al., BioTechniques, 4:320 (1986)); fusion of protoplasts with other entities, either minicells, cells, lysosomes or other fusible lipid-surfaced bodies (e.g. Fraley et al., Biochemistry, December 23;19(26):6021-6029 (1980)); protoplast transformation (EP 0 292 435); direct gene transfer (e.g. Paszkowski et al., Biotechnology 24:387-392 (1992); Potrykus et al., Mol Gen Genet. 199(2):169-177 (1985) including direct gene transfer into protoplasts (e.g. in *Arabidopsis thaliana*, Damm et al., Mol Gen Genet. May;217(1):6-12 (1989); in rice Meijer et al., Plant Mol Biol May;16(5):807-820) (1991)).

In still further embodiments, the vector may also be introduced into the plant cells by electroporation (e.g. Fromm, et al., Proc. Natl. Acad. Sci. USA, September;82 (17):5824-5828 (1985) and Nature February 27-March 5;319(6056):791-793 (1986); Riggs and Bates Proc. Natl. Acad. Sci. USA August;83(15):5602-5606 (1986)). In this technique, plant protoplasts are electroporated in the-presence of plasmids containing the gene construct. Electrical impulses of high field strength reversibly permeabilize biomembranes allowing the introduction of the plasmids. Electroporated plant protoplasts reform the cell wall, divide, and form plant callus.

Examples of biolistic transformation of perennial rye grass, Kentucky bluegrass, and Bermudagrass is demonstrated in PCT Patent WO00/11138; herein incorporated by reference for salt-tolerant transgenic turfgrass and for perennial ryegrass in PCT Patent WO03/076612; and U.S. Pat. No. 5,981,842; all of which are herein incorporated by reference.

In yet other embodiments, the vector is introduced through ballistic particle acceleration using devices (e.g., available from Agracetus, Inc., Madison, Wis. and Dupont, Inc., Wilmington, Del.) (see e.g., U.S. Pat. No. 4,945,050; and McCabe et al., Biotechnology 6:923 (1988); Weissinger et al., Annual Rev. Genet. 22:421 (1988); Sanford et al., Particulate Science and Technology, 5:27 (1987) (onion); Svab et al., Proc. Natl. Acad. Sci. USA, 87:8526 (1990) (tobacco chloroplast); Christou et al., Plant Physiol., 87:671 (1988) (soybean); McCabe et al., Bio/Technology 6:923 (1988) (soybean); Klein et al., Proc. Natl. Acad. Sci. USA, 85:4305 (1988) (maize); Klein et al., Bio/Technology, 6:559 (1988) (maize); Klein et al., Plant Physiol., 91:4404 (1988) (maize); Fromm et al., Bio/Technology, 8:833 (1990); and Gordon-Kamm et al., Plant Cell, 2:603 (1990) (maize); Koziel et al., Biotechnology, 11:194 (1993) (maize); Hill et al., Euphytica, 85:119 (1995) and Koziel et al., Annals of the New York Academy of Sciences 792:164 (1996); Shimamoto et al., Nature 338:274 (1989) (rice); Christou et al., Biotechnology, 9:957 (1991) (rice); Datta et al., Bio/Technology 8:736 (1990) (rice); European Appln. EP 0 332 581 (orchardgrass and other Pooideae); Vasil et al., Biotechnology, 11:1553 (1993) (wheat); Weeks et al., Plant Physiol., 102:1077 (1993) (wheat); Wan et al., Plant Physiol., 104:37 (1994) (barley); Jahne et al., Theor. Appl. Genet. 89:525 (1994) (barley); Knudsen and Muller, Planta, 185:330 (1991) (barley); Umbeck et al., Bio/Technology 5:263 (1987) (cotton); Casas et al., Proc. Natl. Acad. Sci. USA, 90:11212 (1993) (sorghum); Somers et al., BioTechnology 10:1589 (1992) (oat); Torbert et al., Plant Cell Reports, 14:635 (1995) (oat); Weeks et al., Plant Physiol., 102:1077 (1993) (wheat); Chang et al., WO 94/13822 (wheat) and Nehra et al., The Plant Journal, 5:285 (1994) (wheat); all of which are herein incorporated by reference).

In addition to direct transformation, in some embodiments, the vectors comprising a nucleic acid sequence encoding a cbf3 gene are transferred using *Agrobacterium*-mediated transformation (Hinchee et al., Biotechnology, 6:915 (1988); Ishida et al., Nature Biotechnology June; 14(6):745-50 (1996), all of which are herein incorporated by reference). Heterologous genetic sequences (e.g., nucleic acid sequences operatively linked to a promoter of the present invention) can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell, Science, 237:1176 (1987)). Species, which are susceptible infection by Agrobacterium, may be transformed in vitro.

Further examples of methods for transforming ryegrasses, turfgrasses and plants of the present invention are U.S. Pat. Nos. 6,486,384; 5,981,842; 5,948,956; 6,646,185; 6,489, 166; 6,646,185; U.S. patent application Pub. Nos. 20020188964A; 20030106108A1; 20030217386A1; 20030101644A1; 20040003434A1; 20040010816A1; 20030106108A1; all of which are herein incorporated by reference.

4. Regeneration.

After selecting for transformed plant material that can express a heterologous gene encoding a cbf3 gene, or a cbf gene or variant thereof, whole plants are regenerated. Plant regeneration from cultured protoplasts is described in Evans et al., Handbook of Plant Cell Cultures, Vol. 1: (MacMillan Publishing Co., New York, 1983); and Vasil I. R. (ed.), Cell Culture and Somatic Cell Genetics of Plants, Acad. Press, Orlando, Vol. I, 1984, and Vol. III, 1986, herein incorporated by reference. It is known that many plants can be regenerated from cultured cells or tissues or parts, including but not limited to all major species of turfgrass, sedges, rushes, ornamental grasses, ornamental sedges, ornamental rushes, warm (hot) season grasses, cool (cold) season grasses, fodder plants, and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

5. Generation of Transgenic Lines.

Transgenic lines can be established from transgenic plants by tissue culture propagation. The presence of nucleic acid sequences encoding an exogenous cbf3 gene, or a cbf-like gene or mutants or variants thereof may be transferred to related varieties by traditional plant breeding techniques. Examples of transgenic lines are described herein. These transgenic lines are then utilized for evaluation of environmental stress tolerance, cold tolerance, drought tolerance, phenotype, height, nutrient content and other agronomic traits.

B. Evaluation of Environmental Stress Tolerance.

The transgenic plants and lines are tested for the effects of the transgene on environmental stress tolerance and phenotype. The parameters evaluated for environmental stress tolerance are compared to those in control untransformed plants and lines. Parameters evaluated include ranges of environmental tolerance, effects of heat, cold, drought, salt, light; effects on altering cold tolerance and effects on growth rates and nutrient production. Ranges of cold tolerance can be expressed as a temperature per unit of time, or in a particular tissue or as a developmental state; for example, cold tolerance in ryegrass can be measured cold germination rates. These tests were conducted in the greenhouse and can be conducted in the field.

Experimental

The following examples serve to illustrate certain embodiments and aspects of the present invention and are not to be construed as liming the scope thereof. In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); pg (picograms); L and l (liters); ml (milliliters); μl (microliters); cm (centimeters); mm (millimeters); μm (micrometers); nm (nanometers); U (units); min (minute); s and sec (second); k (kilometer); deg (degree); ° C. (degrees Centigrade/Celsius).

EXAMPLE 1

Materials and Methods

I. Methods for Identifying Plants with Enhanced Cold Tolerance.

The present invention provides methods for identifying genes involved in environmental tolerance. Specifically a gene was identified that is associated with enhanced cold tolerance in plants. These methods include first screening populations of plants by testing seeds (referenced by PI and accession number) for their ability to germinate in a cold environment (for example, perennial ryegrass (*Lolium perenne*—Lp) seeds (see, Example 2, FIGS. 1-2).

The present invention provides methods for determining the lethal temperature for perennial ryegrass plants. Seeds from the PI accessions whose seeds germinated under cold treatment (Example 2) were grown into plants and further tested for freezing tolerance (Example 3). Of these, a plant demonstrating the highest freezing tolerance while remaining alive was selected for providing the nucleic acid material for isolating ryegrass cbf3 (Example 4, FIG. 3).

II. Methods for Identifying Genes Involved with Enhancing Cold Tolerance.

Figure 3B:
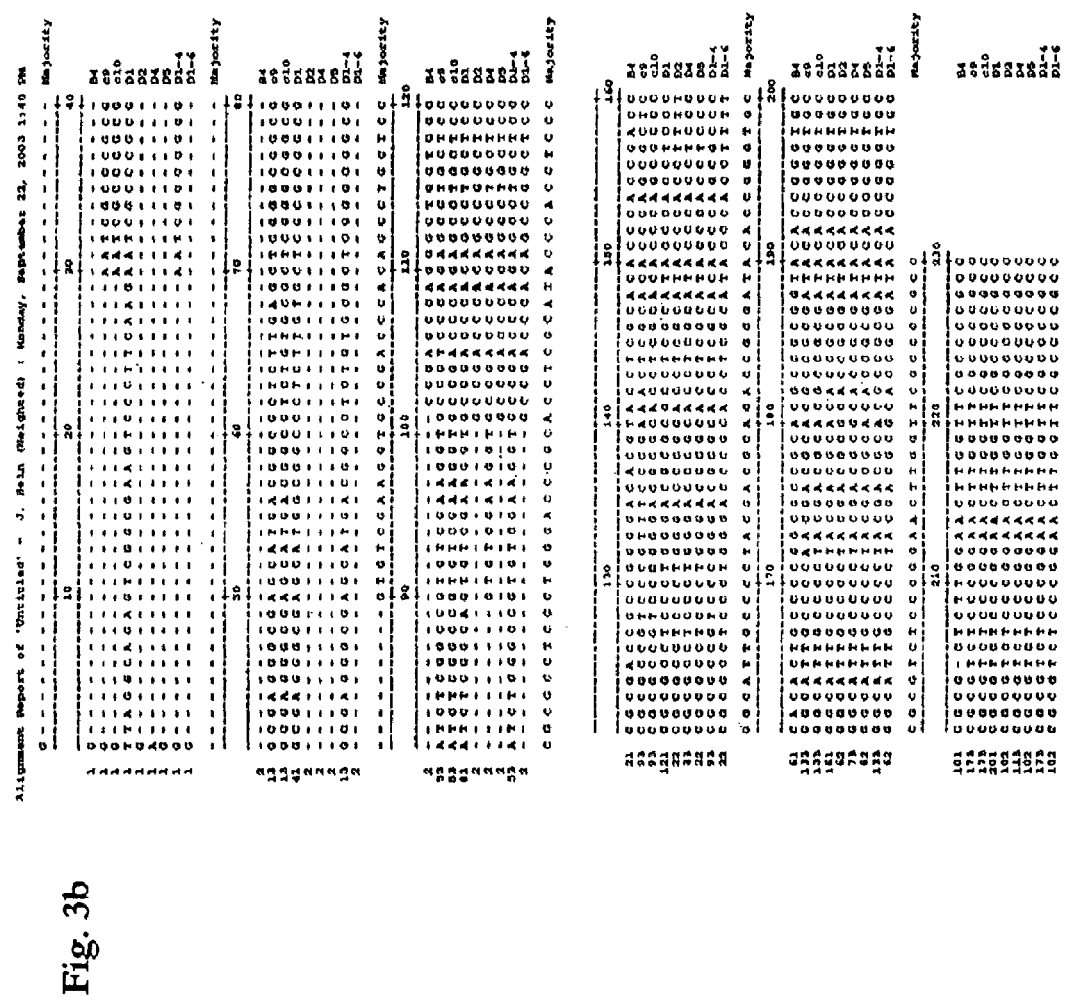

In some embodiments, PCR primers were derived from conserved regions of rice CBF3 and *Arabidopsis* CBF3 (e.g., SEQ ID NO: 49-52 in FIG. 11) then used to isolate numerous ryegrass gene fragments (FIG. 3*a*) that were sequenced and aligned (FIG. 3*b*). The association of these ryegrass fragments to cold tolerance were demonstrated when cold treatment of perennial ryegrass plants increased the amount of hybridized transcript (e.g. Lpcbf3-D1) as shown in Example 5 (e.g. FIG. 4*a*) and increased amount of hybridized transcript for a CBF3 downstream gene transcript (e.g. homologous to wheat cor39) as shown in Example 5 (e.g. FIG. 4*b*), a classic response for a gene affecting environmental stress tolerance. Using this phenotypic information combined with the gene's sequence similarity to CBF3 genes from rice and CBF-like genes in other plants, this gene was designated a ryegrass cbf-like gene and specifically a cbf3 gene that would function as a cbf3 gene and whose encoded protein would function as CBF3. This sequence similarity was demonstrated using NCBI BLAST searches comprising partial and full-length perennial ryegrass nucleic acid and amino acid sequences of the present invention. Additional sequence identities determined by using the sequence comparison program MultAlin (Multiple sequence alignment) program (Corpet, Nucl. Acids Res., 16 (22), 10881-10890 (1988).

A. Characterization and the Identification of cbf3.

The identity of ryegrass cbf3 was initially demonstrated by molecular characterization analysis. Primers based on rice CBF gene and derived degenerate primes based upon *Arabidopsis* cbf genes were used to identify, amplify and clone ryegrass cbf3 (FIGS. 3-7, 11, and 15). Sequences of ryegrass cbf3 was verified by comparing its sequence to known cbf and cbf-like genes through NCBI BLAST analysis (FIGS. 3*c*, 3*d*, 7*d*, and 7*e*). The genes and their deduced proteins of the present invention identified numerous CBF/DREB family proteins in genomic databases from a wide variety of monocots and dicots including tall fescue, *Arabidopsis*, rice, barley spp., wheat spp., rye, maize, soybean, bell pepper, tomato, *B. napsis* spp. (canola oil—rape), shepherd's purse, upland cotton, sweet cherry, and *T. salsuginea* (FIGS. 13 and 14).

B. cbf3 Encodes an AP2 Binding Domain.

Figure 9:
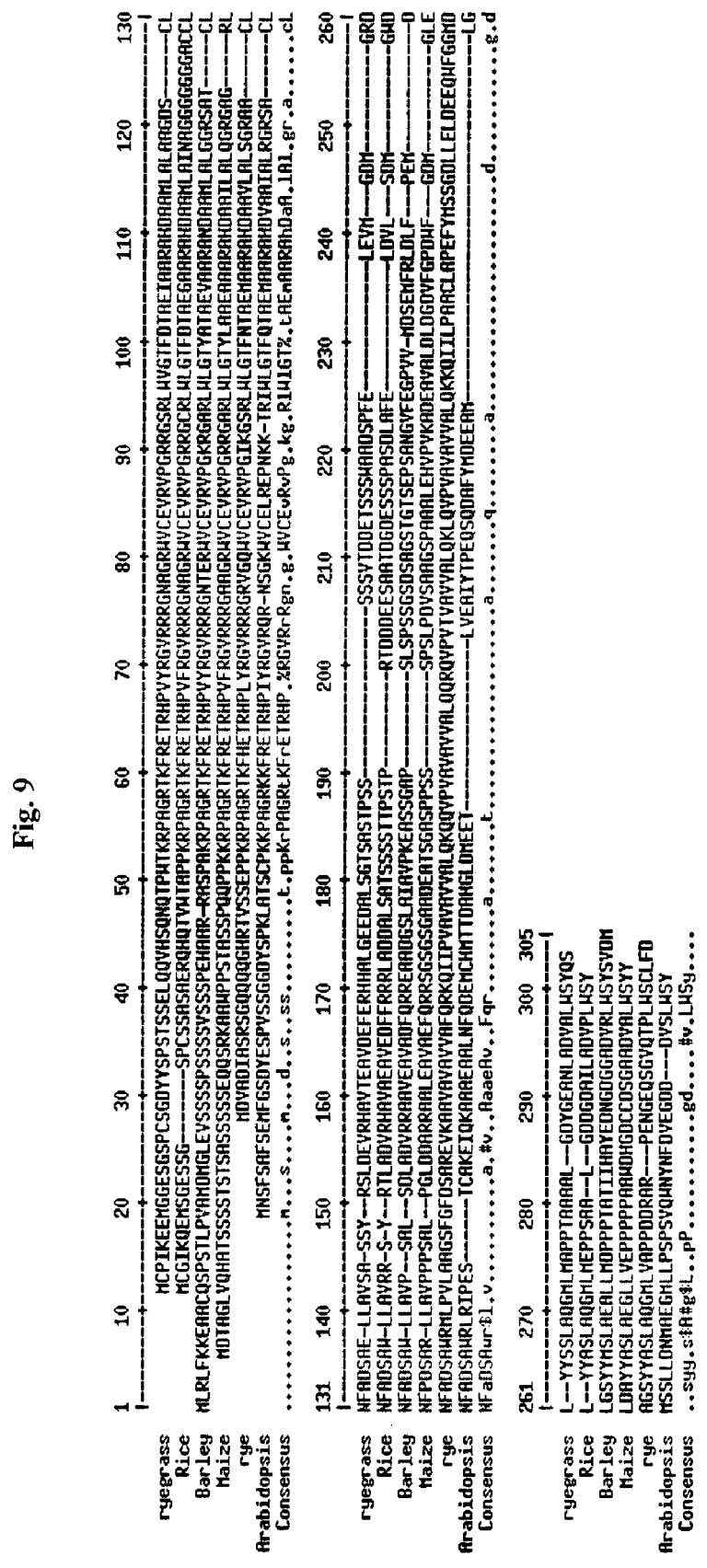

The deduced amino acid sequence of ryegrass CBF3 contains several features characteristic of AP2 binding domain family (see, FIG. 9). The ryegrass CBF3 AP2 binding domain motif comprises SEQ ID NO: 03.

An alignment of the CBF proteins from *Arabidopsis thaliana*, *B. napus*, wheat, rye, and tomato revealed the presence of conserved amino acid sequences, RPAGRxK-FxETRHP (SEQ ID NO:151) and DSAWR (SEQ ID NO:152) motifs comprising SEQ ID NO:04, known as "signature sequences" that bracket the AP2/EREBP DNA binding domains of proteins and distinguish them from other members of a large AP2/EREBP protein family (Jaglo- Ottosen et al. Science 280:104-106 (1998); Gilmour et al., Plant J. 1998 Nov; 16(4):433-42 (1998)).

The following is a description of exemplary materials and methods that were used in subsequent Examples.

EXAMPLE 2

FIG. 1. is an example of a screen over 300 PI accessions of perennial ryegrass (*Lolium perenne*) for seed germination in a cold environment using a thermogradient plate.

Seed Germination at Cold Temperature.

Over 300 PI accessions of perennial ryegrass, *Lolium perenne*, were obtained from the Western Regional Plant Introduction (PI) Station (United States Department of Agriculture—Agricultural Research Service in Pullman, Wash., USA) and tested for germination at cold temperatures. Germination in response to a range of temperatures was evaluated using a one-way thermogradient plate. Tall fescue *Festuca arundinacea* Schreb commercial cultivar "Fan" was also included in the test as a positive control. The procedure used was a modified version of that described by Wade et al. (Field Crops Research 31:295-308 (1993)). At the cold region of the plate, 50% distilled water and 50% ethylene glycol was distributed using a VWR brand refrigerated circulator by Polyscience, model 1140A. For the hot region, a VWR brand immersion circulator by Polyscience, model 1112, was used to circulate 100% distilled water through the coils of the heating coils of the thermogradient plate.

The experiment was a completely randomized block design, with three replications of each accession/cultivar. The thermogradient plate was marked such that petri dishes could be placed equidistantly across the apparatus, allowing seeds to be tested at temperatures of approximately 5, 11, 16, 22, 27, 31, 37, and 42° Celsius. At each of the eight temperature regimes, three petri dishes were randomly placed in three blocks for a total of nine petri dishes per temperature regime. Eleven accessions/cultivars could be tested per run plus Fawn, a tall fescue cultivar used that germinates in these ranges. One week constituted one run of the experiment. The petri dishes were lined with Whatman Number 4 filter paper, which was divided into four equal quadrants. Five seeds were placed in each quadrant, and then covered with another layer of the filter paper. The petri dishes were then covered with strips of steel blue blotter paper. Seeds at temperatures of 5, 11, 16, and 22° C. were watered daily with tap water. At temperatures of 27, 31, 37, and 41° C. seeds were watered with distilled water twice a day. Temperatures were recorded at least twice a day using a Bamant DuaLog R thermocouple thermometer, model 600-1050, and Omega type E or type T probes. At the end of one week, seeds were scored as germinated or not germinated. Germination was defined as the emergence of a radicle from the seed coat. Germination data was analyzed by analysis of variance (ANOVA), using the proc mixed procedure in SAS (SAS Institute, 1990. SAS/STAT user's guide. Ver. 6, 4th ed., Vol. 2. SAS Inst., Cary, N.C.). The data was analyzed by treatment, and ranked according to the least square means estimate. A multiple comparison with the best treatment procedure was also conducted as a check to the proc mixed procedure. From these results, 40 PI accessions from both the hot and cold regions were chosen for the following freezing study.

EXAMPLE 3

Figure 2:
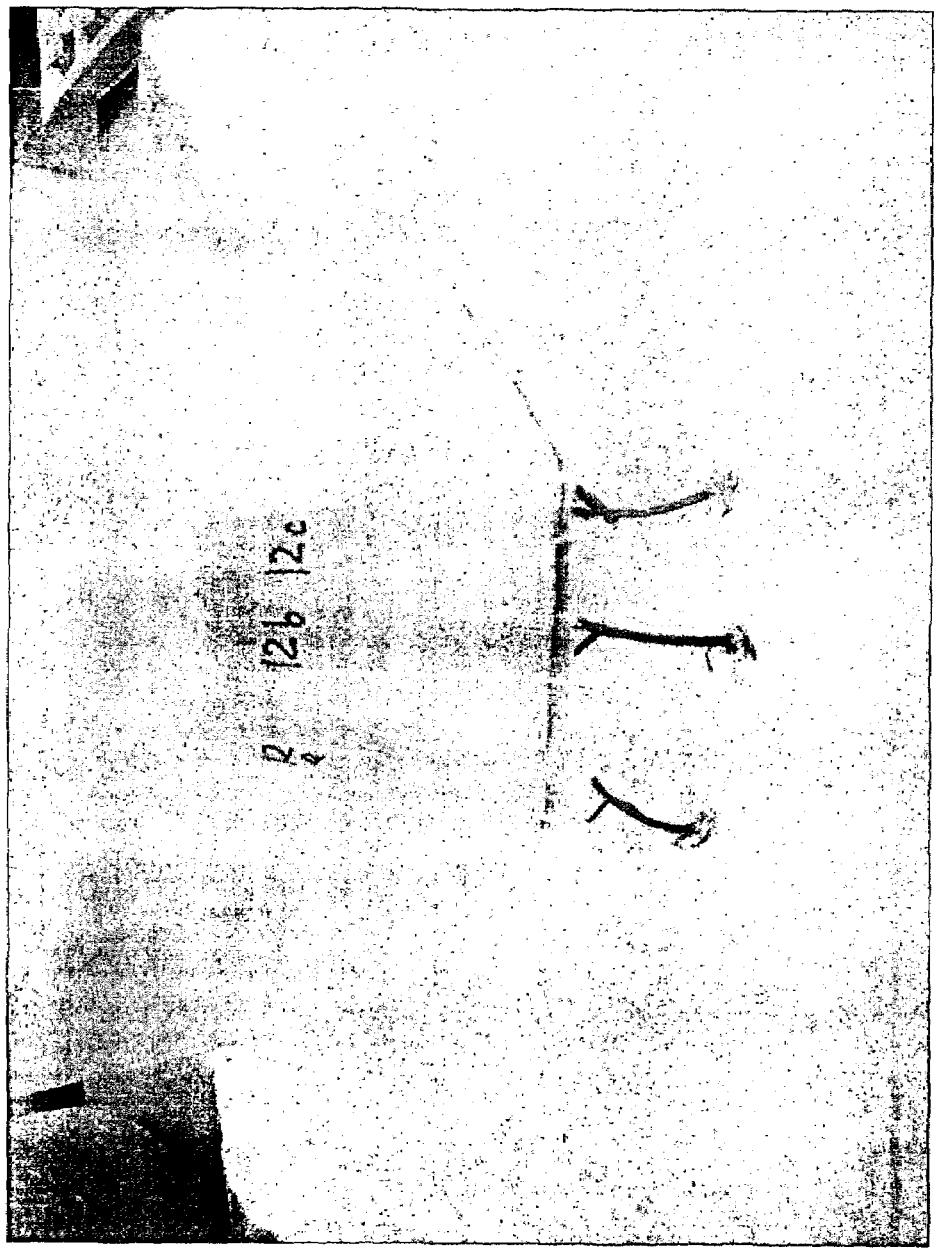
FIG. 2. shows embodiments of 40 PIs that were germinated in a greenhouse; PI 598441 shows the most tolerant to the cold treatment in these materials.

FIG. 2. is an example of PIs that were germinated in a greenhouse under normal conditions. From statistical analysis and actual observations, plants from PI 598441 showed the strongest ability to survive freezing treatments.

Ryegrass Freezing Study.

Of the 40 ryegrass PI accession whose seeds germinated in the cold, seedlings were obtained for this freezing study by planting representative seeds in plates filled with soil for germination and growth at regular temperature without cold treatment in a greenhouse at Michigan State University. When two-weeks old, seedlings were individually transplanted in 2×2 inch plastic pots for further growth. There were approximately 24 plants from each of the 40 PI accessions (960 plants total). When these plants were three-months old, plants were transferred into a cold growth chamber with light for cold pre-treatment at 4° C. (cold acclimation) for one week. After the cold pre-treatment, plants were removed from their pots; their tillers were washed, separated and prepared for further testing.

Tillers were prepared for freezing tests by the following methods. While on ice, the roots of each tiller were cut off approximately 1 cm below the base of the crown, and then tops were cut off at 5 cm above the base of the crown. Ten-twelve plants of each accession provided 70 tillers total at 5 replicates for 14 temperatures The 70 tillers for each accession (200 tillers per temperature) were prepared for 14 freezing temperature treatments, −1, −2, −3, −4, −5, −6, −7, −8, −9, −10, −11, −12, −13, and 0° C. as a control. There were 5 tillers (replications) for each temperature (14) and each PI accession (40). Five tillers of each PI accession for the same temperature treatment were randomly placed in two test tubes (2 tillers in one test tube and 3 tillers in a second test tube)), and kept on ice in a cool location (e.g. Styrofoam cooler). Small amounts of ice were added to the test tubes and the tubes were sealed using parafilm before freezing treatment. Freezing treatment was conducted in 13 sub-zero ethylene glycol baths one each set at one of the 13 freezing temperature treatments where one $14^{th}$ "master bath" was designated and whose temperature was dropped approximately 1 degree per hour beginning at 0° C. and a cool location (e.g. Styrofoam cooler) where tillers for 0° C. treatments were held on ice throughout the freezing experiment. The tubes of tillers were initially placed in a master bath at 0° C. set to decrease to −1° C. within the hour. At −1° C. the 80 test tubes with tillers for −1° C. treatment were transferred into the 1° C. bath for one hour then into the cool location. Then after the master bath reached −2° C., the 80 test tubes with tillers for −2° C. treatment were transferred into the bath previously set at −2° C. for one hour before transfer into the cool location. This treatment was repeated until all tillers had been exposed to the appropriate temperatures. After all freezing treatments, the cooler was moved in the cold growth chamber, uncovered, and kept at 4° C. overnight. Next day, plants were transplanted back in 2×2 inches plastic pots filled with soil and managed in the greenhouse at 20-25° Celsius. Plants were watered every other day and fertilized once every two weeks without mowing. One month after planting, surviving plants were counted to identify the most cold tolerant plants (plants that survive exposure to the coldest temperature) and to estimate lethal temperature for these ryegrass plants, the temperature at which virtually all plants died. The lethal temperature for these plants was −13° Celsius with one surviving plant. Using statistical and actual results, the surviving plant for PI 598441 was chosen for CBF3 gene isolation procedures.

EXAMPLE 4

Figure 3C:
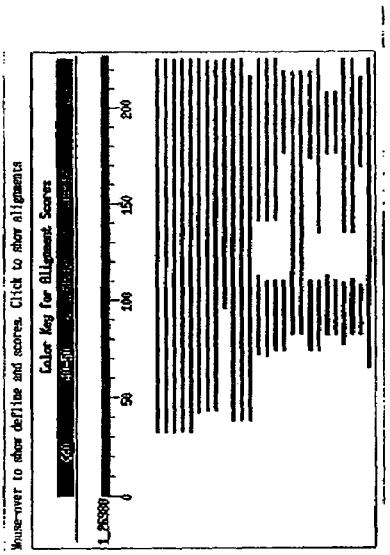
FIG. 3a (SEQ ID NOS:49-52), FIG. 3b (SEQ ID NOS: 171-180), FIG. 3c, and FIG. 3d (SEQ ID NOS:181-182) show embodiments in which ryegrass cbƒ3 gene conserved region from PI 598441 (the accession group of a ryegrass plant that tolerated the coldest treatment) was obtained, sequenced, and identified as cbƒ3.
Figure 4A:
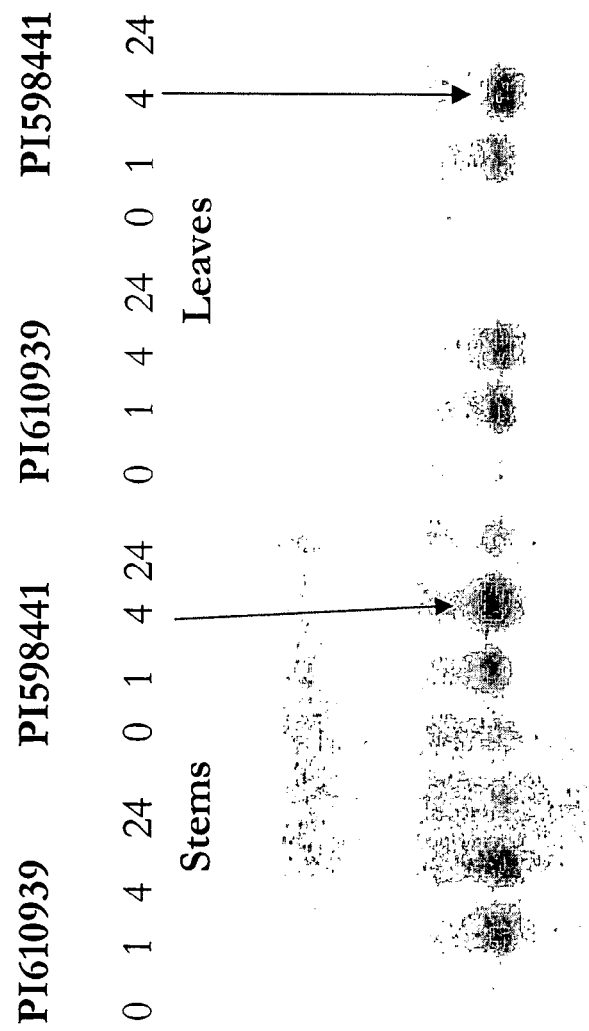
FIG. 4(a-b) shows exemplary embodiments in which Northern analysis confirmed the association of the ryegrass cbƒ3 gene fragment with cold treatment of PI 598441 plants.

FIG. 3(*a-d*) shows examples in which a ryegrass cbf3 gene conserved region from PI 598441, the plant that survived the coldest treatments (most tolerant to the cold treatment), was obtained based on primers derived from rice CBF (DREB1a) and degenerate primers derived from *Arabidopsis* CBF (DREB1a) sequence primers (FIG. 3*a*). These fragments were sequenced and compared to derive a majority gene sequence (see, FIG. 3*b*). This majority sequence was used to search gene databases for the most similar sequences using NCBI BLAST analysis. Results are shown in FIGS. 3*c* and 3*d*.

Experimental Protocol:

Ryegrass cbf3 was obtained using nucleic acid extracted from the surviving PI 598441 plant in Example 3 and used for the following PCR reactions.

PCR Protocol:

Primers used were designed based upon the rice CBF conserved sequences and used for gene amplification in a PCR reaction (Jaglo et al., Plant Physiol 127:910-927 (2001)); O18065: GGCCGGCGGGGCGAACCAAGTTCC (SEQ ID NO:49) and O18066: AGGCAGAGTCGGC-GAAGTTGAGGC (SEQ ID NO:50).

PCR reactions were performed in 25-µL volumes containing 10 mM Tris-HCl (pH 8.3), 50 mM KCl, 1.5 µM MgCl$_2$, 200 µM of each deoxynucleotide, 50 ng of each primer, about 50 ng template DNA, and 1 U Taq DNA polymerase. The amplification was performed in a Thermocycler using the following program: 94° C. for 2 min. followed by 40 cycles at 94° C. for 1 min., 70° C. for 1 min. and 72° C. for 1 min. and 50 seconds, with a final extension at 72° C. for 5 minutes. PCR products were separated on 1.4% (w/v) agarose gels and visualized under UV light after ethidium bromide staining.

PCR Protocol:

The primers used in this reaction were two degenerate primers based on Arabidopsis CBF conserved sequences (Jaglo et al., Plant Physiol 127:910-927 (2001); a CBF Forward Primer: CC(AGCT)AA(AG)AA(AG)CC(AGCT)GC(ACGT)GG(ACGT) (SEQ ID NO:51) and CBF Reverse Primer: GG(AGCT)A(AG)(AGCT)A(AG)CAT(AGCT)CC(CT)TC(AGCT)GCC (SEQ ID NO:52).

PCR reactions were performed in 25-µL volumes containing 10 mM Tris-HCl (pH 8.3), 50 mM KCl, 1.5 µM MgCl$_2$, 200 µM of each deoxynucleotide, 50 ng of each primer, about 50 ng template DNA, and 1 U Taq DNA polymerase. The amplification was performed in a Thermocycler using the following program: 94° C. for 2 min. followed by 40 cycles at 94° C. for 1 min., 50° C. for 1 min. and 72° C. for 1 min. and 50 seconds, with a final extension at 72° C. for 5 minutes. PCR products were separated on 1.4% (w/v) agarose gels and visualized under UV light after ethidium bromide staining.

B4, C9, C10, D1, D2, D4, and D5 sequences (see FIG. 3*b*) were amplified from ryegrass genome by rice CBF primers (see, FIG. 3*a*). D1-4 and D1-6 sequences (see, FIG. 3*b*) were amplified from ryegrass using *Arabidopsis* cbf primers (see FIG. 3*a*). The specific bands (~200 bp) were inserted into pGEM-T easy vector (Promega) by following the kit manual for ligating, transforming and then isolating plasmids to use for sequencing. The inserts were sequenced in the Michigan State University (Genomics Technology Support Facility). Ryegrass sequences were identified as cbf3 by comparing them to gene databases using NCBI BLAST at the Internet web site of NCBI.

EXAMPLE 5

FIG. 4(*a-b*) shows an example in which Northern analysis confirmed that amplified cbf core sequence (from Example 4) are related to cold treatment.

Experimental Protocol:

PI610939 *Lolium Perenne* "Most Cold Sensitive."

Type: Collected. Date: 05 Jul. 1994. From: Sardinia, Italy. Locality: Near Aggius, 3 k north of Aggius on road SS127 to Trinita. Habitat: Grazed. Slope 0-5%, aspect North. Area open. Soil loam, alluvial, pH 5.0. Rainfall 1000 mm. Seasonally dry, alluvial fan. Vegetation closed, seasonal tall grass. Surrounding vegetation is closed evergreen scrub with scattered trees. Latitude: 40 deg. 56 min. 12 sec. North (40.937), Longitude: 009 deg. 03 min. 20 sec. East (9.056). Elevation: 550 meters. Comment: Dominant tree species *Quercus suber* (Cork Oak). Dominant shrub sp. Oleander. Dominant herb/grass sp. *Trifolium repens*, annual grasses. Associated sp. white clover, Medic, *Lotus palustris*.

PI598441 *Lolium Perenne* "Most Cold Tolerant."

Type: Collected. From: Switzerland. Locality: Semsales. Latitude: 46 degrees 35 minutes North (46.583), Longitude: 006 degrees 56 minutes East (6.933). Elevation: 860 meters.

More information for each accession can be found by going to "Accession Area Queries" at http:,followed by,//www.ars-grin.gov/npgs/searchgrin., followed by,html (http:, followed by,//www.ars-grin.gov/npgs/acc/acc queries.,followed by,html).

Northern Method

Figure 4B:
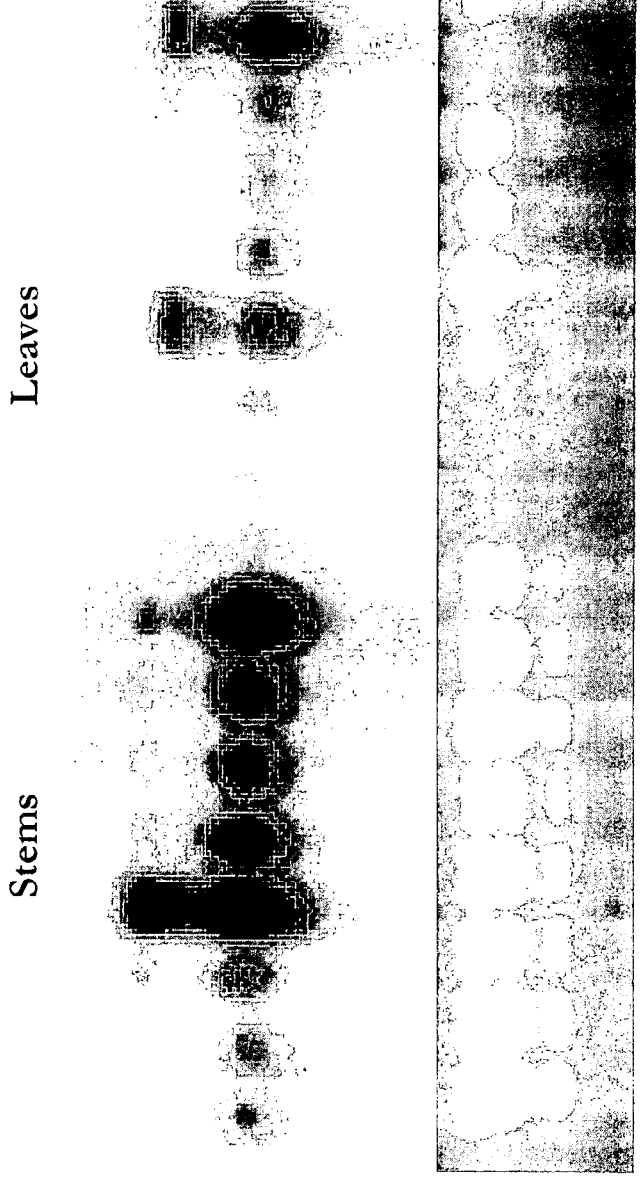

A ryegrass Lpcbf3 probe was prepared from a conserved cbf core region SEQ ID NO:150 (fragment D1 as in FIG. 3*b*) (FIG. 4*a*) and a cbf downstream gene (cor39 homologous gene) SEQ ID NO: 146 (FIG. 4*b*).

Total RNA was extracted from the designated ryegrass plant parts, then separated on 1.0% formaldehyde gel and transferred to Hybond-N extra membranes (Amersham, Buckinghamshire, UK). Filters were pre-hybridized in 50% formamide, 5×SSC, 0.1% SDS, 20 mM of sodium phosphate pH 6.5, 0.1% Ficoll, 0.1% polyvinylpyrolidone, 1% glycine, 250 µg/ml of denatured salmon sperm DNA at 42° C. for at least 2 hours. Hybridization was performed at 42° C. overnight in the pre-hybridized solution with $^{32}$P-labeled probes (>10$^7$ cpm specific activity, cpm/µg DNA). cDNAs were labeled with ($\alpha$-$^{32}$P)-dCTP (1,000 Ci/mmol, Amersham, Buckinghamshire, UK) using the Prime-a-Gene Labeling System (Promega, Madison, Wis., USA). Then, the filters were washed three times in 2×SSC, 0.1% SDS at room temperature for 10 min. and then two washes in 0.1 SSC, 0.1% SDS at 65° C. for 30 minutes each.

EXAMPLE 6

FIG. 5. shows an example where Southern analysis showed polymorphisms between cold tolerant and non-tolerant plant materials. R cold tolerant plants are PI598441 and PI577270. S non-cold tolerant plants are PI 598890 and PI 610939.

Experimental Protocol:

The DNA and protein sequence alignments were conducted with MultiAlin and BLAST as described herein.

PI610939 and PI598441 are Described in Example 5.

PI577270 *Lolium Perenne* "Cold Tolerant."

Type: Collected. From: Norway. Locality: Sola. Latitude: 58 degrees 53 minutes North (58.883), Longitude: 005 degrees 36 minutes. East (5.600). Elevation: 25 meters.

PI598890 *Lolium Perenne* "Cold Sensitive."

Type: Collected. Date: 21 Jul. 1994. From: Morocco. Locality: Near Arhbalou-N-Serdane, next to village Arhbalou on P33, 45 k west of Zeida to K. Tadla. Habitat: Grazed/hay. Slope 0-5%, aspect North. Area open. Soil clay on limestone, pH 10.0. Rainfall 350 mm. Moist, seasonally flooded, basin-swale. Vegetation closed, seasonal tall grass. Surrounding vegetation is evergreen open forest with closed lower layers. Latitude: 32 degrees 40 minutes 35 seconds North (32.676), Longitude: 005 deg. 17 minutes 32 seconds West (−5.292). Elevation: 1675 meters. Comment: Dominant tree species degraded *Quercus ilex* (Holm Oak and Evergreen Oak). Dominant shrub degraded *Juniperus phoenicea*. Dominant herb/grass strawberry clover, tall fescue. Associated sp. *Juncus* sp., *Agropyron* r., *Brachypodium, Potentilla* c., *M lup., Melilotus* sp., *M. poly.*

More information for each accession can be found by going to "Accession Area Queries" at the Internet web site of ars-grin.

Southern Analysis:

A ryegrass Lpcbƒ3 probe was prepared from a conserved cbƒ core region SEQ ID NO:150 (fragment D1).

DNA was extracted, digested with restriction enzymes, then separated on 0.8% agarose gels and transferred to Hybond-N extra membranes (Amersham, Buckinghamshire, UK). Filters were pre-hybridized in 50% formamide, 5×SSC, 0.1% SDS, 20 mM of sodium phosphate pH 6.5, 0.1% Ficoll, 0.1% polyvinylpyrolidone, 1% glycine, 250 µg/ml of denatured salmon sperm DNA at 42° C. for at least 2 hours. Hybridization was performed at 42° C. overnight in the pre-hybridized solution with $^{32}$P-labeled probes (>10$^7$ cpm specific activity, cpm/µg DNA). cDNAs were labeled with ($\alpha$-$^{32}$P)-dCTP (1,000 Ci/mmol, Amersham, Buckinghamshire, UK) using the Prime-a-Gene Labeling System (Promega, Madison, Wis., USA). Then, the filters were washed three times in 2×SSC, 0.1% SDS at room temperature for 10 min. and then two washes in 0.1 SSC, 0.1% SDS at 65° C. for 30 min. each.

EXAMPLE 7

Figure 6B:
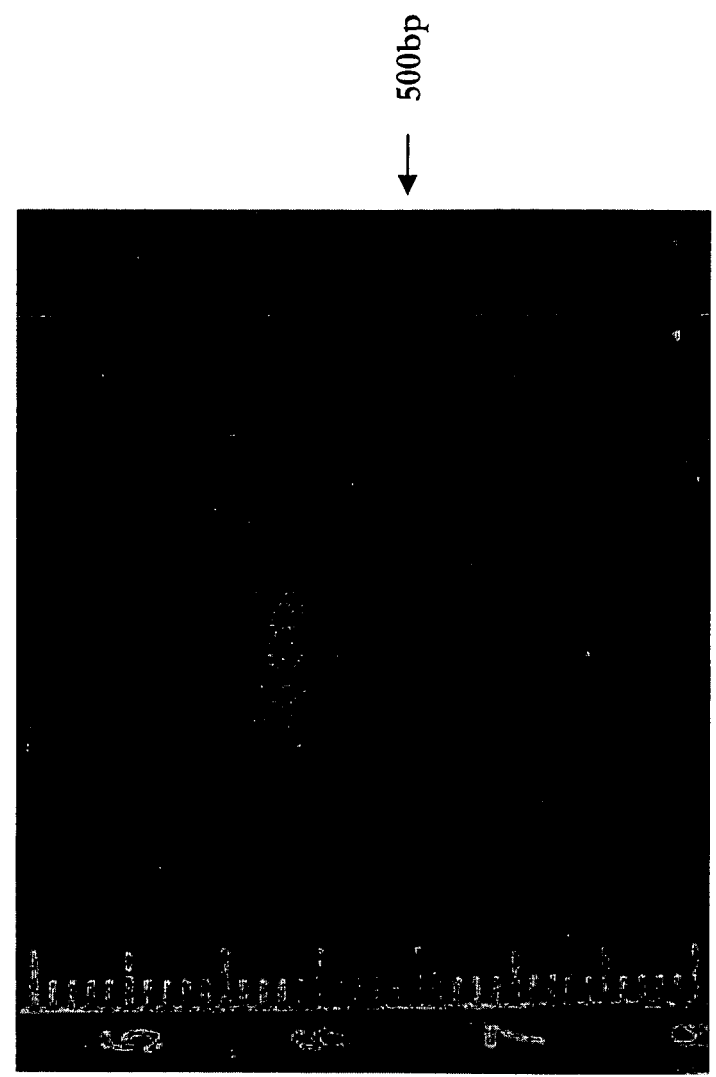
FIG. 6a (SEQ ID NOS:183-190) and FIG. 6b show exemplary embodiments using 5' and 3' RACE to obtain the flanking sequences of ryegrass cbƒ3.
Figure 7A:
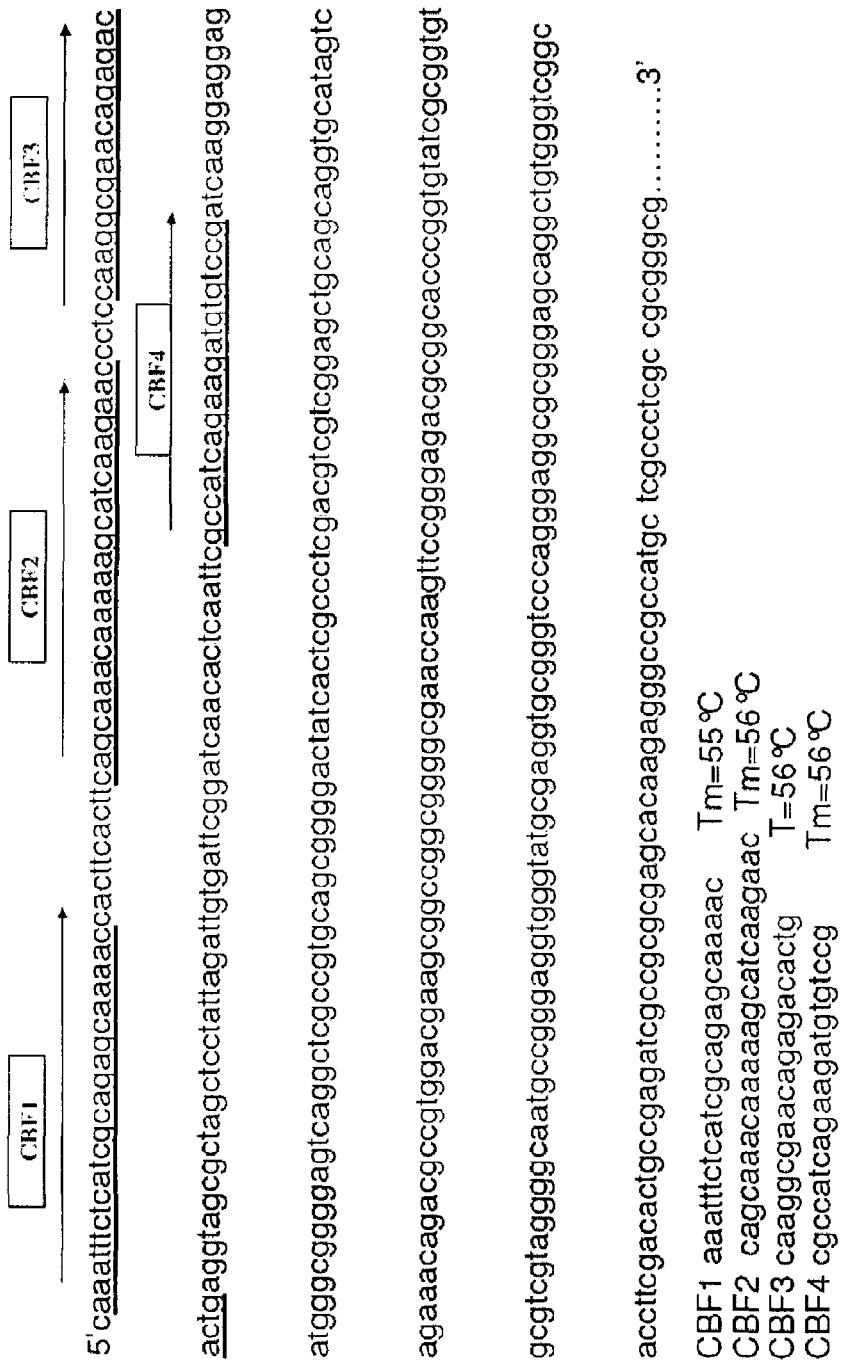
FIG. 7. shows exemplary embodiments that demonstrate primers based on 5' and 3' sequences (SEQ ID NOS:191-195) (a) used to amplify the corresponding ends of cbƒ3 that was sequenced to derive a full-length cbƒ3 cDNA (b-c), whose DNA and protein sequences were compared to corresponding databases using BLAST analysis (d-e).
Figure 7B:
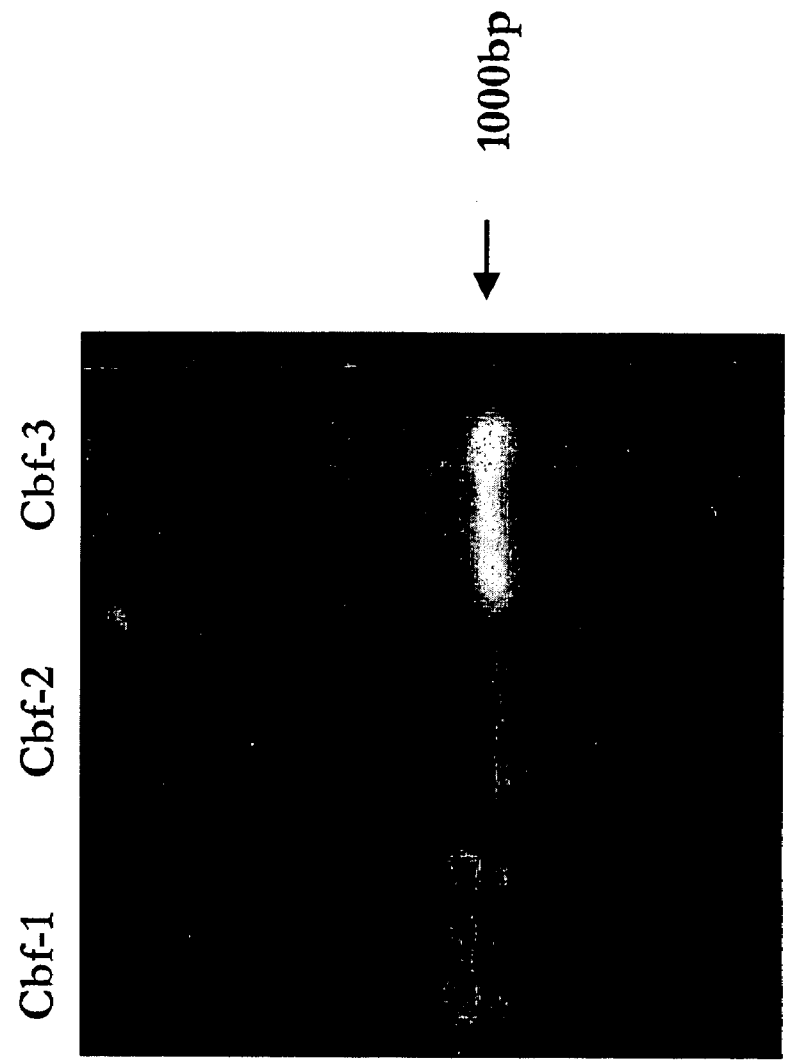
Figure 7C:
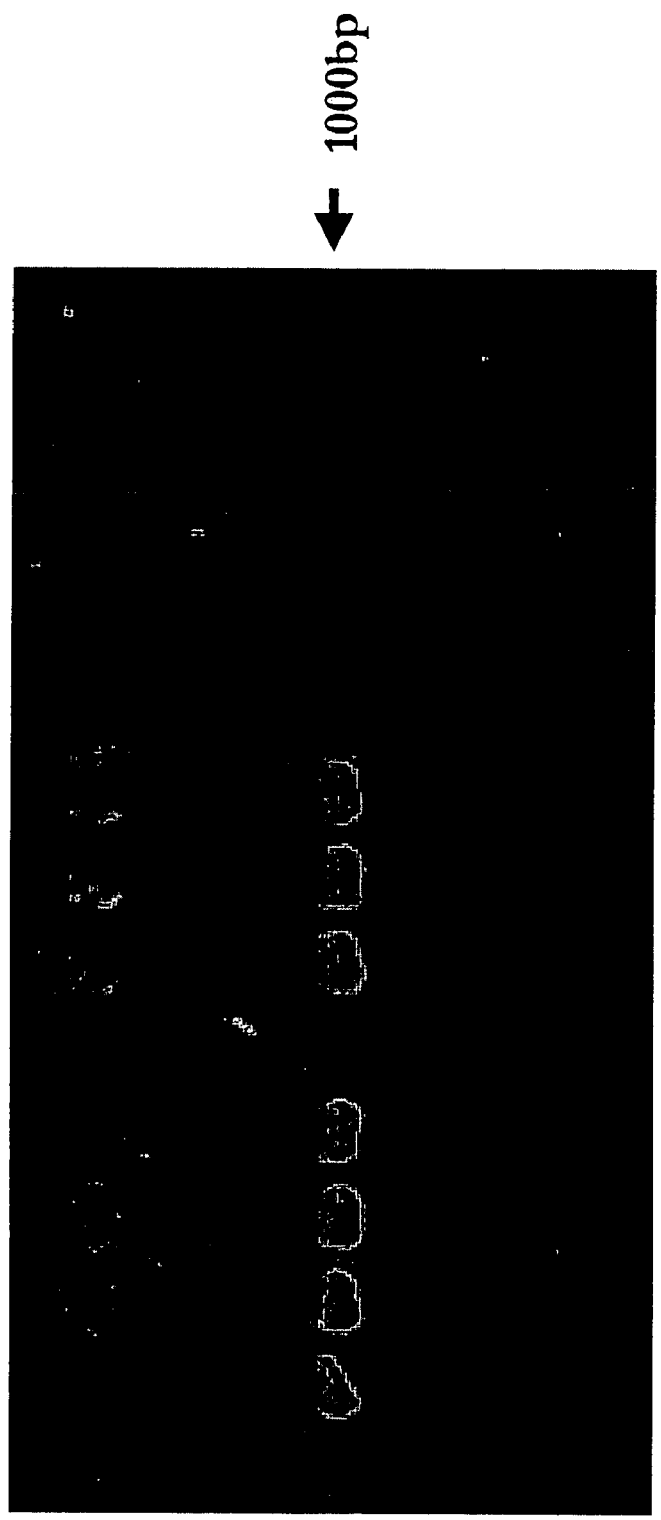
Figure 7D:
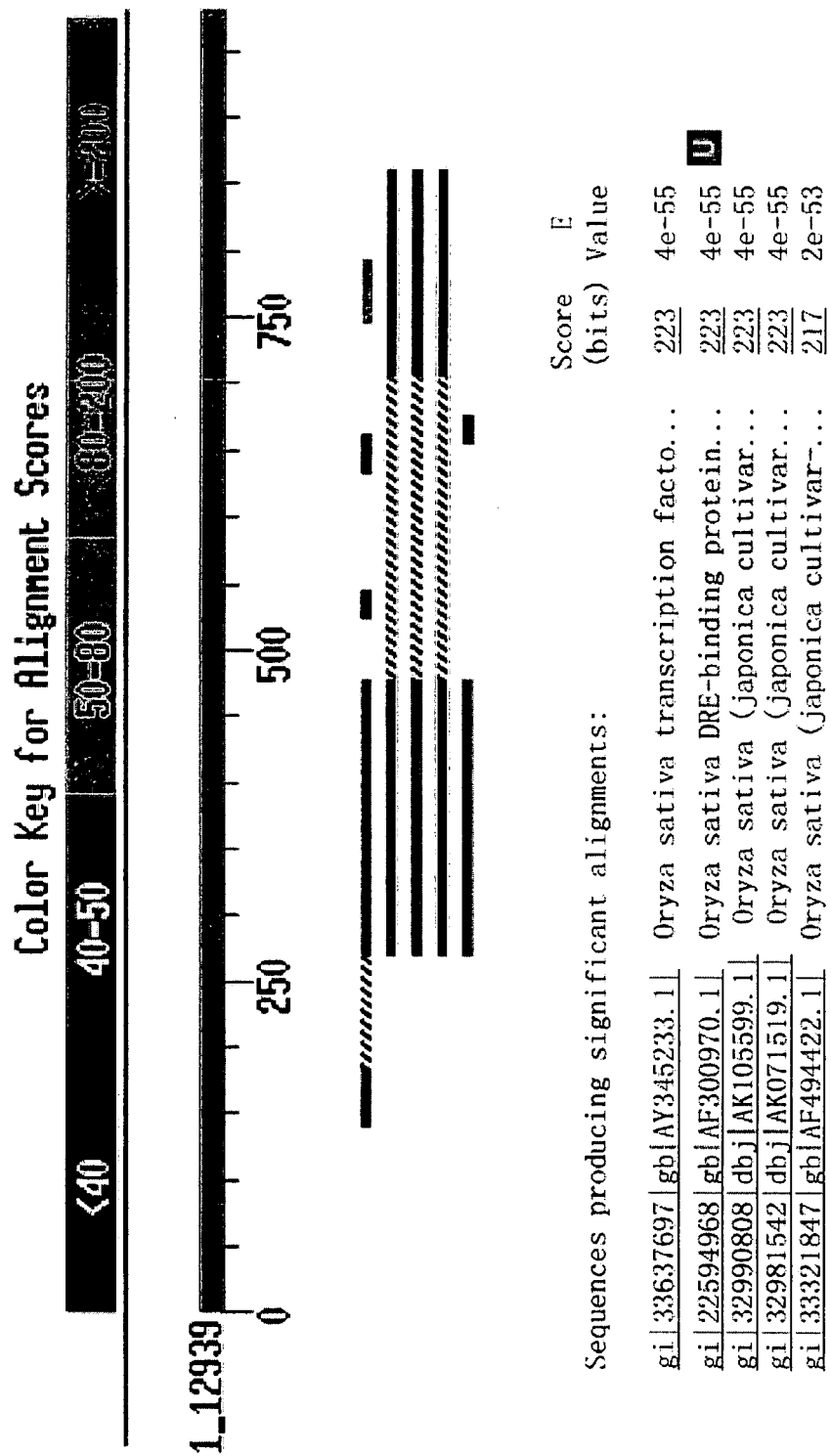
Figure 7E:
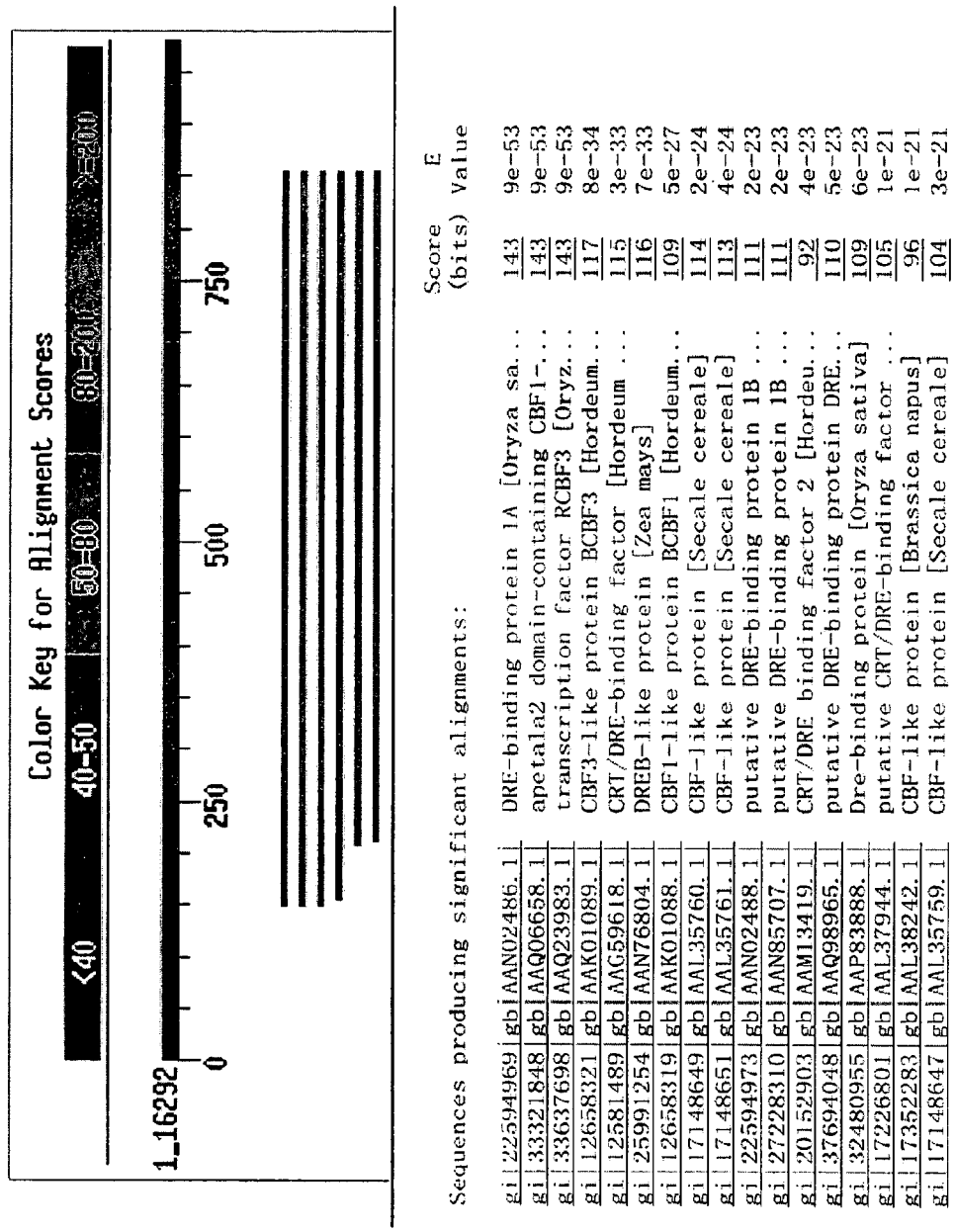

FIG. 6(*a-b*) shows exemplary embodiments using 5' and 3' RACE to obtain the flanking sequences of ryegrass cbƒ3.

Experimental Protocol:

The 5', 3' RACE primers were designed by using the identical (majority) sequence of the sequenced core regions. The ryegrass primers were based upon the identical sequences because sequences from same locus may have slight variety due to heterogeneity of ryegrass species.

5' and 3' RACE:

Full-length cDNA was prepared from mRNA extracted from plants then used to isolate ryegrass cbƒ3 using primers based on the partial gene sequences using 5' and 3' RACE techniques (5'/3' cDNA amplification kit, Roche, German). The sense and anti-sense primers used were Sp1: CCCGCG-GCGAGGGCGAGCATGGCGGC (SEQ ID NO:53) and Sp5R: GGCGGGGCGAACCAAGTTCC (SEQ ID NO:57) for amplifying 5' and 3' sequences of Lpcbf3 gene.

PCR Protocol:

PCR reactions were performed in 25-µl volumes containing 10 mM Tris-HCl (pH 8.3), 50 mM KCl, 1.5 µM MgCl$_2$, 200 µM of each deoxynucleotide, 50 ng of each primer, about 50 ng template DNA, and 1 U Taq DNA polymerase. The amplification was performed in a Thermocycler using the following program: 94° C. for 2 min. followed by 40 cycles at 94° C. for 1 min., 65° C. for 1 min. and 72° C. for 1 min. and 50 seconds, with a final extension at 72° C. for 5 minutes. PCR products were separated on 1.4% (w/v) agarose gels and visualized under UV light after ethidium bromide staining.

The specific bands (~200bp, 500bp) were inserted pGEM-T easy vector (Promega) followed directions provided in the kit manual for insertion, transformation and selection. Cloned genes were harvested and sequenced in the Michigan State University (Genomics Technology Support Facility). The sequences were blasted on http:,followed by,//www.ncbi.nlm.nih.gov/,followed by,blast/.

Alignments of DNA and protein were conducted by the MultiAlin (Multiple sequence alignment) program (Corpet, Nucl. Acids Res., 16 (22), 10881-10890 (1988).

EXAMPLE 8

How to obtain a full-length cbƒ3 coding sequence. FIG. 7. shows exemplary embodiments that demonstrate primers based on 5' and 3' sequences (a) used to amplify the corresponding ends of cbƒ3 that was sequenced to derive a full-length cbƒ3 cDNA (b-c), whose DNA and protein sequences were compared to corresponding databases using BLAST analysis (d-e).

The full-length Lpcbƒ3 was synthesized by PCR using the following protocol.

Experimental Protocol:

In order to obtain a full-length sequence of cbƒ3, the forward-primer CBF4: CGCCATCAGAAGATGTGTCCG (SEQ ID NO:64) and the reverse-primer Cbf3-4R: CACAATCACATTACCAGAAACTGC (SEQ ID NO:170) were designed and used for PCR amplification.

PCR Protocol:

PCR reactions were performed in 25-µl volumes containing 10 mM Tris-HCl (pH 8.3), 50 mM KCl, 1.5 µM MgCl$_2$, 200 µM of each deoxynucleotide, 50 ng of each primer, about 50 ng template DNA, and 1 U Taq DNA polymerase. The amplification was performed in a Thermocycler using the following program: 94° C. for 2 min. followed by 40 cycles at 94° C. for 1 min., 65° C. for 1 min. and 72° C. for 1 min. and 50 seconds, with a final extension at 72° C. for 5 minutes. PCR products were separated on 1.4% (w/v) agarose gels and visualized under UV light after ethidium bromide staining. The full-length sequence was inserted pGEM-T easy vector (Promega) followed directions provided in the kit manual for insertion, transformation and selection. Cloned genes were harvested and sequenced in Michigan State University Genomics Technology Support Facility. The DNA sequence and protein were compared to database information using NCBI BLAST.

EXAMPLE 9

FIG. 9. shows exemplary embodiments that demonstrate sequence alignments comparing ryegrass cbƒ3 with cbƒ genes from other plants.

Experimental Protocol:

Homologous plant cbƒ3 and cbƒ-like genes from various plants were obtained by using a Lpcbƒ3 sequence (SEQ ID NO: 01) for an NCBI BLAST analysis. Homologous plant sequences were then aligned with Lpcbf3 nucleic acid and protein sequences. The MultAlin program was used for alignment.

EXAMPLE 10

FIG. 12. shows percent identities of ryegrass cbf3 (Lpcbf3) compared to other plant CBF proteins.

Experimental Protocol:

The percent identities of ryegrass CBF3 compared to other plant CBF proteins are based on the results of MultAlin program at http:,followed by,//prodes.toulouse.inra.fr/, followed by,multalin/multalin.,followed by,html and NCBI BLAST at http:,followed by,//www.ncbi.nlm.nih.gov/,followed by,blast/.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in botany, biochemistry, molecular biology, plant biology, and chemistry or related fields are intended to be within the scope of the following claims.

The invention claimed is:

1. An isolated nucleic acid molecule selected from the group consisting of SEQ ID NO:1 and sequences encoding a polypeptide having at least 95% sequence identity to SEQ ID NO:2, wherein said nucleic acid encodes a protein that binds to a C-repeat/dehydration-responsive element.

2. The nucleic acid molecule of claim 1, wherein said polypeptide comprises an AP2 binding domain having the amino acid sequence of SEQ ID NO:3.

3. A vector construct comprising the nucleic acid of claim 1.

4. The vector of claim 3, wherein said nucleic acid is operably linked to an exogenous promoter.

5. The vector of claim 4, wherein said exogenous promoter is a eukaryotic promoter.

6. The vector of claim 5, wherein said eukaryotic promoter is active in a plant.

7. The vector of claim 3, wherein said vector is a eukaryotic vector.

8. The eukaryotic vector of claim 7, wherein said eukaryotic vector is a plant vector.

9. The plant vector of claim 8, wherein said plant vector is a T-DNA vector.

10. The vector of claim 3, wherein said vector is a prokaryotic vector.

11. The vector of claim 3, wherein said polypeptide comprises an AP2 binding domain having the amino acid sequence of SEQ ID NO:3, and wherein said nucleic acid molecule is operably linked to an exogenous promoter.

12. The nucleic acid molecule of claim 1, wherein said isolated nucleic acid molecule is SEQ ID NO:1.

13. The nucleic acid molecule of claim 1, wherein said polypeptide is SEQ ID NO:2.

* * * * *

```
                          SEQUENCE LISTING

<160> NUMBER OF SEQ ID NOS: 199

<210> SEQ ID NO 1
<211> LENGTH: 974
<212> TYPE: DNA
<213> ORGANISM: Lolium perenne

<400> SEQUENCE: 1
attaaatttc tcatcgcaga gcaaaaccac ttcacttcag caaacaaaaa gcatcaagag      60
ccctccaagg cgaacagaga cactgaggta gcgctagctc ctattagatt gtgattcgga     120
tcaacactca attcgccatc agaagatgtg tccgatcaag gaggagatgg gcggggagtc     180
aggctcgccg tgcagcgggg actattactc gccctcgacg tcgtcggagc tgcagcaggt     240
gcatagtcag aaccagacgc cgtggacgaa gcggccggcg gggcggacca agttcaggga     300
gacgcggcac ccggtgtatc gcggtgtgcg tcgtaggggc aatgccggga ggtgggtatg     360
cgaggtgcgc gtcccaggga ggcgcgggag caggctgtgg gtcggcacct tcgacactgc     420
cgagatcgcc gcgcgagcac acgacgccgc catgctcgcc ctcgccgcgg gcgattcctg     480
cctcaacttc gctgactccg ctgagctgct cgccgtgtcg gcatcctcct accgcagcct     540
cgacgaggtg cgccacgctg tcaccgaggc cgtcgacgaa ttcgagcgac accacgcgct     600
gggcgaggag gacgccctgt ccggcacgtc ggcgtcgacg ccctcctcct cttcctccgt     660
caccgacgac gagacgtcgt cttcgtgggc cgcggattcg cccttcgagc tggaagtcat     720
gggtgatatg ggcagggatc tgtactactc gagcttggcg cagggaatgc tcatggcgcc     780
gccgaccgca gctgcagcgc tcggtgatta cggcgaggcc aacctcgccg atgtggcact     840
gtggagttac cagagctagt tttgttcgcg ccacttcaaa ttttacctct ctccttcggt     900
gtcgtcttgg acaaattttg gttctgtacg gtcactgcta gcagtttctg gtaatgtgat     960
tgtgcaaatt cagg                                                      974

<210> SEQ ID NO 2
<211> LENGTH: 237
<212> TYPE: PRT
<213> ORGANISM: Lolium perenne

<400> SEQUENCE: 2

Met Cys Pro Ile Lys Glu Glu Met Gly Gly Glu Ser Gly Ser Pro Cys
  1               5                  10                  15

Ser Gly Asp Tyr Tyr Ser Pro Ser Thr Ser Ser Glu Leu Gln Gln Val
             20                  25                  30
```

-continued

```
His Ser Gln Asn Gln Thr Pro Trp Thr Lys Arg Pro Ala Gly Arg Thr
                 35                  40                  45

Lys Phe Arg Glu Thr Arg His Pro Val Tyr Arg Gly Val Arg Arg Arg
 50                  55                  60

Gly Asn Ala Gly Arg Trp Val Cys Glu Val Arg Val Pro Gly Arg Arg
 65                  70                  75                  80

Gly Ser Arg Leu Trp Val Gly Thr Phe Asp Thr Ala Glu Ile Ala Ala
                 85                  90                  95

Arg Ala His Asp Ala Ala Met Leu Ala Leu Ala Ala Gly Asp Ser Cys
                100                 105                 110

Leu Asn Phe Ala Asp Ser Ala Glu Leu Leu Ala Val Ser Ala Ser Ser
                115                 120                 125

Tyr Arg Ser Leu Asp Glu Val Arg His Ala Val Thr Glu Ala Val Asp
                130                 135                 140

Glu Phe Glu Arg His His Ala Leu Gly Glu Glu Asp Ala Leu Ser Gly
145                 150                 155                 160

Thr Ser Ala Ser Thr Pro Ser Ser Ser Ser Val Thr Asp Asp Glu
                165                 170                 175

Thr Ser Ser Trp Ala Ala Asp Ser Pro Phe Glu Leu Glu Val Met
                180                 185                 190

Gly Asp Met Gly Arg Asp Leu Tyr Tyr Ser Ser Leu Ala Gln Gly Met
                195                 200                 205

Leu Met Ala Pro Pro Thr Ala Ala Ala Leu Gly Asp Tyr Gly Glu
    210                 215                 220

Ala Asn Leu Ala Asp Val Ala Leu Trp Ser Tyr Gln Ser
225                 230                 235
```

```
<210> SEQ ID NO 3
<211> LENGTH: 60
<212> TYPE: PRT
<213> ORGANISM: Lolium perenne

<400> SEQUENCE: 3
```

```
Val Tyr Arg Gly Val Arg Arg Gly Asn Ala Gly Arg Trp Val Cys
  1               5                  10                  15

Glu Val Arg Val Pro Gly Arg Arg Gly Ser Arg Leu Trp Val Gly Thr
                 20                  25                  30

Phe Asp Thr Ala Glu Ile Ala Ala Arg Ala His Asp Ala Ala Met Leu
                 35                  40                  45

Ala Leu Ala Ala Gly Asp Ser Cys Leu Asn Phe Ala
     50                  55                  60
```

```
<210> SEQ ID NO 4
<211> LENGTH: 82
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (18)..(77)
<223> OTHER INFORMATION: Xaa can be any naturally occurring amino acid
```

-continued

```
<400> SEQUENCE: 4

Pro Lys Lys Arg Pro Ala Gly Arg Xaa Lys Phe Xaa Glu Thr Arg His
1               5                   10                  15

Pro Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Asp Ser Ala
65                  70                  75                  80

Trp Arg

<210> SEQ ID NO 5
<211> LENGTH: 79
<212> TYPE: PRT
<213> ORGANISM: Lolium perenne
<220> FEATURE:
<221> NAME/KEY: misc_feature
<222> LOCATION: (15)..(74)
<223> OTHER INFORMATION: Xaa can be any naturally occurring amino acid

<400> SEQUENCE: 5

Trp Thr Lys Arg Pro Ala Gly Arg Thr Lys Phe Arg His Pro Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Asp Ser Ala Glu Leu
65                  70                  75

<210> SEQ ID NO 6
<211> LENGTH: 64
<212> TYPE: PRT
<213> ORGANISM: Lolium perenne

<400> SEQUENCE: 6

Phe Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
            20                  25                  30

Asp Thr Ala Glu Ile Ala Ala Arg Ala His Asp Ala Ala Met Leu Ala
        35                  40                  45

Leu Ala Ala Gly Asp Ser Cys Leu Asn Phe Ala Asp Ser Ala Glu Leu
    50                  55                  60

<210> SEQ ID NO 7
<211> LENGTH: 64
<212> TYPE: PRT
<213> ORGANISM: Lolium perenne

<400> SEQUENCE: 7

Tyr Arg Gly Val Arg Gln Arg Gly Asn Ala Gly Arg Trp Val Cys Glu
1               5                   10                  15

Val Arg Val Pro Gly Arg Arg Gly Ser Arg Leu Trp Val Gly Thr Phe
```

```
              20                  25                  30

Asp Thr Ala Glu Ile Ala Ala Arg Ala His Asp Ala Ala Met Leu Ala
         35                  40                  45

Leu Ala Ala Gly Asp Ser Cys Leu Asn Phe Ala Asp Ser Ala Glu Leu
     50                  55                  60

<210> SEQ ID NO 8
<211> LENGTH: 63
<212> TYPE: PRT
<213> ORGANISM: Lolium perenne

<400> SEQUENCE: 8

Tyr Arg Gly Val Arg Arg Asn Ser Gly Lys Trp Val Cys Glu Val
1               5                   10                  15

Arg Val Pro Gly Arg Arg Gly Ser Arg Leu Trp Val Gly Thr Phe Asp
             20                  25                  30

Thr Ala Glu Ile Ala Ala Arg Ala His Asp Ala Ala Met Leu Ala Leu
         35                  40                  45

Ala Ala Gly Asp Ser Cys Leu Asn Phe Ala Asp Ser Ala Glu Leu
     50                  55                  60

<210> SEQ ID NO 9
<211> LENGTH: 64
<212> TYPE: PRT
<213> ORGANISM: Lolium perenne

<400> SEQUENCE: 9

Tyr Arg Gly Val Arg Arg Gly Ala Ala Gly Arg Trp Val Cys Glu
1               5                   10                  15

Val Arg Val Pro Gly Arg Gly Ser Arg Leu Trp Val Gly Thr Phe
             20                  25                  30

Asp Thr Ala Glu Ile Ala Ala Arg Ala His Asp Ala Ala Met Leu Ala
         35                  40                  45

Leu Ala Ala Gly Asp Ser Cys Leu Asn Phe Ala Asp Ser Ala Glu Leu
     50                  55                  60

<210> SEQ ID NO 10
<211> LENGTH: 64
<212> TYPE: PRT
<213> ORGANISM: Lolium perenne

<400> SEQUENCE: 10

Tyr Arg Gly Val Arg Arg Gly Arg Val Gly Gln Trp Val Cys Glu
1               5                   10                  15

Val Arg Val Pro Gly Arg Arg Gly Ser Arg Leu Trp Val Gly Thr Phe
             20                  25                  30

Asp Thr Ala Glu Ile Ala Ala Arg Ala His Asp Ala Ala Met Leu Ala
         35                  40                  45

Leu Ala Ala Gly Asp Ser Cys Leu Asn Phe Ala Asp Ser Ala Glu Leu
     50                  55                  60

<210> SEQ ID NO 11
<211> LENGTH: 64
<212> TYPE: PRT
<213> ORGANISM: Lolium perenne

<400> SEQUENCE: 11

Tyr Arg Gly Val Arg Arg Arg Gly Asn Thr Glu Arg Trp Val Cys Glu
1               5                   10                  15
```

Val Arg Val Pro Gly Arg Arg Gly Ser Arg Leu Trp Val Gly Thr Phe
            20                  25                  30

Asp Thr Ala Glu Ile Ala Ala Arg Ala His Asp Ala Ala Met Leu Ala
            35                  40                  45

Leu Ala Ala Gly Asp Ser Cys Leu Asn Phe Ala Asp Ser Ala Glu Leu
        50                  55                  60

<210> SEQ ID NO 12
<211> LENGTH: 64
<212> TYPE: PRT
<213> ORGANISM: Lolium perenne

<400> SEQUENCE: 12

Tyr Arg Gly Val Arg Arg Gly Asn Ala Gly Arg Trp Val Cys Glu
1               5                   10                  15

Leu Arg Glu Pro Gly Arg Arg Gly Ser Arg Leu Trp Val Gly Thr Phe
            20                  25                  30

Asp Thr Ala Glu Ile Ala Ala Arg Ala His Asp Ala Ala Met Leu Ala
            35                  40                  45

Leu Ala Ala Gly Asp Ser Cys Leu Asn Phe Ala Asp Ser Ala Glu Leu
        50                  55                  60

<210> SEQ ID NO 13
<211> LENGTH: 63
<212> TYPE: PRT
<213> ORGANISM: Lolium perenne

<400> SEQUENCE: 13

Tyr Arg Gly Val Arg Arg Gly Asn Ala Gly Arg Trp Val Cys Glu
1               5                   10                  15

Val Arg Val Pro Asn Lys Lys Thr Arg Leu Trp Val Gly Thr Phe Asp
            20                  25                  30

Thr Ala Glu Ile Ala Ala Arg Ala His Asp Ala Ala Met Leu Ala Leu
            35                  40                  45

Ala Ala Gly Asp Ser Cys Leu Asn Phe Ala Asp Ser Ala Glu Leu
        50                  55                  60

<210> SEQ ID NO 14
<211> LENGTH: 64
<212> TYPE: PRT
<213> ORGANISM: Lolium perenne

<400> SEQUENCE: 14

Tyr Arg Gly Val Arg Arg Gly Asn Ala Gly Arg Trp Val Cys Glu
1               5                   10                  15

Val Arg Val Pro Gly Arg Arg Gly Ser Arg Ile Trp Val Gly Thr Phe
            20                  25                  30

Asp Thr Ala Glu Ile Ala Ala Arg Ala His Asp Ala Ala Met Leu Ala
            35                  40                  45

Leu Ala Ala Gly Asp Ser Cys Leu Asn Phe Ala Asp Ser Ala Glu Leu
        50                  55                  60

<210> SEQ ID NO 15
<211> LENGTH: 64
<212> TYPE: PRT
<213> ORGANISM: Lolium perenne

<400> SEQUENCE: 15

Tyr Arg Gly Val Arg Arg Gly Asn Ala Gly Arg Trp Val Cys Glu
1               5                   10                  15

-continued

Val Arg Val Pro Gly Ile Lys Gly Ser Arg Leu Trp Val Gly Thr Phe
              20                  25                  30

Asp Thr Ala Glu Ile Ala Ala Arg Ala His Asp Ala Ala Met Leu Ala
          35                  40                  45

Leu Ala Ala Gly Asp Ser Cys Leu Asn Phe Ala Asp Ser Ala Glu Leu
      50                  55                  60

<210> SEQ ID NO 16
<211> LENGTH: 64
<212> TYPE: PRT
<213> ORGANISM: Lolium perenne

<400> SEQUENCE: 16

Tyr Arg Gly Val Arg Arg Gly Asn Ala Gly Arg Trp Val Cys Glu
1               5                   10                  15

Val Arg Val Pro Gly Arg Arg Gly Cys Arg Leu Trp Val Gly Thr Phe
              20                  25                  30

Asp Thr Ala Glu Ile Ala Ala Arg Ala His Asp Ala Ala Met Leu Ala
          35                  40                  45

Leu Ala Ala Gly Asp Ser Cys Leu Asn Phe Ala Asp Ser Ala Glu Leu
      50                  55                  60

<210> SEQ ID NO 17
<211> LENGTH: 64
<212> TYPE: PRT
<213> ORGANISM: Lolium perenne

<400> SEQUENCE: 17

Tyr Arg Gly Val Arg Arg Gly Asn Ala Gly Arg Trp Val Cys Glu
1               5                   10                  15

Val Arg Val Pro Gly Arg Arg Gly Ala Arg Leu Trp Val Gly Thr Phe
              20                  25                  30

Asp Thr Ala Glu Ile Ala Ala Arg Ala His Asp Ala Ala Met Leu Ala
          35                  40                  45

Leu Ala Ala Gly Asp Ser Cys Leu Asn Phe Ala Asp Ser Ala Glu Leu
      50                  55                  60

<210> SEQ ID NO 18
<211> LENGTH: 64
<212> TYPE: PRT
<213> ORGANISM: Lolium perenne

<400> SEQUENCE: 18

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Leu Gly Thr Phe
              20                  25                  30

Asp Thr Ala Glu Ile Ala Ala Arg Ala His Asp Ala Ala Met Leu Ala
          35                  40                  45

Leu Ala Ala Gly Asp Ser Cys Leu Asn Phe Ala Asp Ser Ala Glu Leu
      50                  55                  60

<210> SEQ ID NO 19
<211> LENGTH: 64
<212> TYPE: PRT
<213> ORGANISM: Lolium perenne

<400> SEQUENCE: 19

Tyr Arg Gly Val Arg Arg Arg Gly Asn Ala Gly Arg Trp Val Cys Glu

```
                1               5                   10                  15
        Val Arg Val Pro Gly Arg Arg Gly Ser Arg Leu Trp Val Gly Thr Tyr
                        20                  25                  30

Asp Thr Ala Glu Ile Ala Ala Arg Ala His Asp Ala Ala Met Leu Ala
                        35                  40                  45

Leu Ala Ala Gly Asp Ser Cys Leu Asn Phe Ala Asp Ser Ala Glu Leu
                50                      55                  60

<210> SEQ ID NO 20
<211> LENGTH: 64
<212> TYPE: PRT
<213> ORGANISM: Lolium perenne

<400> SEQUENCE: 20

Tyr Arg Gly Val Arg Arg Gly Asn Ala Gly Arg Trp Val Cys Glu
        1               5                   10                  15

Val Arg Val Pro Gly Arg Arg Gly Ser Arg Leu Trp Val Gly Thr Phe
                        20                  25                  30

Asp Thr Ala Glu Gly Ala Ala Arg Ala His Asp Ala Ala Met Leu Ala
                        35                  40                  45

Leu Ala Ala Gly Asp Ser Cys Leu Asn Phe Ala Asp Ser Ala Glu Leu
                50                      55                  60

<210> SEQ ID NO 21
<211> LENGTH: 64
<212> TYPE: PRT
<213> ORGANISM: Lolium perenne

<400> SEQUENCE: 21

Tyr Arg Gly Val Arg Arg Gly Asn Ala Gly Arg Trp Val Cys Glu
        1               5                   10                  15

Val Arg Val Pro Gly Arg Arg Gly Ser Arg Leu Trp Val Gly Thr Phe
                        20                  25                  30

Ala Thr Ala Glu Val Ala Ala Arg Ala His Asp Ala Ala Met Leu Ala
                        35                  40                  45

Leu Ala Ala Gly Asp Ser Cys Leu Asn Phe Ala Asp Ser Ala Glu Leu
                50                      55                  60

<210> SEQ ID NO 22
<211> LENGTH: 64
<212> TYPE: PRT
<213> ORGANISM: Lolium perenne

<400> SEQUENCE: 22

Tyr Arg Gly Val Arg Arg Gly Asn Ala Gly Arg Trp Val Cys Glu
        1               5                   10                  15

Val Arg Val Pro Gly Arg Arg Gly Ser Arg Leu Trp Val Gly Thr Phe
                        20                  25                  30

Leu Ala Ala Glu Ala Ala Ala Arg Ala His Asp Ala Ala Met Leu Ala
                        35                  40                  45

Leu Ala Ala Gly Asp Ser Cys Leu Asn Phe Ala Asp Ser Ala Glu Leu
                50                      55                  60

<210> SEQ ID NO 23
<211> LENGTH: 64
<212> TYPE: PRT
<213> ORGANISM: Lolium perenne

<400> SEQUENCE: 23
```

-continued

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
                20                  25                  30

Asp Thr Ala Glu Met Ala Ala Arg Ala His Asp Ala Ala Met Leu Ala
            35                  40                  45

Leu Ala Ala Gly Asp Ser Cys Leu Asn Phe Ala Asp Ser Ala Glu Leu
    50                  55                  60

<210> SEQ ID NO 24
<211> LENGTH: 64
<212> TYPE: PRT
<213> ORGANISM: Lolium perenne

<400> SEQUENCE: 24

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
                20                  25                  30

Asn Thr Ala Glu Ile Ala Ala Arg Ala His Asp Ala Ala Met Leu Ala
            35                  40                  45

Leu Ala Ala Gly Asp Ser Cys Leu Asn Phe Ala Asp Ser Ala Glu Leu
    50                  55                  60

<210> SEQ ID NO 25
<211> LENGTH: 64
<212> TYPE: PRT
<213> ORGANISM: Lolium perenne

<400> SEQUENCE: 25

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
                20                  25                  30

Gln Thr Ala Glu Ile Ala Ala Arg Ala His Asp Ala Ala Met Leu Ala
            35                  40                  45

Leu Ala Ala Gly Asp Ser Cys Leu Asn Phe Ala Asp Ser Ala Glu Leu
    50                  55                  60

<210> SEQ ID NO 26
<211> LENGTH: 64
<212> TYPE: PRT
<213> ORGANISM: Lolium perenne

<400> SEQUENCE: 26

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
                20                  25                  30

Asn Thr Ala Glu Met Ala Ala Arg Ala His Asp Ala Ala Met Leu Ala
            35                  40                  45

Leu Ala Ala Gly Asp Ser Cys Leu Asn Phe Ala Asp Ser Ala Glu Leu
    50                  55                  60

<210> SEQ ID NO 27
<211> LENGTH: 64
<212> TYPE: PRT
<213> ORGANISM: Lolium perenne

<400> SEQUENCE: 27

```
Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
            20                  25                  30

Gln Thr Ala Glu Met Ala Ala Arg Ala His Asp Ala Ala Met Leu Ala
        35                  40                  45

Leu Ala Ala Gly Asp Ser Cys Leu Asn Phe Ala Asp Ser Ala Glu Leu
    50                  55                  60
```

<210> SEQ ID NO 28
<211> LENGTH: 64
<212> TYPE: PRT
<213> ORGANISM: Lolium perenne

<400> SEQUENCE: 28

```
Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
            20                  25                  30

Asp Thr Ala Glu Ile Ala Ala Arg Ala Asn Asp Ala Ala Met Leu Ala
        35                  40                  45

Leu Ala Ala Gly Asp Ser Cys Leu Asn Phe Ala Asp Ser Ala Glu Leu
    50                  55                  60
```

<210> SEQ ID NO 29
<211> LENGTH: 64
<212> TYPE: PRT
<213> ORGANISM: Lolium perenne

<400> SEQUENCE: 29

```
Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
            20                  25                  30

Asp Thr Ala Glu Ile Ala Ala Arg Ala His Asp Val Ala Ile Ala
        35                  40                  45

Leu Ala Ala Gly Asp Ser Cys Leu Asn Phe Ala Asp Ser Ala Glu Leu
    50                  55                  60
```

<210> SEQ ID NO 30
<211> LENGTH: 64
<212> TYPE: PRT
<213> ORGANISM: Lolium perenne

<400> SEQUENCE: 30

```
Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
            20                  25                  30

Asp Thr Ala Glu Ile Ala Ala Arg Ala His Asp Ala Ala Ile Leu Ala
        35                  40                  45

Leu Ala Ala Gly Asp Ser Cys Leu Asn Phe Ala Asp Ser Ala Glu Leu
    50                  55                  60
```

<210> SEQ ID NO 31
<211> LENGTH: 64
<212> TYPE: PRT
<213> ORGANISM: Lolium perenne

```
<400> SEQUENCE: 31

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
            20                  25                  30

Asp Thr Ala Glu Ile Ala Ala Arg Ala His Asp Ala Ala Val Leu Ala
        35                  40                  45

Leu Ala Ala Gly Asp Ser Cys Leu Asn Phe Ala Asp Ser Ala Glu Leu
    50                  55                  60

<210> SEQ ID NO 32
<211> LENGTH: 64
<212> TYPE: PRT
<213> ORGANISM: Lolium perenne

<400> SEQUENCE: 32

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
            20                  25                  30

Asp Thr Ala Glu Ile Ala Ala Arg Ala His Asp Ala Ala Met Leu Ala
        35                  40                  45

Ile Asn Ala Gly Ala Cys Cys Leu Asn Phe Ala Asp Ser Ala Glu Leu
    50                  55                  60

<210> SEQ ID NO 33
<211> LENGTH: 67
<212> TYPE: PRT
<213> ORGANISM: Lolium perenne

<400> SEQUENCE: 33

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
            20                  25                  30

Asp Thr Ala Glu Ile Ala Ala Arg Ala His Asp Ala Ala Met Leu Ala
        35                  40                  45

Leu Gly Gly Arg Ser Ala Thr Cys Leu Asn Phe Ala Asp Ser Asp Ser
    50                  55                  60

Ala Glu Leu
65

<210> SEQ ID NO 34
<211> LENGTH: 65
<212> TYPE: PRT
<213> ORGANISM: Lolium perenne

<400> SEQUENCE: 34

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
            20                  25                  30

Asp Thr Ala Glu Ile Ala Ala Arg Ala His Asp Ala Ala Met Leu Ala
        35                  40                  45

Leu Gln Gly Arg Gly Ala Gly Arg Leu Asn Phe Ala Asp Ser Ala Glu
    50                  55                  60

Leu
65
```

<210> SEQ ID NO 35
<211> LENGTH: 64
<212> TYPE: PRT
<213> ORGANISM: Lolium perenne

<400> SEQUENCE: 35

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
                20                  25                  30

Asp Thr Ala Glu Ile Ala Ala Arg Ala His Asp Ala Ala Met Leu Ala
            35                  40                  45

Leu Ser Gly Arg Ala Ala Cys Leu Asn Phe Ala Asp Ser Ala Glu Leu
        50                  55                  60

<210> SEQ ID NO 36
<211> LENGTH: 64
<212> TYPE: PRT
<213> ORGANISM: Lolium perenne

<400> SEQUENCE: 36

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
                20                  25                  30

Asp Thr Ala Glu Ile Ala Ala Arg Ala His Asp Ala Ala Met Leu Ala
            35                  40                  45

Leu Arg Gly Arg Ser Ala Cys Leu Asn Phe Ala Asp Ser Ala Glu Leu
        50                  55                  60

<210> SEQ ID NO 37
<211> LENGTH: 64
<212> TYPE: PRT
<213> ORGANISM: Lolium perenne

<400> SEQUENCE: 37

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
                20                  25                  30

Asp Thr Ala Glu Ile Ala Ala Arg Ala His Asp Ala Ala Met Leu Ala
            35                  40                  45

Leu Ala Gly Arg Asp Ala Cys Leu Asn Phe Pro Asp Ser Ala Glu Leu
        50                  55                  60

<210> SEQ ID NO 38
<211> LENGTH: 65
<212> TYPE: PRT
<213> ORGANISM: Lolium perenne

<400> SEQUENCE: 38

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
                20                  25                  30

Asp Thr Ala Glu Ile Ala Ala Arg Ala His Asp Ala Ala Met Leu Ala
            35                  40                  45

Leu Ala Gly Arg Gly Ala Gly Arg Leu Asn Phe Pro Asp Ser Ala Glu

```
                    50                  55                  60

Leu
 65

<210> SEQ ID NO 39
<211> LENGTH: 64
<212> TYPE: PRT
<213> ORGANISM: Lolium perenne

<400> SEQUENCE: 39

Tyr Arg Gly Val Arg Arg Gly Asn Ala Gly Arg Trp Val Cys Glu
 1               5                  10                  15

Val Arg Val Pro Gly Arg Arg Gly Ser Arg Leu Trp Val Gly Thr Phe
                20                  25                  30

Asp Thr Ala Glu Ile Ala Ala Arg Ala His Asp Ala Ala Met Leu Ala
            35                  40                  45

Leu Ala Ala Gly Asp Ser Arg Leu Asn Phe Pro Asp Ser Ala Glu Leu
        50                  55                  60

<210> SEQ ID NO 40
<211> LENGTH: 64
<212> TYPE: PRT
<213> ORGANISM: Lolium perenne

<400> SEQUENCE: 40

Tyr Arg Gly Val Arg Arg Gly Asn Ala Gly Arg Trp Val Cys Glu
 1               5                  10                  15

Val Arg Val Pro Gly Arg Arg Gly Ser Arg Leu Trp Val Gly Thr Phe
                20                  25                  30

Asp Thr Ala Glu Ile Ala Ala Arg Ala His Asp Ala Ala Met Leu Ala
            35                  40                  45

Leu Ala Ala Gly Asp Ser Cys Leu Asn Phe Pro Asp Ser Ala Glu Leu
        50                  55                  60

<210> SEQ ID NO 41
<211> LENGTH: 64
<212> TYPE: PRT
<213> ORGANISM: Lolium perenne

<400> SEQUENCE: 41

Tyr Arg Gly Val Arg Arg Gly Asn Ala Gly Arg Trp Val Cys Glu
 1               5                  10                  15

Val Arg Val Pro Gly Arg Arg Gly Ser Arg Leu Trp Val Gly Thr Phe
                20                  25                  30

Asp Thr Ala Glu Ile Ala Ala Arg Ala His Asp Ala Ala Met Leu Ala
            35                  40                  45

Leu Ala Ala Gly Asp Ser Cys Leu Asn Phe Ala Asp Ser Ala Trp Leu
        50                  55                  60

<210> SEQ ID NO 42
<211> LENGTH: 64
<212> TYPE: PRT
<213> ORGANISM: Lolium perenne

<400> SEQUENCE: 42

Tyr Arg Gly Val Arg Arg Gly Asn Ala Gly Arg Trp Val Cys Glu
 1               5                  10                  15

Val Arg Val Pro Gly Arg Arg Gly Ser Arg Leu Trp Val Gly Thr Phe
                20                  25                  30
```

```
Asp Thr Ala Glu Ile Ala Ala Arg Ala His Asp Ala Ala Met Leu Ala
            35                  40                  45

Leu Ala Ala Gly Asp Ser Cys Leu Asn Phe Ala Asp Ser Ala Arg Leu
 50                  55                  60

<210> SEQ ID NO 43
<211> LENGTH: 64
<212> TYPE: PRT
<213> ORGANISM: Lolium perenne

<400> SEQUENCE: 43

Tyr Arg Gly Val Arg Arg Gly Asn Ala Gly Arg Trp Val Cys Glu
 1               5                  10                  15

Val Arg Val Pro Gly Arg Arg Gly Ser Arg Leu Trp Val Gly Thr Phe
            20                  25                  30

Asp Thr Ala Glu Ile Ala Ala Arg Ala His Asp Ala Ala Met Leu Ala
            35                  40                  45

Leu Ala Ala Gly Asp Ser Cys Leu Asn Phe Pro Asp Ser Ala Arg Leu
 50                  55                  60

<210> SEQ ID NO 44
<211> LENGTH: 65
<212> TYPE: PRT
<213> ORGANISM: Lolium perenne

<400> SEQUENCE: 44

Tyr Arg Gly Val Arg Arg Gly Asn Ala Gly Arg Trp Val Cys Glu
 1               5                  10                  15

Val Arg Val Pro Gly Arg Arg Gly Ser Arg Leu Trp Val Gly Thr Phe
            20                  25                  30

Asp Thr Ala Glu Ile Ala Ala Arg Ala His Asp Ala Ala Met Leu Ala
            35                  40                  45

Leu Ala Ala Gly Asp Ser Cys Leu Asn Phe Ala Asp Ser Ala Trp Arg
 50                  55                  60

Leu
 65

<210> SEQ ID NO 45
<211> LENGTH: 65
<212> TYPE: PRT
<213> ORGANISM: Lolium perenne

<400> SEQUENCE: 45

Tyr Arg Gly Val Arg Arg Gly Asn Ala Gly Arg Trp Val Cys Glu
 1               5                  10                  15

Val Arg Val Pro Gly Arg Arg Gly Ser Arg Leu Trp Val Gly Thr Phe
            20                  25                  30

Asp Thr Ala Glu Ile Ala Ala Arg Ala His Asp Ala Ala Met Leu Ala
            35                  40                  45

Leu Ala Ala Gly Asp Ser Cys Leu Asn Phe Ala Asp Ser Ala Trp Arg
 50                  55                  60

Met
 65

<210> SEQ ID NO 46
<211> LENGTH: 64
<212> TYPE: PRT
<213> ORGANISM: Lolium perenne

<400> SEQUENCE: 46
```

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Ala Gly Thr Phe
            20                  25                  30

Asp Thr Ala Glu Ile Ala Ala Arg Ala His Asp Ala Ala Met Leu Ala
        35                  40                  45

Leu Ala Ala Gly Asp Ser Cys Leu Asn Phe Ala Asp Ser Ala Glu Leu
    50                  55                  60

<210> SEQ ID NO 47
<211> LENGTH: 64
<212> TYPE: PRT
<213> ORGANISM: Lolium perenne

<400> SEQUENCE: 47

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Val Gly Thr Phe
            20                  25                  30

Asp Thr Ala Arg Ile Ala Ala Arg Ala His Asp Ala Ala Met Leu Ala
        35                  40                  45

Leu Ala Ala Gly Asp Ser Cys Leu Asn Phe Ala Asp Ser Ala Glu Leu
    50                  55                  60

<210> SEQ ID NO 48
<211> LENGTH: 64
<212> TYPE: PRT
<213> ORGANISM: Lolium perenne

<400> SEQUENCE: 48

Tyr Arg Gly Val Arg Arg Gly Asn Ala Gly Arg Trp Val Cys Glu
1               5                   10                  15

Val Arg Val Pro Gly Arg Arg Gly Ser Arg Leu Trp Ala Gly Thr Phe
            20                  25                  30

Asp Thr Ala Arg Ile Ala Ala Arg Ala His Asp Ala Ala Met Leu Ala
        35                  40                  45

Leu Ala Ala Gly Asp Ser Cys Leu Asn Phe Ala Asp Ser Ala Glu Leu
    50                  55                  60

<210> SEQ ID NO 49
<211> LENGTH: 24
<212> TYPE: DNA
<213> ORGANISM: Artificial Sequence
<220> FEATURE:
<223> OTHER INFORMATION: Synthetic

<400> SEQUENCE: 49
ggccggcggg gcgaaccaag ttcc                                  24

<210> SEQ ID NO 50
<211> LENGTH: 24
<212> TYPE: DNA
<213> ORGANISM: Artificial Sequence
<220> FEATURE:
<223> OTHER INFORMATION: Synthetic

<400> SEQUENCE: 50
aggcagagtc ggcgaagttg aggc                                  24

<210> SEQ ID NO 51

```
<211> LENGTH: 32
<212> TYPE: DNA
<213> ORGANISM: Artificial Sequence
<220> FEATURE:
<223> OTHER INFORMATION: Synthetic

<400> SEQUENCE: 51
ccagctaaag aaagccagct gcacgtggac gt                                      32

<210> SEQ ID NO 52
<211> LENGTH: 36
<212> TYPE: DNA
<213> ORGANISM: Artificial Sequence
<220> FEATURE:
<223> OTHER INFORMATION: Synthetic

<400> SEQUENCE: 52
ggagctaaga gctaagcata gctcccttca gctgcc                                  36

<210> SEQ ID NO 53
<211> LENGTH: 26
<212> TYPE: DNA
<213> ORGANISM: Artificial Sequence
<220> FEATURE:
<223> OTHER INFORMATION: Synthetic

<400> SEQUENCE: 53
cccgcggcga gggcgagcat ggcggc                                             26

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gctcgcgcgg cgatctcggc                                                    20

<210> SEQ ID NO 55
<211> LENGTH: 16
<212> TYPE: DNA
<213> ORGANISM: Artificial Sequence
<220> FEATURE:
<223> OTHER INFORMATION: Synthetic

<400> SEQUENCE: 55
tacaccgggt gccgcg                                                        16

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
ggaacttggt tcgccccgcc                                                    20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
```
ggcggggcga accaagttcc                                                20

<210> SEQ ID NO 58
<211> LENGTH: 16
<212> TYPE: DNA
<213> ORGANISM: Artificial Sequence
<220> FEATURE:
<223> OTHER INFORMATION: Synthetic

<400> SEQUENCE: 58
cgcggcaccc ggtgta                                                    16

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gccgagatcg ccgcgcgagc                                                20

<210> SEQ ID NO 60
<211> LENGTH: 24
<212> TYPE: DNA
<213> ORGANISM: Artificial Sequence
<220> FEATURE:
<223> OTHER INFORMATION: Synthetic

<400> SEQUENCE: 60
aaatttctca tcgcagagca aaac                                           24

<210> SEQ ID NO 61
<211> LENGTH: 24
<212> TYPE: DNA
<213> ORGANISM: Artificial Sequence
<220> FEATURE:
<223> OTHER INFORMATION: Synthetic

<400> SEQUENCE: 61
cagcaaacaa aaagcatcaa gaac                                           24

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
caaggcgaac agagacactg                                                20

<210> SEQ ID NO 63
<211> LENGTH: 21
<212> TYPE: DNA
<213> ORGANISM: Artificial Sequence
<220> FEATURE:
<223> OTHER INFORMATION: Synthetic

<400> SEQUENCE: 63
cgccatcaga agatgtgtcc g                                              21

<210> SEQ ID NO 64
<211> LENGTH: 24
<212> TYPE: DNA

```
<213> ORGANISM: Artificial Sequence
<220> FEATURE:
<223> OTHER INFORMATION: Synthetic

<400> SEQUENCE: 64
actgaggtag cgctagctcc tatt                                              24

<210> SEQ ID NO 65
<211> LENGTH: 8
<212> TYPE: DNA
<213> ORGANISM: Artificial Sequence
<220> FEATURE:
<223> OTHER INFORMATION: Synthetic

<400> SEQUENCE: 65 tggccgac                                                                 8

<210> SEQ ID NO 66
<211> LENGTH: 9
<212> TYPE: DNA
<213> ORGANISM: Artificial Sequence
<220> FEATURE:
<223> OTHER INFORMATION: Synthetic

<400> SEQUENCE: 66 taccgacat                                                                9

<210> SEQ ID NO 67
<211> LENGTH: 5
<212> TYPE: DNA
<213> ORGANISM: Artificial Sequence
<220> FEATURE:
<223> OTHER INFORMATION: Synthetic

<400> SEQUENCE: 67 ccgac                                                                    5

<210> SEQ ID NO 68
<211> LENGTH: 11
<212> TYPE: DNA
<213> ORGANISM: Artificial Sequence
<220> FEATURE:
<223> OTHER INFORMATION: Synthetic

<400> SEQUENCE: 68
taagagccgc c                                                            11

<210> SEQ ID NO 69
<211> LENGTH: 7
<212> TYPE: DNA
<213> ORGANISM: Artificial Sequence
<220> FEATURE:
<223> OTHER INFORMATION: Synthetic

<400> SEQUENCE: 69 agccgcc                                                                  7

<210> SEQ ID NO 70
<211> LENGTH: 238
<212> TYPE: PRT
<213> ORGANISM: Oryza sativa

<400> SEQUENCE: 70

Met Cys Gly Ile Lys Gln Glu Met Ser Gly Glu Ser Ser Gly Ser Pro
1               5                   10                  15
```

```
Cys Ser Ser Ala Ser Ala Glu Arg Gln His Gln Thr Val Trp Thr Ala
             20                  25                  30

Pro Pro Lys Arg Pro Ala Gly Arg Thr Lys Phe Arg Glu Thr Arg His
         35                  40                  45

Pro Val Phe Arg Gly Val Arg Arg Gly Asn Ala Gly Arg Trp Val
 50                  55                  60

Cys Glu Val Arg Val Pro Gly Arg Arg Gly Cys Arg Leu Trp Leu Gly
 65                  70                  75                  80

Thr Phe Asp Thr Ala Glu Gly Ala Ala Arg Ala His Asp Ala Ala Met
                 85                  90                  95

Leu Ala Ile Asn Ala Gly Gly Gly Gly Gly Ala Cys Cys Leu
                100                 105                 110

Asn Phe Ala Asp Ser Ala Trp Leu Leu Ala Val Pro Arg Ser Tyr Arg
                115                 120                 125

Thr Leu Ala Asp Val Arg His Ala Val Ala Glu Ala Val Glu Asp Phe
 130                 135                 140

Phe Arg Arg Arg Leu Ala Asp Asp Ala Leu Ser Ala Thr Ser Ser Ser
145                 150                 155                 160

Ser Thr Thr Pro Ser Thr Pro Arg Thr Asp Asp Glu Glu Ser Ala
                165                 170                 175

Ala Thr Asp Gly Asp Glu Ser Ser Pro Ala Ser Asp Leu Ala Phe
                180                 185                 190

Glu Leu Asp Val Leu Ser Asp Met Gly Trp Asp Leu Tyr Tyr Ala Ser
                195                 200                 205

Leu Ala Gln Gly Met Leu Met Glu Pro Pro Ser Ala Ala Leu Gly Asp
 210                 215                 220

Asp Gly Asp Ala Ile Leu Ala Asp Val Pro Leu Trp Ser Tyr
225                 230                 235

<210> SEQ ID NO 71
<211> LENGTH: 246
<212> TYPE: PRT
<213> ORGANISM: Oryza sativa

<400> SEQUENCE: 71

Met Cys Gly Ile Lys Gln Glu Met Ser Gly Glu Ser Ser Gly Ser Pro
 1               5                  10                  15

Cys Ser Ser Ala Ser Ala Glu Arg Gln His Gln Thr Val Trp Thr Ala
             20                  25                  30

Pro Pro Lys Arg Pro Ala Gly Arg Thr Lys Phe Arg Glu Phe Thr Thr
         35                  40                  45

Arg His Pro Val Phe Arg Gly Val Arg Arg Gly Asn Ala Gly Arg
 50                  55                  60

Trp Val Cys Glu Val Arg Val Pro Gly Arg Arg Gly Cys Arg Leu Trp
 65                  70                  75                  80

Leu Gly Thr Phe Asp Thr Ala Glu Gly Ala Ala Arg Ala His Asp Ala
                 85                  90                  95

Ala Met Leu Ala Ile Asn Ala Gly Gly Gly Phe Thr Gly Gly Gly
                100                 105                 110

Ala Cys Cys Leu Asn Phe Ala Asp Ser Ala Trp Leu Leu Ala Val Arg
                115                 120                 125

Arg Ser Tyr Arg Thr Leu Ala Asp Val Arg His Ala Val Ala Glu Ala
                130                 135                 140

Val Glu Asp Phe Phe Arg Arg Arg Leu Ala Asp Asp Ala Leu Ser Ala
145                 150                 155                 160
```

-continued

```
Thr Ser Ser Ser Thr Thr Phe Thr Pro Ser Thr Pro Arg Thr Asp
            165                 170                 175
Asp Asp Glu Glu Ser Ala Ala Thr Asp Gly Asp Glu Ser Ser Ser Pro
            180                 185                 190
Ala Ser Asp Leu Ala Phe Glu Leu Asp Val Leu Ser Asp Met Gly Trp
            195                 200                 205
Asp Leu Tyr Tyr Ala Ser Leu Ala Gln Gly Met Leu Met Glu Pro Pro
            210                 215                 220
Ser Ala Ala Leu Phe Thr Gly Asp Asp Gly Asp Ala Ile Leu Ala Asp
225                 230                 235                 240
Val Pro Leu Trp Ser Tyr
                245

<210> SEQ ID NO 72
<211> LENGTH: 293
<212> TYPE: PRT
<213> ORGANISM: Hordeum vulgare

<400> SEQUENCE: 72

Met Ser Pro Thr Leu Ser Leu Lys Leu Lys Ser Ser His Thr Pro
1               5                   10                  15
Gln Ser Ser Val Ser Ser Ser Thr Met Leu Arg Leu Phe Lys Lys Glu
            20                  25                  30
Ala Ala Cys Gln Ser Pro Ser Thr Leu Pro Val Ala Met Asp Met Gly
            35                  40                  45
Leu Glu Val Ser Ser Ser Pro Ser Ser Ser Val Ser Ser Ser
    50                  55                  60
Pro Glu His Ala Ala Arg Arg Ala Ser Pro Ala Lys Arg Pro Ala Gly
65                  70                  75                  80
Arg Thr Lys Phe Arg Glu Thr Arg His Pro Val Tyr Arg Gly Val Arg
                85                  90                  95
Arg Arg Gly Asn Thr Glu Arg Trp Val Cys Glu Val Arg Val Pro Gly
            100                 105                 110
Lys Arg Gly Ala Arg Leu Trp Leu Gly Thr Tyr Ala Thr Ala Glu Val
            115                 120                 125
Ala Ala Arg Ala Asn Asp Ala Ala Met Leu Ala Leu Gly Gly Arg Ser
            130                 135                 140
Ala Thr Cys Leu Asn Phe Ala Asp Ser Ala Trp Leu Leu Ala Val Pro
145                 150                 155                 160
Ser Ala Leu Ser Asp Leu Ala Asp Val Arg Arg Ala Ala Val Glu Ala
                165                 170                 175
Val Ala Asp Phe Gln Arg Arg Glu Ala Ala Asp Gly Ser Leu Ala Ile
            180                 185                 190
Ala Val Pro Lys Glu Ala Ser Ser Gly Ala Pro Ser Leu Ser Pro Ser
            195                 200                 205
Ser Gly Ser Asp Ser Ala Gly Ser Thr Gly Thr Ser Glu Pro Ser Ala
            210                 215                 220
Asn Gly Val Phe Glu Gly Pro Val Val Met Asp Ser Glu Met Phe Arg
225                 230                 235                 240
Leu Asp Leu Phe Pro Glu Met Asp Leu Gly Ser Tyr Tyr Met Ser Leu
                245                 250                 255
Ala Glu Ala Leu Leu Met Asp Pro Pro Thr Ala Thr Ile Ile His
            260                 265                 270
Ala Tyr Glu Asp Asn Gly Asp Gly Gly Ala Asp Val Arg Leu Trp Ser
```

```
                    275                 280                 285

Tyr Ser Val Asp Met
        290

<210> SEQ ID NO 73
<211> LENGTH: 249
<212> TYPE: PRT
<213> ORGANISM: Hordeum vulgare

<400> SEQUENCE: 73

Met Asp Met Gly Leu Glu Val Ser Ser Ser Pro Ser Ser Ser
1               5                   10                  15

Val Ser Ser Pro Glu His Ala Ala Arg Arg Ala Ser Pro Ala Lys
            20                  25                  30

Arg Pro Ala Gly Arg Thr Lys Phe Arg Glu Thr Arg His Pro Val Tyr
        35                  40                  45

Arg Gly Val Arg Arg Gly Asn Thr Glu Arg Trp Val Cys Glu Val
    50                  55                  60

Arg Val Pro Gly Lys Arg Gly Ala Arg Leu Trp Leu Gly Thr Tyr Ala
65                  70                  75                  80

Thr Ala Glu Val Ala Ala Arg Ala Asn Asp Ala Ala Met Leu Ala Leu
                85                  90                  95

Gly Gly Arg Ser Ala Thr Cys Leu Asn Phe Ala Asp Ser Ala Trp Leu
            100                 105                 110

Leu Ala Val Pro Ser Ala Leu Ser Asp Leu Ala Asp Val Arg Arg Ala
        115                 120                 125

Ala Val Glu Ala Val Ala Asp Phe Gln Arg Arg Glu Ala Ala Asp Gly
    130                 135                 140

Ser Leu Ala Ile Ala Val Pro Lys Glu Ala Ser Ser Gly Ala Pro Ser
145                 150                 155                 160

Leu Ser Pro Ser Ser Gly Ser Asp Ser Ala Gly Ser Thr Gly Thr Ser
                165                 170                 175

Glu Pro Ser Ala Asn Gly Val Phe Glu Gly Pro Val Val Met Asp Ser
            180                 185                 190

Glu Met Phe Arg Leu Asp Leu Phe Pro Glu Met Asp Leu Gly Ser Tyr
        195                 200                 205

Tyr Met Ser Leu Ala Glu Ala Leu Leu Met Asp Pro Pro Thr Ala
    210                 215                 220

Thr Ile Ile His Ala Tyr Glu Asp Asn Gly Asp Gly Ala Asp Val
225                 230                 235                 240

Arg Leu Trp Ser Tyr Ser Val Asp Met
                245

<210> SEQ ID NO 74
<211> LENGTH: 238
<212> TYPE: PRT
<213> ORGANISM: Oryza sativa

<400> SEQUENCE: 74

Met Cys Gly Ile Lys Gln Glu Met Ser Gly Glu Ser Ser Gly Ser Pro
1               5                   10                  15

Cys Ser Ser Ala Ser Ala Glu Arg Gln His Gln Thr Val Trp Thr Ala
            20                  25                  30

Pro Pro Lys Arg Pro Ala Gly Arg Thr Lys Phe Arg Glu Thr Arg His
        35                  40                  45

Pro Val Phe Arg Gly Val Arg Arg Arg Gly Asn Ala Gly Arg Trp Val
```

```
              50                  55                  60
Cys Glu Val Arg Val Pro Gly Arg Arg Gly Cys Arg Leu Trp Leu Gly
 65                  70                  75                  80

Thr Phe Asp Thr Ala Glu Gly Ala Ala Arg Ala His Asp Ala Ala Met
                 85                  90                  95

Leu Ala Ile Asn Ala Gly Gly Gly Gly Gly Ala Cys Cys Leu
                100                 105                 110

Asn Phe Ala Asp Ser Ala Trp Leu Leu Ala Val Pro Arg Ser Tyr Arg
                115                 120                 125

Thr Leu Ala Asp Val Arg His Ala Val Ala Glu Ala Val Glu Asp Phe
                130                 135                 140

Phe Arg Arg Leu Ala Asp Asp Ala Leu Ser Ala Thr Ser Ser Ser
145                 150                 155                 160

Ser Thr Thr Pro Ser Thr Pro Arg Thr Asp Asp Glu Glu Ser Ala
                165                 170                 175

Ala Thr Asp Gly Asp Glu Ser Ser Pro Ala Ser Asp Leu Ala Phe
                180                 185                 190

Glu Leu Asp Val Leu Ser Asp Met Gly Trp Asp Leu Tyr Tyr Ala Ser
                195                 200                 205

Leu Ala Gln Gly Met Leu Met Glu Pro Pro Ser Ala Ala Leu Gly Asp
                210                 215                 220

Asp Gly Asp Ala Ile Leu Ala Asp Val Pro Leu Trp Ser Tyr
225                 230                 235

<210> SEQ ID NO 75
<211> LENGTH: 253
<212> TYPE: PRT
<213> ORGANISM: Oryza sativa

<400> SEQUENCE: 75

Met Glu Lys Asn Thr Ala Ala Ser Gly Gln Leu Met Thr Ser Ser Ala
 1               5                  10                  15

Glu Ala Thr Pro Ser Ser Pro Lys Arg Pro Ala Gly Arg Thr Lys Phe
                20                  25                  30

Gln Glu Thr Arg His Leu Val Phe Arg Gly Val Arg Trp Arg Gly Cys
            35                  40                  45

Ala Gly Arg Trp Val Cys Lys Val Arg Val Pro Gly Ser Arg Gly Asp
         50                  55                  60

Arg Phe Trp Ile Gly Thr Ser Asp Thr Ala Glu Glu Thr Ala Arg Thr
 65                  70                  75                  80

His Asp Ala Ala Met Leu Ala Leu Cys Gly Ala Ser Ala Ser Leu Asn
                 85                  90                  95

Phe Ala Asp Ser Ala Trp Leu Leu His Val Pro Arg Ala Pro Val Val
                100                 105                 110

Ser Gly Leu Arg Pro Pro Ala Ala Arg Cys Ala Thr Arg Cys Leu Gln
                115                 120                 125

Gly His Arg Arg Val Pro Ala Pro Gly Arg Gly Ser Thr Ala Thr Ala
                130                 135                 140

Thr Ala Thr Ser Gly Asp Ala Ala Ser Thr Ala Pro Pro Ser Ala Pro
145                 150                 155                 160

Val Leu Ser Ala Lys Gln Cys Glu Phe Ile Phe Leu Ser Ser Leu Asp
                165                 170                 175

Cys Trp Met Leu Met Ser Lys Leu Ile Ser Ser Ser Arg Ala Lys Gly
                180                 185                 190
```

```
Ser Leu Cys Leu Arg Lys Asn Pro Ile Ser Phe Cys Met Val Thr Asn
        195                 200                 205

Ser Tyr Thr Ala Leu Leu Glu Tyr Ile Ile Leu Gln Met Asn Ser
        210                 215                 220

Met Ile Val Leu Ile His Glu Leu Ser Lys Tyr Gln Val Phe Leu Leu
225                 230                 235                 240

Leu Thr Met Ile Thr His His Leu Phe Gln Trp Arg Arg
                245                 250

<210> SEQ ID NO 76
<211> LENGTH: 423
<212> TYPE: PRT
<213> ORGANISM: Oryza sativa

<400> SEQUENCE: 76

Met Ser Gly Gly Ala Ala Thr Val Ala Pro Gly Trp Arg Arg Glu
1               5                   10                  15

Leu Ala Gly Leu Leu Val Pro Leu Val Arg Ser Ala Met Glu Ala Arg
                20                  25                  30

Gly Cys Gly His His His Arg Asp Arg Leu Asp Ala Ser Ala Ile Lys
            35                  40                  45

Ser Leu Pro Ser Val Met Thr Val Arg Ser Cys Gly Gln Arg Gly Arg
        50                  55                  60

Gln Arg Arg Tyr Ala Arg Met Pro Ser Pro Ser Ser Pro Pro Pro
65                  70                  75                  80

Thr Leu Thr Asn Cys Leu Arg Arg Thr Arg His Gly Glu Glu His
                85                  90                  95

Arg Arg Gln Arg Ala Ile Asp Asp Leu Leu Arg Gly Gly Asp Ala Val
                100                 105                 110

Val Ala Glu Ala Ala Gly Gly Ala Asn Gln Val Pro Gly Asp Glu Ala
            115                 120                 125

Pro Ser Val Pro Trp Gly Ala Met Ala Trp Val Arg Gly Ala Val Gly
        130                 135                 140

Val Gln Gly Thr Ser Asp Thr Ala Glu Glu Thr Ala Arg Thr His Asp
145                 150                 155                 160

Ala Ala Met Leu Ala Leu Cys Gly Ala Ser Ala Ser Leu Asn Phe Ala
                165                 170                 175

Asp Ser Ala Trp Leu Leu His Val Pro Arg Ala Pro Val Val Ser Gly
                180                 185                 190

Leu Arg Pro Pro Ala Ala Arg Cys Ala Thr Arg Cys Leu Gln Gly His
            195                 200                 205

Arg Arg Val Pro Ala Pro Gly Arg Gly Ser Thr Ala Thr Ala Thr Ala
        210                 215                 220

Thr Ser Gly Asp Ala Ala Ser Thr Ala Pro Pro Ser Ala Pro Val Leu
225                 230                 235                 240

Ser His Ala Ser Ser Ser Ser Met Leu Ala Thr Ser Val Gln Gln Leu
                245                 250                 255

Asn Arg Leu Ala Thr Ser Ser His Leu Ser Pro Pro Ser His Glu Arg
                260                 265                 270

Thr Met Arg Pro Ser Gly Ala Glu Ser Leu Ala Pro Leu Leu Pro Ile
            275                 280                 285

Arg Ser Arg Ala Arg Leu Leu Leu Ser Pro Pro Leu Arg His Arg Ala
        290                 295                 300

Arg Pro Pro Thr Pro Pro Arg Pro Ala Ala Val Leu Pro Phe Ser His
305                 310                 315                 320
```

-continued

Val Ser Ala Ala Ala Ser Leu Leu Pro His Arg Arg Gln Ala Val Lys
            325                 330                 335

Pro Pro Cys Ser His Val Ala Ala Met Gln Val Glu Thr Gly Glu
            340                 345                 350

Ala Pro Gly His Gly Gly Ala Gln Arg Ser Pro Ile Gly Trp
            355                 360                 365

Leu Ser His Ser Leu Leu Pro Ala Ala Ala Leu Leu Pro Arg Gln
            370                 375                 380

Pro Ser Val Arg His Ser Ser Pro Ala Gly Cys Ala Pro Arg Glu Glu
385                 390                 395                 400

Lys Ser Glu Arg Gly Lys Glu Arg Arg Glu Arg Gly Cys Trp Glu Arg
                405                 410                 415

Gly Ser Ala Asp Val Ala Ser
            420

<210> SEQ ID NO 77
<211> LENGTH: 216
<212> TYPE: PRT
<213> ORGANISM: Schedonorus arundinaceus

<400> SEQUENCE: 77

Met Asp Ala Ala Val Ala Ala Ser Leu Ser Leu Gln Ser Gly Glu Gln
1               5                   10                  15

Glu Tyr Arg Thr Val Trp Ser Glu Pro Pro Lys Pro Arg Ser Gly Arg
                20                  25                  30

Thr Lys Phe Gln Glu Thr Arg His Pro Val Tyr Arg Gly Val Arg Arg
            35                  40                  45

Arg Gly Arg Ala Gly Gln Trp Val Cys Glu Met Arg Val His Gly Thr
    50                  55                  60

Lys Gly Ser Arg Leu Trp Leu Gly Thr Phe Asp Thr Ala Glu Met Ala
65                  70                  75                  80

Ala Arg Ala His Asp Ala Ala Leu Ala Leu Ser Gly Arg Asp Ala
                85                  90                  95

Cys Leu Asn Phe Ala Asp Ser Ala Trp Arg Met Gln Pro Val Leu Pro
                100                 105                 110

Ala Gly Ala Gly Ser Val Cys Phe Gly Gly Ala Gln Glu Val Lys Asp
            115                 120                 125

Ala Val Ala Ala Val Glu Ala Phe Gln Glu Glu His His Val
            130                 135                 140

Glu Ser Thr Ala Glu Thr Ala Lys Asp Glu Glu Ser Ala Leu Ser Met
145                 150                 155                 160

Ser Ser Asp Leu Ser Glu His Asp Asp Glu Arg Trp Ile Asp Gly Met
                165                 170                 175

Asp Ala Gly Ser Tyr Tyr Ala Ser Leu Ala Gln Gly Met Leu Val Glu
            180                 185                 190

Pro Pro Asp Ala Gly Ala Trp Arg Glu Asp Gly Glu His Gly Gly Val
            195                 200                 205

Glu Thr Ser Leu Trp Ser Tyr Leu
        210                 215

<210> SEQ ID NO 78
<211> LENGTH: 268
<212> TYPE: PRT
<213> ORGANISM: Secale cereale

<400> SEQUENCE: 78

```
Met Asp Val Ala Asp Ile Ala Ser Arg Ser Gly Gln Gln Gln Gly
1               5                   10                  15

His Arg Thr Val Ser Ser Glu Pro Pro Lys Arg Pro Ala Gly Arg Thr
                20                  25                  30

Lys Phe His Glu Thr Arg His Pro Leu Tyr Arg Gly Val Arg Arg Arg
            35                  40                  45

Gly Arg Val Gly Gln Trp Val Cys Glu Val Arg Val Pro Gly Ile Lys
        50                  55                  60

Gly Ser Arg Leu Trp Leu Gly Thr Phe Asn Thr Ala Glu Met Ala Ala
65                  70                  75                  80

Arg Ala His Asp Ala Ala Val Leu Ala Leu Ser Gly Arg Ala Ala Cys
                85                  90                  95

Leu Asn Phe Ala Asp Ser Ala Trp Arg Met Leu Pro Val Leu Ala Ala
            100                 105                 110

Gly Ser Phe Gly Phe Asp Ser Ala Arg Glu Val Lys Ala Ala Val Ala
        115                 120                 125

Val Ala Val Ala Phe Gln Arg Lys Gln Ile Ile Pro Val Ala Val
130                 135                 140

Ala Val Val Ala Leu Gln Lys Gln Gln Val Pro Val Ala Val Ala Val
145                 150                 155                 160

Val Ala Leu Gln Gln Arg Gln Val Pro Val Thr Val Ala Val Val Ala
                165                 170                 175

Leu Gln Lys Leu Gln Val Pro Val Ala Val Ala Val Val Ala Leu Gln
            180                 185                 190

Lys Lys Gln Ile Ile Leu Pro Ala Ala Cys Leu Ala Pro Glu Phe Tyr
        195                 200                 205

Met Ser Ser Gly Asp Leu Leu Glu Leu Asp Glu Glu Gln Trp Phe Gly
    210                 215                 220

Gly Met Asp Ala Gly Ser Tyr Tyr Ala Ser Leu Ala Gln Gly Met Leu
225                 230                 235                 240

Val Ala Pro Pro Asp Asp Arg Ala Arg Pro Glu Asn Gly Glu Gln Ser
                245                 250                 255

Gly Val Gln Thr Pro Leu Trp Ser Cys Leu Phe Asp
            260                 265

<210> SEQ ID NO 79
<211> LENGTH: 278
<212> TYPE: PRT
<213> ORGANISM: Triticum aestivum

<400> SEQUENCE: 79

Met Glu Thr Gly Gly Ser Lys Arg Glu Gly Asp Cys Pro Gly Gln Glu
1               5                   10                  15

Arg Lys Lys Lys Val Arg Arg Ser Thr Gly Pro Asp Ser Val Ala
                20                  25                  30

Glu Thr Ile Lys Lys Trp Lys Glu Asn Gln Lys Leu Gln Gln Glu
            35                  40                  45

Asn Gly Ser Arg Lys Ala Pro Ala Lys Gly Ser Lys Lys Gly Cys Met
    50                  55                  60

Ala Gly Lys Gly Gly Pro Glu Asn Ser Asn Cys Ala Tyr Arg Gly Val
65                  70                  75                  80

Arg Gln Arg Thr Trp Gly Lys Trp Val Ala Glu Ile Arg Glu Pro Asn
                85                  90                  95

Arg Gly Asn Arg Leu Trp Leu Gly Ser Phe Pro Thr Ala Val Glu Ala
```

-continued

```
                100                 105                 110
Ala Arg Ala Tyr Asp Asp Ala Arg Ala Met Tyr Gly Ala Lys Ala
            115                 120                 125

Arg Val Asn Phe Ser Glu Gln Ser Pro Asp Ala Asn Ser Gly Cys Thr
130                 135                 140

Leu Ala Pro Pro Leu Pro Met Ser Asn Gly Ala Thr Ala Ala Ser His
145                 150                 155                 160

Pro Ser Asp Gly Lys Asp Glu Ser Glu Ser Pro Pro Ser Leu Ile Ser
                165                 170                 175

Asn Ala Pro Thr Ala Ala Leu His Arg Ser Asp Ala Lys Asp Glu Ser
            180                 185                 190

Glu Ser Ala Gly Thr Val Ala Arg Lys Val Lys Lys Glu Val Ser Asn
            195                 200                 205

Asp Leu Arg Ser Thr His Glu Glu His Lys Thr Leu Glu Val Ser Gln
        210                 215                 220

Pro Lys Gly Lys Ala Leu His Lys Ala Ala Asn Val Ser Tyr Asp Tyr
225                 230                 235                 240

Phe Asn Val Glu Glu Val Leu Asp Met Ile Ile Val Glu Leu Ser Ala
                245                 250                 255

Asp Val Lys Met Glu Ala His Glu Glu Tyr Gln Asp Gly Asp Asp Gly
            260                 265                 270

Phe Ser Leu Phe Ser Tyr
            275
```

<210> SEQ ID NO 80
<211> LENGTH: 250
<212> TYPE: PRT
<213> ORGANISM: Brassica napus

<400> SEQUENCE: 80

```
Met Asn Ser Val Ser Thr Phe Ser Glu Leu Leu Gly Ser Glu Asn Glu
1               5                   10                  15

Ser Pro Val Gly Gly Asp Tyr Cys Pro Met Leu Ala Ala Ser Cys Pro
                20                  25                  30

Lys Lys Pro Ala Gly Arg Lys Lys Phe Arg Glu Thr Arg His Pro Ile
            35                  40                  45

Tyr Arg Gly Val Arg Leu Arg Lys Ser Gly Lys Trp Val Cys Glu Val
        50                  55                  60

Arg Glu Pro Asn Lys Lys Ser Arg Ile Trp Leu Gly Thr Phe Lys Thr
65                  70                  75                  80

Ala Glu Ile Ala Ala Arg Ala His Asp Val Ala Ala Leu Ala Leu Arg
                85                  90                  95

Gly Arg Gly Ala Cys Leu Asn Phe Ala Asp Ser Ala Trp Arg Leu Arg
            100                 105                 110

Ile Pro Glu Thr Thr Cys Ala Lys Asp Ile Gln Lys Ala Ala Ala Glu
        115                 120                 125

Ala Ala Leu Ala Phe Glu Ala Glu Lys Ser Asp Thr Thr Asn Asp
            130                 135                 140

His Gly Met Asn Met Ala Ser Gln Ala Glu Val Asn Asp Thr Thr Asp
145                 150                 155                 160

His Gly Leu Asp Met Glu Glu Thr Met Val Glu Ala Val Phe Thr Glu
                165                 170                 175

Glu Gln Arg Asp Gly Phe Tyr Met Ala Glu Glu Thr Thr Val Glu Gly
            180                 185                 190
```

```
Val Val Pro Glu Glu Gln Met Ser Lys Gly Phe Tyr Met Asp Glu Glu
            195                 200                 205

Trp Met Phe Gly Met Pro Thr Leu Leu Ala Asp Met Ala Ala Gly Met
    210                 215                 220

Leu Leu Pro Pro Pro Ser Val Gln Trp Gly His Asn Asp Asp Phe Glu
225                 230                 235                 240

Gly Asp Val Asp Met Asn Leu Trp Asn Tyr
                245                 250

<210> SEQ ID NO 81
<211> LENGTH: 251
<212> TYPE: PRT
<213> ORGANISM: Brassica napus

<400> SEQUENCE: 81

Met Asn Ser Val Ser Thr Phe Ser Glu Leu Leu Arg Ser Glu Asn Glu
1               5                   10                  15

Ser Pro Val Asn Thr Glu Gly Gly Asp Tyr Ile Leu Ala Ala Ser Cys
            20                  25                  30

Pro Lys Lys Pro Ala Gly Arg Lys Lys Phe Gln Glu Thr Arg His Pro
        35                  40                  45

Ile Tyr Arg Gly Val Arg Leu Arg Lys Ser Gly Lys Trp Val Cys Glu
    50                  55                  60

Val Arg Glu Pro Asn Lys Lys Ser Arg Ile Trp Leu Gly Thr Phe Lys
65                  70                  75                  80

Thr Ala Glu Ile Ala Ala Arg Ala His Asp Val Ala Ala Leu Ala Leu
                85                  90                  95

Arg Gly Arg Gly Ala Cys Leu Asn Phe Ala Asp Ser Ala Trp Arg Leu
            100                 105                 110

Arg Ile Pro Glu Thr Thr Cys Ala Lys Asp Ile Gln Lys Ala Ala Ala
        115                 120                 125

Glu Ala Ala Leu Ala Phe Glu Ala Lys Ser Asp Thr Thr Thr Asn
    130                 135                 140

Asp His Gly Met Asn Met Ala Ser Gln Val Glu Val Asn Asp Thr Thr
145                 150                 155                 160

Asp His Asp Leu Asp Met Glu Glu Thr Ile Val Glu Ala Val Phe Arg
                165                 170                 175

Glu Glu Gln Arg Glu Gly Phe Tyr Met Ala Glu Glu Thr Thr Val Val
            180                 185                 190

Gly Val Val Pro Glu Glu Gln Met Ser Lys Gly Phe Tyr Met Asp Glu
        195                 200                 205

Glu Trp Met Phe Gly Met Pro Thr Leu Leu Ala Asp Met Ala Ala Gly
    210                 215                 220

Met Leu Leu Pro Leu Pro Ser Val Gln Trp Gly His Asn Asp Asp Phe
225                 230                 235                 240

Glu Gly Asp Ala Asp Met Asn Leu Trp Asn Tyr
                245                 250

<210> SEQ ID NO 82
<211> LENGTH: 214
<212> TYPE: PRT
<213> ORGANISM: Brassica napus

<400> SEQUENCE: 82

Met Thr Ser Phe Ser Thr Phe Ser Glu Met Leu Gly Ser Glu Tyr Glu
1               5                   10                  15
```

```
Ser Pro Val Thr Leu Gly Gly Glu Tyr Cys Pro Lys Leu Ala Ala Ser
            20                  25                  30

Cys Pro Lys Lys Pro Ala Gly Arg Lys Lys Phe Arg Glu Thr Arg His
        35                  40                  45

Pro Val Tyr Arg Gly Val Arg Leu Arg Asn Ser Gly Lys Trp Val Cys
    50                  55                  60

Glu Val Arg Glu Pro Asn Lys Lys Ser Arg Ile Trp Leu Gly Thr Phe
65                  70                  75                  80

Leu Thr Ala Glu Ile Ala Ala Arg Ala His Asp Val Ala Ala Ile Ala
                85                  90                  95

Leu Arg Gly Lys Ser Ala Cys Leu Asn Phe Ala Asp Ser Ala Trp Arg
            100                 105                 110

Leu Arg Ile Pro Glu Thr Thr Cys Pro Lys Glu Ile Gln Lys Ala Ala
        115                 120                 125

Ala Glu Ala Ala Leu Ala Phe Gln Ala Glu Ile Asn Asn Thr Thr Thr
    130                 135                 140

Asp His Gly Leu Asp Met Glu Glu Thr Ile Val Glu Ala Ile Phe Thr
145                 150                 155                 160

Glu Glu Asn Asn Asp Val Phe Tyr Met Asp Glu Glu Ser Met Leu Glu
                165                 170                 175

Met Pro Ala Leu Leu Ala Ser Met Ala Glu Gly Met Leu Leu Pro Pro
            180                 185                 190

Pro Ser Val His Phe Gly His Asn Tyr Asp Phe Asp Gly Asp Ala Asp
        195                 200                 205

Val Ser Leu Trp Ser Tyr
    210

<210> SEQ ID NO 83
<211> LENGTH: 174
<212> TYPE: PRT
<213> ORGANISM: Glycine max

<400> SEQUENCE: 83

Met Glu Asp Arg Asp His Cys Cys Ser Asn Asn Ser Thr Met Ile Thr
1               5                   10                  15

Thr Thr Lys Lys Arg Thr Gly Arg Arg Ser Pro Thr Ser Asp Lys Leu
            20                  25                  30

Lys Asn Gln His Arg Glu Lys Gln Ser Met Lys Pro Tyr Arg Gly Ile
        35                  40                  45

Arg Met Arg Lys Trp Gly Lys Trp Val Ala Glu Ile Arg Glu Pro Asn
    50                  55                  60

Lys Arg Ser Arg Ile Trp Leu Gly Ser Tyr Thr Thr Pro Val Ala Ala
65                  70                  75                  80

Ala Arg Ala Tyr Asp Thr Ala Val Phe Tyr Leu Arg Gly Pro Thr Ala
                85                  90                  95

Arg Leu Asn Phe Pro Glu Leu Leu Phe Gln Asp Asp Gln Glu Gly
            100                 105                 110

Ser Asp Ser Val Gln His Gly Ala Ala Gly Asn Met Ser Ala Asp Ser
        115                 120                 125

Ile Arg Arg Lys Ala Thr Gln Val Gly Ala Arg Val Asp Ala Leu Gln
    130                 135                 140

Thr Ala Leu His His His Ala Pro Ser Thr Asn Ser Leu Asn Leu Lys
145                 150                 155                 160

Pro Asp Leu Asn Glu Phe Pro Lys Leu Glu Glu Leu Gln Asp
                165                 170
```

```
<210> SEQ ID NO 84
<211> LENGTH: 215
<212> TYPE: PRT
<213> ORGANISM: Capsicum annuum

<400> SEQUENCE: 84

Met Asn Ile Phe Arg Ser Tyr Tyr Ser Asp Pro Leu Thr Glu Ser Ser
1               5                   10                  15

Ser Ser Phe Ser Asp Ser Ser Ile Tyr Ser Pro Asn Arg Ala Ile Phe
            20                  25                  30

Ser Asp Glu Glu Val Ile Leu Ala Ser Asn Asn Pro Lys Lys Pro Ala
        35                  40                  45

Gly Arg Lys Lys Phe Arg Glu Thr Arg His Pro Val Tyr Arg Gly Val
    50                  55                  60

Arg Lys Arg Asn Ser Gly Lys Trp Val Cys Glu Val Arg Glu Pro Asn
65                  70                  75                  80

Lys Lys Ser Arg Ile Trp Leu Gly Thr Phe Pro Thr Ala Glu Met Ala
                85                  90                  95

Ala Arg Ala His Asp Val Ala Ala Ile Ala Leu Arg Gly Arg Ser Ala
            100                 105                 110

Cys Leu Asn Phe Ala Asp Ser Ala Trp Arg Leu Pro Val Pro Ala Ser
        115                 120                 125

Ser Asp Thr Lys Asp Ile Gln Lys Ala Ala Ala Glu Ala Ala Glu Ala
    130                 135                 140

Phe Arg Pro Leu Lys Leu Glu Gly Ile Ser Lys Glu Ser Ser Ser Ser
145                 150                 155                 160

Thr Pro Glu Ser Met Phe Phe Met Asp Glu Glu Ala Leu Phe Cys Met
                165                 170                 175

Pro Gly Leu Leu Thr Asn Met Ala Glu Gly Leu Met Leu Pro Pro Pro
            180                 185                 190

Gln Cys Ala Glu Ile Gly Asp His Val Glu Thr Ala Asp Ala Asp Thr
        195                 200                 205

Pro Leu Trp Ser Tyr Ser Ile
    210                 215

<210> SEQ ID NO 85
<211> LENGTH: 215
<212> TYPE: PRT
<213> ORGANISM: Capsicum annuum

<400> SEQUENCE: 85

Met Asn Ile Phe Arg Ser Tyr Tyr Ser Asp Pro Leu Thr Glu Ser Ser
1               5                   10                  15

Ser Ser Phe Ser Asp Ser Ser Ile Tyr Ser Pro Asn Arg Ala Ile Phe
            20                  25                  30

Ser Asp Glu Glu Val Ile Leu Ala Ser Asn Asn Pro Lys Lys Pro Ala
        35                  40                  45

Gly Arg Lys Lys Phe Arg Glu Thr Arg His Pro Val Tyr Arg Gly Val
    50                  55                  60

Arg Lys Arg Asn Ser Gly Lys Trp Val Cys Glu Val Arg Glu Pro Asn
65                  70                  75                  80

Lys Lys Ser Arg Ile Trp Leu Gly Thr Phe Pro Thr Ala Glu Met Ala
                85                  90                  95

Ala Arg Ala His Asp Val Ala Ala Ile Ala Leu Arg Gly Arg Ser Ala
            100                 105                 110
```

```
Cys Leu Asn Phe Ala Asp Ser Ala Trp Arg Leu Pro Val Pro Ala Ser
        115                 120                 125

Ser Asp Thr Lys Asp Ile Gln Lys Ala Ala Glu Ala Ala Glu Ala
    130                 135                 140

Leu Arg Pro Leu Lys Leu Glu Gly Ile Ser Lys Glu Ser Ser Ser
145                 150                 155                 160

Thr Pro Glu Ser Met Phe Phe Met Asp Glu Ala Leu Phe Cys Met
                165                 170                 175

Pro Gly Leu Leu Thr Asn Met Ala Glu Gly Leu Met Leu Pro Pro Pro
                180                 185                 190

Gln Cys Ala Glu Ile Gly Asp His Val Glu Thr Ala Asp Ala Asp Thr
        195                 200                 205

Pro Leu Trp Ser Tyr Ser Ile
    210                 215

<210> SEQ ID NO 86
<211> LENGTH: 210
<212> TYPE: PRT
<213> ORGANISM: Lycopersicon esculentum

<400> SEQUENCE: 86

Met Asn Ile Phe Glu Thr Tyr Tyr Ser Asp Ser Leu Ile Leu Thr Glu
1               5                   10                  15

Ser Ser Ser Ser Ser Ser Ser Ser Phe Ser Glu Glu Glu Val Ile
            20                  25                  30

Leu Ala Ser Asn Asn Pro Lys Lys Pro Ala Gly Arg Lys Lys Phe Arg
        35                  40                  45

Glu Thr Arg His Pro Ile Tyr Arg Gly Ile Arg Lys Arg Asn Ser Gly
    50                  55                  60

Lys Trp Val Cys Glu Val Arg Glu Pro Asn Lys Lys Thr Arg Ile Trp
65                  70                  75                  80

Leu Gly Thr Phe Pro Thr Ala Glu Met Ala Ala Arg Ala His Asp Val
                85                  90                  95

Ala Ala Leu Ala Leu Arg Gly Arg Ser Ala Cys Leu Asn Phe Ser Asp
                100                 105                 110

Ser Ala Trp Arg Leu Pro Ile Pro Ala Ser Ser Asn Ser Lys Asp Ile
        115                 120                 125

Gln Lys Ala Ala Gln Ala Val Glu Ile Phe Arg Ser Glu Glu Val
    130                 135                 140

Ser Gly Glu Ser Pro Glu Thr Ser Glu Asn Val Gln Glu Ser Ser Asp
145                 150                 155                 160

Phe Val Asp Glu Glu Ala Ile Phe Phe Met Pro Gly Leu Leu Ala Asn
                165                 170                 175

Met Ala Glu Gly Leu Met Leu Pro Pro Pro Gln Cys Ala Glu Met Gly
                180                 185                 190

Asp His Cys Val Glu Thr Asp Ala Tyr Met Ile Thr Leu Trp Asn Tyr
        195                 200                 205

Ser Ile
    210

<210> SEQ ID NO 87
<211> LENGTH: 300
<212> TYPE: PRT
<213> ORGANISM: Lycopersicon esculentum

<400> SEQUENCE: 87
```

Met Ala Ile Met Asp Glu Ala Ala Asn Met Val Cys Val Pro Leu Asp
1               5                   10                  15

Tyr Ser Arg Lys Arg Lys Ser Arg Ser Arg Arg Asp Arg Thr Lys Asn
            20                  25                  30

Val Glu Glu Thr Leu Ala Lys Trp Lys Glu Tyr Asn Glu Lys Leu Asp
            35                  40                  45

Asn Glu Gly Lys Gly Lys Pro Val Arg Lys Val Pro Ala Lys Gly Ser
50                      55                  60

Lys Lys Gly Cys Met Arg Gly Lys Gly Pro Glu Asn Trp Arg Cys
65                  70                  75                  80

Lys Tyr Arg Gly Val Arg Gln Arg Ile Trp Gly Lys Trp Val Ala Glu
                85                  90                  95

Ile Arg Glu Pro Lys Arg Gly Ser Arg Leu Trp Leu Gly Thr Phe Gly
                100                 105                 110

Thr Ala Ile Glu Ala Ala Leu Ala Tyr Asp Asp Ala Ala Arg Ala Met
            115                 120                 125

Tyr Gly Pro Cys Ala Arg Leu Asn Leu Pro Asn Tyr Ala Cys Asp Ser
130                 135                 140

Val Ser Trp Ala Thr Thr Ser Ala Ser Ala Ser Ala Ser Asp Cys Thr
145                 150                 155                 160

Val Ala Ser Gly Phe Gly Glu Val Cys Pro Val Asp Gly Ala Leu His
                165                 170                 175

Glu Ala Asp Thr Pro Leu Ser Ser Val Lys Asp Glu Gly Thr Ala Met
            180                 185                 190

Asp Ile Val Glu Pro Thr Ser Ile Asp Glu Asp Thr Leu Lys Ser Gly
            195                 200                 205

Trp Asp Cys Leu Asp Lys Leu Asn Met Asp Glu Met Phe Asp Val Asp
            210                 215                 220

Glu Leu Leu Ala Met Leu Asp Ser Thr Pro Val Phe Thr Lys Asp Tyr
225                 230                 235                 240

Asn Ser Asp Gly Lys His Asn Asn Met Val Ser Asp Ser Gln Cys Gln
                245                 250                 255

Glu Pro Asn Ala Val Val Asp Pro Met Thr Val Asp Tyr Gly Phe Asp
            260                 265                 270

Phe Leu Lys Pro Gly Arg Gln Glu Asp Leu Asn Phe Ser Ser Asp Asp
            275                 280                 285

Leu Ala Phe Ile Asp Leu Asp Ser Glu Leu Val Val
            290                 295                 300

<210> SEQ ID NO 88
<211> LENGTH: 229
<212> TYPE: PRT
<213> ORGANISM: Cucumis melo

<400> SEQUENCE: 88

Met Ser Ser Ser Lys Glu Gln Ser Pro Ser Pro Glu Thr Glu Ser Ser
1               5                   10                  15

Ser Ser Ser Ser Asp Ser Asn Lys Lys Pro Lys Arg Ile Asn Ser
            20                  25                  30

Asn Ser Ser Ser Asn Ser Lys His Ala Val Tyr Arg Gly Val Arg Met
            35                  40                  45

Arg Asn Trp Gly Lys Trp Val Ser Glu Ile Arg Glu Pro Arg Lys Lys
50                  55                  60

Ser Arg Ile Trp Leu Gly Thr Phe Pro Ser Pro Glu Met Ala Ala Arg

-continued

```
                65                  70                  75                  80
Ala His Asp Val Ala Ala Leu Ser Ile Lys Gly Asn Ser Ala Ile Leu
                    85                  90                  95

Asn Phe Pro Asp Leu Val His Leu Leu Pro Arg Pro Val Ser Leu Ala
                100                 105                 110

Pro Arg Asp Val Gln Ala Ala Ala Lys Ala Ala His Met His Asn
                115                 120                 125

Leu Ser Ser Asn Ala Asn Thr Asn Asn His Asn Thr Asn Ser Asn Ser
        130                 135                 140

Ser Ser Ala Phe Ser Asp Glu Leu Ser Glu Ile Val Glu Leu Pro Ala
145                 150                 155                 160

Leu Gly Thr Ser Tyr Asp Gly Gly Val Gly Val Gly Gly Glu Phe Val
                165                 170                 175

Phe Val Glu Ser Glu Leu Glu Ser Ala Ala Trp Leu Tyr Gln Pro Pro
                180                 185                 190

Trp Val Gln Ser Leu Gln Glu Asp Tyr Asp Asp Ile Asp Gly Asp Gly
                195                 200                 205

Asp Cys Gly Lys Leu Gly Met Gly Phe Val Ser Asn Gly Phe Lys Gly
        210                 215                 220

Phe Leu Phe Asp Tyr
225
```

<210> SEQ ID NO 89
<211> LENGTH: 267
<212> TYPE: PRT
<213> ORGANISM: Zea mays

<400> SEQUENCE: 89

```
Met Asp Thr Ala Gly Leu Val Gln His Ala Thr Ser Ser Ser Ser Thr
1               5                   10                  15

Ser Thr Ser Ala Ser Ser Ser Ser Glu Gln Gln Ser Arg Lys Ala
            20                  25                  30

Ala Trp Pro Pro Ser Thr Ala Ser Ser Pro Gln Gln Pro Pro Lys Lys
        35                  40                  45

Arg Pro Ala Gly Arg Thr Lys Phe Arg Glu Thr Arg His Pro Val Phe
    50                  55                  60

Arg Gly Val Arg Arg Gly Ala Ala Gly Arg Trp Val Cys Glu Val
65                  70                  75                  80

Arg Val Pro Gly Arg Arg Gly Ala Arg Leu Trp Leu Gly Thr Tyr Leu
                85                  90                  95

Ala Ala Glu Ala Ala Ala Arg Ala His Asp Ala Ala Ile Leu Ala Leu
                100                 105                 110

Gln Gly Arg Gly Ala Gly Arg Leu Asn Phe Pro Asp Ser Ala Arg Leu
            115                 120                 125

Leu Ala Val Pro Pro Ser Ala Leu Pro Gly Leu Asp Asp Ala Arg
    130                 135                 140

Arg Ala Ala Leu Glu Ala Val Ala Glu Phe Gln Arg Arg Ser Gly Ser
145                 150                 155                 160

Gly Ser Gly Ala Ala Asp Glu Ala Thr Ser Gly Ala Ser Pro Pro Ser
                165                 170                 175

Ser Ser Pro Ser Leu Pro Asp Val Ser Ala Ala Gly Ser Pro Ala Ala
            180                 185                 190

Ala Leu Glu His Val Pro Val Lys Ala Asp Glu Ala Val Ala Leu Asp
        195                 200                 205
```

Leu Asp Gly Asp Val Phe Gly Pro Asp Trp Phe Gly Asp Met Gly Leu
    210                 215                 220

Glu Leu Asp Ala Tyr Tyr Ala Ser Leu Ala Glu Gly Leu Leu Val Glu
225                 230                 235                 240

Pro Pro Pro Pro Ala Ala Trp Asp His Gly Asp Cys Cys Asp Ser
            245                 250                 255

Gly Ala Ala Asp Val Ala Leu Trp Ser Tyr Tyr
            260                 265

<210> SEQ ID NO 90
<211> LENGTH: 281
<212> TYPE: PRT
<213> ORGANISM: Zea mays

<400> SEQUENCE: 90

Met Ala Gln Glu Leu His Glu Thr Ser Ser Cys Ser Ala Thr Thr Thr
1               5                   10                  15

Ser Ser Cys Thr Thr Ser Cys Cys Ser Ser Thr Val Thr Asp Ser Ser
            20                  25                  30

Ser Ser Pro Pro Ser Pro Ala Ala Ala Asn Ala Ala Pro Ala Thr Arg
        35                  40                  45

Lys Arg Gln Ala Leu Glu Ala Glu Ala Glu Ala Gly Gly Glu
50                  55                  60

Glu Glu Glu Glu Glu Glu Gly Cys Ala Gly Asn Lys Ala Ala Pro
65                  70                  75                  80

Ala Lys Lys Arg Pro Arg Gly Ser Glu Gly Lys His Pro Thr Phe Arg
                85                  90                  95

Gly Val Arg Met Arg Ala Trp Gly Lys Trp Val Ser Glu Ile Arg Glu
            100                 105                 110

Pro Arg Lys Lys Ser Arg Ile Trp Leu Gly Thr Phe Pro Thr Ala Glu
        115                 120                 125

Met Ala Ala Arg Ala His Asp Val Ala Ala Leu Ala Ile Lys Gly Arg
    130                 135                 140

Ala Ala His Leu Asn Phe Pro Asp Leu Ala Gly Ala Leu Pro Arg Ala
145                 150                 155                 160

Ala Ser Ala Ala Pro Lys Asp Val Gln Ala Ala Ala Leu Ala Ala
                165                 170                 175

Ala Phe Thr Ser Pro Ser Ser Glu Pro Gly Ala Gly Ala His Glu Glu
            180                 185                 190

Pro Ala Ala Lys Asp Gly Ala Ala Pro Glu Glu Ala Ala Ala Asp Ala
        195                 200                 205

Gln Ala Pro Val Pro Val Ala Leu Pro Pro Ala Ala Ser Arg Pro
    210                 215                 220

Gly Thr Pro Ser Ser Gly Val Glu Asp Glu Arg Gln Leu Phe Asp Leu
225                 230                 235                 240

Pro Asp Leu Leu Asp Ile Arg Asp Gly Phe Gly Arg Phe Pro Pro
                245                 250                 255

Met Trp Ala Pro Leu Thr Asp Val Glu Glu Val Val Asn Ala Glu Leu
            260                 265                 270

Arg Leu Glu Glu Pro Leu Leu Trp Glu
        275                 280

<210> SEQ ID NO 91
<211> LENGTH: 216
<212> TYPE: PRT
<213> ORGANISM: Gossypium hirsutum

```
<400> SEQUENCE: 91

Met Asp Phe Val Val Gln Asp Tyr Asp Met Val Asp Ser Gly Ser Val
1               5                   10                  15

Ser Glu Ser Gly Thr Asp Arg Pro Val Asn Phe Ser Asp Glu Tyr Val
            20                  25                  30

Met Leu Ala Ser Ser Tyr Pro Lys Arg Pro Ala Gly Arg Lys Lys Phe
        35                  40                  45

Arg Glu Thr Arg His Pro Val Tyr Arg Gly Val Arg Arg Asn Pro
    50                  55                  60

Gly Lys Trp Val Ser Glu Val Arg Glu Pro Asn Lys Lys Ser Arg Ile
65              70                  75                  80

Trp Leu Gly Thr Phe Pro Lys Ala Asp Met Ala Ala Arg Ala His Asp
                85                  90                  95

Val Ala Ala Ile Ala Leu Arg Gly Lys Ser Ala Cys Leu Asn Phe Ala
            100                 105                 110

Asp Ser Ala Trp Lys Leu Pro Val Pro Ala Ser Ser Asp Pro Lys Asp
        115                 120                 125

Ile Gln Lys Thr Val Ala Glu Val Ala Glu Thr Phe Arg Thr Ala Glu
130                 135                 140

His Ser Gly Asn Ser Arg Asn Asp Ala Lys Arg Ser Glu Asn Thr
145                 150                 155                 160

Glu Met Glu Lys Gly Phe Tyr Leu Asp Glu Ala Leu Phe Gly Thr
                165                 170                 175

Gln Arg Phe Trp Ala Asn Met Ala Ala Gly Met Met Ser Pro Pro
            180                 185                 190

Arg Ser Gly His Asp Gly Gly Trp Glu Glu His Glu Val Asp Asp Tyr
            195                 200                 205

Val Pro Leu Trp Ser Tyr Ser Ile
    210                 215

<210> SEQ ID NO 92
<211> LENGTH: 219
<212> TYPE: PRT
<213> ORGANISM: Capsella bursa-pastoris

<400> SEQUENCE: 92

Met Asn Ser Ser Phe Ser Ala Phe Ser Glu Met Phe Gly Ser Glu Tyr
1               5                   10                  15

Glu Ser Pro Val Ser Ser Gly Gly Asp Tyr Cys Pro Thr Leu Ala
            20                  25                  30

Thr Ser Cys Pro Lys Lys Pro Ala Gly Arg Lys Lys Phe Arg Glu Thr
        35                  40                  45

Arg His Pro Val Tyr Arg Gly Val Arg Arg Asn Ser Gly Lys Trp
    50                  55                  60

Val Cys Glu Val Arg Glu Pro Asn Lys Lys Ser Arg Ile Trp Leu Gly
65              70                  75                  80

Thr Phe Pro Thr Ala Asp Met Ala Ala Arg Ala His Asp Val Ala Ala
                85                  90                  95

Ile Ala Leu Arg Gly Arg Ser Ala Cys Leu Asn Phe Ala Asp Ser Ala
            100                 105                 110

Trp Arg Leu Arg Ile Pro Glu Ser Thr Gly Ala Lys Glu Ile Gln Lys
        115                 120                 125

Ala Ala Ala Glu Ala Ala Leu Ala Phe Gln Asp Glu Met Met Met Ser
    130                 135                 140
```

```
Asp Thr Thr Thr Asp His Gly Phe Asp Met Glu Glu Thr Phe Val
145                 150                 155                 160

Glu Ala Ile Val Thr Ala Glu Gln Ser Ala Ser Leu Tyr Ile Asp Glu
            165                 170                 175

Glu Asp Met Phe Gly Met Pro Ser Leu Met Ala Ser Met Ala Glu Gly
        180                 185                 190

Met Leu Leu Pro Leu Pro Ser Val Gln Trp Asn His Asn Tyr Asp Ile
    195                 200                 205

Asp Gly Asp Asp Asp Val Ser Leu Trp Ser Tyr
    210                 215
```

<210> SEQ ID NO 93
<211> LENGTH: 240
<212> TYPE: PRT
<213> ORGANISM: Prunus avium

<400> SEQUENCE: 93

```
Met Asp Met Phe Phe Ser Gln Leu Ser Asp Ser Val Asp Gln Pro Gln
1               5                   10                  15

Ser Ser Leu Leu Ser Asp Ala Ser Val Thr Thr Arg Gly Ala Ser Cys
            20                  25                  30

Ser Asp Gly Asp Val Ile Leu Ala Ser Ser Arg Pro Lys Lys Arg Ala
        35                  40                  45

Gly Arg Arg Val Phe Lys Glu Thr Arg His Pro Val Tyr Arg Gly Val
    50                  55                  60

Arg Arg Arg Asn Asn Asp Lys Trp Val Cys Glu Met Arg Glu Pro Asn
65                  70                  75                  80

Lys Lys Lys Ser Arg Ile Trp Leu Gly Thr Tyr Pro Thr Ala Glu Met
            85                  90                  95

Ala Ala Arg Ala His Asp Val Ala Ala Leu Ala Phe Arg Gly Lys Leu
        100                 105                 110

Ala Cys Ile Asn Phe Ala Asp Ser Ala Trp Arg Leu Pro Val Pro Ala
    115                 120                 125

Ser Met Asp Thr Met Asp Ile Arg Arg Ala Ala Glu Ala Ala Glu
130                 135                 140

Gly Phe Arg Pro Val Glu Phe Gly Gly Val Cys Ser Gly Ser Ser Asp
145                 150                 155                 160

Glu Lys Glu Arg Met Val Val Gln Val Glu Glu Lys Asn Lys Lys Gly
            165                 170                 175

Ser Val Asn Leu Glu Arg Ser Arg Ser Leu Ser Leu Ser Tyr Trp Asp
        180                 185                 190

Glu Glu Glu Val Phe His Met Pro Arg Leu Leu His Asp Met Ala Glu
    195                 200                 205

Gly Leu Leu Leu Ser Pro Ser Gln Cys Leu Gly Gly Tyr Met Asn Leu
    210                 215                 220

Asp Asp Met Gly Thr Asp Ala Asp Val Lys Leu Trp Ser Phe Ser Ile
225                 230                 235                 240
```

<210> SEQ ID NO 94
<211> LENGTH: 232
<212> TYPE: PRT
<213> ORGANISM: Prunus avium

<400> SEQUENCE: 94

```
Met Asp Met Ile Tyr Ser Gln Leu Ser Asp Leu Ala Ser Met Glu Asn
1               5                   10                  15
```

-continued

```
Pro Asp Thr Ser Ser Phe Ser Asp Ala Ser Val Thr Ala Arg Arg Ala
            20                  25                  30

Ser Leu Ser Asp Glu Glu Val Ile Leu Ala Ser Ser Cys Pro Lys Arg
        35                  40                  45

Arg Ala Gly Arg Arg Val Phe Lys Glu Thr Arg His Pro Val Tyr Arg
    50                  55                  60

Gly Val Arg Arg Arg Asn Asn Asn Lys Trp Val Cys Glu Leu Arg Ala
65                  70                  75                  80

Pro Asn Asn Lys Lys Ala Arg Ile Trp Leu Gly Thr Tyr Pro Thr Ala
                85                  90                  95

Glu Met Ala Ala Arg Ala His Asp Val Ala Val Leu Ala Phe Arg Gly
            100                 105                 110

Lys Leu Ala Cys Leu Asn Phe Ala Asp Ser Ala Trp Arg Leu Pro Val
        115                 120                 125

Pro Ala Ser Thr Asp Ala Ala Glu Ile Arg Arg Ala Ala Thr Glu Ala
    130                 135                 140

Ala Glu Ala Phe Arg Gln Ala Glu Asp Gly Gly Val Asp Glu Lys Glu
145                 150                 155                 160

Ser Lys Ala Val Val Ser Glu Glu Lys Gly Cys Val Gly Met Glu Gly
                165                 170                 175

Ser Ser Asn Leu Phe Tyr Leu Asp Glu Asp Glu Ile Phe Glu Met Pro
            180                 185                 190

Arg Leu Leu Asp Asp Met Ala Asp Gly Ile Met Leu Cys Pro Pro Gln
        195                 200                 205

Cys Leu Asp Gly Tyr Met Asp Trp Asn Asp Val Glu Thr Val Asp Asp
    210                 215                 220

Leu Lys Leu Trp Ser Phe Ser Ile
225                 230

<210> SEQ ID NO 95
<211> LENGTH: 216
<212> TYPE: PRT
<213> ORGANISM: Arabidopsis thaliana

<400> SEQUENCE: 95

Met Asn Ser Phe Ser Ala Phe Ser Glu Met Phe Gly Ser Asp Tyr Glu
1               5                   10                  15

Ser Ser Val Ser Ser Gly Gly Asp Tyr Ile Pro Thr Leu Ala Ser Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Arg Arg Asn Ser Gly Lys Trp Val Cys
    50                  55                  60

Glu Val Arg Glu Pro Asn Lys Lys Thr Arg Ile Trp Leu Gly Thr Phe
65                  70                  75                  80

Gln Thr Ala Glu Met Ala Ala Arg Ala His Asp Val Ala Ala Leu Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Asp Ile Gln Lys Ala Ala
        115                 120                 125

Ala Glu Ala Ala Leu Ala Phe Gln Asp Glu Met Cys Asp Ala Thr Thr
    130                 135                 140

Asp Tyr Gly Phe Asp Met Glu Glu Thr Leu Val Glu Ala Ile Tyr Thr
```

```
                145                 150                 155                 160
Ala Glu Gln Ser Glu Asn Ala Phe Tyr Met His Asp Glu Ala Met Phe
                165                 170                 175

Glu Met Pro Ser Leu Leu Ala Asn Met Ala Glu Gly Met Leu Leu Pro
                180                 185                 190

Leu Pro Ser Val Gln Trp Asn His Asn His Glu Val Asp Gly Asp Asp
                195                 200                 205

Asp Asp Val Ser Leu Trp Ser Tyr
        210                 215

<210> SEQ ID NO 96
<211> LENGTH: 216
<212> TYPE: PRT
<213> ORGANISM: Arabidopsis thaliana

<400> SEQUENCE: 96

Met Asn Ser Phe Ser Ala Phe Ser Glu Met Phe Gly Ser Asp Tyr Glu
1               5                   10                  15

Ser Ser Val Ser Ser Gly Gly Asp Tyr Ile Pro Thr Leu Ala Ser Ser
                20                  25                  30

Cys Pro Lys Lys Pro Ala Gly Arg Lys Lys Phe Arg Glu Thr Arg His
            35                  40                  45

Pro Ile Tyr Arg Gly Val Arg Arg Asn Ser Gly Lys Trp Val Cys
        50                  55                  60

Glu Val Arg Glu Pro Asn Lys Lys Thr Arg Ile Trp Leu Gly Thr Phe
65                  70                  75                  80

Gln Thr Ala Glu Met Ala Ala Arg Ala His Asp Val Ala Ala Leu Ala
                85                  90                  95

Leu Arg Gly Arg Ser Ala Cys Leu Asn Phe Ala Asp Ser Ala Trp Arg
                100                 105                 110

Leu Arg Ile Pro Glu Ser Thr Cys Ala Lys Asp Ile Gln Lys Ala Ala
            115                 120                 125

Ala Glu Ala Ala Leu Ala Phe Gln Asp Glu Met Cys Asp Ala Thr Thr
        130                 135                 140

Asp His Gly Phe Asp Met Glu Glu Thr Leu Val Glu Ala Ile Tyr Thr
145                 150                 155                 160

Ala Glu Gln Ser Glu Asn Ala Phe Tyr Met His Asp Glu Ala Met Phe
                165                 170                 175

Glu Met Pro Ser Leu Leu Ala Asn Met Ala Glu Gly Met Leu Leu Pro
                180                 185                 190

Leu Pro Ser Val Gln Trp Asn His Asn His Glu Val Asp Gly Asp Asp
                195                 200                 205

Asp Asp Val Ser Leu Trp Ser Tyr
        210                 215

<210> SEQ ID NO 97
<211> LENGTH: 213
<212> TYPE: PRT
<213> ORGANISM: Arabidopsis thaliana

<400> SEQUENCE: 97

Met Asn Ser Phe Ser Ala Phe Ser Glu Met Phe Gly Ser Asp Tyr Glu
1               5                   10                  15

Pro Gln Gly Gly Asp Tyr Cys Pro Thr Leu Ala Thr Ser Cys Pro Lys
                20                  25                  30

Lys Pro Ala Gly Arg Lys Lys Phe Arg Glu Thr Arg His Pro Ile Tyr
```

-continued

```
            35                  40                  45
Arg Gly Val Arg Gln Arg Asn Ser Gly Lys Trp Val Ser Glu Val Arg
         50                  55                  60
Glu Pro Asn Lys Lys Thr Arg Ile Trp Leu Gly Thr Phe Gln Thr Ala
 65                  70                  75                  80
Glu Met Ala Ala Arg Ala His Asp Val Ala Ala Leu Ala Leu Arg Gly
                 85                  90                  95
Arg Ser Ala Cys Leu Asn Phe Ala Asp Ser Ala Trp Arg Leu Arg Ile
             100                 105                 110
Pro Glu Ser Thr Cys Ala Lys Asp Ile Gln Lys Ala Ala Ala Glu Ala
         115                 120                 125
Ala Leu Ala Phe Gln Asp Glu Thr Cys Asp Thr Thr Thr Thr Asp His
     130                 135                 140
Gly Leu Asp Met Glu Glu Thr Met Val Glu Ala Ile Tyr Thr Pro Glu
145                 150                 155                 160
Gln Ser Glu Gly Ala Phe Tyr Met Asp Glu Thr Met Phe Gly Met
                 165                 170                 175
Pro Thr Leu Leu Asp Asn Met Ala Glu Gly Met Leu Leu Pro Pro Pro
             180                 185                 190
Ser Val Gln Trp Asn His Asn Tyr Asp Gly Glu Gly Asp Gly Asp Val
         195                 200                 205
Ser Leu Trp Ser Tyr
         210

<210> SEQ ID NO 98
<211> LENGTH: 216
<212> TYPE: PRT
<213> ORGANISM: Arabidopsis thaliana

<400> SEQUENCE: 98

Met Asn Ser Cys Ser Ala Phe Ser Glu Met Phe Gly Ser Asp Tyr Glu
  1               5                  10                  15
Ser Pro Val Ser Ser Gly Gly Asp Tyr Ser Pro Lys Leu Ala Thr Ser
                 20                  25                  30
Cys Pro Lys Lys Pro Ala Gly Arg Lys Lys Phe Arg Glu Thr Arg His
             35                  40                  45
Pro Ile Tyr Arg Gly Val Arg Gln Arg Asn Ser Gly Lys Trp Val Cys
         50                  55                  60
Glu Leu Arg Glu Pro Asn Lys Lys Thr Arg Ile Trp Leu Gly Thr Phe
 65                  70                  75                  80
Gln Thr Ala Glu Met Ala Ala Arg Ala His Asp Val Ala Ala Ile Ala
                 85                  90                  95
Leu Arg Gly Arg Ser Ala Cys Leu Asn Phe Ala Asp Ser Ala Trp Arg
             100                 105                 110
Leu Arg Ile Pro Glu Ser Thr Cys Ala Lys Glu Ile Gln Lys Ala Ala
         115                 120                 125
Ala Glu Ala Ala Leu Asn Phe Gln Asp Glu Met Cys His Met Thr Thr
     130                 135                 140
Asp Ala His Gly Leu Asp Met Glu Glu Thr Leu Val Glu Ala Ile Tyr
145                 150                 155                 160
Thr Pro Glu Gln Ser Gln Asp Ala Phe Tyr Met Asp Glu Glu Ala Met
                 165                 170                 175
Leu Gly Met Ser Ser Leu Leu Asp Asn Met Ala Glu Gly Met Leu Leu
             180                 185                 190
```

Pro Ser Pro Ser Val Gln Trp Asn Tyr Asn Phe Asp Val Glu Gly Asp
            195                 200                 205

Asp Asp Val Ser Leu Trp Ser Tyr
210                 215

<210> SEQ ID NO 99
<211> LENGTH: 224
<212> TYPE: PRT
<213> ORGANISM: Arabidopsis thaliana

<400> SEQUENCE: 99

Met Asn Pro Phe Tyr Ser Thr Phe Pro Asp Ser Phe Leu Ser Ile Ser
1               5                   10                  15

Asp His Arg Ser Pro Val Ser Asp Ser Ser Glu Cys Ser Pro Lys Leu
            20                  25                  30

Ala Ser Ser Cys Pro Lys Lys Arg Ala Gly Arg Lys Lys Phe Arg Glu
        35                  40                  45

Thr Arg His Pro Ile Tyr Arg Gly Val Arg Gln Arg Asn Ser Gly Lys
    50                  55                  60

Trp Val Cys Glu Val Arg Glu Pro Asn Lys Lys Ser Arg Ile Trp Leu
65                  70                  75                  80

Gly Thr Phe Pro Thr Val Glu Met Ala Ala Arg Ala His Asp Val Ala
                85                  90                  95

Ala Leu Ala Leu Arg Gly Arg Ser Ala Cys Leu Asn Phe Ala Asp Ser
            100                 105                 110

Ala Trp Arg Leu Arg Ile Pro Glu Thr Thr Cys Pro Lys Glu Ile Gln
        115                 120                 125

Lys Ala Ala Ser Glu Ala Ala Met Ala Phe Gln Asn Glu Thr Thr Thr
    130                 135                 140

Glu Gly Ser Lys Thr Ala Ala Glu Ala Glu Glu Ala Ala Gly Glu Gly
145                 150                 155                 160

Val Arg Glu Gly Glu Arg Arg Ala Glu Glu Gln Asn Gly Gly Val Phe
                165                 170                 175

Tyr Met Asp Asp Glu Ala Leu Leu Gly Met Pro Asn Phe Phe Glu Asn
            180                 185                 190

Met Ala Glu Gly Met Leu Leu Pro Pro Glu Val Gly Trp Asn His
        195                 200                 205

Asn Asp Phe Asp Gly Val Gly Asp Val Ser Leu Trp Ser Phe Asp Glu
    210                 215                 220

<210> SEQ ID NO 100
<211> LENGTH: 216
<212> TYPE: PRT
<213> ORGANISM: Thellungiella salsuginea

<400> SEQUENCE: 100

Met Asn Ser Phe Ser Ala Phe Ala Glu Met Phe Gly Ser Glu Tyr Glu
1               5                   10                  15

Ser Pro Val Thr Val Gly Gly Asp Tyr Cys Pro Thr Leu Ala Thr Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Arg Asn Ser Gly Lys Trp Val Cys
    50                  55                  60

Glu Val Arg Glu Pro Asn Lys Lys Ser Arg Ile Trp Leu Gly Thr Phe
65                  70                  75                  80

```
Pro Thr Ala Glu Met Ala Ala Arg Ala His Asp Val Ala Ala Ile Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Asp Ile Gln Lys Ala Ala
            115                 120                 125

Ala Glu Ala Ala Val Ala Phe Gln Ala Glu Met Ser Asp Thr Met Thr
130                 135                 140

Ser Asp His Gly Leu Asp Met Glu Glu Thr Thr Val Glu Val Ile Val
145                 150                 155                 160

Thr Glu Glu Glu Gln Ser Glu Gly Phe Tyr Met Asp Glu Glu Ala Met
                165                 170                 175

Phe Gly Met Pro Arg Leu Leu Ala Asn Met Ala Glu Gly Met Leu Leu
            180                 185                 190

Pro Pro Pro Ser Val Gln Trp Gly His Asn Tyr Asp Cys Asp Gly Asp
            195                 200                 205

Ala Asp Val Ser Leu Trp Ser Tyr
210                 215

<210> SEQ ID NO 101
<211> LENGTH: 253
<212> TYPE: PRT
<213> ORGANISM: Oryza sativa

<400> SEQUENCE: 101

Met Glu Lys Asn Thr Ala Ala Ser Gly Gln Leu Met Thr Ser Ser Ala
1               5                   10                  15

Glu Ala Thr Pro Ser Ser Pro Lys Arg Pro Ala Gly Arg Thr Lys Phe
            20                  25                  30

Gln Glu Thr Arg His Leu Val Phe Arg Gly Val Arg Trp Arg Gly Cys
                35                  40                  45

Ala Gly Arg Trp Val Cys Lys Val Arg Val Pro Gly Ser Arg Gly Asp
50                  55                  60

Arg Phe Trp Ile Gly Thr Ser Asp Thr Ala Glu Glu Thr Ala Arg Thr
65                  70                  75                  80

His Asp Ala Ala Met Leu Ala Leu Cys Gly Ala Ser Ala Ser Leu Asn
                85                  90                  95

Phe Ala Asp Ser Ala Trp Leu Leu His Val Pro Arg Ala Pro Val Val
            100                 105                 110

Ser Gly Leu Arg Pro Pro Ala Ala Arg Cys Ala Thr Arg Cys Leu Gln
            115                 120                 125

Gly His Arg Arg Val Pro Ala Pro Gly Arg Gly Ser Thr Ala Thr Ala
130                 135                 140

Thr Ala Thr Ser Gly Asp Ala Ala Ser Thr Ala Pro Pro Ser Ala Pro
145                 150                 155                 160

Val Leu Ser Ala Lys Gln Cys Glu Phe Ile Phe Leu Ser Ser Leu Asp
                165                 170                 175

Cys Trp Met Leu Met Ser Lys Leu Ile Ser Ser Arg Ala Lys Gly
            180                 185                 190

Ser Leu Cys Leu Arg Lys Asn Pro Ile Ser Phe Cys Met Val Thr Asn
            195                 200                 205

Ser Tyr Thr Ala Leu Leu Glu Tyr Ile Ile Leu Gln Met Asn Ser
210                 215                 220

Met Ile Val Leu Ile His Glu Leu Ser Lys Tyr Gln Val Phe Leu Leu
225                 230                 235                 240
```

```
Leu Thr Met Ile Thr His His Leu Phe Gln Trp Arg Arg
            245                 250

<210> SEQ ID NO 102
<211> LENGTH: 218
<212> TYPE: PRT
<213> ORGANISM: Oryza sativa

<400> SEQUENCE: 102

Met Glu Val Glu Glu Ala Ala Tyr Arg Thr Val Trp Ser Glu Pro Pro
1               5                   10                  15
Lys Arg Pro Ala Gly Arg Thr Lys Phe Arg Glu Thr Arg His Pro Val
                20                  25                  30
Tyr Arg Gly Val Arg Arg Gly Gly Arg Pro Gly Ala Ala Gly Arg
            35                  40                  45
Trp Val Cys Glu Val Arg Val Pro Gly Ala Arg Gly Ser Arg Leu Trp
50                  55                  60
Leu Gly Thr Phe Ala Thr Ala Glu Ala Ala Arg Gly His Asp Ala
65                  70                  75                  80
Ala Ala Leu Ala Leu Arg Gly Arg Ala Ala Cys Leu Asn Phe Ala Asp
                85                  90                  95
Phe Ala Trp Arg Met Pro Pro Val Pro Ala Ser Ala Ala Leu Ala Gly
            100                 105                 110
Ala Arg Gly Val Arg Asp Pro Val Ala Val Ala Val Glu Ala Phe Gln
        115                 120                 125
Arg Gln Ser Ala Ala Pro Ser Ser Pro Ala Glu Thr Phe Ala Asn Asp
    130                 135                 140
Gly Asp Glu Glu Glu Ala Asn Lys Glu Val Leu Pro Val Ala Ala Ala
145                 150                 155                 160
Glu Val Phe Asp Ala Gly Ala Phe Glu Leu Asp Asp Gly Phe Arg Phe
                165                 170                 175
Gly Gly Met Asp Ala Gly Ser Tyr Tyr Ala Ser Leu Ala Gln Gly Leu
            180                 185                 190
Leu Val Glu Pro Pro Ala Ala Gly Ala Trp Trp Glu Asp Gly Glu Leu
        195                 200                 205
Ala Asp Ser Asp Met Pro Leu Trp Ser Tyr
    210                 215

<210> SEQ ID NO 103
<211> LENGTH: 291
<212> TYPE: PRT
<213> ORGANISM: Oryza sativa

<400> SEQUENCE: 103

Met Ala Ala Ala Ile Asp Leu Ser Gly Glu Glu Leu Met Arg Ala Leu
1               5                   10                  15
Glu Pro Phe Ile Arg Asp Ala Ser Gly Ser Pro Val Cys Ser Gln
                20                  25                  30
Phe Ser Pro Thr Ser Pro Phe Ser Phe Pro His Ala Leu Ala Tyr Gly
            35                  40                  45
Gly Gly Leu Ala Gln Gln Pro Glu Leu Ser Pro Ala Gln Met His Tyr
        50                  55                  60
Ile Gln Ala Arg Leu His Leu Gln Arg Gln Ala Ala Gln Ala Gly Pro
65                  70                  75                  80
Leu Gly Pro Arg Ala Gln Pro Met Lys Ala Ser Ser Ser Ser Ala Ser
                85                  90                  95
```

```
Ala Ala Gly Ala Ala Ala Thr Pro Pro Arg Pro Gln Lys Leu Tyr Arg
            100                 105                 110

Gly Val Arg Gln Arg His Trp Gly Lys Trp Val Ala Glu Ile Arg Leu
        115                 120                 125

Pro Arg Asn Arg Thr Arg Leu Trp Leu Gly Thr Phe Asp Thr Ala Glu
    130                 135                 140

Glu Ala Ala Leu Ala Tyr Asp Gln Ala Ala Tyr Arg Leu Arg Gly Asp
145                 150                 155                 160

Ala Ala Arg Leu Asn Phe Pro Asp Asn Ala Ala Ser Arg Gly Pro Leu
                165                 170                 175

His Ala Ser Val Asp Ala Lys Leu Gln Thr Leu Cys Gln Asn Ile Ala
            180                 185                 190

Ala Ala Lys Asn Ala Lys Lys Ser Val Ser Ala Ser Ala Ala Ala
        195                 200                 205

Thr Ser Ser Ala Pro Thr Ser Asn Cys Ser Ser Pro Ser Ser Asp Asp
    210                 215                 220

Ala Ser Ser Cys Leu Glu Ser Ala Asp Ser Ser Pro Ser Leu Ser Pro
225                 230                 235                 240

Ser Ser Ala Ala Thr Thr Ala Glu Thr Pro Ala Thr Val Pro Glu Met
                245                 250                 255

Gln Gln Leu Asp Phe Ser Glu Ala Pro Trp Asp Glu Ala Ala Phe
            260                 265                 270

Ala Leu Thr Lys Tyr Pro Ser Tyr Glu Ile Asp Trp Asp Ser Leu Leu
        275                 280                 285

Ala Ala Asn
    290

<210> SEQ ID NO 104
<211> LENGTH: 238
<212> TYPE: PRT
<213> ORGANISM: Oryza sativa

<400> SEQUENCE: 104

Met Cys Gly Ile Lys Gln Glu Met Ser Gly Glu Ser Ser Gly Ser Pro
1               5                   10                  15

Cys Ser Ser Ala Ser Ala Glu Arg Gln His Gln Thr Val Trp Thr Ala
            20                  25                  30

Pro Pro Lys Arg Pro Ala Gly Arg Thr Lys Phe Arg Glu Thr Arg His
        35                  40                  45

Pro Val Phe Arg Gly Val Arg Arg Gly Asn Ala Gly Arg Trp Val
    50                  55                  60

Cys Glu Val Arg Val Pro Gly Arg Gly Cys Arg Leu Trp Leu Gly
65                  70                  75                  80

Thr Phe Asp Thr Ala Glu Gly Ala Ala Arg Ala His Asp Ala Ala Met
                85                  90                  95

Leu Ala Ile Asn Ala Gly Gly Gly Gly Gly Ala Cys Cys Leu
            100                 105                 110

Asn Phe Ala Asp Ser Ala Trp Leu Leu Ala Val Pro Arg Ser Tyr Arg
        115                 120                 125

Thr Leu Ala Asp Val Arg His Ala Val Ala Glu Ala Val Glu Asp Phe
    130                 135                 140

Phe Arg Arg Arg Leu Ala Asp Asp Ala Leu Ser Ala Thr Ser Ser Ser
145                 150                 155                 160

Ser Thr Thr Pro Ser Thr Pro Arg Thr Asp Asp Asp Glu Glu Ser Ala
```

```
                        165                 170                 175
Ala Thr Asp Gly Asp Glu Ser Ser Pro Ala Ser Asp Leu Ala Phe
            180                 185                 190
Glu Leu Asp Val Leu Ser Asp Met Gly Trp Asp Leu Tyr Tyr Ala Ser
            195                 200                 205
Leu Ala Gln Gly Met Leu Met Glu Pro Pro Ser Ala Ala Leu Gly Asp
            210                 215                 220
Asp Gly Asp Ala Ile Leu Ala Asp Val Pro Leu Trp Ser Tyr
225                 230                 235

<210> SEQ ID NO 105
<211> LENGTH: 279
<212> TYPE: PRT
<213> ORGANISM: Oryza sativa

<400> SEQUENCE: 105

Ala Ala Ala Ile Glu Gly Asn Leu Met Arg Ala Leu Gly Glu Ala Pro
1               5                   10                  15
Ser Pro Gln Met Gln Lys Ile Ala Pro Pro Phe His Pro Gly Leu
            20                  25                  30
Pro Pro Ala Pro Ala Asn Phe Ser Ser Ala Gly Val His Gly Phe His
            35                  40                  45
Tyr Met Gly Pro Ala Gln Leu Ser Pro Ala Gln Ile Gln Arg Val Gln
        50                  55                  60
Ala Gln Leu His Met Gln Arg Gln Ala Gln Ser Gly Leu Gly Pro Arg
65                  70                  75                  80
Ala Gln Pro Met Lys Pro Ala Ser Ala Ala Pro Ala Ala Ala
                85                  90                  95
Ala Arg Ala Gln Lys Leu Tyr Arg Gly Val Arg Gln Arg His Trp Gly
                100                 105                 110
Lys Trp Val Ala Glu Ile Arg Leu Pro Arg Asn His Pro Arg Leu Trp
            115                 120                 125
Leu Gly Thr Phe Asp Thr Ala Glu Glu Ala Ala Leu Thr Tyr Gly Gln
        130                 135                 140
Ala Ala Tyr Arg Leu Arg Gly Asp Ala Ala Arg Leu Asn Phe Pro Asp
145                 150                 155                 160
Asn Ala Ala Ser Arg Gly Pro Leu Asp Ala Ala Val Asp Ala Lys Leu
                165                 170                 175
Gln Ala Ile Cys Asp Thr Ile Ala Ala Ser Lys Asn Ala Ser Ser Arg
            180                 185                 190
Ser Arg Gly Gly Ala Gly Arg Ala Met Pro Ile Asn Ala Pro Leu Val
        195                 200                 205
Ala Ala Ala Ser Ser Ser Ser Gly Ser Asp His Ser Gly Gly Gly Asp
            210                 215                 220
Asp Gly Gly Ser Glu Thr Ser Ser Ser Ser Ala Ala Ala Ser Pro Leu
225                 230                 235                 240
Ala Glu Met Glu Gln Leu Asp Phe Ser Glu Val Pro Trp Asp Glu Ala
                245                 250                 255
Glu Gly Phe Ala Leu Thr Lys Tyr Pro Ser Tyr Glu Ile Asp Trp Asp
            260                 265                 270
Ser Leu Leu Asn Asn Asn Asn
        275

<210> SEQ ID NO 106
<211> LENGTH: 218
```

-continued

<212> TYPE: PRT
<213> ORGANISM: Oryza sativa

<400> SEQUENCE: 106

Met Glu Val Glu Glu Ala Ala Tyr Arg Thr Val Trp Ser Glu Pro Pro
1               5                   10                  15

Lys Arg Pro Ala Gly Arg Thr Lys Phe Arg Glu Thr Arg His Pro Val
            20                  25                  30

Tyr Arg Gly Val Arg Arg Arg Gly Arg Pro Gly Ala Ala Gly Arg
        35                  40                  45

Trp Val Cys Glu Val Arg Val Pro Gly Ala Arg Gly Ser Arg Leu Trp
    50                  55                  60

Leu Gly Thr Phe Ala Thr Ala Glu Ala Ala Arg Ala His Asp Ala
65                  70                  75                  80

Ala Ala Leu Ala Leu Arg Gly Arg Ala Ala Cys Leu Asn Phe Ala Asp
                85                  90                  95

Phe Ala Trp Arg Met Pro Pro Val Pro Ala Ser Ala Ala Leu Ala Gly
            100                 105                 110

Ala Arg Gly Val Arg Asp Pro Val Ala Val Ala Val Glu Ala Phe Gln
        115                 120                 125

Arg Gln Ser Ala Ala Pro Ser Ser Pro Ala Glu Thr Phe Ala Asn Asp
    130                 135                 140

Gly Asp Glu Glu Glu Ala Asn Lys Asp Val Leu Pro Val Ala Ala Ala
145                 150                 155                 160

Glu Val Phe Asp Ala Gly Ala Phe Glu Leu Asp Asp Gly Phe Arg Phe
                165                 170                 175

Gly Gly Met Asp Ala Gly Ser Tyr Tyr Ala Ser Leu Ala Gln Gly Leu
            180                 185                 190

Leu Val Glu Pro Pro Ala Ala Gly Ala Trp Trp Glu Asp Gly Glu Leu
        195                 200                 205

Ala Gly Ser Asp Met Pro Leu Trp Ser Tyr
    210                 215

<210> SEQ ID NO 107
<211> LENGTH: 218
<212> TYPE: PRT
<213> ORGANISM: Oryza sativa

<400> SEQUENCE: 107

Met Glu Val Glu Glu Ala Ala Tyr Arg Thr Val Trp Ser Glu Pro Pro
1               5                   10                  15

Lys Arg Pro Ala Gly Arg Thr Lys Phe Arg Glu Thr Arg His Pro Val
            20                  25                  30

Tyr Arg Gly Val Arg Arg Arg Gly Arg Pro Gly Ala Ala Gly Arg
        35                  40                  45

Trp Val Cys Glu Val Arg Val Pro Gly Ala Arg Gly Ser Arg Leu Trp
    50                  55                  60

Leu Gly Thr Phe Ala Thr Ala Glu Ala Ala Arg Ala His Asp Ala
65                  70                  75                  80

Ala Ala Leu Ala Leu Arg Gly Arg Ala Ala Cys Leu Asn Phe Ala Asp
                85                  90                  95

Ser Ala Trp Arg Met Pro Pro Val Pro Ala Ser Ala Ala Leu Ala Gly
            100                 105                 110

Ala Arg Gly Val Arg Asp Ala Val Ala Val Ala Val Glu Ala Phe Gln
        115                 120                 125

```
Arg Gln Ser Ala Ala Pro Ser Ser Pro Ala Glu Thr Phe Ala Asp Asp
    130                 135                 140

Gly Asp Glu Glu Asp Asn Lys Asp Val Leu Pro Val Ala Ala Ala
145                 150                 155                 160

Glu Val Phe Asp Ala Gly Ala Phe Glu Leu Asp Asp Gly Phe Arg Phe
                165                 170                 175

Gly Gly Met Asp Ala Gly Ser Tyr Tyr Ala Ser Leu Ala Gln Gly Leu
            180                 185                 190

Leu Val Glu Pro Pro Ala Ala Gly Ala Trp Trp Glu Asp Gly Glu Leu
        195                 200                 205

Ala Gly Ser Asp Met Pro Leu Trp Ser Tyr
    210                 215
```

<210> SEQ ID NO 108
<211> LENGTH: 274
<212> TYPE: PRT
<213> ORGANISM: Oryza sativa

<400> SEQUENCE: 108

```
Met Glu Arg Gly Glu Gly Arg Arg Gly Asp Cys Ser Val Gln Val Arg
1               5                   10                  15

Lys Lys Arg Thr Arg Arg Lys Ser Asp Gly Pro Asp Ser Ile Ala Glu
            20                  25                  30

Thr Ile Lys Trp Trp Lys Glu Gln Asn Gln Lys Leu Gln Glu Glu Asn
        35                  40                  45

Ser Ser Arg Lys Ala Pro Ala Lys Gly Ser Lys Lys Gly Cys Met Ala
    50                  55                  60

Gly Lys Gly Gly Pro Glu Asn Ser Asn Cys Ala Tyr Arg Gly Val Arg
65                  70                  75                  80

Gln Arg Thr Trp Gly Lys Trp Val Ala Glu Ile Arg Glu Pro Asn Arg
                85                  90                  95

Gly Arg Arg Leu Trp Leu Gly Ser Phe Pro Thr Ala Leu Glu Ala Ala
            100                 105                 110

His Ala Tyr Asp Glu Ala Ala Arg Ala Met Tyr Gly Pro Thr Ala Arg
        115                 120                 125

Val Asn Phe Ala Asp Asn Ser Thr Asp Ala Asn Ser Gly Cys Thr Ser
    130                 135                 140

Ala Pro Ser Leu Met Met Ser Asn Gly Pro Ala Thr Ile Pro Ser Asp
145                 150                 155                 160

Glu Lys Asp Glu Leu Glu Ser Pro Pro Phe Ile Val Ala Asn Gly Pro
                165                 170                 175

Ala Val Leu Tyr Gln Pro Asp Lys Lys Asp Val Leu Glu Arg Val Val
            180                 185                 190

Pro Glu Val Gln Asp Val Lys Thr Glu Gly Ser Asn Gly Leu Lys Arg
        195                 200                 205

Val Cys Gln Glu Arg Lys Asn Met Glu Val Cys Glu Ser Glu Gly Ile
    210                 215                 220

Val Leu His Lys Glu Val Asn Ile Ser Tyr Asp Tyr Phe Asn Val His
225                 230                 235                 240

Glu Ile Val Glu Met Ile Ile Val Glu Leu Ser Ala Asp Gln Lys Thr
                245                 250                 255

Glu Val His Glu Glu Tyr Gln Glu Gly Asp Asp Gly Phe Ser Leu Phe
            260                 265                 270

Ser Tyr
```

-continued

<210> SEQ ID NO 109
<211> LENGTH: 895
<212> TYPE: DNA
<213> ORGANISM: Oryza sativa

<400> SEQUENCE: 109

| | | | | | |
|---|---|---|---|---|---|
| cactcgagca | gagcaaatac | agttcaggaa | tcaggagcaa | gcagaaacac | acacacaaat | 60 |
| ccgaagatgt | gcgggatcaa | gcaggagatg | agcggcgagt | cgtcgggtc | gccgtgcagc | 120 |
| tcggcgtcgg | cggagcggca | gcaccagacg | gtgtggacgg | cgccgccgaa | gaggccggcg | 180 |
| gggcggacca | agttcaggga | gacgaggcac | ccggtgttcc | gcggcgtgcg | gcggagggcc | 240 |
| aatgccggga | ggtgggtgtg | cgaggtgcgg | gtgcccgggc | ggcgcggctg | caggctctgg | 300 |
| ctcggcacgt | tcgacaccgc | cgagggcgcg | gcgcgcgcgc | acgacgccgc | catgctcgcc | 360 |
| atcaacgccg | gcggcggcgg | cggcggggga | gcatgctgcc | tcaacttcgc | cgactccgcg | 420 |
| tggctcctcg | ccgtgccgcg | ctcctaccgc | accctcgccg | acgtccgcca | cgccgtcgcc | 480 |
| gaggccgtcg | aggacttctt | ccggcgccgc | ctcgccgacg | acgcgctgtc | cgccacgtcg | 540 |
| tcgtcctcga | cgacgccgtc | caccccacgc | accgacgacg | acgaggagtc | cgccgccacc | 600 |
| gacggcgacg | agtcctcctc | cccggccagc | gacctggcgt | tcgaactgga | cgtcctgagt | 660 |
| gacatgggct | gggacctgta | ctacgcgagc | ttggcgcagg | ggatgctcat | ggagccacca | 720 |
| tcggcggcgc | tcggcgacga | cggtgacgcc | atcctcgccg | acgtcccact | ctggagctac | 780 |
| tagagctcaa | tcaactgtac | aattttgcct | cttttttctc | tcttttctgg | cttccgatgc | 840 |
| caaaattttg | gtactgtacg | gacactactt | tcggtaatgt | gatggaacaa | gttgc | 895 |

<210> SEQ ID NO 110
<211> LENGTH: 955
<212> TYPE: DNA
<213> ORGANISM: Oryza sativa

<400> SEQUENCE: 110

| | | | | | |
|---|---|---|---|---|---|
| aaaaaaaaaa | aaaaaaaaaa | aaaaaaaaaa | aaaaatcgc | cattaccaca | ctcgagcaga | 60 |
| gcaaatacag | ttcaggaatc | aggagcaagc | agaaacacac | acacaaatcc | gaagatgtgc | 120 |
| gggatcaagc | aggagatgag | cggcgagtcg | tcgggtcgc | cgtgcagctc | ggcgtcggcg | 180 |
| gagcggcagc | accagacggt | gtggacggcg | ccgccgaaga | ggccggcggg | gcggaccaag | 240 |
| ttcagggaga | cgaggcaccc | ggtgttccgc | ggcgtgcggc | ggagggcaa | tgccgggagg | 300 |
| tgggtgtgcg | aggtgcgggt | gcccggcgg | cgcggctgca | ggctctggct | cggcacgttc | 360 |
| gacaccgccg | agggcgcggc | gcgcgcgcac | gacgccgcca | tgctcgccat | caacgccggc | 420 |
| ggcggcggcg | gcggggagc | atgctgcctc | aacttcgccg | actccgcgtg | gctcctcgcc | 480 |
| gtgccgcgct | cctaccgcac | cctcgccgac | gtccgccacg | ccgtcgccga | ggccgtcgag | 540 |
| gacttcttcc | ggcgccgcct | cgccgacgac | gcgctgtccg | ccacgtcgtc | gtcctcgacg | 600 |
| acgccgtcca | ccccacgcac | cgacgacgac | gaggagtccg | ccgccaccga | cggcgacgag | 660 |
| tcctcctccc | cggccagcga | cctggcgttc | gaactggacg | tcctgagtga | catgggctgg | 720 |
| gacctgtact | acgcgagctt | ggcgcagggg | atgctcatgg | agccaccatc | ggcggcgctc | 780 |
| ggcgacgacg | gtgacgccat | cctcgccgac | gtcccactct | ggagctacta | gagctcaatc | 840 |
| aactgtacaa | ttttgcctct | tttttctctc | ttttctggct | tccgatgcca | aaattttggt | 900 |
| actgtacgga | cactactttc | ggtaatgtga | tggaacaagt | tgcaaaacac | agagc | 955 |

<210> SEQ ID NO 111
<211> LENGTH: 988
<212> TYPE: DNA
<213> ORGANISM: Schedonorus arundinaceus

<400> SEQUENCE: 111

| | | | | | |
|---|---|---|---|---|---|
| aatccaaaat | aacctccacc | cctccagcta | agaacatact | agtaccttcg | cctcaccaga | 60 |
| gcaacccaca | agcaagcatc | tccactatat | atcgacgctg | cgagtgatgg | acgctgccgt | 120 |
| tgccgcctcg | ctgtcgctgc | agtcggggga | gcaagagtac | aggacggtat | ggtcggagcc | 180 |
| gccgaagcca | cgatcgggc | gcaccaagtt | ccaggacg | cggcacccgg | tgtaccgcgg | 240 |
| cgttcggcgc | cggggcgtg | ccgggcagtg | ggtgtgcgag | atgcgcgtcc | acgggacgaa | 300 |
| ggggtccagg | ctctggctcg | gcaccttcga | caccgctgag | atggctgcac | gcgcgcacga | 360 |
| cgccgccgcg | ctcgcgctct | ccggccgcga | cgcatgcctc | aacttcgctg | actccgcctg | 420 |
| gcggatgcag | cccgtcctcc | ctgccggtgc | cgggtcggtc | tgcttcggcg | gagcgcagga | 480 |
| ggtcaaggac | gccgtcgccg | ccgccgtcga | ggcgttccag | gaggaggagc | accacgttga | 540 |
| gtccacggcg | gagacggcca | aggacgagga | gagcgcgctg | tccatgtcca | gcgacttgtc | 600 |
| ggagcacgac | gacgagcgct | ggattgacgg | catggacgcc | gggtcgtact | acgcgagctt | 660 |
| ggcgcagggc | atgctcgtgg | agccaccgga | cgccggagcg | tggcgggagg | acggcgaaca | 720 |
| cggcggtgtc | gagacgtcgc | tatggagcta | cttgtagtgt | acgtggagtt | ttaccaggaa | 780 |
| ctactactag | aactagttct | gttctcgctt | ccaaatatgg | gaagacgcag | agtaatcatc | 840 |
| gagggcaatt | tttaccccat | atgtgaaagg | aaaacgctct | ctttcctccg | gacgatacga | 900 |
| cgcgatgcgt | cctccgcctt | gcgcacgcaa | cacgtgtctg | ggggcccacc | tccaccgctt | 960 |
| caaaaaaaaa | aaaaaaaaa | aaaaaaaa | | | | 988 |

<210> SEQ ID NO 112
<211> LENGTH: 895
<212> TYPE: DNA
<213> ORGANISM: Oryza sativa

<400> SEQUENCE: 112

| | | | | | |
|---|---|---|---|---|---|
| cactcgagca | gagcaaatac | agttcaggaa | tcaggagcaa | gcagaaacac | acacacaaat | 60 |
| ccgaagatgt | gcgggatcaa | gcaggagatg | agcggcgagt | cgtcgggtc | gccgtgcagc | 120 |
| tcggcgtcgg | cggagcggca | gcaccagacg | gtgtggacgg | cgccgccgaa | gaggccggcg | 180 |
| gggcggacca | agttcaggga | gacgaggcac | ccggtgttcc | gcggcgtgcg | gcggaggggc | 240 |
| aatgccggga | ggtgggtgtg | cgaggtgcgg | gtgcccgggc | ggcgcggctg | caggctctgg | 300 |
| ctcggcacgt | tcgacaccgc | cgagggcgcg | gcgcgcgcgc | acgacgccgc | catgctcgcc | 360 |
| atcaacgccg | gcggcggcgg | cggcggggga | gcatgctgcc | tcaacttcgc | cgactccgcg | 420 |
| tggctcctcg | ccgtgccgcg | ctcctaccgc | accctcgccg | acgtccgcca | cgccgtcgcc | 480 |
| gaggccgtcg | aggacttctt | ccggcgccgc | ctcgccgacg | acgcgctgtc | cgccacgtcg | 540 |
| tcgtcctcga | cgacgccgtc | caccccacgc | accgacgacg | acgaggagtc | cgccgccacc | 600 |
| gacggcgacg | agtcctcctc | cccggccagc | gacctggcgt | tcgaactgga | cgtcctgagt | 660 |
| gacatgggct | gggacctgta | ctacgcgagc | ttggcgcagg | ggatgctcat | ggagccacca | 720 |
| tcggcggcgc | tcggcgacga | cggtgacgcc | atcctcgccg | acgtcccact | ctggagctac | 780 |
| tagagctcaa | tcaactgtac | aatttttgcct | ctttttctc | tcttttctgg | cttccgatgc | 840 |
| caaaattttg | gtactgtacg | gacactactt | tcggtaatgt | gatggaacaa | gttgc | 895 |

<210> SEQ ID NO 113
<211> LENGTH: 717
<212> TYPE: DNA
<213> ORGANISM: Oryza sativa

<400> SEQUENCE: 113

| | | | | | |
|---|---|---|---|---|---|
| atgtgcggga | tcaagcagga | gatgagcggc | gagtcgtcgg | ggtcgccgtg | cagctcggcg | 60 |
| tcggcggagc | ggcagcacca | gacggtgtgg | acggcgccgc | cgaagaggcc | ggcggggcgg | 120 |
| accaagttca | gggagacgag | gcacccggtg | ttccgcggcg | tgcggcggag | gggcaatgcc | 180 |
| gggaggtggg | tgtgcgaggt | acgggtgccc | ggcggcgcg | gctgcaggct | ctggctcggc | 240 |
| acgttcgaca | ccgccgaggg | cgcggcgcgc | gcgcacgacg | ccgccatgct | cgccatcaac | 300 |
| gccggcggcg | gcggcggcgg | gggagcatgc | tgcctcaact | tcgccgactc | cgcgtggctc | 360 |
| ctcgccgtgc | gcgctcccta | ccgcaccctc | gccgacgtcc | gccacgccgt | cgccgaggcc | 420 |
| gtcgaggact | tcttccggcg | ccgcctcgcc | gacgacgcg | tgtccgccac | gtcgtcgtcc | 480 |
| tcgacgacgc | cgtccacccc | acgcaccgac | gacgaggagg | agtccgccgc | caccgacggc | 540 |
| gacgagtcct | cctccccggc | cagcgacctg | gcgttcgaac | tggacgtcct | gagtgacatg | 600 |
| ggctgggacc | tgtactacgc | gagcttggcg | caggggatgc | tcatggagcc | accatcggcg | 660 |
| gcgctcggcg | acgacggtga | cgccatcctc | gccgacgtcc | cactctggag | ctactag | 717 |

<210> SEQ ID NO 114
<211> LENGTH: 850
<212> TYPE: DNA
<213> ORGANISM: Oryza sativa

<400> SEQUENCE: 114

| | | | | | |
|---|---|---|---|---|---|
| cgagcagagg | aaatacagtt | taggaatccg | gagcaagcag | aaacacacac | acaaatccga | 60 |
| agatgtgcgg | gatcaagcag | gagatgagcg | gcgagtcgtc | ggggtcgccg | tgcagctcgg | 120 |
| cgtcggcgga | gcggcagcac | cagacggtgt | ggacggcgcc | gccgaagagg | ccggcggggc | 180 |
| ggaccaagtt | cagggagacg | aggcacccgg | tgttccgcgg | cgtgcggcgg | aggggcaatg | 240 |
| ccgggaggtg | ggtgtgcgag | gtgcgggtgc | ccggcggcgg | cggctgcagg | ctctggctcg | 300 |
| gcacgttcga | caccgccgag | ggcgcggcgc | gcgcgcacga | cgccgccatg | ctcgccatca | 360 |
| acgccggcgg | cggcggcggc | gggggagcat | gctgcctcaa | cttcgccgac | tccgcgtggc | 420 |
| tcctcgccgt | gcgcgctccc | taccgcaccc | tcgccgacgt | ccgccacgcc | gtcgccgagg | 480 |
| ccgtcgagga | cttcttccgg | cgccgcctcg | ccgacgacgc | gctgtccgcc | acgtcgtcgt | 540 |
| cctcgacgac | gccgtccacc | ccacgcaccg | acgacgacga | ggagtccgcc | gccaccgacg | 600 |
| gcgacgagtc | ctcctccccg | gccagcgacc | tggcgttcga | actggacgtc | ctgagtgaca | 660 |
| tgggctggga | cctgtactac | gcgagcttgg | cgcaggggat | gctcatggag | ccaccatcgg | 720 |
| cggcgctcgg | cgacgacggt | gacgccatcc | tcgccgacgt | cccactctgg | agctactaga | 780 |
| gctcaatcaa | ctgtacaatt | ttgcctcttt | tttctctctt | ttctgccttc | cgatgccaaa | 840 |
| attttttaa | | | | | | 850 |

<210> SEQ ID NO 115
<211> LENGTH: 904
<212> TYPE: DNA
<213> ORGANISM: Oryza sativa

<400> SEQUENCE: 115

| | | | | | |
|---|---|---|---|---|---|
| actgcttgag | acgtcgcaca | cgtcatggag | aagaacaccg | ccgccagcgg | gcaattgatg | 60 |

-continued

| | |
|---|---|
| acctcctccg cggaggcgac gccgtcgtcg ccgaagcggc cggcggggcg aaccaagttc | 120 |
| caggagacga ggcacctagt gttccgtggg gtgcgatggc gtgggtgcgc ggggcggtgg | 180 |
| gtgtgcaagg tgcgtgtccc gggcagccgc ggtgaccgtt tctggatagg cacgtctgac | 240 |
| accgccgagg agaccgcgcg cacgcacgac gccgccatgc tcgccttgtg cggggcctcc | 300 |
| gccagcctca acttcgccga ctctgcctgg ctgctccacg tcccgcgcgc cccgtcgtc | 360 |
| tccggactcc ggccaccagc tgcccgatgt gcaacgcgct gcctgcaagg ccatcgccga | 420 |
| gttccagcgc cgggccgggg gagcaccgcc actgccactg ccacctccgg cgatgctgca | 480 |
| tcgaccgctc ctccgtcggc acccgttctg tcagccaaac aatgcgaatt catctttctt | 540 |
| tcttcactag attgttggat gttaatgtca aagcttatca gcagtagcag agcaaaagga | 600 |
| tcgttgtgcc tgcgaaaaaa tcccatttca ttttgcatgg ttacaaattc ttacactgct | 660 |
| cttttgctcg aatacattat attgcagatg aattcaatga tcgtttaat ccacgaatta | 720 |
| tcaaaatatc aagtctttct gctactaacc atgataacac accaccttt tcaatggagg | 780 |
| aggtaggcgc ggacgccctc gccatcatcg tcgatgtcgc cactgatgac gaggtccgcg | 840 |
| ccgctcacca gctcgcacgc ctcgtcgtcg tccatgctcg ccacctcggt ccagcagctg | 900 |
| aacc | 904 |

<210> SEQ ID NO 116
<211> LENGTH: 1655
<212> TYPE: DNA
<213> ORGANISM: Oryza sativa

<400> SEQUENCE: 116

| | |
|---|---|
| atgtcaggtg gtgcggccgc gacggtggct cccgggtggc ggcgcgagct cgccggcctc | 60 |
| ctcgtccccc tcgtgcggtc ggcgatggag gcgcgcggct gcggccatca tcaccgagat | 120 |
| cgactcgacg cctctgccat caagtcgctg ccgtcggtga tgacggtgcg cagctgtggc | 180 |
| caacggggga ggcagaggag gtacgcacgg atgccctcgc cccgtcgtc gccgccgcca | 240 |
| acactaacca actgcttgag acgtcgcaca cgtcatggag aagaacaccg ccgccagcgg | 300 |
| gcaattgatg acctcctccg cggaggcgac gccgtcgtcg ccgaagcggc cggcggggcg | 360 |
| aaccaagttc caggagacga ggcacctagt gttccgtggg gtgcgatggc gtgggtgcgc | 420 |
| ggggcggtgg gtgtgcaagg tgcgtgtccc gggcagccgc ggtgaccgtt tctggatagg | 480 |
| cacgtctgac accgccgagg agaccgcgcg cacgcacgac gccgccatgc tcgccttgtg | 540 |
| cggggcctcc gccagcctca acttcgccga ctctgcctgg ctgctccacg tcccgcgcgc | 600 |
| cccgtcgtc tccggactcc ggccaccagc tgcccgatgt gcaacgcgct gcctgcaagg | 660 |
| ccatcgccga gttccagcgc cgggccgggg gagcaccgcc actgccactg ccacctccgg | 720 |
| cgatgctgca tcgaccgctc ctccgtcggc acccgttctg tcagccaaac aatgcgaatt | 780 |
| catctttctt tcttcactag attgttggat gttaatgtca aagcttatca gcagtagcag | 840 |
| agcaaaagga tcgttgtgcc tgcgaaaaaa tcccatttca ttttgcatgg ttacaaattc | 900 |
| ttacactgct cttttgctcg aatacattat attgcagatg aattcaatga tcgtttaat | 960 |
| ccacgaatta tcaaaatatc aagtctttct gctactaacc atgataacac accacctttt | 1020 |
| tcaatggagg aggtaggcgc ggacgccctc gccatcatcg tcgatgtcgc cactgatgac | 1080 |
| gaggtccgcg ccgctcacca gctcgcacgc ctcgtcgtcg tccatgctcg ccacctcggt | 1140 |
| ccagcagctg aaccgcctgg cgacgtcctc tcacctcagt cctccctccc agtgagcgaa | 1200 |

| | |
|---|---:|
| caatgaggcc gagcggcgca gagtcgttgg cgccgctgct ccccatccgc agccgcgctc | 1260 |
| gcctgctgct gtcgccgcct ctccgccacc gcgctcgccc gccgacgccg cctcgccccg | 1320 |
| ccgccgtcct ccctttctcc catgtctccg ccgccgcgtc gctgctgcca catcgccggc | 1380 |
| aggctgtcaa acctccctgc tcccacgtcg ccgctgcgat gcaagtggag actggagagg | 1440 |
| ccccgggggca tggtggaggg gcacagcgtt ctcccctat cggctggctg tcgcactccc | 1500 |
| tcctgccggc cgcggcggcc ctcctacccc ggcagccgtc ggtgcggcac tcctcccctg | 1560 |
| ccggttgtgc tcctcgagag gagaaaagtg agagaggaaa ggaaggagg gagaggggct | 1620 |
| gctgggagag agggagtgct gatgtggcat cctga | 1655 |

<210> SEQ ID NO 117
<211> LENGTH: 1922
<212> TYPE: DNA
<213> ORGANISM: Hordeum vulgare

<400> SEQUENCE: 117

| | |
|---|---:|
| acaattcaca tctaaatttg tcttttcttg tttttcaatg tgtatttaga atttgcatgt | 60 |
| gaaattttg ggggatgtgc attcatgcga tgtggacatc cgcaattatt ttcagaactt | 120 |
| tttgagatgt ttaaaattaa tattttttgaa tgatatcatg gaagcatttg gaagatggta | 180 |
| tcaccggata ctctccctct cggggaacaa gacgacctca ttcagcagtg accgctgtct | 240 |
| tctctttctg gccgatcagc cggcggacca atcaggcaag gcaatcaccg ctgcattaac | 300 |
| actgttaagc cagaagaaag ttcgcttttt tttcttttga gaggagcagg aagttgcctt | 360 |
| ttttgcttaa cactgcaatg ccaaaagccc ccacacgccc agcaggagaa aagtctcatg | 420 |
| aacaccactt gatttcatcc cattgtcacc agctgtccgg acaccgcatc cctaccgccg | 480 |
| tcccaagcgc gttcatacac ttcaacctcc agcaccacgc atacctataa atatgtctcc | 540 |
| cacactctcg ctcaagctca agaaatcatc tcacactcct cagtcctcag taagctcaag | 600 |
| caccatgctc agactgttca agaaggaagc cgcctgccaa tcacccagca ctctgccggt | 660 |
| agccatggac atgggccttg aggtctcgag ctcctccccc tcctcctcgt cggtgtcgtc | 720 |
| ctcgcccgag cacgcggcga ggcgggcgtc gccggcgaag cgccccgctg ggcgcaccaa | 780 |
| gttccgggag acgcggcacc cggtgtaccg cggcgtgcgg cgccggggca acaccgaacg | 840 |
| gtgggtctgc gaggtgcgcg tccccggcaa gcgcggtgct cggctctggc tcgggacgta | 900 |
| cgccacggct gaggtcgccg cgcgcgcgaa cgacgctgcc atgctcgccc tgggcggccg | 960 |
| ctccgccacg tgcctcaact tcgccgattc cgcgtggctg ctcgccgtgc cgtccgccct | 1020 |
| gtccgatctc gcagacgtcc ggcgcgcggc tgtcgaggcc gtcgcggatt tccagcgacg | 1080 |
| ggaggctgcc gatggctccc tcgccatcgc tgtccctaag gaggcctcct ctggcgctcc | 1140 |
| ttcactatct ccgtcgtctg ggtccgacag tgccggttcg acggggacgt cggaaccttc | 1200 |
| cgccaatgga gtgttcgagg ggcccgttgt aatggacagt gaaatgttca ggcttgactt | 1260 |
| gttcccggaa atggacctgg gctcgtacta catgagcctc gcggaggcgc tgctcatgga | 1320 |
| cccgccgcct acagcgacca tcatccacgc gtacgaagac aacggcgacg ggggagctga | 1380 |
| tgtccggctc tggagctata gtgtcgatat gtgatttccc agatgattct gctctgtttt | 1440 |
| gactgtgtac tgactgctga gtagtttttt tgtttcctta ggaaagtttt cctcttttag | 1500 |
| agtgaagatg ttgtagctaa taaactgaag ctgcttccaa tccagcactg aatgaaacag | 1560 |
| ttttagtcgc tgcaattctt atgccacctt tatgactccg gctctttat tcctgaaaca | 1620 |
| tttcgtgcaa tttcaaacta taaaaggaa aacaagaacg acagatcaaa gcagatactt | 1680 |

-continued

| | |
|---|---|
| tgttggttga gatttgagac gggttgcaaa ggattccaga acagaaagt gttccttcat | 1740 |
| gcgccatgac cttagaacat ctacaatcag acccttcata ctgatttaaa agctcgtgca | 1800 |
| agtcgtccgg tcactaaccg gtcatagaat tttgacccag ctagaccttc gaaatgggct | 1860 |
| caaacttccg ggttgacata taccccttac atccagccca aatataagga ggatatggaa | 1920 |
| gc | 1922 |

<210> SEQ ID NO 118
<211> LENGTH: 1015
<212> TYPE: DNA
<213> ORGANISM: Hordeum vulgare

<400> SEQUENCE: 118

| | |
|---|---|
| gcacactcct cagtcctcag taagctcaag caccatgctc agactgttca agaaggaagc | 60 |
| cgcctgccaa tcacccagca ctctgccggt agccatggac atgggccttg aggtctcgag | 120 |
| ctcctccccc tcctcctcgt cggtgtcgtc ctcgcccgag cacgcggcga ggcgggcgtc | 180 |
| gccggcgaag cgccccgctg gcgcaccaa gttccgggag acgcggcacc cggtgtaccg | 240 |
| cggcgtgcgg cgccggggca acaccgaacg gtgggtctgc gaggtgcgcg tccccggcaa | 300 |
| gcgcggtgct cggctctggc tcgggacgta cgccacggct gaggtcgccg cgcgcgcgaa | 360 |
| cgacgctgcc atgctcgccc tgggcggccg ctccgccacg tgcctcaact tcgccgattc | 420 |
| cgcgtggctg ctcgccgtgc cgtccgccct gtccgatctc gcagacgtcc ggcgcgcggc | 480 |
| tgtcgaggcc gtcgcggatt ccagcgacg ggaggctgcc gatggctccc tcgccatcgc | 540 |
| tgtccctaag gaggcctcct ctggcgctcc ttcactatct ccgtcgtctg gtccgacag | 600 |
| tgccggttcg acggggacgt cggaaccttc cgccaatgga gtgttcgagg ggcccgttgt | 660 |
| aatggacagt gaaatgttca ggcttgactt gttcccggaa atggacctgg gctcgtacta | 720 |
| catgagcctc gcggaggcgc tgctcatgga cccgccgcct acagcgacca tcatccacgc | 780 |
| gtacgaagac aacggcgacg ggggagctga tgtccggctc tggagctata gtgtcgatat | 840 |
| gtgatttccc agatgattct gctctgtttt gactgtgtac tgactgctga gtagttttt | 900 |
| tgtttcctta ggaaagtttt cctcttttag agtgaagatg ttgtagctaa taaactgaag | 960 |
| ctgcttccaa tccagcactg aatgaaacag ttttagtcgc tgcaattctt atgcc | 1015 |

<210> SEQ ID NO 119
<211> LENGTH: 1040
<212> TYPE: DNA
<213> ORGANISM: Secale cereale

<400> SEQUENCE: 119

| | |
|---|---|
| accgatcgat caaaacctcc caacacagct gctgattcca gtactagtac tactccacac | 60 |
| ctctcacgag catcatctcc gccagctctc gactcggatg gacgtcgccg acatcgcctc | 120 |
| ccggtctggc cagcagcagc aggggcaccg gaccgtgtcg tcggagccgc cgaagcgccc | 180 |
| cgcggggagg accaagttcc acgagacgcg ccacccgctg taccgcggcg tgcggcgccg | 240 |
| tggccgcgtc gggcagtggg tgtgcgaggt gcgcgtgccc gggatcaagg gctccaggct | 300 |
| ctggctcggc accttcaaca cggccgagat ggcggcgcgc gcgcacgacg ctgccgtgct | 360 |
| cgcgctctcc ggccgcgccg cctgcctcaa cttcgccgac tccgcctggc ggatgctgcc | 420 |
| cgtgctcgcg gccggctcct tcggctttga tagcgcgcgg gaggtcaagg ccgccgtcgc | 480 |
| cgtcgccgtc gtcgcgttcc agcggaaaca gattattcca gtcgccgtcg ctgtcgttgc | 540 |

| | |
|---|---|
| tctccagaag cagcaggttc cggtcgccgt ggccgtcgtg gcgctccagc agaggcaggt | 600 |
| tccggtcacc gtcgccgtcg tggcgctcca gaagctgcag gttccggtcg ccgtcgccgt | 660 |
| cgtggcgctc cagaagaagc agattattct tccagccgcg tgtctggcgc cggagtttta | 720 |
| catgtcttcc ggcgacctgt tggagctcga cgaggagcag tggtttggcg gcatggacgc | 780 |
| cgggtcgtac tacgccagct tggcgcaggg gatgctcgtg gcgccgccgg acgacagagc | 840 |
| gaggccggag aacggcgagc agagcggcgt ccagactccg ctatggagct gcttgttcga | 900 |
| ctaatttagc accacaactg tcaagttgta gatagtcgtg ttcttcccga tttggaagaa | 960 |
| gcagagtaga gttcccgatt tctacttttg gggaaaaggg ctatattgct tactcgagta | 1020 |
| atacattttc ttttgatttt | 1040 |

<210> SEQ ID NO 120
<211> LENGTH: 1292
<212> TYPE: DNA
<213> ORGANISM: Triticum aestivum

<400> SEQUENCE: 120

| | |
|---|---|
| caaaaccaag gcggcggcag cggggcggga gagcggggag caccgaccga caccggccga | 60 |
| cagggtgggc tgcatgcgga gctgaggcga ggcgaggcga ggcggggaga gatccggcgc | 120 |
| gggtgccacc gccggccggc cgcgggagat ctggttggtg gcgccgcccg gataagggag | 180 |
| aggcggcgag gggagagcag ccgggggaga ccgaggcgag aggagatctc tctcgtccct | 240 |
| cttctcgctc catggagacc gggggtagca agcgggaagg agactgcccc ggcaggaaa | 300 |
| ggaagaagaa agtgcgcagg agaagcactg gtcctgattc ggttgctgaa accatcaaga | 360 |
| agtggaagga ggaaaaccag aagctccagc aagagaatgg atcccggaaa gcaccggcca | 420 |
| agggttccaa gaaagggtgc atggcaggga aggaggtcc agagaattca aactgcgctt | 480 |
| accgcggtgt gaggcagagg acgtggggga aatgggttgc tgagatccgt gagcccaacc | 540 |
| gtggcaatcg gctgtggctt ggttcattcc ctaccgcagt cgaagctgca cgtgcatatg | 600 |
| atgatgcggc aagggcaatg tatgcgccaa agcacgtgt caacttctca gagcagtccc | 660 |
| cggatgccaa ctctggttgc acgctggcac ctccattgcc gatgtctaat ggggcaaccg | 720 |
| ctgcgtcaca tccttctgat gggaaggatg aatcggagtc tcctccttct cttatctcaa | 780 |
| atgcgccgac agctgcgctg catcggtctg atgctaagga tgagtctgag ctgcaggga | 840 |
| ccgtggcacg taaggtgaaa aaagaagtga gcaatgattt gagaagtacc catgaggagc | 900 |
| acaagaccct ggaagtatcc caaccaaaag ggaaggcttt acataaagca gcgaacgtaa | 960 |
| gttatgatta cttcaacgtc gaggaagttc ttgacatgat aattgtggaa ttgagtgctg | 1020 |
| atgtaaaaat ggaagcacat gaagagtacc aagatggtga tgatgggttt agtcttttct | 1080 |
| catattaggg ttttagctat gagggttgca gtcatgcgga gcaataggga taactttcat | 1140 |
| tctagctgct aggaaatact tcaaatctgc aacccgaagc tttgtagtca cttatggttt | 1200 |
| tcatcttact ggagagaata gctttatacc ataagtcaac gggtacaaga agttgtcctg | 1260 |
| tgcgttgagt tcatgtacta tggtaaaagt tg | 1292 |

<210> SEQ ID NO 121
<211> LENGTH: 874
<212> TYPE: DNA
<213> ORGANISM: Brassica napus

<400> SEQUENCE: 121

| | |
|---|---|
| gtaattcgat taccgctcga gtacttacta tactacactc agccttatcc agtttttcaa | 60 |

```
aagaagtttt caactatgaa ctcagtctct actttttctg aacttcttgg ctctgagaac    120
gagtctccgg taggtggtga ttactgtccc atgttggcgg cgagctgtcc gaagaagccg    180
gcgggtagga agaagtttcg ggagacacgt cacccattt accgaggagt tcgccttaga     240
aaatcaggta agtgggtgtg tgaagtgagg gaaccaaaca aaaaatctag gatttggctc    300
ggaactttca aaacagctga gatcgcagct cgtgctcacg acgtcgccgc cttagctctc    360
cgtggaagag gcgcctgcct caacttcgcc gactcggctt ggcggctccg tatcccggag    420
acaacctgcg ccaaggatat ccagaaggct gctgctgaag ccgcattggc ttttgaggcc    480
gagaagagtg ataccacgac gaatgatcat ggcatgaaca tggcttctca ggccgaggtt    540
aatgacacaa cggatcatgg cctggacatg gaggagacga tggtggaggc tgttttact    600 gaggagcaga gagacgggtt ttacatggcg gaggagacga cggtggaggg tgttgttccg    660
gaggaacaga tgagcaaagg gttttacatg gacgaggagt ggatgttcgg gatgccgacc    720
ttgttggctg atatggcggc agggatgctc ttaccgccgc cgtccgtaca atggggacat    780
aatgatgact cgaaggaga tgttgacatg aacctctgga attattagta ctcatatttt     840
tttaaattat ttttttgaacg aataatatt tatt                                874

<210> SEQ ID NO 122
<211> LENGTH: 898
<212> TYPE: DNA
<213> ORGANISM: Brassica napus

<400> SEQUENCE: 122
aataaatatc ttatcaaacc agtcagaaca gagatcttgt tacttactat actacactca    60
gccttatcca gtttttcaaaa aaagtattca acgatgaact cagtctctac tttttctgaa    120
ctgctccgct ccgagaacga gtctccggtt aatacggaag gtggtgatta cattttggcg   180
gcgagctgtc ccaagaaacc tgctggtagg aagaagtttc aggagacacg ccacccatt    240 tacagaggag ttcgtctgag gaagtcaggt aagtgggtgt gtgaagtgag gaaccaaac    300 aagaaatcta gaatttggct cggaactttc aaaacagctg gatcgcagc tcgtgctcac    360 gacgttgccg ccttagctct ccgtggaaga ggcgcctgcc tcaacttcgc cgactcggct   420
tggcggctcc gtatcccgga gacgacctgc gccaaggata tccagaaggc tgctgctgaa   480
gccgcattgg cttttgaggc cgagaagagt gataccacga cgaatgatca tggcatgaac   540
atggcttctc aggttgaggt taatgacacg acggatcatg acctggacat ggaggagacg   600
atagtggagg ctgttttag ggaggaacag agagaagggt tttacatggc ggaggagacg   660
acggttgtgg gtgttgttcc ggaggaacag atgagcaaag gttttacat ggacgaggag    720 tggatgttcg ggatgccgac cttgttggct gatatggcgg cagggatgct cttaccgctg   780
ccgtccgtac aatggggaca taatgatgac ttcgaaggag atgctgacat gaacctctgg   840
aattattagt actcatattt ttttaaatta ttttttgaac gaataatatt ttattgaa     898

<210> SEQ ID NO 123
<211> LENGTH: 967
<212> TYPE: DNA
<213> ORGANISM: Brassica napus

<400> SEQUENCE: 123
ggcacgagga taaattaaac atttatcaaa ccaacgaaac atagatcttt gtagttactt    60
atccagttta ttttttaaaa aattataaag agatttcaac aatgacctca ttttctacct    120
```

```
tttctgaaat gttgggctcc gagtatgagt ctccggttac gttaggcgga gagtattgtc    180
cgaagctggc cgcgagctgt ccgaagaaac cagccggtcg taagaagttt cgggagacgc    240
gtcacccagt ttatagagga gttcgtctga gaaactcagg taaatgggtg tgtgaagtga    300
gggagccaaa caagaaatcc aggatttggc tcggtacttt cttaaccgcc gagatcgcag    360
ctcgtgctca cgacgtcgcc gccatagccc tccgcggcaa atcagcttgt ctcaattttg    420
ctgactcggc ttggcggctc cgtatcccgg agacaacatg ccccaaggag attcagaagg    480
cggctgctga agccgccttg cttttcagg ctgagataaa taatacgacg acggatcatg     540
gcctggacat ggaggagacg atcgtggagg ctattttcac ggaggaaaac aacgatgtgt    600
tttatatgga cgaggagtcc atgttagaga tgccggcctt gttggctagt atggcggaag    660
gaatgctttt gccgccgccg tccgtacatt tcggacataa ctatgacttt gacgagatg     720 ctgacgtgtc cctttggagt tattagtgca aggttttttt ttcaattttt tcgtataata    780
cttcttttgg attttcggat tctgcctttt tatgggaatc ttttttttt tggtaatgtg     840 gaagctgagt gtgaatgttt aaacaattgt gttatcaaat gctagtattt ttttgtgcag    900
cataatcatc ttattggctc tccaaaaaaa aaaaaaaaa aaaaaaaaaa aaaaaaaaa      960 aaaaaaa                                                              967

<210> SEQ ID NO 124
<211> LENGTH: 910
<212> TYPE: DNA
<213> ORGANISM: Glycine max

<400> SEQUENCE: 124
gcacctctat atatacatag acacatgtaa atggttgcaa agaaagataa gataggtacc    60
agctttcaca tagtttattt aatccgttat atgccacctg atatataggc atattagcta    120
gttaggtagg tatagtagtt aagttaattc aaccatggaa gacagggatc actgttgttc    180
caacaattca acgatgatca caacaacaaa gaaaagaacg ggtagaagaa gtccaacatc    240
ggataagctc aagaatcaac accgcgagaa gcagtcgatg aaaccttacc gtggaataag    300
gatgcggaag tggggaagt gggtggcgga gatcagagaa cccaacaaaa ggtcgaggat     360
atggttgggt tcttacacga cacccgtggc cgccgcacgt gcctacgaca ccgctgtctt    420
ttacctccgg ggtcccaccg cgcgccttaa cttccccgaa ctcttgttcc aggacgacga    480
ccaggagggc agtgattcgg tgcagcacgg cgcagcaggg aacatgtccg ctgattccat    540
tcgccgaaaa gccacgcaag tcggcgccag agtcgacgct ctccaaaccg cgcttcacca    600
ccacgcgcca agtaccaact ctctcaatct caagcccgac ttgaacgagt ttccaaaact    660
cgaagagctt caagattgat ataaatcaaa tatcaatatc aatcaatata tttaatttcc    720
taagttcttt attaatatat agtttatgt gtgtatatat agatgatgat gcctcggagt     780
tggggcttga aactaattaa ccccttccct tcccttaat ttagatatat ccttttctt      840 gttttttccgt atcttcaatc ataatatcaa atcaagaag tattattatt ttctaaaaaa    900
aaaaaaaaaa                                                           910

<210> SEQ ID NO 125
<211> LENGTH: 809
<212> TYPE: DNA
<213> ORGANISM: Cucumis melo

<400> SEQUENCE: 125
aaaaacccca aatccaaaaa tcccctgttt tctctcctct aaaatcacca ataatgagta    60
```

-continued

```
gtagtaaaga acagagccct tctccggaaa cagagtcctc ttcttcatct tcttccgatt     120
caaacaaaaa acccaaaaga attaattcca attccagttc caattcaaaa cacgcagttt     180
acagaggagt tcgaatgaga aattggggga aatgggtatc agaaattcga gaaccaagaa     240
agaaatcccg catttggtta gggactttcc ccagccctga aatggctgct cgagctcatg     300
atgttgctgc cctaagcatc aaaggaaatt ccgccattct taatttccct gatcttgttc     360
atcttcttcc tcgtcctgtt tctcttgctc ctcgtgatgt tcaagctgct gctgctaaag     420
ctgctcatat gcataatctt tcatctaatg ctaaatactaa caaccataat actaattcta     480
attcctcctc tgccttttcc gatgaactta gtgagattgt tgagttgccg gctctgggaa     540
cgagttacga cggcggagtt ggtgttggtg gggagtttgt gtttgttgag tcggaattgg     600
aatcagcggc ttggctttac cagccaccgt gggtgcagag cttgcaggag gattatgatg     660
atatagatgg agatggagat tgtggtaagt tgggaatggg atttgtttcc aatggattta     720
aagggtttct gtttgattat tgaaaaaaaa atattttgta tttaaaaaaa aaaaaaaaaa     780
aaaaaaaaaa aaaaaaaaaa aaaaaaaaa                                      809
```

<210> SEQ ID NO 126
<211> LENGTH: 1281
<212> TYPE: DNA
<213> ORGANISM: Capsicum annuum

<400> SEQUENCE: 126

```
ggcacgagcc aacataccat aaataataa tgaacatctt tagaagctat tattcggacc      60
cacttactga atcttcatca tcttttctg atagtagcat ttactcccct aatagagcta     120 tttttctga tgaggaagtt atattagcat caaataaccc gaaaaagcca gctggggaga     180
agaagtttcg agaaactcga catccagtat acaggggagt taggaagagg aattcaggca     240
aatgggtttg tgaagtcaga gaacccaata agaaatcaag aatttggctt ggtacttttc     300
ctacagctga aatggctgct agagctcatg acgtggcggc tatagcatta agaggtcgtt     360
ctgcttgttt gaactttgct gattctgctt ggaggttgcc tgttccggct tcctctgaca     420
ctaaagatat tcaaaaggcg gccgctgagg ccgcggaagc cttccgacca ttgaagttgg     480
aaggaatttc aaaagaatca tctagcagta ctccagagag tatgttcttt atggatgagg     540
aagcgctctt ctgcatgccg ggattactta cgaatatggc tgaagggcta atgttaccac     600
cacctcaatg tgcagaaatt ggagatcatg tggaaactgc tgatgcggat acccctttat     660
ggagctattc catttaagta attatgttac tacttatttt ggatgcagta ctcttctagc     720
tatgatcttc cctataagta taatcagatt aatgctgaaa aagttccttt aaattaggat     780
atacttcgtg ctcaatattt gggtatggtg cgaattattg taaaggtatt gtaatatgtg     840
gatattataa gtatgtattt ctatctatta tatacgtgta gcagcataag taagtggttg     900
gggctaaatg aaaatcattg gcctagagcg tgcggataag actatgatat ttatgacggt     960
ggtctaaagt ttttttctag tttaggcaag tgaaaagtag atttgtggag tctattttc     1020 aagttggtag ttgtatttga atgaaataaa tgggcaagtt tttgaaacct attttcttct     1080
gtttttgaat tctcaatatc ttttgggcaa gttacctatt tcaactgcca atgtacggca     1140
gtatatagga gcatttagaa gaagaccaag ctttgttttg gtcaaagatt ttgtaagtat     1200
tttttgaaaa aattcagcat taactttaaa tttgggaatt ggtgcaacgt ttgatagagt     1260
tttaaaaaaa aaaaaaaaaa a                                              1281
```

-continued

<210> SEQ ID NO 127
<211> LENGTH: 1085
<212> TYPE: DNA
<213> ORGANISM: Capsicum annuum

<400> SEQUENCE: 127

| | | | | | |
|---|---|---|---|---|---|
| ggcacgagga | taccataaaa | taataatgaa | catctttaga | agctattatt | cggacccact | 60 |
| tactgaatct | tcatcatctt | tttctgatag | tagcatttac | tcccctaata | gagctatttt | 120 |
| ttctgatgag | gaagttatat | tagcatcaaa | taacccgaaa | aagccagctg | ggaggaagaa | 180 |
| gtttcgagaa | actcgacatc | cagtatacag | gggagttagg | aagaggaatt | caggcaaatg | 240 |
| ggtttgtgaa | gtcagagaac | ccaataagaa | atcaagaatt | tggcttggta | cttttcctac | 300 |
| agctgaaatg | gctgctagag | ctcatgacgt | ggcggctata | gcattaagag | gtcgttctgc | 360 |
| ttgtttgaac | tttgctgatt | ctgcttggag | gttgcctgtt | ccggcttcct | ctgacactaa | 420 |
| agatattcaa | aaggcggccg | ctgaggccgc | ggaagccctc | cgaccattga | agttggaagg | 480 |
| aatttcaaaa | gaatcatcta | gcagtactcc | agagagtatg | ttctttatgg | atgaggaagc | 540 |
| gctcttctgc | atgccgggat | tacttacgaa | atatggctgaa | gggctaatgt | taccaccacc | 600 |
| tcaatgtgca | gaaattggag | atcatgtgga | aactgctgat | gcggatacccc | ctttatggag | 660 |
| ctattccatt | taagtaatta | tgttactact | tattttggat | gcagtactct | tctagctatg | 720 |
| atcttcccta | aagtataat | cagattaatg | ctgaaagaag | ttccttaaat | taggatatac | 780 |
| ttcgtgctca | atatttgggt | atggtgcgaa | ttattgtaaa | ggtattgtaa | tatgtggata | 840 |
| ttataagtat | gtatttctat | ctattatata | cgtgtagcag | cataagtaag | tggttgggc | 900 |
| taaatgaaaa | tcattggcct | agagcgtgcg | gataagacta | tgatatttat | gacggtggtc | 960 |
| taaagttttt | ttctagttta | ggcaagtgaa | aagtagattt | gtggagtcta | tttttcaagt | 1020 |
| tggtagttgt | atttgtaatg | aaataaatgg | gcaagttttt | gaaacctaaa | aaaaaaaaa | 1080 |
| aaaaa | | | | | | 1085 |

<210> SEQ ID NO 128
<211> LENGTH: 776
<212> TYPE: DNA
<213> ORGANISM: Lycopersicon esculentum

<400> SEQUENCE: 128

| | | | | | |
|---|---|---|---|---|---|
| ggcaccagct | ttctatttt | agctctcaac | aacaatgaat | atctttgaaa | cctattattc | 60 |
| agactcgtta | attttaaccg | aatcatcttc | ttcttcatcg | tcatcgtcgt | tttctgaaga | 120 |
| ggaagttatt | ttagcttcga | ataacccgaa | aaagccagct | ggcaggaaga | agtttcgaga | 180 |
| aacacggcat | ccgatataca | ggggaatcag | gaagaggaat | tcaggaaaat | gggtttgtga | 240 |
| agtcagagaa | ccaaataaga | agacaaggat | ttggcttggt | acttttccta | cggctgaaat | 300 |
| ggcggctaga | gctcatgacg | tggcggcttt | agcattaaga | ggccgttctg | cttgtttgaa | 360 |
| tttctctgat | tctgcttgga | ggctgcctat | ccctgcttcc | tccaactcta | aagatattca | 420 |
| aaaggcggcc | gctcaggccg | tcgaaatctt | ccgatcggaa | gaagtttcag | gagaatctcc | 480 |
| tgaaacgtca | gaaaatgtgc | aagagagtag | tgacttcgtg | gatgaggagg | cgatcttttt | 540 |
| catgccagga | ttacttgcaa | atatggcaga | aggacttatg | ctacctccac | ctcaatgtgc | 600 |
| agaaatggga | gatcattgtg | tggaaactga | tgcctacatg | ataactttat | ggaattattc | 660 |
| tatctaaaat | agtagtacaa | tttatcaaat | tactaggatt | tagaagattt | tggtagtttt | 720 |
| tggtattcag | tatttagata | ctaagaatgt | atattattag | tatttttatt | ttggcc | 776 |

-continued

<210> SEQ ID NO 129
<211> LENGTH: 1782
<212> TYPE: DNA
<213> ORGANISM: Lycopersicon esculentum

<400> SEQUENCE: 129

| | | | | | |
|---|---|---|---|---|---|
| ctctacaagc | tttttgttaa | gagactaaaa | aaaacaaaaa | aaccttgaag | aactcaccaa | 60 |
| tttgatcaat | tcatttatta | aaaaaaaaaa | cagagaagaa | aagagaaatg | gctattatgg | 120 |
| atgaagctgc | taatatggtt | tgtgtgccgt | tggattatag | tagaaagagg | aaatcaagga | 180 |
| gtagaaggga | cagaacaaaa | aatgtggaag | agacactagc | taaatggaag | gagtataatg | 240 |
| agaaactaga | caatgaaggg | aaagggaagc | cagtgcgtaa | agttcctgct | aaaggttcaa | 300 |
| agaagggtg | tatgagaggt | aaaggggac | cagaaaattg | gcggtgtaaa | tacagaggtg | 360 |
| ttagacagag | gatatgggt | aaatggggttg | ctgagattag | ggaacctaaa | agaggtagta | 420 |
| ggttatggtt | gggtacattt | ggtacagcaa | ttgaagctgc | tttagcatat | gatgatgctg | 480 |
| caagagctat | gtatggtcct | tgtgcaaggc | ttaatttgcc | aaattacgcg | tgtgattctg | 540 |
| tttcctgggc | aactacatct | gcatctgcat | ctgcatctga | ttgcaccgtt | gcttctggtt | 600 |
| tcggcgaggt | atgtccggtt | gatggtgctc | ttcatgaagc | tgacacacca | ttgagctcag | 660 |
| tgaaagacga | agggaccgcg | atggatattg | ttgaacctac | gagtattgat | gaagatacgc | 720 |
| ttaagtctgg | atgggattgt | ctagataaat | taaatatgga | tgagatgttt | gatgtagatg | 780 |
| agctattggc | tatgttagat | tctactccag | ttttcaccaa | ggactacaat | tcagatggaa | 840 |
| agcacaacaa | tatggtatca | gattcgcaat | gtcaggagcc | gaatgcagtg | gtagatccta | 900 |
| tgactgttga | ctatggcttt | gattttctga | aaccaggcag | gcaagaagat | cttaatttca | 960 |
| gttcggatga | ccttgcattc | atagacttgg | attctgaact | tgtcgtttga | tagttttcgc | 1020 |
| agttgaaaga | tgcaatgcaa | gataacatgt | atcgtcattg | attgagatat | aggacgcgag | 1080 |
| gaagagaaaa | ctcgagatgt | tgagtttgga | caatgttttc | gtatcgttca | attttttttt | 1140 |
| atttcatgtt | gggcagcatt | ggttgcccctt | ttcccaggcc | agctgattct | cgataagttt | 1200 |
| ttgcatcgaa | gattatgcat | ttggtgttct | ggaggactaa | tcttgtacag | atctaaccgg | 1260 |
| cctagtgagt | caataattgt | tcgttttggt | gtgttgatat | gacgaataaa | gatgtttctg | 1320 |
| ggattcatag | tttgttgtaa | agtttgcttg | acaattagag | gtactgatttt | ttgtgctttc | 1380 |
| attggaacaa | tgtagaatgc | attgacggca | tttacagttc | attcataact | tgaacaataa | 1440 |
| gtttggcagt | gtgtatttgt | gttactttgt | gaagtattcc | caggggattc | gccaacgaat | 1500 |
| gctgtgttgt | gtgttcaagt | gtttcgagta | gatcagagaa | gtactggaag | cagtggtgct | 1560 |
| atagtgtttt | atgttagccc | tcatcgtggt | ttggtagatt | tgtgtagttc | tgttttgcac | 1620 |
| ttaggctttt | ttatctctat | cagaagttgt | actcaggatg | taatagtaga | cgttttgaga | 1680 |
| cgtttcaaaa | tgttccagtt | catgttcttt | accacattgt | aattcaataa | attctgcggt | 1740 |
| aatcttaaga | tgtggaaaaa | aaaaaaaaaa | aaaaaaaaaa | aa | | 1782 |

<210> SEQ ID NO 130
<211> LENGTH: 1388
<212> TYPE: DNA
<213> ORGANISM: Zea mays

<400> SEQUENCE: 130

| | | | | | |
|---|---|---|---|---|---|
| ccagagtacc | agacaccact | gcgcatcagt | gcaaagaggt | agctacccta | tctgccatgg | 60 |

| | |
|---|---:|
| ctcaagagct ccacgaaacg tcctcttgct ctgccaccac cacctcgtcg tgcaccacat | 120 |
| cctgctgctc gtccactgtc acagactcgt cctcttcgcc cccgtcaccg gcggcggcca | 180 |
| atgccgcgcc cgcgacacgg aagcggcagg cgttggaggc cgaggccgag gccgaggcgg | 240 |
| gcggtgagga ggaggaggag gaggaggaag gctgtgctgg taataaggcg cgccggcca | 300 |
| agaagcgacc gcggggcagc gaggggaagc acccgacgtt ccgcggcgtg cggatgcggg | 360 |
| cgtgggcaa gtgggtgtcg gagatccgcg agccgcgcaa gaagtcgcgc atatggctcg | 420 |
| gcacgttccc caccgccgag atggccgcgc gcgcccacga cgtcgcggcg ctcgccatca | 480 |
| agggccgcgc cgcgcacctc aacttcccgg acctcgccgg cgcgctcccg cgcgccgcgt | 540 |
| ccgcggcgcc caaggacgtc caggcagccg ccgcattggc cgctgcgttc acgtcgccgt | 600 |
| catcggagcc cggcgccggc gcgcacgagg agcccgctgc caaggacggc gccgcgcccg | 660 |
| aggaggcagc cgccgacgca caggcaccag taccagtagc actaccaccg ccggcggcct | 720 |
| ctcggccagg gacgccgtcg agcggcgtgg aggacgagcg gcagctgttc gacctgccgg | 780 |
| acctgctcct cgacatccgg gacgggttcg ggcgcttccc gccgatgtgg gccccgctca | 840 |
| ctgacgtgga ggaggtggtc aatgcggagc tgcgcctcga ggagccgctg ctttgggagt | 900 |
| agcggtcaga gatgctcgtt gcctgcattg caaacgaggt ctaaacaata gtagcagtgg | 960 |
| tatcccattt cttctcgttt tgcttctcgc cctctccttt ttttctctct ttcttgctta | 1020 |
| ctttgggggg aaaacagcta gttcttttt tcttcttctt cttcttcttt tattaaattg | 1080 |
| agttttaata agtataaaca tatataaacg agagagagat ataagctgtg tacttaaaag | 1140 |
| tgtaagacga gtacctatca gttcattatt acgtatctac tagtggtacc agtagtgatc | 1200 |
| atgttgtccc ggccgtgtgt gaattccagc ggtagttgtt gaccttgcta gatttttata | 1260 |
| gttgcttgtg ttgtgtgctg taccaaaatt ccccagggaa aaagggcagg aagcaaacga | 1320 |
| atgtaacggg aacacaagca gcatctaatc tctattactg ctgacaacga aaaaaaaaa | 1380 |
| aaaaaaaa | 1388 |

<210> SEQ ID NO 131
<211> LENGTH: 1085
<212> TYPE: DNA
<213> ORGANISM: Zea mays

<400> SEQUENCE: 131

| | |
|---|---:|
| gctcaagctc gagacaagaa accagaacca gctcactcct cactccactt ccactcccaa | 60 |
| cagcaagctc aagcagtcag tcaccggcag gggtcagggt cacagtcaca gcagcagcca | 120 |
| tggacacggc cggcctcgtc cagcacgcga cctcctcgtc ttccacctcc acctcggcgt | 180 |
| cgtcgtcctc gtccgagcag cagagccgca aggcggcgtg gccgccgtcg accgcttcct | 240 |
| caccacagca gccgcccaag aagcgccccg cggggcgcac aaagttccgg gagacgcggc | 300 |
| acccggtgtt ccgcggcgtg cggcggcggg gcgccgcggg ccgtgggtg tgcgaggtgc | 360 |
| gcgtcccggg gaggcgcggc gcgcggctgt ggctcggcac ctacctcgcc gccgaggcgg | 420 |
| cggcgcgcgc gcacgacgcc gcgatactcg ccctgcaggg ccgcggcgcg ggcgcctca | 480 |
| acttcccgga ctccgcgcgg ctgctcgccg tgccgccccc gtccgcgctc ccgggcctgg | 540 |
| acgacgcccg ccgcgcggcg ctcgaggccg tcgcggagtt ccagccgcgc tctgggtccg | 600 |
| ggtccgggc cgccgacgaa gcgacctcgg cgcgtctcc tccctcctcg tcgccgtcgc | 660 |
| tgccggacgt ttctgcgggct ggctcgccgg cggcggcgct tgagcacgtg cctgtgaagg | 720 |
| ccgacgaagc agtggcgttg gacttggacg gcgacgtgtt cgggcccgac tggttcgggg | 780 |

```
acatgggcct ggagttggat gcgtactacg ccagcctcgc ggaagggttg ctcgtggagc      840
cgccgccgcc gccggcggcc tgggatcatg gagactgctg tgactccgga gctgcggacg      900
tcgcgctctg gagctactac tagcaaagtt aacaataata agcttgacag ccaaccccaa      960
aagcccccca actgattgta ttcacctctg taacaaaatt caaattgatt tcccagcaaa     1020
tgaacttcaa agaagtctt tggttccgat ttaaaaaaaa aaaaaaaaaa aaaaaaaaa      1080 aaaaa                                                                 1085

<210> SEQ ID NO 132
<211> LENGTH: 1102
<212> TYPE: DNA
<213> ORGANISM: Gossypium hirsutum

<400> SEQUENCE: 132
ggccattacg gccggggaga aaagaaagc tcatttagtt aatatttcc cttgcatttc        60 caaattcgga agttcataca gcaagtgatt tcctaaaata cttggatcct aagtacgaat      120
atccttttct tgaaatatac tcttttaag tcaaagctt tgtttaactg aaacttaaac       180
tgattactgt ttgggttttt tttttaaatg gattttgtag ttcaagatta tgatatggtt     240
gattctgggt cggtttctga agtggaact gatcgtccgg tgaattttc cgatgaatat       300 gtgatgttag cttcgagtta tccaaagagg cccgcgggaa ggaagaagtt ccggagact      360 cgacacccgg tgtaccgtgg agttcgccgg aggaatcccg ggaagtgggt ttctgaagtg     420
agggagccta ataagaagtc gaggatttgg cttggaactt tcccgaaggc ggatatggcg     480
gcgcgtgctc acgacgtggc agctatagca ctgagaggga agtcagcttg tttgaacttc     540
gctgactcag cttggaagct tccggtcccg gcttcttccg acccaaagga tatccaaaag     600
acggtggcgg aggtggcgga gactttcaga acggctgagc attgagcgg gaattctaga      660 aacgatgcaa agagaagtga aaacacggag atggagaaag ggttttactt ggacgaagaa     720
gcgttgtttg ggacacaaag attttgggca aatatggctg ccggtatgat gatgtcacct     780
cctcgttccg gtcatgacgg aggatgggag gaacatgaag tcgatgatta tgtacccttta   840 tggagttatt ctatttaaaa gtaaaatttt tcagacattt tcaagcattc attggaattt    900
ttagttcaca gaaatcgcca ccggcaattg ccctttatgt tttgtacgta caacgatttt    960
tttggattgt acgggtagtg ctgtaagtaa aaagattaat gtgtatatat acgatgtata   1020
tatacttcat agcttctcca aacaataaat ttatagcttc atatctattt taccatcaaa   1080
aaaaaaaaaa aaaaaaaaaa aa                                             1102

<210> SEQ ID NO 133
<211> LENGTH: 1034
<212> TYPE: DNA
<213> ORGANISM: Capsella bursa-pastoris

<400> SEQUENCE: 133
acgcgggttc ttctaactac aaacttaaac aagaatccac ctgaaaagaa aatagggaga     60
gagaaatata tatatatata tattaacaac taaagagatt tcttctttta gttactctct    120
acttttatcc agttttttt cttctttatc tcgaacagag tattctcaaa caatgaactc     180
atctttctct gctttctctg aaatgtttgg ttccgagtac gagtctccgg tttcttcagg    240
cggcggagat tactgtccga cgctggccac gagctgtccc aaaaaccag cgggtaggaa     300 gaagtttcgt gagacccgtc acccagttta cagaggagtt cgtcggagaa actccggcaa    360
```

| | |
|---|---|
| gtgggtttgt gaggttagag agccaaacaa gaaatctagg atttggctcg gaactttccc | 420 |
| tacggccgat atggctgctc gtgctcacga cgtcgccgct atagccctcc gtggcaggtc | 480 |
| agcctgtctc aatttcgctg actctgcttg gcggctacgg atccccgagt caacaggcgc | 540 |
| caaggaaatc cagaaggcgg cggctgaagc tgcgctggct tttcaggatg agatgatgat | 600 |
| gagcgatacc acgacgacgg atcatggctt tgacatggag gaaacgtttg tggaagcaat | 660 |
| tgtgacggcg aacagagcg cttcgttata tatagacgaa gaggacatgt tcggtatgcc | 720 |
| gagtttgatg gctagtatgg ccgaaggtat gcttttgcct ctgccgtccg tacaatggaa | 780 |
| ccataactat gacatcgacg gcgatgatga cgtctcgcta tggagttatt aaacttttct | 840 |
| gattttctc atctccatta atattttgg tactactgtg tgatatttat ttttgtttgg | 900 |
| atccttttt agaacggatc cttcatttgt tgttgtttgg gtagttgtga gaagtgaatg | 960 |
| taaatgattc agtatggctg gattttactt aaatgcaaag agtgcagaaa aagttcatga | 1020 |
| tcaaaaaaaa aaaa | 1034 |

<210> SEQ ID NO 134
<211> LENGTH: 1917
<212> TYPE: DNA
<213> ORGANISM: Prunus avium

<400> SEQUENCE: 134

| | |
|---|---|
| tacttacttt tgctgtgact accactctct ctcacctcct tctctctaga ccaccaactt | 60 |
| ttcgactttt actctctctc tctctctctc tctctctctc tgctttgttg ataagatttt | 120 |
| gagttatgag taagcactgt gggacctcag ctgagcttgg gagtgggagc cagttacagt | 180 |
| aataaaatat cacatttcag aagcacttaa atgcaggggc aaaatagtat ttttatatta | 240 |
| tttttaattt ttatcatcag aatatttctt tcattaaaaa aataaaaat aaaaactgaa | 300 |
| aaaccttctt cgtatcctcg ccatcactgg atggtgggta tgatttgagc gggggtatgg | 360 |
| gttgtgagag caccatcagt tgttgcgggg gtggtgggtt atttggctcg gtgtcgggta | 420 |
| gagattgacc atgactttgt tgaaatagtc agattgtgaa aattaaaatt aatacaaaaa | 480 |
| ataaaaaacc attttgtacc tgtatttaat ataaaaaatt aacaaaactg acaacatgac | 540 |
| catttctcct aataaaacta aaattgaaaa tcatggaaac aatttaaaaa attaaggaat | 600 |
| caaaatacaa ataggtcaa aattatggtg atattgaacc taaaaacccc acttgccccc | 660 |
| cactatactt tttaaacttg cgccccaatt tacttagact agttagttca gtgtgtgttt | 720 |
| cccgccacgt ggcggagcca agtctaatct attttctttt cctccatctc tcctccaatc | 780 |
| cccttttgtc tgttttgtga agggaacttg ctgagccaca ttccgacctg gccccaccgg | 840 |
| cctcctcaca ctccgtgtta tcgtgtccac acctgggccc acctgccacg caatccctaa | 900 |
| tctataaaag ccattctccc tcacttccaa tttcagctca aggaaactca acaagctaa | 960 |
| aacaccaaac cattcataca taaagcttag tctaatggaa atgttcttct ctcaactttc | 1020 |
| agactcggtc gaccagcccc agtcgagttt gttgtccgac gccagcgtca ccactcgagg | 1080 |
| ggcttcttgt tccgacgggg acgtcatatt ggcgtcgagc cggccgaaga agcgagcggg | 1140 |
| gaggagggtt ttcaaggaga cgaggcaccc ggtttatagg ggtgtgagga ggaggaacaa | 1200 |
| tgacaagtgg gtgtgtgaaa tgagagagcc aacaagaag aagtccagga tatggctcgg | 1260 |
| gacttatccg acggcggaga tggctgctcg tgcccatgac gtggccgcat tggcgtttag | 1320 |
| agggaagctt gcatgcatca actttgctga ctcagcgtgg aggctgcccg tgccggcttc | 1380 |
| catggatacc atggatattc ggagggcggc cgcagaggca gctgagggggt ttaggccggt | 1440 |

-continued

| | |
|---|---|
| ggagtttggt ggagtgtgca gcggcagcag tgatgagaag gagagaatgg tggtgcaggt | 1500 |
| ggaagagaag aacaagaagg gtagtgtgaa cttggaaaga agcagaagct tgagcttgtc | 1560 |
| ctattgggat gaggaggaag tgtttcacat gcccaggttg cttcatgaca tggctgaagg | 1620 |
| gcttcttctt tctccatcgc aatgcttagg tggctacatg aatttggatg acatgggcac | 1680 |
| cgatgctgat gtcaaattgt ggagtttctc catttaataa tcgacgttta ttttagtcga | 1740 |
| ttactagaat ttatttattg tttgattctt atgcatttat ttacttgtaa caaaaaagat | 1800 |
| taaccttggt tgttcgctgt aagtggacag attggaaata tattttttgga tatttgtggt | 1860 |
| cgagatagat attttggggtt atatactgca caaaagtttc ctaaatttag aattatt | 1917 |

<210> SEQ ID NO 135
<211> LENGTH: 1650
<212> TYPE: DNA
<213> ORGANISM: Prunus avium

<400> SEQUENCE: 135

| | |
|---|---|
| atgatattgt attaagtaag gtcttgcagt tcaagtagtt aagactatttt tattcattca | 60 |
| tatgagattt taagttcgac tcttctctcc ctgactatcg tttatatcta aaaaataatt | 120 |
| attgtaatcg aaattatatt tacaaatttt gacctagcct ccttacgata cataaactaa | 180 |
| ccccaaaaag agtttccttg ccatttttcta ttttgaagta tatgatttta catataccgc | 240 |
| cgtcctttcc acagaacaaa aagaggagaa tgcattcgat tcgaagatat acaaatactt | 300 |
| gtgatttcct ctaagtgaga caacaaaagc gaagaagacg atgaaaaatt tattgcagga | 360 |
| tttgagttgg gcaccacctc acacacattg cacacgttgc attaaaaaac gtgacaaatt | 420 |
| ttgtaaccaa aaaatcacac gtgctaaata cccactttac ttagcttagt aagtcaagcc | 480 |
| aaagccaaag tcaaattaat ctattttctc tacaatcctc tttgctttcc agtgtgaaca | 540 |
| cgcccacatt aggccgctga tttccatgtg gcgtctcgcc aaatcatcac gctccgtgtt | 600 |
| cgcgcgtcca cttcgcataa acatggccca acccaaaatc tataaaaaag ccaccaccac | 660 |
| actcgaactc tctccatttt cagcccagaa aaacccaaac cctactaaaa cacaaagtcg | 720 |
| gaaagcttta cactaagggc ttgcaaaaat ggacatgatc tacagccagc tctctgattt | 780 |
| agcttctatg gaaaacccgg atacgtcttc gttttcggac gccagcgtta cggcccggcg | 840 |
| agcttctctt tcagatgagg aggtcatact ggcgtccagc tgcccgaaaa ggcgggcggg | 900 |
| gaggagggtt ttcaaggaga ccaggcaccc ggtttatagg ggtgtgagga ggaggaacaa | 960 |
| caacaagtgg gtgtgtgagc tgagagcccc caacaacaag aaggccagga tatggctcgg | 1020 |
| gacttatccg acggctgaga tggcggctcg tgcccatgat gtcgctgtat ggcgtttag | 1080 |
| ggggaagctt gcctgcctca actttgctga ctcggcttgg cggctgcctg tgcctgcctc | 1140 |
| caccgatgcc gcggagatta ggagggcggc caccgaggcc gctgaagcgt ttaggcaggc | 1200 |
| ggaggatggt ggtgttgatg agaaggagag taaggcagtg gtgagtgagg agaagggttg | 1260 |
| tgtaggaatg gagggaagca gcaacttgtt ttatttggac gaggacgaaa tatttgagat | 1320 |
| gccaaggttg cttgatgaca tggctgatgg gattatgctt tgtccacctc aatgcttaga | 1380 |
| tggctacatg gattggaatg acgtggaaac tgttgacgat ttgaaactgt ggagtttttc | 1440 |
| tatttgatcg acctctatag aaatcccaca ttctatagta aatcagaatg attgtaattt | 1500 |
| gtaggcccta cttactttat tttttaaatg gaaacatatt tatgttttag accctactta | 1560 |
| cttttgctgt gactaccact ctctctcacc tccttctctc tagaccacca acttttcgac | 1620 |

-continued

| | |
|---|---|
| ttttactctc tctctctctc tctctctctc | 1650 |

<210> SEQ ID NO 136
<211> LENGTH: 3334
<212> TYPE: DNA
<213> ORGANISM: Arabidopsis thaliana
<220> FEATURE:
<221> NAME/KEY: misc_feature
<222> LOCATION: (2698)..(2698)
<223> OTHER INFORMATION: n is a, c, g, or t

<400> SEQUENCE: 136

| | |
|---|---|
| atttttgagt gagaggagtg cgctggctgg agagaaagag aggaaaggag tttcgaagtg | 60 |
| agagagaggg cgttgagatt gtggatcaac ttaatgtaat atgttctttt attaacattt | 120 |
| tcttttgtc ataactca aacctttac tatttgttt cataatcta acacacccca | 180 |
| ccatttgtta atgcatgatg gtagaaaata ttaaatataa ttaactactt ttatgtgatc | 240 |
| aaaattaggt ttcagactcg tttcgcgatc cgatctacaa ttacaactgc atgcttctaa | 300 |
| ttgatctaaa ttctaaattt tttatacata ttaaaaaaac aactttttgt taaattctca | 360 |
| atcatcattt ttgtgattaa caattttta taactctaaa ccaataatat ttgattattt | 420 |
| attttatatg tataatgatg attgagaatt ttaattagca gtctatttag ggttttccta | 480 |
| aagttacaat atgttgttac ccttctagtt aaatttttcca aaataccata tttcataact | 540 |
| tttcaaactg tttattaatt caaccgtaaa aagcactaaa atgttacatt tgatcattca | 600 |
| cccaaattaa attcaaaagt ttttccgcca aaactacttg gtgacttacg tgcttatata | 660 |
| cggacgacta ttattatgtt ctatactttt ttatactttg ttgcacaaat atctactctc | 720 |
| ccaattcata ttctagaagg atgtgctata agaatgggag aaattacaca agaagagcat | 780 |
| ctttaaatat cctctcacaa tctttatgtc taatacacgg gtgaacaatt aacgacaatt | 840 |
| tcttttattca ggaatataat aatgaataac ggttacccta cacctagtac actaaatcct | 900 |
| taacagccac acattcatac gcaaagagtt tataaaactc ataaggtat aataataacg | 960 |
| agtgaataag tcaaaaaaag tcttctctgg acacatggca gatcttaatg agtgaatcct | 1020 |
| taaactactc attttacaat tgcttcgctg tgtatagttt acgtggcatt accagagaca | 1080 |
| caaactccgt cttcgccttt tcttttgcct ctaaaatatc ttccgccatt ataaaacagc | 1140 |
| atgctctcac tccaactttt atttatctac aaacattaaa tccacctgaa ctagaacaga | 1200 |
| aagagagaga aactattatt tcagcaaacc ataccaacaa aaaagacaga gatcttttag | 1260 |
| ttaccttatc cagtttcttg aaacagagta ctcttctgat caatgaactc attttctgct | 1320 |
| ttttctgaaa tgtttggctc cgattacgag tcttcggttt cctcaggcgg tgattatatt | 1380 |
| ccgacgcttg cgagcagctg ccccaagaaa ccggcgggtc gtaagaagtt tcgtgagact | 1440 |
| cgtcacccaa tatacagagg agttcgtcgg agaaactccg gtaagtgggt ttgtgaggtt | 1500 |
| agagaaccaa acaagaaaac aaggatttgg ctcggaacat tcaaaccgc tgagatggca | 1560 |
| gctcgagctc acgacgttgc cgctttagcc cttcgtggcc gatcagcctg tctcaatttc | 1620 |
| gctgactcgg cttggagact ccgaatcccg gaatcaactt gcgctaagga catccaaaag | 1680 |
| gcggcggctg aagctgcgtt ggcgtttcag gatgagatgt gtgatgcgac gacggattat | 1740 |
| ggcttcgaca tggaggagac gttggtggag gctatttaca cggcggaaca gagcgaaaat | 1800 |
| gcgttttata tgcacgatga ggcgatgttt gagatgccga gtttgttggc taatatggca | 1860 |
| gaagggatgc ttttgccgct tccgtccgta cagtggaatc ataatcatga agtcgacggc | 1920 |
| gatgatgacg acgtatcgtt atggagttat taaaaactcag attattattt ccattttag | 1980 |

```
tacgatactt tttatttttat tattattttt agatccttttt ttagaatgga atcttcatta    2040
tgtttgtaaa actgagaaac gagtgtaaat taaattgatt cagtttcagt ataagtgtgg    2100
gctattctta aatgcaagta ttttagagc agtaacaaaa aaatgttgtt taaattagag    2160
tataaaaccg aaacaaccga ttcagcaaaa cctccaataa tagaccgtac accataaaca    2220
gaaatatggg tcccacaaga gagcactgtc cgtagcttcc ccttcattgg ccctctacgt    2280
ggctcctctt gtaaccaatg tcatgtcatt ttcaagtttt actttctttt tttatactaa    2340
tatcttgttt gtcgttttct gtaccttaag gtcctaaacc actttctttc gcgcaccatt    2400
ccttgtcgta ttatttctcc gaatatgtca ataccgtgag acgacaattg atagcgagag    2460
gtagcgagag agagaaacgt tcgttgtgaa gatattttat tgctgttgtt gagattgaga    2520
tattttatag ctattattgg aatttgaaag tgatgtataa cttgctacta tatcggctaa    2580
atccttgggc ttaaaccagt ttttatttag taaatttat gctcctgtat tattatctgg    2640
aagtattttt ctccgaaata tatgagtcga gtttaaggaa tatataagcg aaaaaccnca    2700
aattatatat ataagcgggg ttaatagatc accacaatca atttaatttg gactttagaa    2760
ttaataaaat tgtttcttcg taattattat tatttttgtt gttctggcaa atctgataat    2820
ccagattatt attagacaag tagcgaaggg acggtgaaca tttatgatttt taatttgtat    2880 gttgtaagga aaacaaaaca aataagttct gtaaaaaagg tttaccttttc tactttgccg    2940 gaaaactcaa ctcacggtgg cgtccggcga gttttcagac caaaaagaag gttggaagaa    3000
atgaagatga gaggagagg acaaaagata gagatggtgg ttgaacaaaa gaagagtaaa    3060
gaggacgaag acgctctaag tctaagccaa gggggagaag aagagaagag gtatgaggag    3120
gaaccatact tttgttagag agatgctgga aattgtgatc aactacatgc aaaatgtctt    3180
ttcgcctaac cacttaccat atttgatatt ttccttttgc caaattacac aaaccctatc    3240
ttgtctctca catatatatc caattaatac accctgcca cttgttaatt ctcgaccatg    3300
tatgtatact tatgtaaaga atatccaaaa gctt                                 3334
```

<210> SEQ ID NO 137
<211> LENGTH: 908
<212> TYPE: DNA
<213> ORGANISM: Arabidopsis thaliana
<220> FEATURE:
<221> NAME/KEY: misc_feature
<222> LOCATION: (851)..(851)
<223> OTHER INFORMATION: n is a, c, g, or t

<400> SEQUENCE: 137

```
cctgaactag aacagaaaga gagagaaact attatttcag caaaccatac caacaaaaaa      60
gacagagatc ttttagttac cttatccagt ttcttgaaac agagtactct tctgatcaat     120
gaactcattt tctgcttttt ctgaaatgtt tggctccgat tacgagtctt cggtttcctc     180
aggcggtgat tatattccga cgcttgcgag cagctgcccc aagaaaccgg cgggtcgtaa     240
gaagtttcgt gagactcgtc acccaatata cagaggagtt cgtcggagaa actccggtaa     300
gtgggtttgt gaggttagag aaccaaacaa gaaaacaagg atttggctcg gaacatttca     360
aaccgctgag atggcagctc gagctcacga cgttgccgct ttagcccttc gtggccgatc     420
agcctgtctc aatttcgctg actcggcttg gagactccga atcccggaat caacttgcgc     480
taaggacatc caaaggcgg cggctgaagc tgcgttggcg tttcaggatg agatgtgtga     540
tgcgacgacg gatcatggct tcgacatgga ggagacgttg gtggaggcta tttacacggc     600
```

| | |
|---|---:|
| ggaacagagc gaaaatgcgt tttatatgca cgatgaggcg atgtttgaga tgccgagttt | 660 |
| gttggctaat atggcagaag ggatgctttt gccgcttccg tccgtacagt ggaatcataa | 720 |
| tcatgaagtc gacggcgatg atgacgacgt atcgttatgg agttattaaa actcagatta | 780 |
| ttatttccat ttttagtacg atacttttta ttttattatt attttagat ccttttttag | 840 |
| aatggaatct ncattatgtt tgtaaaactg agaaacgagt gtaaattaaa ttgattcagt | 900 |
| ttcagtat | 908 |

<210> SEQ ID NO 138
<211> LENGTH: 908
<212> TYPE: DNA
<213> ORGANISM: Arabidopsis thaliana

<400> SEQUENCE: 138

| | |
|---|---:|
| cctgaactag aacagaaaga gagagaaact attatttcag caaaccatac caacaaaaaa | 60 |
| gacagagatc ttttagttac cttatccagt ttcttgaaac agtactctct tctgatcaat | 120 |
| gaactcattt tctgcttttt ctgaaatgtt tggctccgat tacgagtctt cggtttcctc | 180 |
| aggcggtgat tatattccga cgcttgcgag cagctgcccc aagaaaccgg cgggtcgtaa | 240 |
| gaagtttcgt gagactcgtc acccaatata cagaggagtt cgtcggagaa actccggtaa | 300 |
| gtgggtttgt gaggttagag aaccaaacaa gaaaacaagg atttggctcg aacatttca | 360 |
| aaccgctgag atggcagctc gagctcacga cgttgccgct ttagcccttc gtggccgatc | 420 |
| agcctgtctc aatttcgctg actcggcttg gagactccga atcccggaat caacttgcgc | 480 |
| taaggacatc caaaaggcgg cggctgaagc tgcgttggcg tttcaggatg agatgtgtga | 540 |
| tgcgacgacg gatcatggct tcgacatgga ggagacgttg gtggaggcta tttacacggc | 600 |
| ggaacagagc gaaaatgcgt tttatatgca cgatgaggcg atgtttgaga tgccgagttt | 660 |
| gttggctaat atggcagaag ggatgctttt gccgcttccg tccgtacagt ggaatcataa | 720 |
| tcatgaagtc gacggcgatg atgacgacgt atcgttatgg agttattaaa actcagatta | 780 |
| ttatttccat ttttagtacg atacttttta ttttattatt attttagat ccttttttag | 840 |
| aatggaatct tcattatgtt tgtaaaactg agaaacgagt gtaaattaaa ttgattcagt | 900 |
| ttcagtat | 908 |

<210> SEQ ID NO 139
<211> LENGTH: 902
<212> TYPE: DNA
<213> ORGANISM: Arabidopsis thaliana

<400> SEQUENCE: 139

| | |
|---|---:|
| ctagaacaga aagagagaga aactattatt tcagcaaacc ataccaacaa aaagacaga | 60 |
| gatcttttag ttaccttatc cagtttcttg aaacagagta ctcttctgat caatgaactc | 120 |
| attttctgct ttttctgaaa tgtttggctc cgattacgag tcttcggttt cctcaggcgg | 180 |
| tgattatatt ccgacgcttg cgagcagctg ccccaagaaa ccggcgggtc gtaagaagtt | 240 |
| tcgtgagact cgtcacccaa tatacagagg agttcgtcgg agaaactccg gtaagtgggt | 300 |
| ttgtgaggtt agagaaccaa acaagaaaac aaggatttgg ctcggaacat ttcaaaccgc | 360 |
| tgagatggca gctcgagctc acgacgttgc cgctttagcc cttcgtggcc gatcagcctg | 420 |
| tctcaatttc gctgactcgg cttggagact ccgaatcccg gaatcaactt gcgctaagga | 480 |
| catccaaaag gcggcggctg aagctgcgtt ggcgtttcag gatgagatgt gtgatgcgac | 540 |
| gacggatcat ggcttcgaca tggaggagac gttggtggag gctatttaca cggcggaaca | 600 |

```
gagcgaaaat gcgttttata tgcacgatga ggcgatgttt gagatgccga gtttgttggc      660
taatatggca aagggatgc ttttgccgct tccgtccgta cagtggaatc ataatcatga       720
agtcgacggc gatgatgacg acgtatcgtt atggagttat aaaactcag attattattt       780 ccattttag tacgatactt tttatttat tattattttt agatcctttt ttagaatgga        840
atcttcatta tgtttgtaaa actgagaaac gagtgtaaat taaattgatt cagtttcagt      900
at                                                                     902

<210> SEQ ID NO 140
<211> LENGTH: 8729
<212> TYPE: DNA
<213> ORGANISM: Arabidopsis thaliana

<400> SEQUENCE: 140
aacatatcat cacacgtgga atgagaacga gtttcgactt ttcaaatatg ccataaagcc       60
tcaattatct tcttatctag cttgaatatg caacaaaaag ctattaagat attcataaaa      120
tagaggcgtc tcaaatctac caacaaaaag ctacaaaaga tccagtccaa tccactgaag      180
aatcccaaaa cagagtagaa acccaaacaa cccgattcag caaataattc aaaaacgaac      240
gtccgtacga ttttccaaaa acagaaagat gggttccaca agataatgcg tgggacgtc       300 aaaatcctct aaacccgtgg ttcggccgcg gaaacactgt ccctaccttc cccaccagcc      360
ttcactggcc ccatacgtca ctctcaagct ttactttcta ttttccacta aagccaattt      420
tgttgttttc ttcaccttac cactcttttt ttccctcttt gttgtgtctt cttttctcct     480
aaatgtcaat aacgtgagag cgagaggtaa cgagagagat attttgtca gcgaatatat      540 ttcatgcata tcttattgtg aagatttttt ataccttttt tttgtcaata caatatagct     600
attattgaga ttgagatatt ttgtggaatt attgggattc aagataactt gctattttgt     660
attggtctta tccttcgctt agtcctgtcc tggtccattt acatgttttt ggttatagtt      720
tgtttaaact gaataatttt gttcatcata tgcattaatg actcattttt aaccgtccat      780
cgaaattgat aattatccat taccaaatct gattaatttt tttaaaaaat caagcttttc      840
tatattgtag tattattttt ggttaaatat taggacatct acttccaata caaatactac      900
atgagtattt aaaatatcat ttcacagaga tatttatgtc tattatgtta tagacgggtg     960
acaattaatg acaatttgtt tattcatagg aatttaaaaa cgattgtaac aacagcagcc    1020
agccaaccac acaggcacac actcgataga atttaaagaa ctcataaagg ttaacgagtg    1080
aagagtcaaa agtctcttta caagggtcaa aggacacacg tcagacagcg agtggaacat    1140
cgtgggattg cttcgctatg tactatacac gtgtcattca cagagacaaa aactccgtgt    1200
gcaccccaca tatccgttat ctctcctccg gccaatataa acaccaattc tcactctcac    1260
tttttatact aactacacac ttgaaaaaga atctacctga aaagaaaaaa aagagagaga    1320
gatataaata gctttaccaa gacagatata ctatctttta ttaatccaaa aagactgaga    1380
actctagtaa ctacgtacta cttaaaccct atccagtttc ttgaaacaga gtactctgat    1440
caatgaactc attttcagct ttttctgaaa tgtttggctc cgattacgag cctcaaggcg    1500
gagattattg tccgacgttg gccacgagtt gtccgaagaa accggcgggc cgtaagaagt    1560
ttcgtgagac tcgtcaccca atttacagag gagttcgtca aagaaactcc ggtaagtggg    1620
tttctgaagt gagagagcca aacaagaaaa ccaggatttg gctcgggact ttccaaaccg    1680
ctgagatggc agctcgtgct cacgacgtcg ctgcattagc cctccgtggc cgatcagcat    1740
```

-continued

```
gtctcaactt cgctgactcg gcttggcggc tacgaatccc ggagtcaaca tgcgccaagg   1800
atatccaaaa agcggctgct gaagcggcgt tggcttttca agatgagacg tgtgatacga   1860
cgaccacgga tcatggcctg acatggagg agacgatggt ggaagctatt tatacaccgg    1920
aacagagcga aggtgcgttt tatatggatg aggagacaat gtttgggatg ccgactttgt   1980
tggataatat ggctgaaggc atgcttttac cgccgccgtc tgttcaatgg aatcataatt   2040
atgacggcga aggagatggt gacgtgtcgc tttggagtta ctaatattcg atagtcgttt   2100
ccatttttgt actatagttt gaaaatattc tagttccttt tttagaatgg ttccttcatt   2160
ttattttatt ttattgttgt agaaacgagt ggaaaataat tcaatacaaa acaaatcgtt   2220
ttctacttct ttgcttcaca taagttaaaa gtcaaatatt taacaaaaaa gatattaaaa   2280
gtcatattgt agttgctttc aaggcaaaat atgtggacag aatcattaca cgtggatgat   2340
gtttgtaaat atgccacaaa acctgcatta cattatttta ttctatctca tgtaagttac   2400
agatcttaca atttagcaa cagaaagcca caaaatatta cataaattgg ctcgtctcga    2460
atctagcaac caaaaaaatt cagtccagtt cactataaag aataaaaaaa aagtttcct    2520
aaaatagtgt ataaaaccga aacaaactaa ttcaacaaac ccgaaataaa caaatccgta   2580
cgacaaccaa aaatatcttt cagatggtt ccacaagata acccagtgcc aatcagaatt    2640
ctgaaagcgt ggctcgaccg cggaaaccat tgtccatacc ttctcttctt tgtccccct    2700
tacgtggctc gctgtggagt ctcgtaccac gtgtcgcgtc acttcactct ttactttcta   2760
ttttccacta aaatcataat ttgtctttttt cttgaccata cccactcttt tttcttctcg   2820
ttgtcgtctt gcttctccta aatatctcaa ataacgtgag agacttgagt gtgagaggta   2880
ggtaacgagg cagactttt ttggaagcga atataactta tgctgatatt ttatttagct    2940
ttctgattgg agttgagata ttatataggt attattgaga tattatatac gtattattga   3000
gatttgagat attttgtaga ttttatagtt ctatcggact aattcttggc ttaatccact   3060
aacatgtttt tgtttagtta attaaactga ttattttctg cgctatagtt ttgttaaaca   3120
ccttttagac gtaacaaagc aattacgctt gatcattcat cgtagactct tttcttttt    3180
ttacatctca tagaagtttt gtttaaacac agcaggaagt aaattatttt cttattacgt   3240
acgtatgatt gttttagac tattttagta ctttgagaag taaaattggg gatacgagat    3300
aaaagacaat tgattaacat gcttttttatt ttgacttccg aaactaatca tggttgtcta   3360
tgtttataaa ttgtgttatt tttgttgaaa aacttagata attattaaat cagtagcgaa   3420
tggatggaga acacatgatt ttagattgca taccgtaaaa caaaaaaaaa tcatgatgga   3480
tgtagaacat tcaaatggat caaataaata agtatgtgat caaagaaag tatgtaatca    3540
aaagggttag cacgagtacc ttgggaggaa attcttctaa ttatgaatta tgcaagaatt   3600
ttcgtcaagg gaaggtgggg aagaggtagc taaattaaag aatagagaat catatgacta   3660
aggacgtggt ggttgaagga atgagagaa tacatgaaga agagaaactt ctttgagtga    3720
gaaggaagtg cgctggctga aggcaataga gagaaagag tttcgagtga gagagagggc    3780
gttgagattg tgatcaactt aatgtaatat gttcttttat tacattttct ttttgtcata   3840
tactcaaacc ttttactatt ttgtctcata aatctaacac accccaccat tgttaatgc    3900
atgatggtag aaaatattaa atataattaa ctactttat gtgatcaaaa ttaggtttca    3960
gactcgtttc gcgatccgat ttacaattac aactgcatgc ttctaattga tctaaattct   4020
aagttttta tacatattaa aaaataact ttttgttaaa ttctcaatca tcattttgt      4080
gattaacaat ttttttataac tctaaaccaa taatatttga ttatttattt tatatgtata   4140
```

```
atgatgattg agaattttaa ttagcagtct atttagggtt ttcctaaagt tacaatatgt    4200
tgttacccct ctagttaaat tttccaaaat accatatttc ataacttttc aaactgttta    4260
ttaattcaac cgtaaaaagc actaaaatgt tacatttgat cattcaccca aattaaattc    4320
aaaagttttt ccgccaaaac tacttggtga cttacgtgct tatatacgga cgactattat    4380
tatgttctat acttttttat actttgttgc acaaatatct actctcccaa ttcatattct    4440
agaaggatgt gctataagaa tgggagaaat tacacaagaa gagcatcttt aaatatcctc    4500
tcacaatctt tatgtctaat acacgggtga acaattaacg acaatttctt tattcaggaa    4560
tataataatg aataacggtt accctacacc tagtacacta aatccttaac agccacacat    4620
tcatacgcaa agagtttata aaactcataa aggtataata ataacgagtg ataagtcaa    4680 aaaaagtctt ctctggacac atggcagatc ttaatgagtg aatccttaaa ctactcattt    4740
tacaattgct tcgctgtgta tagtttacgt ggcattacca gagacacaaa ctccgtcttc    4800
gccttttctt ttgcctctaa aatatcttcc gccattataa aacagcatgc tctcactcca    4860
acttttattt atctacaaac attaaatcca cctgaactag aacagaaaga gagagaaact    4920
attatttcag caaaccatac caacaaaaaa gacagagatc ttttagttac cttatccagt    4980
ttcttgaaac agagtactct tctgatcaat gaactcattt tctgctttt ctgaaatgtt    5040 tggctccgat tacgagtctt cggtttcctc aggcggtgat tatattccga cgcttgcgag    5100
cagctgcccc aagaaaccgg cgggtcgtaa gaagtttcgt gagactcgtc acccaatata    5160
cagaggagtt cgtcggagaa actccggtaa gtgggtttgt gaggttagag aaccaaacaa    5220
gaaaacaagg atttggctcg gaacatttca aaccgctgag atggcagctc gagctcacga    5280
cgttgccgct ttagcccttc gtggccgatc agcctgtctc aatttcgctg actcggcttg    5340
gagactccga atcccggaat caacttgcgc taaggacatc caaaaggcgg cggctgaagc    5400
tgcgttggcg tttcaggatg agatgtgtga tgcgacgacg gatcatggct tcgacatgga    5460
ggagacgttg gtggaggcta tttacacggc ggaacagagc gaaaatgcgt tttatatgca    5520
cgatgaggcg atgtttgaga tgccgagttt gttggctaat atggcagaag ggatgctttt    5580
gccgcttccg tccgtacagt ggaatcataa tcatgaagtc gacggcgatg atgacgacgt    5640
atcgttatgg agttattaaa actcagatta ttatttccat ttttagtacg atactttta    5700 ttttattatt attttagat cctttttag aatggaatct tcattatgtt tgtaaaactg    5760
agaaacgagt gtaaattaaa ttgattcagt ttcagtataa gtgtgggcta ttcttaaatg    5820
caagtatttt tagagcagta acaaaaaat gttgtttaaa ttagagtata aaaccgaaac    5880
aaccgattca gcaaaacctc caataataga ccgtacacca taaacagaaa tatgggtccc    5940
acaagagagc actgtccgta gcttccctt cattggccct ctacgttgct cctctgtaac    6000
caatgtcatg tcattttcaa gttttacttt cttttttat actaatatct tgttgtcgt    6060 tttctgtacc ttaaggtcct aaaccacttt ctttcgcgca ccattccttg tcgtattatt    6120
tctccgaata tgtcaatacc gtgagacgac aattgatagc gagaggtagc gagagagaga    6180
aacgttcgtt gtgaagatat tttattgctg ttgttgagat ttgagatatt ttatagctat    6240
tattggaatt tgaaagtgat gtataacttg ctactatatc ggtctaatcc ttggcttaaa    6300
ccagttttta tttagtaatt taaactcaat gtccttatgc tcctgtatta ttattcggtg    6360
gaagtatttt tttctcaaaa aatatatgag tcgagtttaa gaaatatata agcgaaaaaa    6420
caaaaaaata tatataagcg gggttaatag atcaaccaca atcaatttaa tttggacttt    6480
```

```
agaattaata aaattgttta cttcgtaatt attattattt ttgttgttct ggcaaatctg    6540
ataatccaga ttattattag acaagtagca aagggacggt gaacatttat gattttaatt    6600
tgtatgttgt gaggaaaaca aaacaaataa gttctgtaaa aaaggtttac ctttctactt    6660
tgccggaaaa ctcaactcac ggtggcgtcc ggcgagtttt cagaccaaaa agaaggttgg    6720
aagaaatgaa gatgaagagg agaggacaaa agatagagat ggtggttgaa caaaagaaga    6780
gtaaagagga cgaagacgct ctaagtctaa gccaaggggg agaagaagag aagaggtatg    6840
aggaggaacc atactttgt tagagagatg ctggaaattg tgatcaacta catgcaaaat     6900
gtcttttcgc ctaaccactt accatatttg atattttcct tttgccaaat tacacaaacc    6960
ctatcttgtc tctcacatat atatccaatt aatacacccc tgccacttgt taattctcga    7020
ccatgtatgt atacttatgt aaagaatatc caaaagcttt cttttgttc cttcgatttt     7080 aagcaacttg tgttctcatt tctaatata ttaaagaaat cctgagtaaa agttatagcc     7140
tccgtgaatc ttaggaaatt actctagcat attcaaattt tttgagacaa tatataaatt    7200
tttctgaata attaaattta catatctatg ctacgaaact tgattaatta aattaaatat    7260
atatatataa taataataat aataataata taacatttt tttaggacac aaatatctaa     7320
tctcactata ctctagaagt atttgcaatg cacgatatgt gaatggagaa aagacagaaa    7380
gagcatttga aaatatctcg tttcacggat cattatgtct aattattta ccatagaaaa     7440 gcgacaatta taaacaattt gttattcgtg gaaaataat atttaataat ggttgtcgta     7500
ccctataaac tacagccaca cattcataca ataagaagtt aaaaaaattc ataccctaaa    7560
ggcatcaacc agtgaagggt cagaaacttc ccaagatggg tcaaaggaca catgtcagat    7620
tctcagtgat tgacagcctt gataattaca aaaccgtggg atcgcttagc tgtttcttat    7680
ccacgtggca ttcacagaga cagaaactcc gcgttcgacc ccacaaatat ccaaatatct    7740
tccggccaat ataaacagca agctctcact ccaacatttc tataacttca aacacttacc    7800
tgaattagaa aagaaagata gagagagaaa taaatatttt atcataccat acaaaaaaag    7860
acagagatct ttctacttac tctactctca taaaccttat ccagtttctt gaaacagagt    7920
actcttctga tcaatgaact catgttctgc ttttctgaa atgtttggct ccgattacga     7980
gtctccggtt tcctcaggcg gtgattacag tccgaagctt gccacgagct gccccaagaa    8040
accagcggga aggaagaagt tcgtgagac tcgtcaccca atttacagag gagttcgtca     8100
aagaaactcc ggtaagtggg tgtgtgagtt gagagagcca aacaagaaaa cgaggatttg    8160
gctcgggact ttccaaaccg ctgagatggc agctcgtgct cacgacgtcg ccgccatagc    8220
tctccgtggc agatctgcct gtctcaattt cgctgactcg gcttggcggc tacgaatccc    8280
ggaatcaacc tgtgccaagg aaatccaaaa ggcggcggct gaagccgcgt tgaattttca    8340
agatgagatg tgtcatatga cgacggatgc tcatggtctt gacatggagg agaccttggt    8400
ggaggctatt tatacgccgg aacagagcca agatgcgttt tatatggatg aagaggcgat    8460
gttggggatg tctagtttgt tggataacat ggccgaaggg atgctttac cgtcgccgtc     8520 ggttcaatgg aactataatt ttgatgtcga gggagatgat gacgtgtcct tatggagcta    8580
ttaaaattcg attttattt ccatttttgg tattatagct ttttatacat ttgatccttt     8640
tttagaatgg atcttcttct tttttggtt gtgagaaacg aatgtaaatg gtaaagttg      8700 ttgtcaaatg caaatgtttt tgagtgcag                                      8729
```

<210> SEQ ID NO 141
<211> LENGTH: 1040

```
<212> TYPE: DNA
<213> ORGANISM: Thellungiella salsuginea

<400> SEQUENCE: 141
caggccaata taaacaccaa ccctcactcc cactttctt caaactacaa actttaaaat    60
ccaacctgaa aaaaaagag agagataaaa ataaaatatt tctatcaaaa accatcagga   120
cggaagatct tttaacctac tacttaaacc ttatccagtt tttctcaaaa aagagttttc   180
ttttttctt aaagatcaaa aatgaactca ttttctgcgt tcgctgaaat gtttggctcc   240
gagtacgagt ctccggtcac cgtaggcggc gattactgtc cgacgctagc gactagctgt   300
ccgaagaaac cagccggtcg aagaagttt cgggagacac gtcacccaat ctacagagga   360
gttcgtcgga aaactccgg taagtgggtg tgtgaggtta gagagccgaa caagaaatct   420
aggatttggc tcggaacttt tccaacagcc gagatggcag ctcgtgctca tgacgtcgcc   480
gccatagctc tacgtggcag atccgcctgt ctaaatttcg cagactcggc ttggcggctt   540
agaatcccgg agtcaacttg cgctaaagat atacagaaag cggctgctga agcggcggtt   600
gcttttcagg ctgagatgag tgatacgatg acatcggatc atggccttga catggaggag   660
acgacggtgg aggttattgt aacggaggag gaacaaagcg aagggtttta tatggacgag   720
gaagccatgt ttggcatgcc gaggttgctg gctaatatgg cggaaggtat gcttttgcct   780
cctccgtccg tacaatgggg acataattat gactgcgacg gagatgctga cgtgtccctt   840
tggagttatt aaaaaattt ggtactataa tttttttttt tttttctga gattttagga   900
ttccacaatt tttttatagg atgaatccct cttttttttt ttttggtgg tcactgagag   960
acgatgtaaa tctttcaaaa acaatatttt caatgcgagt atttttttgtg caaaaaaaa  1020
aaaaaaaaaa aaaaaaaaa                                              1040

<210> SEQ ID NO 142
<211> LENGTH: 391
<212> TYPE: PRT
<213> ORGANISM: Triticum aestivum

<400> SEQUENCE: 142

Met Glu Asn Gln Ala His Ile Ala Gly Glu Lys Lys Gly Ile Met Glu
1               5                   10                  15

Lys Ile Lys Glu Lys Leu Pro Gly Gly His Gly Asp His Lys Glu Thr
            20                  25                  30

Ala Gly Thr His Gly His Ala Ala Thr Ala Thr His Gly Ala Pro Ala
        35                  40                  45

Thr Gly Gly Ala Tyr Gly Gln Gln Gly His Ala Gly Thr Thr Gly Thr
    50                  55                  60

Gly Leu His Gly Ala His Ala Gly Glu Lys Lys Gly Val Met Glu Asn
65                  70                  75                  80

Ile Lys Asp Lys Leu Pro Gly Gly His Glu Asp His Gln Gln Thr Gly
                85                  90                  95

Gly His Tyr Gly Gln Gln Gly His Ala Gly Thr Ala Thr His Gly Thr
            100                 105                 110

Pro Ala Thr Ala Gly Thr Tyr Gly Gln Gln Gly His Thr Gly Thr Ala
        115                 120                 125

Thr His Gly Thr Pro Ala Thr Gly Gly Thr Tyr Gly Glu Gln Gly His
    130                 135                 140

Thr Gly Val Thr Gly Thr Gly Thr His Gly Thr Gly Glu Lys Lys Gly
145                 150                 155                 160
```

```
Leu Met Glu Asn Ile Lys Glu Lys Leu Pro Gly Gly His Gly Asp His
                165                 170                 175

Gln Gln Thr Ala Gly Thr Tyr Gly Gln Gln Gly His Val Gly Thr Gly
            180                 185                 190

Thr His Gly Ala Pro Ala Thr Gly Gly Ala Tyr Gly Gln His Glu His
        195                 200                 205

Ala Gly Val Ala Gly Ala Gly Thr Tyr Gly Thr Gly Glu Lys Lys Gly
    210                 215                 220

Val Met Glu Asn Ile Lys Asp Lys Leu Pro Gly Gly His Gly Asp His
225                 230                 235                 240

Gln Gln Thr Gly Gly Thr Tyr Gly Gln Gln Gly His Thr Gly Thr Ala
                245                 250                 255

Thr His Gly Thr Pro Ala Gly Gly Thr Tyr Glu Gln His Gly His
            260                 265                 270

Thr Gly Met Thr Gly Thr Gly Thr His Gly Thr Gly Glu Lys Lys Gly
        275                 280                 285

Val Met Glu Asn Ile Lys Glu Lys Leu Pro Gly Gly His Gly Asp His
    290                 295                 300

Gln Gln Thr Gly Gly Ala Tyr Gly Gln Gln Gly His Thr Gly Thr Ala
305                 310                 315                 320

Thr His Gly Thr Pro Ala Gly Gly Thr Tyr Gly Gln His Ala His
                325                 330                 335

Thr Gly Met Thr Gly Thr Glu Thr His Gly Thr Thr Ala Thr Gly Gly
            340                 345                 350

Thr His Gly Gln His Gly His Ala Gly Thr Thr Gly Thr Gly Thr His
        355                 360                 365

Gly Thr Asp Gly Val Gly Glu Lys Lys Ser Leu Met Asp Lys Ile Lys
    370                 375                 380

Asp Lys Leu Pro Gly Gln His
385                 390

<210> SEQ ID NO 143
<211> LENGTH: 261
<212> TYPE: PRT
<213> ORGANISM: Capsella bursa-pastoris

<400> SEQUENCE: 143

Met Ala Glu Glu Asn Lys Asn Asn Val Pro Glu His Glu Thr Pro Lys
1               5                   10                  15

Val Ala Thr Thr Glu Glu Pro Ser Thr Thr Thr Thr Pro Glu Val
            20                  25                  30

Thr Asp Arg Gly Met Phe Asp Phe Leu Ser Lys Lys Glu Glu Val
        35                  40                  45

Lys Pro Gln Glu Thr Thr Thr Leu Glu Ser Glu Phe Asp His Lys Ala
    50                  55                  60

Gln Ile Ser Glu Pro Ala Leu Ala Ala Glu His Glu Val Lys Glu
65                  70                  75                  80

Asn Lys Ile Thr Leu Leu Glu Glu Leu Gln Glu Lys Thr Glu Glu Asp
                85                  90                  95

Glu Glu Asn Lys Pro Ser Val Ile Glu Lys Leu His Arg Ser Asn Ser
            100                 105                 110

Ser Ser Ser Ser Ser Ser Asp Glu Glu Gly Glu Lys Lys Lys Lys
        115                 120                 125

Lys Thr Val Glu Gly Glu Glu Lys Lys Gly Ala Met Asp Lys Ile
    130                 135                 140
```

Lys Glu Lys Leu Pro Gly His His Asp Lys Glu Thr Glu Asp His Asp
145                 150                 155                 160

Val Pro Val Val Ser Thr Ile Gln Val Pro Val Ser Glu Ser Val Val
                165                 170                 175

Glu His His Glu Thr Glu Gly Glu Glu Lys Lys Gly Val Met Asp Lys
            180                 185                 190

Ile Lys Glu Lys Leu Pro Gly Arg Asn Asp Lys Glu Thr Glu Asp Ser
            195                 200                 205

Pro Val Pro Thr Ser Thr Pro Leu Val Val Thr Glu His Pro Val Gly
            210                 215                 220

His Ser Thr Glu Gln Pro Ala Glu Lys Lys Gly Ile Ile Glu Lys Ile
225                 230                 235                 240

Lys Glu Lys Leu Pro Gly Tyr His Ala Lys Thr Glu Glu Lys Lys
                245                 250                 255

Glu Lys Glu Ser Ala
            260

<210> SEQ ID NO 144
<211> LENGTH: 265
<212> TYPE: PRT
<213> ORGANISM: Arabidopsis thaliana

<400> SEQUENCE: 144

Met Ala Glu Glu Tyr Lys Asn Asn Val Pro Glu His Glu Thr Pro Thr
1               5                   10                  15

Val Ala Thr Glu Glu Ser Pro Ala Thr Thr Glu Val Thr Asp Arg
            20                  25                  30

Gly Leu Phe Asp Phe Leu Gly Lys Lys Glu Glu Val Lys Pro Gln
            35                  40                  45

Glu Thr Thr Thr Leu Glu Ser Glu Phe Asp His Lys Ala Gln Ile Ser
    50                  55                  60

Glu Pro Glu Leu Ala Ala Glu His Glu Val Lys Glu Asn Lys Ile
65                  70                  75                  80

Thr Leu Leu Glu Glu Leu Gln Glu Lys Thr Glu Glu Asp Glu Glu Asn
                85                  90                  95

Lys Pro Ser Val Ile Glu Lys Leu His Arg Ser Asn Ser Ser Ser
            100                 105                 110

Ser Ser Ser Asp Glu Glu Gly Glu Glu Lys Lys Glu Lys Lys Lys
            115                 120                 125

Ile Val Glu Gly Glu Glu Asp Lys Lys Gly Leu Val Glu Lys Ile Lys
            130                 135                 140

Glu Lys Leu Pro Gly His His Asp Lys Thr Ala Glu Asp Asp Val Pro
145                 150                 155                 160

Val Ser Thr Thr Ile Pro Val Pro Val Ser Glu Ser Val Val Glu His
                165                 170                 175

Asp His Pro Glu Glu Lys Lys Gly Leu Val Glu Lys Ile Lys Glu
            180                 185                 190

Lys Leu Pro Gly His His Asp Glu Lys Ala Glu Asp Ser Pro Ala Val
            195                 200                 205

Thr Ser Thr Pro Leu Val Val Thr Glu His Pro Val Glu Pro Thr Thr
            210                 215                 220

Glu Leu Pro Val Glu His Pro Glu Glu Lys Lys Gly Ile Leu Glu Lys
225                 230                 235                 240

Ile Lys Glu Lys Leu Pro Gly Tyr His Ala Lys Thr Thr Glu Glu Glu

```
                        245                 250                 255
Val Lys Lys Glu Lys Glu Ser Asp Asp
                260                 265

<210> SEQ ID NO 145
<211> LENGTH: 294
<212> TYPE: PRT
<213> ORGANISM: Arabidopsis thaliana

<400> SEQUENCE: 145

Asn His Leu Lys Ala Thr Thr Gln Val Leu Lys Phe Ser His Ile Phe
1               5                   10                  15

Tyr Leu Leu Tyr Lys Leu Leu Ile Lys Ser Arg Leu Thr Met Ala Glu
                20                  25                  30

Glu Tyr Lys Asn Asn Val Pro Glu His Glu Thr Pro Thr Val Ala Thr
            35                  40                  45

Glu Glu Ser Pro Ala Thr Thr Thr Glu Val Thr Asp Arg Gly Leu Phe
        50                  55                  60

Asp Phe Leu Gly Lys Lys Glu Glu Val Lys Pro Gln Glu Thr Thr
65                  70                  75                  80

Thr Leu Glu Ser Glu Phe Asp His Lys Ala Gln Ile Ser Glu Pro Glu
                85                  90                  95

Leu Ala Ala Glu His Glu Val Lys Glu Asn Lys Ile Thr Leu Leu
            100                 105                 110

Glu Glu Leu Gln Glu Lys Thr Glu Glu Asp Glu Glu Asn Lys Pro Ser
        115                 120                 125

Val Ile Glu Lys Leu His Arg Ser Asn Ser Ser Ser Ser Ser Ser Ser
130                 135                 140

Asp Glu Glu Gly Glu Glu Lys Lys Glu Lys Lys Lys Lys Ile Val Glu
145                 150                 155                 160

Gly Glu Glu Asp Lys Lys Gly Leu Val Glu Lys Ile Lys Glu Lys Leu
                165                 170                 175

Pro Gly His His Asp Lys Thr Ala Glu Asp Asp Val Pro Val Ser Thr
            180                 185                 190

Thr Ile Pro Val Pro Val Ser Glu Ser Val Val Glu His Asp His Pro
        195                 200                 205

Glu Glu Glu Lys Lys Gly Leu Val Glu Lys Ile Lys Glu Lys Leu Pro
    210                 215                 220

Gly His His Asp Glu Lys Ala Glu Asp Ser Pro Ala Val Thr Ser Thr
225                 230                 235                 240

Pro Leu Val Val Thr Glu His Pro Val Glu Pro Thr Thr Glu Leu Pro
                245                 250                 255

Val Glu His Pro Glu Glu Lys Lys Gly Ile Leu Glu Lys Ile Lys Glu
            260                 265                 270

Lys Leu Pro Gly Tyr His Ala Lys Thr Thr Glu Glu Val Lys Lys
        275                 280                 285

Glu Lys Glu Ser Asp Asp
    290

<210> SEQ ID NO 146
<211> LENGTH: 1243
<212> TYPE: DNA
<213> ORGANISM: Triticum aestivum

<400> SEQUENCE: 146
gtaaacacat cagcactagt agatttcacg agtcagaagc tcagcgcaag atggagaacc    60
```

-continued

```
aggcacacat cgccggcgag aagaagggca tcatggagaa gatcaaggag aagctccccg    120
gcggccacgg cgaccacaag gagaccgctg gtacccacgg gcacgccgcc acggcgacgc    180
atggtgcccc ggccaccggt ggtgcctacg ggcagcaggg tcacgctgga accaccggca    240
cggggttgca tggcgcccac gccggcgaga agaagggcgt gatggagaac atcaaggaca    300
agctccctgg tggccacgag gaccaccagc agaccggtgg ccactacggg cagcagggac    360
acgccggcac ggcgacgcat ggcaccccgg ctaccgctgg cacctatggg caacaggggc    420
ataccggcac ggcgacgcat ggcaccccag cgaccggtgg cacctatggg gagcagggac    480
acaccggagt gaccggcacg gggacgcacg gcaccggcga agaagggc ctcatggaga    540 acatcaagga gaagctccct ggtggccatg gtgaccacca gcagaccgct ggcacctacg    600
ggcagcaggg acacgtcggc acggggacac atggcgcccc ggctaccggc ggggcctacg    660
ggcagcatga acacgccgga gtggccggcg cgggaacata cggcaccggc gagaagaagg    720
gcgtcatgga gaacatcaag gacaagctcc ctggcggcca cggcgaccac cagcagaccg    780
gtggcaccta cgggcagcag ggacacaccg gcacggcgac gcatggcacc ccggccggcg    840
gcggcaccta tgagcagcac ggacacaccg ggatgaccgg cacggggaca cacggcaccg    900
gcgagaagaa gggcgtcatg gagaacatca aggagaagct ccccggtggc cacggcgacc    960
accagcagac cggtggagcc tacgggcagc agggacacac cggcacggcg acgcatggca    1020
ctccggctgg cggcgcacc tacgggcagc atgcacacac tggaatgacc ggcacggaga    1080
cgcacggcac cacggccacc ggcggcaccc atgggcagca cggacacgcc ggaacgactg    1140
gcactgggac acacggcacc gacggggtgg gcgagaagaa gagcctcatg gacaagatca    1200
aggacaagct gcctggacag cactgagccc ggtgtgccga cgg    1243

<210> SEQ ID NO 147
<211> LENGTH: 1109
<212> TYPE: DNA
<213> ORGANISM: Capsella bursa-pastoris

<400> SEQUENCE: 147
ggcgccatac gcgggggtct caaacatcga tactcatcat ctcacacaca cctcttcaaa    60
accaatcttt tttagcaact tcaaagttct ttaaactttc tgtttatcaa accgtttcag    120
tccattcaga ttataactat ggcggaagag aacaagaaca acgttcccga gcacgagacc    180
cccaaggttg caacaacaga agagccatca accactacta ctacaccaga ggttacggat    240
cgtgggatgt tcgatttctt gagcaagaag aaagaggaag tgaaacctca agagactacg    300
acgctcgagt ctgagttcga ccataaggct cagatctcag aaccggcgtt agctgcggag    360
cacgaggaag tgaaggagaa caagattact ctcctcgagg agcttcagga gaagaccgag    420
gaagatgagg agaacaagcc tagtgtcatc gaaaagcttc accgatccaa cagctcttct    480
tcctcttcaa gcgatgaaga aggtgaggaa agaaaaaga agaagaccgt tgaaggagaa    540
gaagagaaga aagggcaat ggataagatc aagagaagc ttccaggcca ccacgacaag    600
gaaacagagg atcatgacgt accagtggtc agcaccatcc aggtaccagt atcggagagt    660
gtggtggagc atcacgaaac cgagggcgaa gaaaagaaag gagtaatgga taagatcaag    720
gagaagcttc caggccgcaa cgacaaggag acagaggatt caccctgtccc aaccagcacg    780 ccactggttg taactgagca cccggtggga cactcgacgg agcaaccggc ggagaagaag    840
ggaatcatcg aaaagattaa agagaagctt ccaggttatc acgccaagac agaggaagag    900
```

```
aagaaagaaa aagagtctgc ttaagcaaaa tgatgaaacg atgaaataat gatattggga    960
gtgggacatt tgttgtgttt tgtgatcat tatctttctc ttttttcttt ttaagttgtt   1020
cttgtggctt tcatttgatc ctgtggtttg tattttcatt tttatctttt ttatatatat  1080
aaatggtttg cataaaaaaa aaaaaaaaa                                     1109

<210> SEQ ID NO 148
<211> LENGTH: 1109
<212> TYPE: DNA
<213> ORGANISM: Arabidopsis thaliana

<400> SEQUENCE: 148
ggcgccatac gcggggtct caaacatcga tactcatcat ctcacacaca cctcttcaaa     60
accaatcttt tttagcaact tcaaagttct ttaaactttc tgtttatcaa accgtttcag   120
tccattcaga ttataactat ggcggaagag aacaagaaca acgttcccga gcacgagacc   180
cccaaggttg caacaacaga agagccatca accactacta ctacaccaga ggttacggat   240
cgtgggatgt tcgatttctt gagcaagaag aaagaggaag tgaaacctca agagactacg   300
acgctcgagt ctgagttcga ccataaggct cagatctcag aaccggcgtt agctgcggag   360
cacgaggaag tgaaggagaa caagattact ctcctcgagg agcttcagga agaccgag    420 gaagatgagg agaacaagcc tagtgtcatc gaaaagcttc accgatccaa cagctcttct   480
tcctcttcaa gcgatgaaga aggtgaggaa aagaaaaga agaagaccgt tgaaggagaa   540
gaagagaaga aaggggcaat ggataagatc aagagaagc ttccaggcca ccacgacaag   600
gaaacagagg atcatgacgt accagtggtc agcaccatcc aggtaccagt atcggagagt   660
gtggtggagc atcacgaaac cgagggcgaa gaaaagaaag gagtaatgga taagatcaag   720
gagaagcttc caggccgcaa cgacaaggag acagaggatt caactgtccc aaccagcacg   780
ccactggttg taactgagca cccggtggga cactcgacgg agcaaccggc ggagaagaag   840
ggaatcatcg aaaagattaa agagaagctt ccaggttatc acgccaagac agaggaagag   900
aagaaagaaa aagagtctgc ttaagcaaaa tgatgaaacg atgaaataat gatattggga   960
gtgggacatt tgttgtgttt tgtgatcat tatctttctc ttttttcttt ttaagttgtt   1020
cttgtggctt tcatttgatc ctgtggtttg tattttcatt tttatctttt ttatatatat  1080
aaatggtttg cataaaaaaa aaaaaaaaa                                     1109

<210> SEQ ID NO 149
<211> LENGTH: 1073
<212> TYPE: DNA
<213> ORGANISM: Arabidopsis thaliana

<400> SEQUENCE: 149
aaaaccatct taaagcaact acacaagtct tgaaattttc tcatattttc tatttactat     60
ataaactttt aatcaaatca agattaacta tggctgagga gtacaagaac aacgttcccg   120
agcacgagac accaacggtc gcaacagagg aatcaccagc gacgacaaca gaggttacgg   180
atcgtggatt gtttgatttc ttggggaaga aggaagagga agtgaaacct caagagacaa   240
cgacgctcga gtctgagttc gatcataagg ctcagatctc tgaaccggag ttagctgcgg   300
agcacgagga agtgaaggag aacaagatta ctctgctaga ggagcttcaa gaaagaccg    360 aggaagatga ggagaacaag cctagtgtca tcgaaaagct tcaccgatcc aacagctctt   420
cttcctcttc gagcgatgaa gaaggtgagg aaaagaagga agaagaagaag aagatcgttg   480 aaggagagga agataagaaa ggactagtgg agaagatcaa ggagaagctc ccaggacacc   540
```

```
acgacaagac agcagaggat gatgtaccag tttccactac catcccggta ccagtgtcgg      600
agagtgtggt ggagcatgac catcccgagg aagagaagaa aggattagtt gagaagatca      660
aggagaagct tcctggtcac cacgacgaga agcagagga ttcaccagct gtcacgtcca      720
cgccgttggt tgtaacggag catccggtgg agcctacgac ggagcttcca gtggaacatc      780
cggaggagaa gaaggggatt ttggaaaaga tcaaagagaa gcttccaggt tatcatgcca      840
agaccactga agaggaagtg aagaaagaaa aagagtctga tgattaagca aaatggttaa      900
agaatgaata atgatgtggg agtgggacat tcgctgtgtt ttgtgatcat tatctttctc      960 tttttaagttg ttattgtggc tttcgttgat tgcatttgat cctttatttt gtaatttcat     1020
tctatctttt atataaagtt tgcatatggt ttatacttaa aaaaaaaaaa aaa             1073

<210> SEQ ID NO 150
<211> LENGTH: 230
<212> TYPE: DNA
<213> ORGANISM: Lolium perenne

<400> SEQUENCE: 150
ttaggcagag tcggcgaagt cccttcaaga atcgcccgcg gcgagggcga gcatggcggc       60
cctcttgtgc tcgcgcggcg atctcggcag tgtcgaaggt gccgaccac agcctgctcc      120 cgcgcctccc tgggacgcgc gcctcgcata ccacctccc ggcattgccc ctacgacgca      180
caccgcgata caccgggtgc cgcgtctccc ggaacttggt tcgccccgcc                 230

<210> SEQ ID NO 151
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 151

Arg Pro Ala Gly Arg Xaa Lys Phe Xaa Glu Thr Arg His Pro
1               5                   10

<210> SEQ ID NO 152
<211> LENGTH: 5
<212> TYPE: PRT
<213> ORGANISM: Artificial Sequence
<220> FEATURE:
<223> OTHER INFORMATION: Synthetic

<400> SEQUENCE: 152

Asp Ser Ala Trp Arg
1               5

<210> SEQ ID NO 153
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
```

<223> OTHER INFORMATION: Xaa can be any naturally occurring amino acid

<400> SEQUENCE: 153

Pro Trp Xaa Lys Arg Pro Ala Gly Arg Thr Lys Phe Arg His Pro
1               5                   10                  15

<210> SEQ ID NO 154
<211> LENGTH: 5
<212> TYPE: PRT
<213> ORGANISM: Artificial Sequence
<220> FEATURE:
<223> OTHER INFORMATION: Synthetic

<400> SEQUENCE: 154

Asp Ser Ala Glu Leu
1               5

<210> SEQ ID NO 155
<211> LENGTH: 82
<212> TYPE: PRT
<213> ORGANISM: Artificial Sequence
<220> FEATURE:
<223> OTHER INFORMATION: Synthetic

<400> SEQUENCE: 155

Trp Thr Lys Arg Pro Ala Gly Arg Thr Lys Phe Arg Glu Thr Arg His
1               5                   10                  15

Pro Val Tyr Arg Gly Val Arg Arg Gly Asn Ala Gly Arg Trp Val
            20                  25                  30

Cys Glu Val Arg Val Pro Gly Arg Arg Gly Ser Arg Leu Trp Val Gly
            35                  40                  45

Thr Phe Asp Thr Ala Glu Ile Ala Ala Arg Ala His Asp Ala Ala Met
        50                  55                  60

Leu Ala Leu Ala Ala Gly Asp Ser Cys Leu Asn Phe Ala Asp Ser Ala
65                  70                  75                  80

Glu Leu

<210> SEQ ID NO 156
<211> LENGTH: 83
<212> TYPE: PRT
<213> ORGANISM: Artificial Sequence
<220> FEATURE:
<223> OTHER INFORMATION: Synthetic

<400> SEQUENCE: 156

Pro Trp Thr Lys Arg Pro Ala Gly Arg Thr Lys Phe Arg Glu Thr Arg
1               5                   10                  15

His Pro Val Tyr Arg Gly Val Arg Arg Gly Asn Ala Gly Arg Trp
            20                  25                  30

Val Cys Glu Val Arg Val Pro Gly Arg Arg Gly Ser Arg Leu Trp Val
            35                  40                  45

Gly Thr Phe Asp Thr Ala Glu Ile Ala Ala Arg Ala His Asp Ala Ala
        50                  55                  60

Met Leu Ala Leu Ala Ala Gly Asp Ser Cys Leu Asn Phe Ala Asp Ser
65                  70                  75                  80

Ala Glu Leu

<210> SEQ ID NO 157
<211> LENGTH: 4
<212> TYPE: PRT
<213> ORGANISM: Artificial Sequence

```
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 157

Pro Trp Xaa Lys
1

<210> SEQ ID NO 158
<211> LENGTH: 73
<212> TYPE: PRT
<213> ORGANISM: Artificial Sequence
<220> FEATURE:
<223> OTHER INFORMATION: Synthetic

<400> SEQUENCE: 158

Pro Ala Gly Arg Thr Lys Phe Arg Glu Thr Arg His Pro Val Tyr Arg
1               5                   10                  15

Gly Val Arg Arg Arg Gly Asn Ala Gly Arg Trp Val Cys Glu Val Arg
            20                  25                  30

Val Pro Gly Arg Arg Gly Ser Arg Leu Trp Val Gly Thr Phe Asp Thr
        35                  40                  45

Ala Glu Ile Ala Ala Arg Ala His Asp Ala Ala Met Leu Ala Leu Ala
    50                  55                  60

Ala Gly Asp Ser Cys Leu Asn Phe Ala
65                  70

<210> SEQ ID NO 159
<211> LENGTH: 82
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(77)
<223> OTHER INFORMATION: Xaa can be any naturally occurring amino acid

<400> SEQUENCE: 159

Trp Thr Lys Arg Pro Ala Gly Arg Thr Lys Phe Arg Glu Thr Arg His
1               5                   10                  15

Pro Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Asp Ser Ala
65                  70                  75                  80

Glu Leu

<210> SEQ ID NO 160
<211> LENGTH: 82
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(8)
<223> OTHER INFORMATION: Xaa can be any naturally occurring amino acid
```

```
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(77)
<223> OTHER INFORMATION: Xaa can be any naturally occurring amino acid

<400> SEQUENCE: 160

Trp Thr Lys Xaa Xaa Xaa Xaa Thr Xaa Xaa Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Asp Ser Ala
65                  70                  75                  80

Glu Leu

<210> SEQ ID NO 161
<211> LENGTH: 83
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (19)..(78)
<223> OTHER INFORMATION: Xaa can be any naturally occurring amino acid

<400> SEQUENCE: 161

Pro Trp Thr Xaa Arg Pro Ala Gly Arg Thr Lys Phe Arg Glu Thr Arg
1               5                   10                  15

His Pro Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Asp Ser
65                  70                  75                  80

Ala Glu Leu

<210> SEQ ID NO 162
<211> LENGTH: 83
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
```

```
<221> NAME/KEY: misc_feature
<222> LOCATION: (14)..(78)
<223> OTHER INFORMATION: Xaa can be any naturally occurring amino acid

<400> SEQUENCE: 162

Pro Trp Thr Xaa Xaa Xaa Xaa Xaa Thr Xaa Xaa Arg Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Asp Ser
65                  70                  75                  80

Ala Glu Leu

<210> SEQ ID NO 163
<211> LENGTH: 17
<212> TYPE: PRT
<213> ORGANISM: Artificial Sequence
<220> FEATURE:
<223> OTHER INFORMATION: Synthetic

<400> SEQUENCE: 163

Trp Thr Lys Arg Pro Ala Gly Arg Thr Lys Phe Arg Glu Thr Arg His
1               5                   10                  15

Pro

<210> SEQ ID NO 164
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 164

Trp Thr Lys Xaa Xaa Xaa Xaa Xaa Thr Xaa Xaa Arg
1               5                   10

<210> SEQ ID NO 165
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 165

Pro Trp Thr Xaa Arg Pro Ala Gly Arg Thr Lys Phe Arg Glu Thr Arg
1               5                   10                  15

His Pro
```

```
<210> SEQ ID NO 166
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 166

Pro Trp Thr Xaa Xaa Xaa Xaa Xaa Xaa Thr Xaa Xaa Arg
1               5                   10

<210> SEQ ID NO 167

<400> SEQUENCE: 167

000

<210> SEQ ID NO 168
<211> LENGTH: 14
<212> TYPE: PRT
<213> ORGANISM: Artificial Sequence
<220> FEATURE:
<223> OTHER INFORMATION: Synthetic

<400> SEQUENCE: 168

Arg Pro Ala Gly Arg Thr Lys Phe Arg Glu Thr Arg His Pro
1               5                   10

<210> SEQ ID NO 169
<211> LENGTH: 60
<212> TYPE: PRT
<213> ORGANISM: Artificial Sequence
<220> FEATURE:
<223> OTHER INFORMATION: Synthetic

<400> SEQUENCE: 169

Val Tyr Arg Gly Val Arg Arg Gly Asn Ala Gly Arg Trp Val Cys
1               5                   10                  15

Glu Val Arg Val Pro Gly Arg Arg Gly Ser Arg Leu Trp Val Gly Thr
                20                  25                  30

Phe Asp Thr Ala Glu Ile Ala Ala Arg Ala His Asp Ala Ala Met Leu
        35                  40                  45

Ala Leu Ala Ala Gly Asp Ser Cys Leu Asn Phe Ala
        50                  55                  60

<210> SEQ ID NO 170
<211> LENGTH: 24
<212> TYPE: DNA
<213> ORGANISM: Artificial Sequence
<220> FEATURE:
<223> OTHER INFORMATION: Synthetic

<400> SEQUENCE: 170
cacaatcaca ttaccagaaa ctgc                                    24

<210> SEQ ID NO 171
<211> LENGTH: 142
<212> TYPE: DNA
<213> ORGANISM: Lolium perenne
```

<400> SEQUENCE: 171

```
ggtgtcgaag gtgccgaccc acagcctgct cccgcgcctc cctgggaccc gcacctcgca        60
tacccacctc ccggcattgc ccctacgacg cacaccgcga tacaccgggt gccgcgtctc       120
ccggaacttg gttcgccccg cc                                                142
```

<210> SEQ ID NO 172
<211> LENGTH: 129
<212> TYPE: DNA
<213> ORGANISM: Lolium perenne

<400> SEQUENCE: 172

```
gccgagccag ggctgctcgc cgcgaccgcc ggggacacgt acctcgcaca cccaccgacc        60
cacactgccc cggcgccgca cgccgcggta caccgggtgc cgcgctcttg gaacttggtt       120
cgccccgcc                                                               129
```

<210> SEQ ID NO 173
<211> LENGTH: 202
<212> TYPE: DNA
<213> ORGANISM: Lolium perenne

<400> SEQUENCE: 173

```
gaatcgcccg cggcgagggc gagcatgacg gcgctcttga gctcgggcgg cgatctcggc        60
cgtgtcgaag gtgccgtccc agagcctgct cccgcgccgt cccgtttccc gaaactcgca       120
cacccagcgc tcggcattgc cccaacgacg cacgccgcga tacaccgggt gccgcgtctc       180
ccggaacttg gttcgccccg cc                                                202
```

<210> SEQ ID NO 174
<211> LENGTH: 202
<212> TYPE: DNA
<213> ORGANISM: Lolium perenne

<400> SEQUENCE: 174

```
gaatcgcccg cggcgagggc gagcatgacg gcctctgtgc gctcgggcgg cgatctcggc        60
cgtgtcgaag gtgccgaccc agagcctgct cccgcgccgt cccgggacgc gcacctcgca       120
cacccagcgc ccggcattgc ccctacgacg cacgccgcga tacaccgggt gccgcgtctc       180
ccggaacttg gttcgccccg cc                                                202
```

<210> SEQ ID NO 175
<211> LENGTH: 230
<212> TYPE: DNA
<213> ORGANISM: Lolium perenne

<400> SEQUENCE: 175

```
ttaggcagag tcggcgaagt cccttcaaga atcgcccgcg gcgagggcga gcatggcggc        60
cctcttgtgc tcgcgcggcg atctcggcag tgtcgaaggt gccgacccac agcctgctcc       120
cgcgcctccc tgggacgcgc gcctcgcata cccacctccc ggcattgccc ctacgacgca       180
caccgcgata caccgggtgc cgcgtctccc ggaacttggt tcgccccgcc                  230
```

<210> SEQ ID NO 176
<211> LENGTH: 131
<212> TYPE: DNA
<213> ORGANISM: Lolium perenne

<400> SEQUENCE: 176

```
ggccgaccca cagccggctc ccgcgcctcc ctgggacccg cacctcgcat acccacettt     60 tggcattgcc cctacgacgc gcaccgcgat acaccgggtg ccgcgtctcc cggaacttgg    120
ttcgccccgc c                                                         131
```

```
<210> SEQ ID NO 177
<211> LENGTH: 142
<212> TYPE: DNA
<213> ORGANISM: Lolium perenne

<400> SEQUENCE: 177
agtgtcgaag gtgccgaccc acagcctgct cccgcgcctc cctgggaccc gcacctcgca     60
tacccacctc ccggcattgc cctacgacg cgcaccgcga tacaccgggt gccgcgtctc    120
ccggaacttg gttcgccccg cc                                             142
```

```
<210> SEQ ID NO 178
<211> LENGTH: 131
<212> TYPE: DNA
<213> ORGANISM: Lolium perenne

<400> SEQUENCE: 178
ggccgaccca cagcctgctc ccgcgcctcc ctgggacccg cacctcgcat acccacctcc     60
cggcattgcc cctacgacgc acaccgcgat acaccgggtg ccgcgtctcc cggaacttgg    120
ttcgccccgc c                                                         131
```

```
<210> SEQ ID NO 179
<211> LENGTH: 202
<212> TYPE: DNA
<213> ORGANISM: Lolium perenne

<400> SEQUENCE: 179
gaatcgcccg cggcgagggc gagcatgacg gcctctgtgc gctcgggcgg cgatctcggc     60
cgtgtcgaag gtgccgaccc agagcctgct cccgcgccgt cccgggacgc gcacctcgca    120
cacccagcgc ccggcattgc cctacgacg cacgccgcga tacaccgggt gccgcgtctc    180
ccggaacttg gttcgccccg cc                                             202
```

```
<210> SEQ ID NO 180
<211> LENGTH: 131
<212> TYPE: DNA
<213> ORGANISM: Lolium perenne

<400> SEQUENCE: 180
ggccgaccca cagccggctc ccgcgcctcc ctgggacccg cacctcgcat acccacettt     60 tggcattgcc cctacgacgc gcaccgcgat acaccgggtg ccgcgtctcc cggaacttgg    120
ttcgccccgc c                                                         131
```

```
<210> SEQ ID NO 181
<211> LENGTH: 198
<212> TYPE: DNA
<213> ORGANISM: Artificial Sequence
<220> FEATURE:
<223> OTHER INFORMATION: Synthetic

<400> SEQUENCE: 181
ggcggggcga accaagttcc gggagacgcg gcacccggtg tatcgcggtg tgcgtcgtag     60
gggcaatgcc gggaggtggg tatgcgaggt gcggtccca gggaggcgcg ggagcaggct    120
gtgggtcggc accttcgaca ctgccgagat cgccgcgcga gcacaagagg gccgccatgc    180
```

```
tcgccctcgc cgcgggcg                                                      198

<210> SEQ ID NO 182
<211> LENGTH: 197
<212> TYPE: DNA
<213> ORGANISM: Oryza sativa

<400> SEQUENCE: 182
ggcggggcgg accaagttca gggagacgag gcacccggtg ttccgcggcg tgcggcggag         60
gggcaatgcc gggaggtggg tgtgcgaggt gcgggtgccc gggcggcgcg gctgcaggct        120
ctggctcggc acgttcgaca ccgccagggg cgcggcgcgc gcgcacgacg ccgccatgct        180
cgccatcaac gccggcg                                                      197

<210> SEQ ID NO 183
<211> LENGTH: 198
<212> TYPE: DNA
<213> ORGANISM: Artificial Sequence
<220> FEATURE:
<223> OTHER INFORMATION: Synthetic

<400> SEQUENCE: 183
ggcggggcga accaagttcc gggagacgcg gcacccggtg tatcgcggtg tgcgtcgtag         60
gggcaatgcc gggaggtggg tatgcgaggt gcgggtccca gggaggcgcg ggagcaggct        120
gtgggtcggc accttcgaca ctgccgagat cgccgcgcga gcacaagagg gccgccatgc        180
tcgccctcgc cgcgggcg                                                     198

<210> SEQ ID NO 184
<211> LENGTH: 26
<212> TYPE: DNA
<213> ORGANISM: Artificial Sequence
<220> FEATURE:
<223> OTHER INFORMATION: Synthetic

<400> SEQUENCE: 184
cccgcggcga gggcgagcat ggcggc                                             26

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
gctcgcgcgg cgatctcggc                                                    20

<210> SEQ ID NO 186
<211> LENGTH: 16
<212> TYPE: DNA
<213> ORGANISM: Artificial Sequence
<220> FEATURE:
<223> OTHER INFORMATION: Synthetic

<400> SEQUENCE: 186
tacaccgggt gccgcg                                                        16

<210> SEQ ID NO 187
<211> LENGTH: 20
<212> TYPE: DNA
<213> ORGANISM: Artificial Sequence
<220> FEATURE:
```

```
<223> OTHER INFORMATION: Synthetic

<400> SEQUENCE: 187
ggaacttggt tcgccccgcc                                                      20

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
ggcggggcga accaagttcc                                                      20

<210> SEQ ID NO 189
<211> LENGTH: 16
<212> TYPE: DNA
<213> ORGANISM: Artificial Sequence
<220> FEATURE:
<223> OTHER INFORMATION: Synthetic

<400> SEQUENCE: 189
cgcggcaccc ggtgta                                                          16

<210> SEQ ID NO 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
gccgagatcg ccgcgcgagc                                                      20

<210> SEQ ID NO 191
<211> LENGTH: 472
<212> TYPE: DNA
<213> ORGANISM: Lolium perenne

<400> SEQUENCE: 191
caaatttctc atcgcagagc aaaaccactt cacttcagca acaaaaagc atcaagaacc           60
ctccaaggcg aacagagaca ctgaggtagc gctagctcct attagattgt gattcggatc         120
aacactcaat tcgccatcag aagatgtgtc cgatcaagga ggagatgggc ggggagtcag         180
gctcgccgtg cagcggggac tatcactcgc cctcgacgtc gtcggagctg cagcaggtgc         240
atagtcagaa acagacgccg tggacgaagc ggccggcggg gcgaaccaag ttccgggaga         300
cgcggcaccc ggtgtatcgc ggtgtgcgtc gtaggggcaa tgccgggagg tgggtatgcg         360
aggtgcgggt cccagggagg cgcgggagca ggctgtgggt cggcaccttc gacactgccg         420
agatcgccgc gcgagcacaa gagggccgcc atgctcgccc tcgccgcggg cg                 472

<210> SEQ ID NO 192
<211> LENGTH: 24
<212> TYPE: DNA
<213> ORGANISM: Artificial Sequence
<220> FEATURE:
<223> OTHER INFORMATION: Synthetic

<400> SEQUENCE: 192
aaatttctca tcgcagagca aaac                                                 24
```

<210> SEQ ID NO 193
<211> LENGTH: 24
<212> TYPE: DNA
<213> ORGANISM: Artificial Sequence
<220> FEATURE:
<223> OTHER INFORMATION: Synthetic

<400> SEQUENCE: 193
cagcaaacaa aaagcatcaa gaac                                          24

<210> SEQ ID NO 194
<211> LENGTH: 20
<212> TYPE: DNA
<213> ORGANISM: Artificial Sequence
<220> FEATURE:
<223> OTHER INFORMATION: Synthetic

<400> SEQUENCE: 194
caaggcgaac agagacactg                                               20

<210> SEQ ID NO 195
<211> LENGTH: 21
<212> TYPE: DNA
<213> ORGANISM: Artificial Sequence
<220> FEATURE:
<223> OTHER INFORMATION: Synthetic

<400> SEQUENCE: 195
cgccatcaga agatgtgtcc g                                             21

<210> SEQ ID NO 196
<211> LENGTH: 238
<212> TYPE: PRT
<213> ORGANISM: Oryza sativa

<400> SEQUENCE: 196

Met Cys Gly Ile Lys Gln Glu Met Ser Gly Glu Ser Ser Gly Ser Pro
1               5                   10                  15

Cys Ser Ser Ala Ser Ala Glu Arg Gln His Gln Thr Val Trp Thr Ala
            20                  25                  30

Pro Pro Lys Arg Pro Ala Gly Arg Thr Lys Phe Arg Glu Thr Arg His
        35                  40                  45

Pro Val Phe Arg Gly Val Arg Arg Gly Asn Ala Gly Arg Trp Val
    50                  55                  60

Cys Glu Val Arg Val Pro Gly Arg Arg Gly Cys Arg Leu Trp Leu Gly
65                  70                  75                  80

Thr Phe Asp Thr Ala Glu Gly Ala Ala Arg Ala His Asp Ala Ala Met
                85                  90                  95

Leu Ala Ile Asn Ala Gly Gly Gly Gly Gly Gly Ala Cys Cys Leu
            100                 105                 110

Asn Phe Ala Asp Ser Ala Trp Leu Leu Ala Val Arg Arg Ser Tyr Arg
        115                 120                 125

Thr Leu Ala Asp Val Arg His Ala Val Ala Glu Ala Val Glu Asp Phe
    130                 135                 140

Phe Arg Arg Arg Leu Ala Asp Asp Ala Leu Ser Ala Thr Ser Ser Ser
145                 150                 155                 160

Ser Thr Thr Pro Ser Thr Pro Arg Thr Asp Asp Glu Glu Ser Ala
                165                 170                 175

Ala Thr Asp Gly Asp Glu Ser Ser Ser Pro Ala Ser Asp Leu Ala Phe
            180                 185                 190

```
Glu Leu Asp Val Leu Ser Asp Met Gly Trp Asp Leu Tyr Tyr Ala Ser
            195                 200                 205

Leu Ala Gln Gly Met Leu Met Glu Pro Pro Ser Ala Ala Leu Gly Asp
        210                 215                 220

Asp Gly Asp Ala Ile Leu Ala Asp Val Pro Leu Trp Ser Tyr
225                 230                 235

<210> SEQ ID NO 197
<211> LENGTH: 269
<212> TYPE: PRT
<213> ORGANISM: Hordeum vulgare

<400> SEQUENCE: 197

Met Leu Arg Leu Phe Lys Lys Glu Ala Ala Cys Gln Ser Pro Ser Thr
1               5                   10                  15

Leu Pro Val Ala Met Asp Met Gly Leu Glu Val Ser Ser Ser Ser Pro
            20                  25                  30

Ser Ser Ser Ser Val Ser Ser Pro Glu His Ala Ala Arg Arg Ala
        35                  40                  45

Ser Pro Ala Lys Arg Pro Ala Gly Arg Thr Lys Phe Arg Glu Thr Arg
50                  55                  60

His Pro Val Tyr Arg Gly Val Arg Arg Gly Asn Thr Glu Arg Trp
65                  70                  75                  80

Val Cys Glu Val Arg Val Pro Gly Lys Arg Gly Ala Arg Leu Trp Leu
            85                  90                  95

Gly Thr Tyr Ala Thr Ala Glu Val Ala Ala Arg Ala Asn Asp Ala Ala
            100                 105                 110

Met Leu Ala Leu Gly Gly Arg Ser Ala Thr Cys Leu Asn Phe Ala Asp
        115                 120                 125

Ser Ala Trp Leu Leu Ala Val Pro Ser Ala Leu Ser Asp Leu Ala Asp
130                 135                 140

Val Arg Arg Ala Ala Val Glu Ala Val Ala Asp Phe Gln Arg Arg Glu
145                 150                 155                 160

Ala Ala Asp Gly Ser Leu Ala Ile Ala Val Pro Lys Glu Ala Ser Ser
            165                 170                 175

Gly Ala Pro Ser Leu Ser Pro Ser Ser Gly Ser Asp Ser Ala Gly Ser
        180                 185                 190

Thr Gly Thr Ser Glu Pro Ser Ala Asn Gly Val Phe Glu Gly Pro Val
        195                 200                 205

Val Met Asp Ser Glu Met Phe Arg Leu Asp Leu Phe Pro Glu Met Asp
    210                 215                 220

Leu Gly Ser Tyr Tyr Met Ser Leu Ala Glu Ala Leu Leu Met Asp Pro
225                 230                 235                 240

Pro Pro Thr Ala Thr Ile Ile His Ala Tyr Glu Asp Asn Gly Asp Gly
                245                 250                 255

Gly Ala Asp Val Arg Leu Trp Ser Tyr Ser Val Asp Met
            260                 265

<210> SEQ ID NO 198
<211> LENGTH: 216
<212> TYPE: PRT
<213> ORGANISM: Arabidopsis thaliana

<400> SEQUENCE: 198

Met Asn Ser Phe Ser Ala Phe Ser Glu Met Phe Gly Ser Asp Tyr Glu
1               5                   10                  15
```

-continued

```
Ser Pro Val Ser Ser Gly Gly Asp Tyr Ser Pro Lys Leu Ala Thr Ser
            20                  25                  30

Cys Pro Lys Lys Pro Ala Gly Arg Lys Lys Phe Arg Glu Thr Arg His
            35                  40                  45

Pro Ile Tyr Arg Gly Val Arg Gln Arg Asn Ser Gly Lys Trp Val Cys
            50                  55                  60

Glu Leu Arg Glu Pro Asn Lys Lys Thr Arg Ile Trp Leu Gly Thr Phe
 65                  70                  75                  80

Gln Thr Ala Glu Met Ala Ala Arg Ala His Asp Val Ala Ala Ile Ala
                85                  90                  95

Leu Arg Gly Arg Ser Ala Cys Leu Asn Phe Ala Asp Ser Ala Trp Arg
                100                 105                 110

Leu Arg Ile Pro Glu Ser Thr Cys Ala Lys Glu Ile Gln Lys Ala Ala
                115                 120                 125

Ala Glu Ala Ala Leu Asn Phe Gln Asp Glu Met Cys His Met Thr Thr
                130                 135                 140

Asp Ala His Gly Leu Asp Met Glu Glu Thr Leu Val Glu Ala Ile Tyr
145                 150                 155                 160

Thr Pro Glu Gln Ser Gln Asp Ala Phe Tyr Met Asp Glu Glu Ala Met
                165                 170                 175

Leu Gly Met Ser Ser Leu Leu Asp Asn Met Ala Glu Gly Met Leu Leu
                180                 185                 190

Pro Ser Pro Ser Val Gln Trp Asn Tyr Asn Phe Asp Val Glu Gly Asp
                195                 200                 205

Asp Asp Val Ser Leu Trp Ser Tyr
        210                 215

<210> SEQ ID NO 199
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 199

Pro Ala Gly Arg Xaa Lys Phe Xaa Glu Thr Arg His Pro
 1               5                  10
```